US008188281B2

(12) United States Patent
Salituro et al.

(10) Patent No.: US 8,188,281 B2
(45) Date of Patent: *May 29, 2012

(54) AZAINDOLES USEFUL AS INHIBITORS OF JAK AND OTHER PROTEIN KINASES

(75) Inventors: Francesco Salituro, Marlboro, MA (US); Luc Farmer, Foxboro, MA (US); Randy Bethiel, Lexington, MA (US); Edmund Harrington, Plymouth, MA (US); Jeremy Green, Waltham, MA (US); John Court, Littleton, MA (US); Jon Come, Cambridge, MA (US); David Lauffer, Stow, MA (US); Alex Aronov, Watertown, MA (US); Hayley Binch, San Diego, CA (US); Dean Boyall, Abingdon (GB); Jean-Damien Charrier, Wantage (GB); Simon Everitt, Beaconsfields (GB); Damien Fraysse, Abingdon (GB); Michael Mortimore, Burford (GB); Francoise Pierard, Abingdon (GB); Daniel Robinson, Abingdon (GB); Jian Wang, Newton, MA (US); Joanne Pinder, Abingdon (GB); Tiansheng Wang, Concord, MA (US); Albert Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 90 days.

This patent is subject to a terminal disclaimer.

(21) Appl. No.: 12/273,799

(22) Filed: Nov. 19, 2008

(65) Prior Publication Data
US 2009/0176763 A1    Jul. 9, 2009

Related U.S. Application Data

(63) Continuation of application No. 11/093,821, filed on Mar. 30, 2005, now Pat. No. 7,507,826.

(60) Provisional application No. 60/557,503, filed on Mar. 30, 2004, provisional application No. 60/625,599, filed on Nov. 5, 2004.

(51) Int. Cl.
C07D 471/02 (2006.01)

(52) U.S. Cl. ........................................... 546/113

(58) Field of Classification Search .................. 546/113
See application file for complete search history.

(56) References Cited

U.S. PATENT DOCUMENTS

| 6,265,403 | B1 | 7/2001 | Fraley et al. | |
|---|---|---|---|---|
| 7,507,826 | B2 * | 3/2009 | Salituro et al. | 546/113 |
| 7,767,816 | B2 * | 8/2010 | Farmer et al. | 546/113 |
| 2002/0147189 | A1 | 10/2002 | Hui et al. | |

| 2005/0137201 | A1 | 6/2005 | Aronov et al. |
| 2006/0003968 | A1 | 1/2006 | Green et al. |
| 2007/0207995 | A1 | 9/2007 | Salituro et al. |

FOREIGN PATENT DOCUMENTS

| EP | 0557171 | 8/1993 |
|---|---|---|
| WO | WO 88/01997 | 3/1988 |
| WO | WO 95/33748 | 12/1995 |
| WO | WO 99/21859 | 5/1999 |
| WO | WO 00/40581 | 7/2000 |
| WO | WO 00/43393 | 7/2000 |
| WO | WO 01/01986 | 1/2001 |
| WO | WO 02/051837 | 7/2002 |
| WO | WO 02/072587 | 9/2002 |
| WO | WO 02/085896 | 10/2002 |
| WO | WO 02/085911 | 10/2002 |
| WO | WO 02/088131 | 11/2002 |
| WO | WO 02/088135 | 11/2002 |
| WO | WO 02/088140 | 11/2002 |
| WO | WO 02/088144 | 11/2002 |
| WO | WO 02/092602 | 11/2002 |
| WO | WO 03/000688 | 1/2003 |
| WO | WO 03/091246 | 11/2003 |
| WO | WO 03/101990 | 12/2003 |
| WO | WO 2004/016609 | 2/2004 |
| WO | WO 2004/016610 | 2/2004 |
| WO | WO 2004/043388 | 5/2004 |
| WO | WO 2004/078756 | 9/2004 |
| WO | WO 2004/082638 | 9/2004 |
| WO | WO 2004/089913 | 10/2004 |
| WO | WO 2004/106298 | 12/2004 |
| WO | WO 2005/028475 | 3/2005 |
| WO | WO 2005/044181 | 5/2005 |
| WO | WO 2005/062795 | 7/2005 |
| WO | WO 2005/085244 | 9/2005 |
| WO | WO 2005/095400 | 10/2005 |
| WO | WO 2005/105213 | 11/2005 |
| WO | WO 2006/009755 | 1/2006 |
| WO | WO 2006/030031 | 3/2006 |
| WO | WO 2006/038001 | 4/2006 |
| WO | WO 2006/050076 | 5/2006 |
| WO | WO 2006/124863 | 11/2006 |
| WO | WO 2006/127587 | 11/2006 |
| WO | WO 2007/002433 | 1/2007 |
| WO | WO 2007/117494 | 10/2007 |

OTHER PUBLICATIONS

Alvarez, M., "Synthesis of 3-Aryl-and 3-Heteroaryl-7-azaindoles", Synthesis, 4 (1999), pp. 615-620.
Fernandez et al. Monatshefte Fur Chemie vol. 135, 2004, pp. 615-627.
Fresneda, P., "Synthesis of the Indole Alkaloids Meridianins from the Tunicate Aplidium Meridianum", Tetrahedron, 57 (2001), pp. 2355-2363.
Herber, R. et al., 1H-Pyrrolo[2,3-b]pyridines. Part II. Fragmentation of Some 1H-Pyrrolo[2,3-b]pyridines induced by Electron Impact. J. Chem. Soc. (B) Phys. Org. 1970, 459.
Kelly, T., "Novel Non-Nucleoside Inhibitors of Human Immunodeficiency virus type 1 Reverse Transcriptase. 6. 2-Indo1-3-yl and 2-Azaindol-3-yl-dipyridodiazepinones1", J. Med. Chem., 40 (1997), pp. 2430-2433.

(Continued)

*Primary Examiner* — Nizal Chandrakumar
(74) *Attorney, Agent, or Firm* — Honigman Miller Schwartz and Cohn LLP; Jonathan P. O'Brien; Andrew N. Weber

(57) ABSTRACT

The present invention relates to inhibitors of protein kinases. The invention also provides pharmaceutical compositions comprising the compounds of the invention and methods of using the compositions in the treatment of various disorders.

15 Claims, No Drawings

OTHER PUBLICATIONS

Pungpo, P., "Three-Dimensional Quantitative Structure-Activity Relationship Study on HIV-1 Reverse Transcriptase Inhibitors in the Class of Dipyridodiazepinone Derivatives, Using Comparative Molecular field Analysis" Journal of Molecular Graphics and Modeling 18 (2000), pp. 581-590.

International Search Report, dated Aug. 19, 2005, issued for PCT Application No. PCT/US2005/010846.

International Preliminary Report on Patentability, dated Oct. 12, 2006, issued for PCT Application No. PCT/US2005/010846.

Written Opinion of the International Searching Authority, issued for PCT Application No. PCT/US2005/010846.

* cited by examiner

AZAINDOLES USEFUL AS INHIBITORS OF JAK AND OTHER PROTEIN KINASES

CROSS-REFERENCE TO RELATED APPLICATIONS

This application is a continuation of U.S. application Ser. No. 11/093,821, filed Mar. 30, 2005 now U.S. Pat. No. 7,507,826, which in turn claims the benefit of U.S. Provisional Application No. 60/557,503, filed Mar. 30, 2004 and U.S. Provisional Application No. 60/625,599, filed Nov. 5, 2004.

TECHNICAL FIELD OF THE INVENTION

The present invention relates to inhibitors of protein kinases. The invention also provides pharmaceutical compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank *Mol. Med.* 5, 432-456 (1999) & Seidel, et al, *Oncogene* 19, 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, *Blood* 96, 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, *Nature* 346, 274-276 (1990) & Galli, *N. Engl. J. Med.*, 328, 257-265 (1993)]. A crucial role for JAK3 in IgE receptor-mediated mast cell responses in vitro and in vivo has been established [Malaviya, et al, *Biochem. Biophys. Res. Commun.* 257, 807-813 (1999)]. In addition, the prevention of type I hypersensitivity reactions, including anaphylaxis, mediated by mast cell-activation through inhibition of JAK3 has also been reported [Malaviya et al, *J. Biol. Chem.* 274, 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 33, 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus Kinases (JAK 1 & 3) and that IL-4-associated JAK kinases are expressed in the RA synovium [Muller-Ladner, et al, *J. Immunol.* 164, 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, *Biochem. Biophys. Res. Commun.* 267, 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, *Clin. Cancer Res.* 5, 1569-1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT 1, STAT3, STAT5, and cytokine-independent growth [Schwaller, et al, *EMBO J.* 17, 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, *Proc. Nat. Acad. Sci. U.S.A.* 94, 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, *J. Immunol.* 159, 5206-5210 (1997)]. In addition, IL-6-mediated STAT3 activation was blocked by an inhibitor of JAK, leading to sensitization of myeloma cells to apoptosis [Catlett-Falcone, et al, *Immunity* 10, 105-115 (1999)].

One kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al. *Nature,* 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell. Biol.* 1996, 16, 5313-5327; Amano et al., *Science,* 1997, 275, 1308-1311; Ishizaki et al., *FEBS Lett.* 1997, 404, 118-124) and in down-regulation of myosin phosphatase (Kimura et al., *Science,* 1996, 273, 245-248), platelet activation (Klages et al., *J. Cell. Biol.,* 1999, 144, 745-754), aortic smooth muscle contraction by various stimuli (Fu et al., *FEBS Lett.,* 1998, 440, 183-187), thrombin-induced responses of aortic smooth muscle cells (Seasholtz et al., *Cir. Res.,* 1999, 84, 1186-1193), hypertrophy of cardiomyocytes (Kuwahara et al., *FEBS Lett.,* 1999, 452, 314-318), bronchial smooth muscle contraction (Yoshii et al, *Am. J. Respir. Cell Mol. Biol.,* 1999, 20, 1190-1200), smooth muscle contraction and cytoskeletal reorganization of non-muscle cells (Fukata et al, *Trends in Pharm. Sci* 2001, 22, 32-39), activation of volume-regulated anion channels (Nilius et al., *J. Physiol.,* 1999, 516, 67-74), neurite retraction (Hirose et al., *J. Cell. Biol.,* 1998, 141, 1625-1636), neutrophil chemotaxis (Niggli, *FEBS Lett.,* 1999, 445, 69-72), wound healing (Nobes and Hall, *J. Cell. Biol.,* 1999, 144, 1235-1244), tumor invasion (Itoh et al, *Nat. Med.,* 1999, 5, 221-225) and cell transformation (Sahai et al., *Curr. Biol.,* 1999, 9, 136-145).

More specifically, ROCK has been implicated in various diseases and disorders including hypertension (Satoh et al., *J. Clin. Invest.* 1994, 94, 1397-1403; Mukai et al., *FASEB J.* 2001, 15, 1062-1064; Uehata et al, *Nature* 1997, 389, 990-994; Masumoto et al., *Hypertension,* 2001, 38, 1307-1310), cerebral vasospasm (Sato et al, *Circ. Res.* 2000, 87, 195-200; Miyagi et al., *J. Neurosurg.* 2000, 93, 471-476; Tachibana et al., *Acta Neurochir* (Wien) 1999, 141, 13-19), coronary vasospasm (Shimokawa et al., *Jpn. Cir. J.* 2000, 64, 1-12; Kandabashi et al., *Circulation* 2000, 101, 1319-1323; Katsumata et al., *Circulation* 1997, 96, 4357-4363; Shimokawa et al., *Cardiovasc. Res.* 2001, 51, 169-177; Utsunomiya et al., *J. Pharmacol.* 2001, 134, 1724-1730; Masumoto et al., *Circulation* 2002, 105, 1545-1547), bronchial asthma (Chiba et al., *Comp. Biochem. Physiol. C Pharmacol. Toxicol. Endocrinol.* 1995, 11, 351-357; Chiba et al., *Br. J. Pharmacol.* 1999, 127, 597-600; Chiba et al., *Br. J. Pharmacol.* 2001, 133, 886-890; Tizuka et al., *Eur. J. Pharmacol.* 2000, 406, 273-279), preterm labor (Niro et al., *Biochem. Biophys. Res. Commun.* 1997, 230, 356-359; Tahara et al., *Endocrinology* 2002, 143, 920-929; Kupittayanant et al., *Pflugers Arch.* 2001, 443, 112-114), erectile dysfunction (Chitaley et al., *Nat. Med.* 2001, 7, 119-122; Mills et al., *J. Appl. Physiol.* 2001, 91, 1269-1273), glaucoma (Honjo et al., *Arch. Opthalmol.* 2001, 1171-1178; Rao et al., *Invest. Opthalmol. Vis. Sci.* 2001, 42, 1029-1037), vascular smooth muscle cell proliferation (Shimokawa et al., *Cardiovasc. Res.* 2001, 51, 169-177; Morishige et al, *Arterioscler. Thromb. Vasc. Biol.* 2001, 21, 548-554; Eto et al., *Am. J. Physiol. Heart Circ. Physiol.* 2000, 278, H1744-H1750; Sawada et al., *Circulation* 2000, 101, 2030-2023; Shibata et al., *Circulation* 2001, 103, 284-289), myocardial hypertrophy (Hoshijima et al., *J. Biol. Chem.* 1998, 273, 7725-77230; Sah et al., *J. Biol. Chem.* 1996, 271, 31185-31190; Kuwahara et al., *FEBS Lett.* 1999, 452, 314-318; Yanazume et al., *J. Biol. Chem.* 2002, 277, 8618-8625), malignoma (Itoh et al., *Nat. Med.* 1999, 5, 221-225; Genda et al., *Hepatology* 1999, 30, 1027-1036; Somlyo et al., *Biochem. Biophys. Res. Commun.* 2000, 269, 652-659), ischemia/reperfusion-induced injury (Ikeda et al., *J. of Surgical Res.* 2003, 109, 155-160; Miznuma et al. *Transplantation* 2003, 75, 579-586), endothelial dysfunction (Hernandez-Perera et al, *Circ. Res.* 2000, 87, 616-622; Laufs et al., *J. Biol. Chem.* 1998, 273, 24266-24271; Eto et al., *Circ. Res.* 2001, 89, 583-590), Crohn's Disease and colitis (Segain et al. *Gastroenterology* 2003, 124(5), 1180-1187), neurite outgrowth (Fournier et al. *J. Neurosci.* 2003, 23, 1416-1423), Raynaud's Disease (Shimokawa et al. *J. Cardiovasc. Pharmacol.* 2002, 39, 319-327), angina (Utsunomiya et al. *Br. J. Pharmacol.* 2001, 134, 1724-1730; Masumoto et al, *Circulation* 2002, 105, 1545-1547; Shimokawa et al, *J. Cardiovasc. Pharmacol.,* 2002, 40, 751-761; Satoh et al., *Jpn. J. Pharmacol.,* 2001, 87, 34-40), Alzheimer's disease (Zhou et al., *Science* 2003, 302, 1215-1218), benign prostatic hyperplasia (Rees et al., *J. Urology,* 2003, 170, 2517-2522), and atherosclerosis (Retzer et al. *FEBS Lett.* 2000, 466, 70-74; Ishibashi et al. *Biochim. Biophys. Acta* 2002, 1590, 123-130). Accordingly, the development of inhibitors of ROCK kinase would be useful as therapeutic agents for the treatment of disorders implicated in the ROCK kinase pathway.

The Aurora proteins are a family of three highly related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas. In addition amplification of the AURKA locus that encodes for Aurora-A correlates with poor prognosis for patients with node-negative breast cancer. Furthermore overexpression of Aurora-A has been shown to transform mammalian fibroblasts, giving rise to aneuploid cells containing multipolar spindles.

A number of studies have now demonstrated that depletion or inhibition of Aurora-A or -B in human cancer cell lines by siRNA, dominant negative or neutralising antibodies disrupts progression through mitosis with accumulation of cells with 4N DNA, and in some cases this is followed by endoreduplication and cell death.

Protein kinases are attractive and proven targets for new therapeutic agents to treat a range if human diseases, with examples including Gleevec and Tarceva. The Aurora kinases are especially attractive due to their association with numerous human cancers and the role they play in promoting proliferation of these cancer cells (Harrington et al., *Nature Med.*, 2004, 10: 262-267).

Accordingly, there is a great need to develop inhibitors of JAK, ROCK and Aurora, preferably JAK-3, ROCK and Aurora A, protein kinases that are useful in treating various diseases or conditions associated with JAK, ROCK and Aurora activation, particularly given the inadequate treatments currently available for the majority of these disorders.

SUMMARY OF THE INVENTION

It has now been found that compounds of this invention, and pharmaceutically acceptable compositions thereof, are effective as inhibitors of JAK, ROCK and Aurora protein kinases. In certain embodiments, these compounds are effective as inhibitors of JAK-3, ROCK and Aurora protein kinases. These compounds have the general formula I:

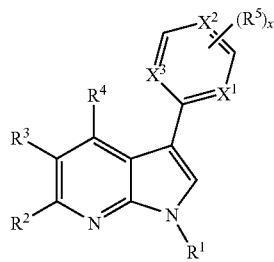

or a pharmaceutically acceptable salt thereof, wherein $R^1$, $R^2$, $R^3$, $R^4$, $X^1$, $X^1$, $X^3$, $R^5$ and x are as defined below and in subsets herein.

These compounds and pharmaceutical compositions thereof are useful for treating or preventing a variety of disorders, including, but not limited to, heart disease, diabetes, Alzheimer's disease, immunodeficiency disorders, inflammatory diseases, hypertension, allergic diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, ovarian cancer, breast cancer and endometrial cancer), liver disease including hepatic ischemia, heart disease such as myocardial infarction and congestive heart failure, pathologic immune conditions involving T cell activation, and neurodegenerative disorders.

DETAILED DESCRIPTION OF THE INVENTION

1. General Description of Compounds of the Invention

The present invention relates to compounds of formula I:

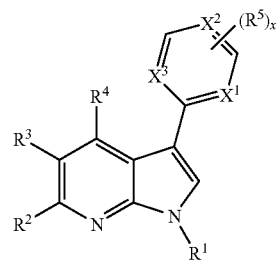

or pharmaceutically acceptable salts thereof, wherein:
$R^1$ is T-R' or is $—Si(R')_3$;
$R^2$, $R^3$, and $R^4$ are each independently halogen, CN, $NO_2$, or V—R';
$X^1$, $X^2$ and $X^3$ are each independently N, or CH, wherein the hydrogen atom of CH is optionally replaced by $R^5$;
x is 1, 2, 3, or 4;
each occurrence of $R^5$ is independently halogen, CN, $NO_2$, or U—R';
T, V, and U are each independently a bond or an optionally substituted $C_1$-$C_6$ alkylidene chain, wherein up to two methylene units of the chain are optionally and independently replaced by —NR'—, —S—, —O—, —CS—, —$CO_2$—, —OCO—, —CO—, —COCO—, —CONR'—, —NR'CO—, —$NR'CO_2$—, —$SO_2NR'$—, —$NR'SO_2$—, —CONR'NR'—, —NR'CONR'—, —OCONR'—, —NR'NR'—, —$NR'SO_2NR'$—, —SO—, —$SO_2$—, —PO—, —$PO_2$—, or —POR'—; and
each occurrence of R' is independently hydrogen or an optionally substituted group selected from a $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur. In certain embodiments, the two occurrences of R' that form a ring will be on a single substituent (e.g., $R^1$, $R^2$, $R^3$, $R^4$ or on a single $R^5$ substituent) and form a monocyclic or bicyclic ring. In other embodiments, the two occurrences of R' are on two substituents (e.g., on two $R^5$ substituents) and can form a bicyclic fused ring with the ring to which the $R^5$ substituents are attached. However, the two occurrences of R' do not form a tricyclic ring whether they are a bound to a single substituent or to two separate substituents.

In certain embodiments, for compounds described directly above:
a. if $R^1$ is substituted cyclopentyl, x is 1, $X^1$ and $X^3$ are CH, then $X^2$ is not C—$R^5$, where $R^5$ is fluoro or OMe;
b. if $R^2$ and $R^3$ are simultaneously H and $R^1$ and $R^4$ are independently selected from H or Me, x is 1, $X^1$ and $X^3$ are CH, then $X^2$ is not C—$R^5$, where $R^5$ is OMe, $NO_2$, or fluoro;
c. if $R^1$, $R^2$ and $R^4$ are simultaneously H, x is 1, $R^5$ is —SMe, $NH_2$ or an optionally substituted NH-piperidine, and $X^1$ and $X^2$ are N, then $X^3$ is not CH;
d. if $R^2$, $R^3$ and $R^4$ are simultaneously H, $X^1$, $X^2$ and $X^3$ are CH, and two $R^5$ form a fused optionally substituted bicyclic ring with the ring to which they are attached, then $R^1$ is not $CH_2CH_2N(Me)_2$.
e. if $R^2$ and $R^3$ are simultaneously H, $R^4$ is $NH_2$, and $X^1$, $X^2$ and $X^3$ are CH, then $R^1$ is not substituted phenyl;
f. if $R^2$, $R^3$ and $R^4$ are simultaneously H, then $R^1$ is not $Si(R')_3$.
g. if $R^1$, $R^2$ and $R^4$ are simultaneously H and (i) $X^2$ and $X^3$ are CH or $CR^5$ or (ii) any one of $X^1$, $X^2$ or $X^3$ are N, then $R^3$ is not phenyl or phenyl substituted with O-phenyl or $N(Me)_2$.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —$R^\circ$; —$OR^\circ$; —$SR^\circ$; phenyl (Ph) optionally substituted with $R^\circ$; —O(Ph) optionally substituted with $R^\circ$; —$(CH_2)_{1-2}$(Ph), optionally substituted with $R^\circ$; —CH=CH(Ph), optionally substituted with $R^\circ$; a 5-6 membered heteroaryl or heterocyclic ring optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2R^\circ$; —$NR^\circ NR^\circ C(O)R^\circ$; —$NR^\circ NR^\circ C(O)N(R^\circ)_2$; —$NR^\circ NR^\circ CO_2R^\circ$; —$C(O)C(O)R^\circ$; —$C(O)CH_2C(O)R^\circ$; —$CO_2R^\circ$; —$C(O)R^\circ$; —$C(S)R^\circ$; —$C(O)N(R^\circ)_2$; —$C(S)N(R^\circ)_2$; —$OC(O)N(R^\circ)_2$; —$OC(O)R^\circ$; —$C(O)N(OR^\circ)R^\circ$; —$C(NOR^\circ)R^\circ$; —$S(O)_2R^\circ$; —$S(O)_3R^\circ$; —$SO_2N(R^\circ)_2$; —$S(O)R^\circ$; —$NR^\circ SO_2N(R^\circ)_2$; —$NR^\circ SO_2R^\circ$; —$N(OR^\circ)R^\circ$; —C(=NH)—$N(R^\circ)_2$; —$P(O)_2R^\circ$; —$PO(R^\circ)_2$; —$OPO(R^\circ)_2$; or —$(CH_2)_{0-2}NHC(O)R^\circ$; wherein each independent occurrence of $R^\circ$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^\circ$, on the same substituent or different substituents, taken together with the atom(s) to which each $R^\circ$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of $R^\circ$ are selected from $NH_2$, $NH(C_{1-4}$aliphatic), $N(C_{1-4}$aliphatic)$_2$, halogen, $C_{1-4}$aliphatic, OH, O($C_{1-4}$aliphatic), $NO_2$, CN, $CO_2H$, $CO_2(C_{1-4}$aliphatic), O(halo$C_{1-4}$ aliphatic), or haloC$_{1-4}$ aliphatic, wherein each of the foregoing $C_{1-4}$aliphatic groups of $R^\circ$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic group.

Unless otherwise defined above and herein, optional substituents on the nitrogen of a non-aromatic heterocyclic ring are generally selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^{+1})_2$, —C(=NH)—$N(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of $R^+$ are selected from —$NH_2$, —$NH(C_{1-4}$ aliphatic), —$N(C_{1-4}$ aliphatic)$_2$, halogen, $C_{1-4}$ aliphatic, —OH, —$O(C_{1-4}$ aliphatic), —$NO_2$, —CN, —$CO_2H$, —$CO_2(C_{1-4}$ aliphatic), —O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As detailed above, in some embodiments, two independent occurrences of $R^\circ$ (or $R^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of $R^\circ$ (or $R^+$, R', R' or any other variable similarly defined herein), are taken together with the atom(s) to which each variable is bound include, but are not limited to the following: a) two independent occurrences of $R^\circ$ (or $R^+$, R, R' or any other variable similarly defined herein) that are bound to the same atom and are taken together with that atom to form a ring, for example, $N(R^\circ)_2$, where both occurrences of $R^\circ$ are taken together with the nitrogen atom to form a piperidin-1-yl, piperazin-1-yl, or morpholin-4-yl group; and b) two independent occurrences of $R^\circ$ (or $R^+$, R, R' or any other variable similarly defined herein) that are bound to different atoms and are taken together with both of those atoms to form a ring, for example where a phenyl group is substituted with two occurrences of $OR^\circ$

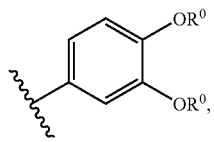

these two occurrences of $R^o$ are taken together with the oxygen atoms to which they are bound to form a fused 6 membered oxygen containing ring:

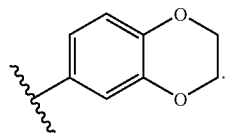

It will be appreciated that a variety of other rings can be formed when two independent occurrences of $R^o$ (or $R^+$, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds

As described generally above, $R^1$ is T-R', or is $-Si(R')_3$. In certain embodiments, when $R^1$ is T-R', T is an optionally substituted $C_1$-$C_6$alkylidene chain wherein up to two methylene units are optionally and independently replaced with $-O-$, $-S-$, $-NR'-$, $-OCO-$, $-COO-$, $-SO_2-$ or $-CO-$, and R' is hydrogen, $C_1$-$C_4$-alkyl, or an optionally substituted 5- or 6-membered aryl or heteroaryl group. In other embodiments of $R^1$, R' may additionally be $C_1$-$C_4$-aliphatic. In other embodiments, when $R^1$ is $-Si(R')_3$, R' is hydrogen, $C_1$-$C_4$-alkyl, or an optionally substituted 5- or 6-membered saturated, partially unsaturated, or fully unsaturated monocyclic ring having 0-3 heteroatoms independently selected from nitrogen, oxygen, or sulfur. In still other embodiments, $R^1$ is hydrogen, $C_1$-$C_4$alkyl, $-COR'$, $-SO_2R'$, or $-Si(R')_3$. In yet other embodiments, $R^1$ is hydrogen, methyl, ethyl, n-propyl, isopropyl, n-butyl, p-toluenesulfonyl (Ts), t-butyldimethylsilyl (TBS), triisopropylsilyl (TIPS), or triethylsilyl (TES). Exemplary $R^1$ groups are also depicted in Tables 1 and 2 herein.

As described generally above, $R^2$, $R^3$, and $R^4$ are each independently halogen, CN, $NO_2$, or V—R'. In certain embodiments, $R^2$, $R^3$, and $R^4$ are each independently hydrogen, R', halogen, CN, $NO_2$, $-N(R')_2$, $-CH_2N(R')_2$, $-OR'$, $-CH_2OR'$, $-SR'$, $-CH_2SR'$, $-COOR'$, $-NR'COR'$, $-CON(R')_2$, $-SO_2N(R')_2$, $-CONR'(CH_2)_2N(R')_2$, $-CONR'(CH_2)_3N(R')_2$, $-CONR'(CH_2)_4N(R')_2$, $-O(CH_2)_2OR'$, $O(CH_2)_3OR'$, $O(CH_2)_4OR'$, $-O(CH_2)_2N(R')_2$, $-O(CH_2)_3N(R')_2$, or $-O(CH_2)_4N(R')_2$. In other embodiments, $R^2$, $R^3$, and $R^4$ are each independently Cl, Br, F, $-CN$, $-COOH$, $-COOMe$, $-NH_2$, $-N(CH_3)_2$, $-N(Et)_2$, $-N(iPr)_2$, $-O(CH_2)_2OCH_3$, $-CONH_2$, $-COOCH_3$, $-OH$, $-CH_2OH$, $-NHCOCH_3$, $-SO_2NH_2$, $-SO_2N(Me)_2$, or an optionally substituted group selected from $C_1$-$C_4$alkyl, $C_1$-$C_4$alkyloxy, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur. In still other embodiments, $R^2$, $R^3$, and $R^4$ are each hydrogen. In other embodiments, one of $R^2$, $R^3$, or $R^4$ is hydrogen. In yet other embodiments, two of $R^2$, $R^3$, or $R^4$ is hydrogen. In yet other embodiments, $R^2$ and $R^4$ are both hydrogen, and $R^3$ is halogen, CN, $NO_2$, or V—R'. In still other embodiments, $R^2$ and $R^4$ are both hydrogen, and $R^3$ is an optionally substituted group selected from a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur. In yet other embodiments, $R^2$ and $R^4$ are both hydrogen, and $R^3$ is an optionally substituted 5- or 6-membered saturated, partially unsaturated, or fully unsaturated ring having 0-3 heteroatoms independently selected from nitrogen, oxygen, or sulfur. In yet other embodiments, $R^2$ and $R^4$ are both hydrogen, and $R^3$ is an optionally substituted ring selected from phenyl, pyridyl, pyrimidinyl, thiazolyl, oxazolyl, thienyl, furyl, pyrrolyl, pyrazolyl, triazolyl, pyrazinyl, thiadiazolyl, or oxadiazolyl. In yet other embodiments, when $R^1$, $R^2$ and $R^4$ are H, then $R^3$ is not an optionally substituted phenyl. In yet other embodiments, when $R^1$, $R^2$ and $R^4$ are H, then $R^3$ is not an aryl, heteroaryl, carbocyclyl or heterocyclyl ring. Exemplary $R^2$, $R^3$, and $R^4$ groups also include those shown below in Tables 1 and 2.

As described above, $R^2$, $R^3$, and $R^4$ are each optionally substituted, and in certain embodiments, $R^2$, $R^3$, and $R^4$ are each optionally and independently substituted with z occurrences of $R^6$, wherein z is 0-5 and $R^6$ is $=O$, $=NR'$, $=S$, halogen, $-CN$, $-NO_2$, or Z—R'', wherein Z is a bond or an optionally substituted $C_1$-$C_6$ alkylidene chain, wherein up to two methylene units of the chain are optionally and independently replaced by $-NR''-$, $-S-$, $-O-$, $-CS-$, $-CO_2-$, $-OCO-$, $-CO-$, $-COCO-$, $-CONR''-$, $-NR''CO-$, $-NR''CO_2-$, $-SO_2NR''-$, $-NR''SO_2-$, $-CONR''NR''-$, $-NR''CONR''-$, $-OCONR''-$, $-NR''NR''-$, $-NR''SO_2NR''-$, $-SO-$, $-SO_2-$, $-PO-$, $-PO_2-$ or $-POR''-$, and each occurrence of R'' is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur. In other embodiments, z is 0, 1, 2, or 3, and each occurrence of $R^6$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR" (CH$_2$)$_2$N(R")$_2$, —CONR(CH$_2$)$_3$N(R")$_2$, —CONR"(CH$_2$)$_4$N (R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR" (CH$_2$)R", —NR"(CH$_2$)$_2$R", —NR"(CH$_2$)$_3$R", —NR"(CH$_2$)$_4$ R", —NR"(CH$_2$)N(R")$_2$, —NR"(CH$_2$)$_2$N(R")$_2$, —NR" (CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR"(CH$_2$)$_4$ OR". In other embodiments, $R^6$ may additionally be —NR"CH(CH$_3$)R". In still other embodiments, z is 1, 2, or 3 and each occurrence of $R^6$ is independently F, Cl, Br, CN, OH, NH$_2$, —CH$_2$OH, C$_1$-C$_6$alkyl, —O(C$_1$-C$_6$alkyl), —CH$_2$O (C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$-phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic. Additional exemplary $R^6$ groups are depicted in Table 1.

As described generally above for compounds of formula I, $X^1$, $X^2$ and $X^3$ are each independently N, or CH, wherein the hydrogen atom of CH is optionally replaced by $R^5$. In certain embodiments, two of $X^1$, $X^2$, or $X^3$ is N, and the remaining one of $X^1$, $X^2$, or $X^3$ is CH, wherein the hydrogen atom of CH is optionally replaced by $R^5$. In certain other embodiments, one of $X^1$, $X^2$, or $X^3$ is N, and the remaining two of $X^1$, $X^2$, or $X^3$ is CH, wherein the hydrogen atom of CH is optionally replaced by $R^5$. In yet other embodiments, each of $X^1$, $X^2$ and $X^3$ is CH, wherein the hydrogen atom of CH is optionally replaced by $R^5$. In certain other exemplary embodiments, compounds have one of formulae I-A, I-B, I-C or I-D:

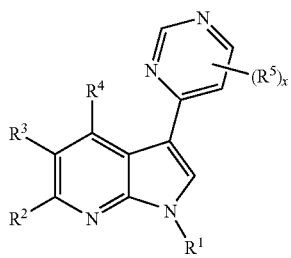

I-A

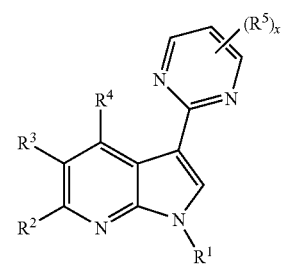

I-B

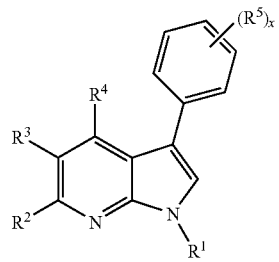

I-C

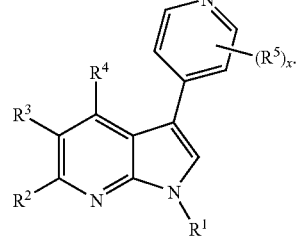

I-D

In other embodiments, compounds have formula I-E:

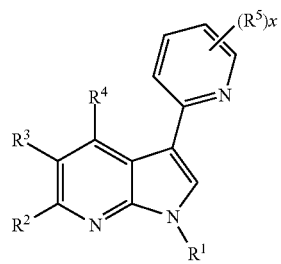

I-E

As described generally for compounds of formula I above, x is 1, 2, 3, or 4; and each occurrence of $R^5$ is independently halogen, CN, NO$_2$, or U—R', wherein each occurrence of U is independently a bond or an optionally substituted C$_1$-C$_6$ alkylidene chain, wherein up to two methylene units of the chain are optionally and independently replaced by —NR'—, —S—, —O—, —CS—, —CO$_2$—, —OCO—, —CO—, —COCO—, —CONR'—, —NR'CO—, —NR'CO$_2$—, —SO$_2$NR'—, —NR'SO$_2$—, —CONR'NR'—, —NR'CONR'—, —OCONR'—, —NR'NR'—, —NR'SO$_2$NR'—, —SO—, —SO$_2$—, —PO—, —PO$_2$—, or —POR'—; and each occurrence of R' is independently hydrogen or an optionally substituted C$_1$-C$_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur. In certain embodiments, each occurrence of $R^5$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COCH$_2$R', —NR'CO(CH$_2$)$_2$ R', —NR'COOR', —CON(R')$_2$, —SO$_2$N(R')$_2$, —CONR'

(CH$_2$)$_2$N(R')$_2$, —CONR(CH$_2$)$_3$N(R')$_2$, —CONR'(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, —O(CH$_2$)$_4$N(R')$_2$, —NR'CH(CH$_2$OH)R', —NR'CH(CH$_2$CH$_2$OH)R', —NR'(CH$_2$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$N(R')$_2$, —NR'(CH$_2$)OR', —NR'(CH$_2$)$_2$OR', —NR'(CH$_2$)$_3$OR', or —NR'(CH$_2$)$_4$OR'. In certain embodiments, R$^5$ may also be —NR'CH(CH$_3$)R', NR'CH(CF$_3$)R', —NR'CH(CH$_3$)C(O)OR', —NR'CH(CF$_3$)C(O)OR', —NR'CH(CH$_2$CH$_3$)R', —NR'CH$_2$C(O)N(R')$_2$, —NR'CH(CH$_3$)C(O)N(R')$_2$, NR'CH(CF$_3$)C(O)N(R')$_2$, —NR'CH(CH$_2$CH$_3$)C(O)N(R')$_2$, —NR'CH(CH(CH$_3$)$_2$)C(O)N(R')$_2$, —NR'CH(C(CH$_3$)$_3$)C(O)N(R')$_2$, —NR'CH(CH$_2$CH(CH$_3$)$_2$)C(O)N(R')$_2$, —NR'CH(CH$_2$OR$^9$)C(O)N(R')$_2$ or —NR'CH(CH$_2$CH$_2$N(Me)$_2$)C(O)N(R')$_2$. In certain exemplary embodiments, x is 1, 2, or 3, and at least one occurrence of R$^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, or —NR'(CH$_2$)$_2$N(R')$_2$. In other embodiments, x is 1, 2, or 3, and at least one occurrence of R$^5$ is —OR'. In other embodiments, x is 1, 2, or 3, and at least one occurrence of R$^5$ is halogen. In yet other embodiments, x is 1, 2, or 3, and at least one occurrence of R$^5$ is —NR'COR', —NR'COCH$_2$R', —NR'CO(CH$_2$)$_2$R', —NR'CH(CH$_2$OH)R', —NR'CH(CH$_2$OMe)R', —NR'CH(CH$_2$OEt)R', —NR'CH(CH$_2$OCF$_3$)R', —NR'CH(CH$_2$CH$_2$OH)R', —NR'CH(CH$_2$CH$_2$OMe)R', —NR'CH(CH$_2$CH$_2$OEt)R', —NR'CH(CH$_2$CH$_2$OCF$_3$)R', —NR'CH(CH$_3$)C(O)OR', —NR'CH(CF$_3$)C(O)OR', —NR'CH(CH$_3$)C(O)N(R')$_2$, —NR'CH(CF$_3$)C(O)N(R')$_2$, —NR'CH(CH$_2$CH$_3$)C(O)N(R')$_2$, —NR'CH(CH$_2$OH)C(O)N(R')$_2$, —NR'CH(CH$_2$OMe)C(O)N(R')$_2$, —NR'CH(CH$_2$OEt)C(O)N(R')$_2$ or —NR'CH(CH$_2$OCF$_3$)C(O)N(R')$_2$, wherein R' is an optionally substituted C$_1$-C$_4$ aliphatic; NHCH$_2$C(O)NHR', —NHCH(CH$_3$)C(O)NHR', —NHCH(CH$_2$CH$_3$)C(O)NHR', —NHCH(CH(CH$_3$)$_2$)C(O)NHR', —NHCH(C(CH$_3$)$_3$)C(O)NHR', —NHCH(CH$_2$CH(CH$_3$)$_2$)C(O)NHR', —NHCH(CH$_2$OH)C(O)NHR', —NHCH(CH$_2$OMe)C(O)NHR' or —NHCH(CH$_2$CH$_2$N(Me)$_2$)C(O)NHR', wherein R' is an optionally substituted C$_1$-C$_4$ aliphatic; —NHR', —NH(CH$_2$)R', —NH(CH$_2$)$_2$R', —NHCH(CH$_3$)R', —NHCH$_2$C(O)NHR', —NHCH(CH$_3$)C(O)NHR', —NHCH(CH$_2$CH$_3$)C(O)NHR', —NHCH(CH(CH$_3$)$_2$)C(O)NHR', —NHCH(C(CH$_3$)$_3$)C(O)NHR', —NHCH(CH$_2$CH(CH$_3$)$_2$)C(O)NHR', —NHCH(CH$_2$OH)C(O)NHR', —NHCH(CH$_2$OMe)C(O)NHR' or —NHCH(CH$_2$CH$_2$N(Me)$_2$)C(O)NHR', wherein R' is an optionally substituted C$_1$-C$_4$ aliphatic; —NHCH(CH$_3$)R', wherein R' is optionally substituted phenyl; H, halogen, CH$_3$, CF$_3$, COOH, COOMe or OR', wherein R' is C$_1$-C$_4$ aliphatic.

In still other embodiments, x is 1, 2, or 3, and at least one occurrence of R$^5$ is an optionally substituted C$_1$-C$_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur.

In yet other embodiments, x is 1 or 2, and each occurrence of R$^5$ is independently halogen, R', CN, —CH$_2$CN, —(CH$_2$)$_2$CN, NO$_2$, —CH$_2$NO$_2$, —(CH$_2$)$_2$NO$_2$, CON(R')$_2$, —CH$_2$CON(R')$_2$, —(CH$_2$)$_2$CON(R')$_2$, COOR', —CH$_2$COOR', —(CH$_2$)$_2$COOR', —SO$_2$N(R')$_2$, —CH$_2$SO$_2$N(R')$_2$, —(CH$_2$)$_2$SO$_2$N(R')$_2$, —NR'SO$_2$R', —CH$_2$NR'SO$_2$R', —(CH$_2$)$_2$NR'SO$_2$R', NR'CON(R')$_2$, —CH$_2$NR'CON(R')$_2$, —(CH$_2$)$_2$NR'CON(R')$_2$, —NR'SO$_2$N(R')$_2$, —CH$_2$NR'SO$_2$N(R')$_2$, —(CH$_2$)$_2$NR'SO$_2$N(R')$_2$, —COCOR', —CH$_2$COCOR', —(CH$_2$)$_2$COCOR', —N(R')$_2$, —CH$_2$N(R')$_2$, —(CH$_2$)$_2$N(R')$_2$, —OR', —CH$_2$OR', —(CH$_2$)$_2$OR', —NR'COR', —NR'COCH$_2$R', —NR'CO(CH$_2$)$_2$R', —CH$_2$NR'COR', or —(CH$_2$)$_2$NR'COR'. In yet other embodiments, R$^5$ is CN, —CH$_2$CN, —(CH$_2$)$_2$CN, —NO$_2$, —CH$_2$NO$_2$, —(CH$_2$)$_2$NO$_2$, OR', —CH$_2$OR', —CON(R')$_2$, —SO$_2$N(R')$_2$, —N(R')$_2$, or R'. In still other embodiments, each occurrence of R$^5$ is independently hydrogen, halogen, CN, —CH$_2$CN, —(CH$_2$)$_2$CN, NO$_2$, —CH$_2$NO$_2$, —(CH$_2$)$_2$NO$_2$, —CONH$_2$, —CON(C$_1$-C$_4$alkyl), —SO$_2$NH$_2$, —SO$_2$N(C$_1$-C$_4$alkyl), NH$_2$, —N(C$_1$-C$_4$alkyl), —OH, —O(C$_1$-C$_4$alkyl), —CH$_2$OH, —CH$_2$O(C$_1$-C$_4$alkyl), or an optionally substituted 5- or 6-membered unsaturated ring wherein 0-3 ring carbon atoms is optionally replaced by oxygen, sulfur, or nitrogen.

As described generally for compounds of formula I above, R$^5$ is optionally substituted with y occurrences of R$^7$, wherein y is 0-5 and R$^7$ is =O, =NR', =S, halogen, —CN, —NO$_2$, or W—R", wherein W is a bond or an optionally substituted C$_1$-C$_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted C$_1$-C$_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R", are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur. In other embodiments, y is 0, 1, 2, or 3, and each occurrence of R$^7$ is independently hydrogen, R', —CH$_2$R", halogen, CN, NO$_2$, —N(R')$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR"(CH$_2$)$_4$OR". In certain embodiments, R$^7$ may also be —NR'CH(CH$_3$)R'. In other embodiments, y is 1, 2, or 3 and each occurrence of R$^7$ is independently F, Cl, Br, CN, OH, NH$_2$, —CH$_2$OH, C$_1$-C$_6$alkyl, —O(C$_1$-C$_6$alkyl), —CH$_2$O(C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$-phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic. Additional exemplary R$^7$ groups are depicted in Table 1.

In still other embodiments, x is 1, 2, or 3; at least one occurrence of R$^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a C$_1$-C$_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R$^7$. In certain embodiments, R' is hydrogen, C$_1$-C$_6$alkyl optionally substituted with 1-3 occurrences of R$^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R$^7$. In other embodiments, R' is hydrogen, C$_1$-C$_4$alkyl optionally substituted with 1-3 occurrences of R$^7$, or is a ring selected from:

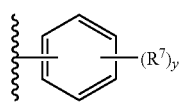
i

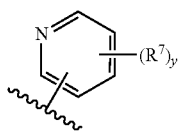
ii

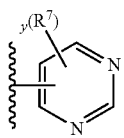
iii

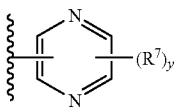
iv

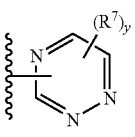
v

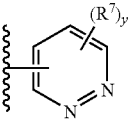
vi

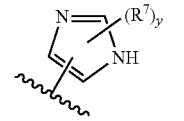
vii

-continued

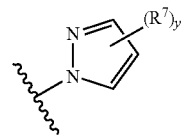
viii

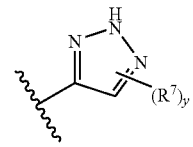
ix

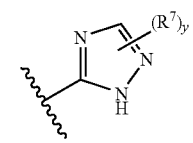
x

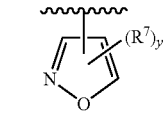
xi

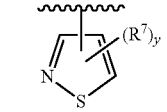
xii

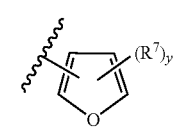
xiii

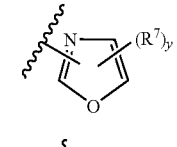
xiv

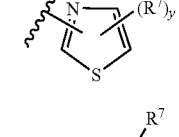
xv

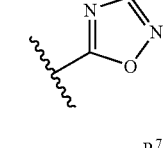
xvi

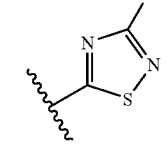
xvii

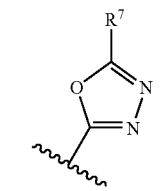
xviii

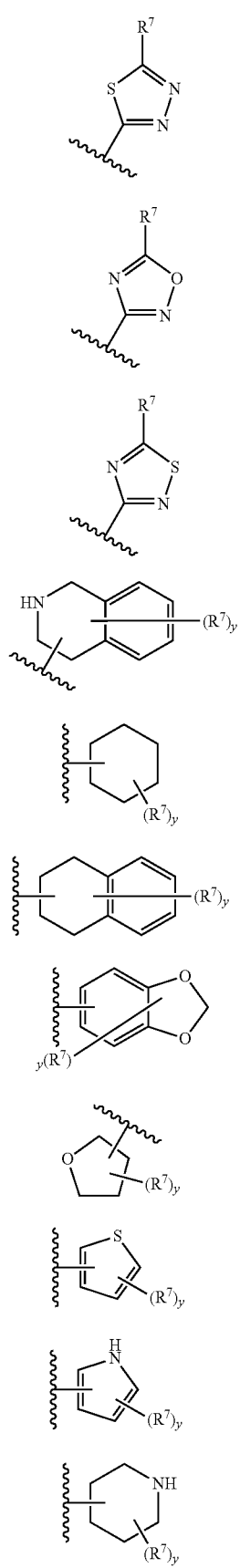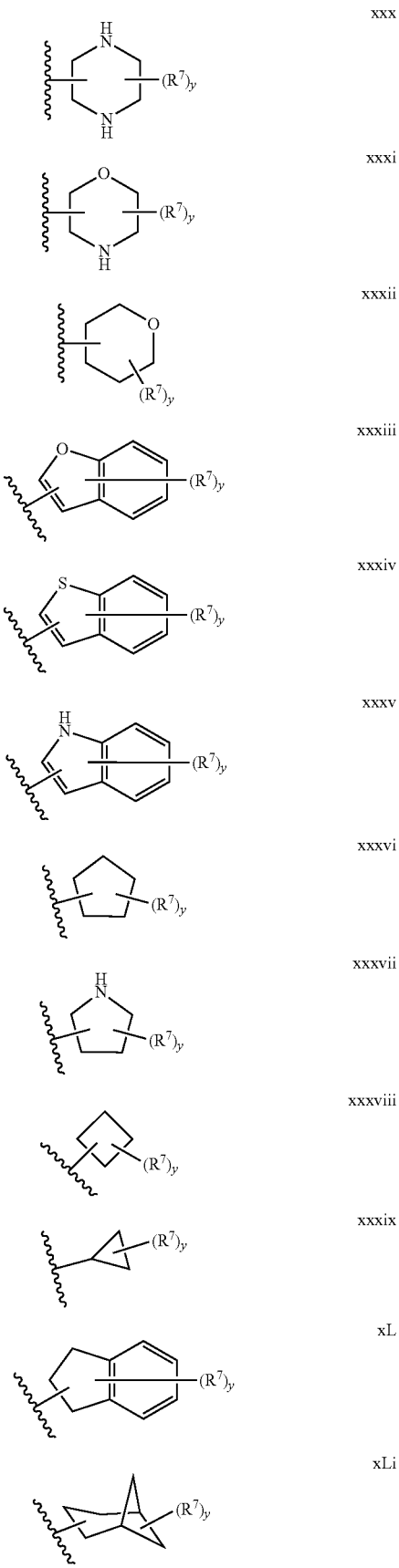

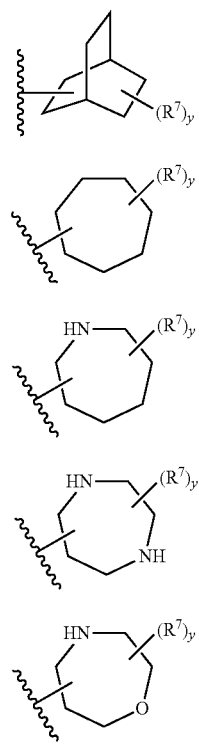

xLii xLiii xLiv xLv xLvi wherein y and R⁷ are described generally and in subsets above.

In another embodiment, R' may be

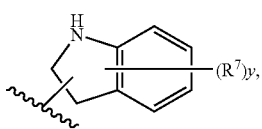

xLvii wherein y and R⁷ are described generally and in subsets above.

In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from:

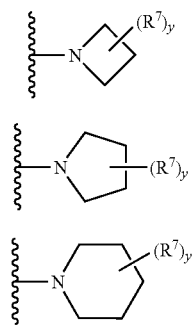

a b c

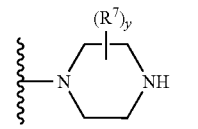

d

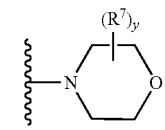

e

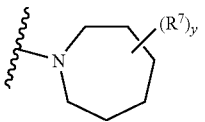

f

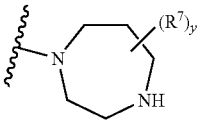

g

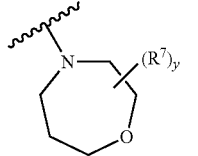

h

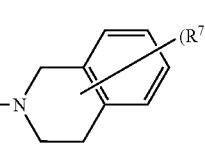

i

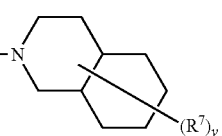

j

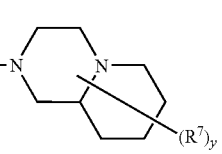

k

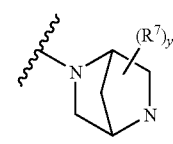

l

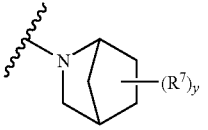

m

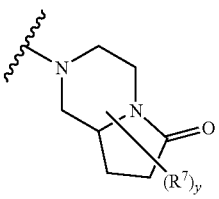

n

-continued

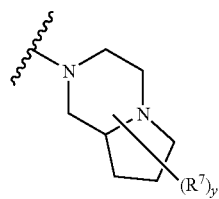

wherein y and R⁷ are described generally and in subsets above. Certain additional subsets of compounds of general formula I include:

I. Compounds of Formula I-A:

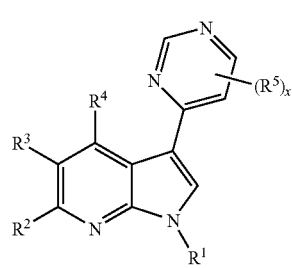

I-A wherein $R^1$, $R^2$, $R^3$, $R^4$, $R^5$ and x are each described generally above and in subsets described above and herein.

In some embodiments, for compounds of formula I-A:

a. $R^1$ is:
  i. T-R', wherein T is a bond or an optionally substituted $C_1$-$C_6$alkylidene chain wherein up to two methylene units are optionally and independently replaced with —O—, —S—, —NR'—, —OCO—, —COO—, —SO₂— or —CO—, and R' is hydrogen, $C_1$-$C_4$-alkyl, or an optionally substituted 5- or 6-membered aryl or heteroaryl group, or
  ii. —Si(R')₃, wherein $R^1$ is hydrogen, $C_1$-$C_4$-alkyl, or an optionally substituted 5- or 6-membered saturated, partially unsaturated, or fully unsaturated monocyclic ring having 0-3 heteroatoms independently selected from nitrogen, oxygen, or sulfur;

b. $R^2$, $R^3$, and $R^4$ are each independently hydrogen, R', halogen, CN, NO₂, —N(R')₂, —CH₂N(R')₂, —OR', —CH₂OR', —SR', —CH₂SR', —COOR', —NR'COR', —NR'COCH₂R', —NR'CO(CH₂)₂R', —CON(R')₂, —SO₂N(R')₂, —CONR'(CH₂)₂N(R')₂, —CONR'(CH₂)₃N(R')₂, —CONR'(CH₂)₄N(R')₂, —O(CH₂)₂OR', O(CH₂)₃OR', O(CH₂)₄OR', —O(CH₂)₂N(R')₂, —O(CH₂)₃N(R')₂, or —O(CH₂)₄N(R')₂; wherein $R^2$, $R^3$, and $R^4$ are each optionally substituted with z occurrences of $R^6$, wherein z is 0-5 and $R^6$ is =O, =NR', =S, halogen, —CN, —NO₂, or Z—R", wherein Z is a bond or an optionally substituted $C_1$-$C_6$ alkylidene chain, wherein up to two methylene units of the chain are optionally and independently replaced by —NR"—, —S—, —O—, —CS—, —CO₂—, —OCO—, —CO—, —COCO—, —CONR"—, —NR"CO—, —NR"CO₂—, —SO₂NR"—, —NR"SO₂—, —CONR"NR"—, —NR"CONR"—, —OCONR"—, —NR"NR"—, —NR"SO₂NR"—, —SO—, —SO₂—, —PO—, —PO₂—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; and c. each occurrence of $R^5$ is independently hydrogen, R', —CH₂R', halogen, CN, NO₂, —N(R')₂, —CH₂N(R')₂, —OR', —CH₂OR', —SR', —CH₂SR', —COOR', —NR'COR', —NR'COCH₂R', —NR'CO(CH₂)₂R', —NR'COOR', —CON(R')₂, —SO₂N(R')₂, —CONR'(CH₂)₂N(R')₂, —CONR(CH₂)₃N(R')₂, —CONR'(CH₂)₄ N(R')₂, —O(CH₂)₂OR', O(CH₂)₃OR', O(CH₂)₄ OR', —O(CH₂)₂N(R')₂, —O(CH₂)₃N(R')₂, —O(CH₂)₄ N(R')₂, —NR'CH(CH₂OH)R', —NR'CH(CH₂CH₂OH) R', —NR'(CH₂)R', —NR'(CH₂)₂R', —NR'(CH₂)₃R', —NR'(CH₂)₄R', —NR'(CH₂)N(R')₂, —NR'(CH₂)₂N (R')₂, —NR'(CH₂)₃N(R')₂, —NR'(CH₂)₄N(R')₂, —NR' (CH₂)OR', —NR'(CH₂)₂OR', —NR'(CH₂)₃OR', or —NR'(CH₂)₄OR', wherein $R^5$ is optionally substituted with y occurrences of $R^7$, wherein y is 0-5 and $R^7$ is =O, =NR', =S, halogen, —CN, —NO₂, or W—R', wherein W is a bond or an optionally substituted $C_1$-$C_6$ alkylidene chain, wherein up to two methylene units of the chain are optionally and independently replaced by —NR"—, —S—, —O—, —CS—, —CO₂—, —OCO—, —CO—, —COCO—, —CONR"—, —NR"CO—, —NR"CO₂—, —SO₂NR"—, —NR"SO₂—, —CONR"NR"—, —NR"CONR"—, —OCONR"—, —NR"NR"—, —NR"SO₂NR"—, —SO—, —SO₂—, —PO—, —PO₂—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In still other embodiments, for compounds of formula I-A:

a. $R^1$ is hydrogen, $C_1$-$C_4$alkyl, —COR', —SO₂R', or —Si (R')₃;

b. $R^2$, $R^3$, and $R^4$ are each independently Cl, Br, F, —CN, —COOH, —COOMe, —NH₂, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, —SO₂N (Me)₂, or an optionally substituted group selected from $C_1$-$C_4$alkyl, $C_1$-$C_4$alkyloxy, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $R^2$, $R^3$, and $R^4$ are each independently and optionally substituted with z occurrences of $R^6$, wherein z is 0, 1, 2, or 3, and each occurrence of $R^6$ is independently hydrogen, R", —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR'(CH$_2$)$_{4-0}$R";

c. each occurrence of $R^5$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COCH$_2$R', —NR'CO(CH$_2$)$_2$R', —NR'COOR', —CON(R')$_2$, —SO$_2$N(R')$_2$, —CONR'(CH$_2$)$_2$N(R')$_2$, —CONR(CH$_2$)$_3$N(R')$_2$, —CONR'(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, —O(CH$_2$)$_4$N(R')$_2$, —NR'CH(CH$_2$OH)R', —NR'CH(CH$_2$CH$_2$OH)R', —NR'(CH$_2$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$N(R')$_2$, —NR'(CH$_2$)OR', —NR'(CH$_2$)$_2$OR', —NR'(CH$_2$)$_3$OR', or —NR'(CH$_2$)$_4$OR', wherein $R^5$ is optionally substituted with y occurrences of $R^7$, wherein y is 0, 1, 2, or 3, and each occurrence of $R^7$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR"(CH$_2$)$_4$OR".

In other embodiments, for compounds of formula I-A and subsets described directly above, $R^1$ is hydrogen, methyl, ethyl, n-propyl, isopropyl, n-butyl, p-toluenesulfonyl (Ts), t-butyldimethylsilyl (TBS), triisopropylsilyl (TIPS), or triethylsilyl (TES).

In still other embodiments, for compounds of formula I-A and subsets described directly above, $R^2$, $R^3$, and $R^4$ are each hydrogen. In other embodiments, one of $R^2$, $R^3$, or $R^4$ is hydrogen. In yet other embodiments, two of $R^2$, $R^3$, or $R^4$ is hydrogen. In yet other embodiments, $R^2$ and $R^4$ are both hydrogen, and $R^3$ is halogen, CN, NO$_2$, or V—R'. In still other embodiments, $R^2$ and $R^4$ are both hydrogen, and $R^3$ is an optionally substituted group selected from a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur. In yet other embodiments, $R^2$ and $R^4$ are both hydrogen, and $R^3$ is an optionally substituted 5- or 6-membered saturated, partially unsaturated, or fully unsaturated ring having 0-3 heteroatoms independently selected from nitrogen, oxygen, or sulfur. In yet other embodiments, $R^2$ and $R^4$ are both hydrogen, and $R^3$ is an optionally substituted ring selected from phenyl, pyridyl, pyrimidinyl, thiazolyl, oxazolyl, thienyl, furyl, pyrrolyl, pyrazolyl, triazolyl, pyrazinyl, thiadiazolyl, or oxadiazolyl. In yet other embodiments, $R^3$ is selected from H, Cl, Br, F, —CN, —COOH, —COOMe, —NH$_2$, —N(R')$_2$, —NO$_2$, —OR', —CON(R')$_2$, —COOR', —OH, —SR', —C(R')$_2$OR', —N(R')COR', —N(R')C(O)OR', —SO$_2$NH$_2$, —SO$_2$N(R')$_2$, or an optionally substituted group selected from C$_1$-C$_4$ aliphatic, C$_1$-C$_4$ alkyloxy or —C≡C—C$_1$-C$_4$ aliphatic. In a further embodiment, $R^2$ and $R^4$ are both hydrogen and $R^3$ is selected from the immediately preceding list.

In other embodiments, for compounds of formula I-A and subsets described directly above, $R^2$, $R^3$, and $R^4$ are each independently and optionally substituted with z occurrences of $R^6$, wherein z is 1, 2, or 3 and each occurrence of $R^6$ is independently F, Cl, Br, CN, OH, NH$_2$, —CH$_2$OH, C$_1$-C$_6$alkyl, —O(C$_1$-C$_6$alkyl), —CH$_2$O(C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$-phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic.

In certain exemplary embodiments, for compounds of formula I-A and subsets described directly above, x is 1, 2, or 3, and at least one occurrence of $R^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, or —NR'(CH$_2$)$_2$N(R')$_2$. In other embodiments, x is 1, 2, or 3, and at least one occurrence of $R^5$ is —OR'. In yet other embodiments, x is 1, 2, or 3, and at least one occurrence of $R^5$ is —NR'COR', —NR'COCH$_2$R', or —NR'CO(CH$_2$)$_2$R'. In still other embodiments, x is 1, 2, or 3, and at least one occurrence of $R^5$ is an optionally substituted C$_1$-C$_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur.

In still other embodiments, for compounds of formula I-A and subsets described directly above, $R^5$ is optionally substituted with y occurrences of $R^7$, wherein y is 1, 2, or 3 and each occurrence of $R^7$ is independently F, Cl, Br, CN, OH, NH$_2$, —CH$_2$OH, C$_1$-C$_6$alkyl, —O(C$_1$-C$_6$alkyl), —CH$_2$O(C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$-phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic. In yet other embodiments, for compounds of formula I-A and subsets described directly above, x is 1, 2, or 3; at least one occurrence of $R^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a C$_1$-C$_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In yet other embodiments, x is 1 and compounds have general formula I-A-i:

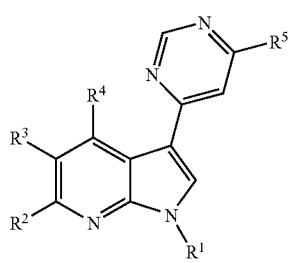

I-A-i wherein $R^1$, $R^2$, $R^3$, and $R^4$ are described generally and in subsets above and herein, and $R^5$ is —N(K)$_2$, —NR'CH(CH$_2$OH)R', —NR'CH(CH$_2$CH$_2$OH)R', —NR'(CH$_2$)R', —NR(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In some embodiments, $R^5$ is N(R')$_2$. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, x is 1 and compounds have general formula I-A-ii:

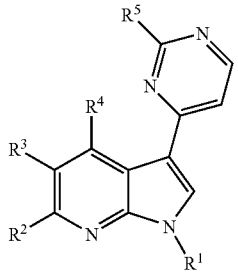

I-A-ii wherein $R^1$, $R^2$, $R^3$, and $R^4$ are described generally and in subsets above and herein, and $R^5$ is —N($R^{12}$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In some embodiments, $R^5$ is N(R')$_2$. In certain embodiments, for each of the subsets described above, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$, $R^3$ and $R^4$ are each hydrogen and compounds of formula I-A-iii are provided:

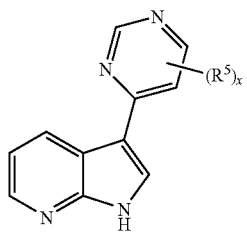

I-A-iii wherein x is 1, 2, or 3; and at least one occurrence of $R^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a C$_1$-C$_6$ aliphatic group optionally substituted with y occurrences of R$^7$, or is a ring selected from (i)-(xLvi) or (xLvii). In yet other embodiments, R$^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodimnts, R$^1$, R$^2$, R$^3$ and R$^4$ are each hydrogen, and x is 1, and compounds of formula I-A-iv are provided:

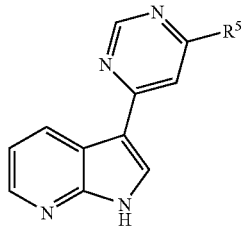

I-A-iv wherein R$^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a C$_1$-C$_6$ aliphatic group optionally substituted with y occurrences of R$^7$ or is a ring selected from (i)-(xLvi) or (xLvii). In yet other embodiments, R$^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, R$^1$, R$^2$, R$^3$ and R$^4$ are each hydrogen, x is 1, and compounds of formula I-A-v are provided:

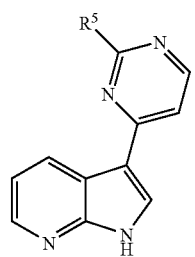

I-A-v wherein R$^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a C$_1$-C$_6$ aliphatic group optionally substituted with y occurrences of R$^7$ or is a ring selected from (i)-(xLvi) or (xLvii). In yet other embodiments, R$^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, R$^1$, R$^2$, and R$^4$ are each hydrogen, and compounds of formula I-A-vi are provided:

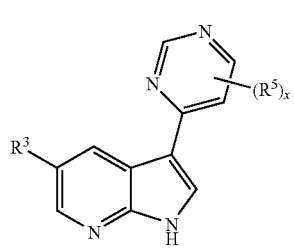

I-A-vi wherein:

R$^3$ is an optionally substituted group selected from a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur;

x is 1, 2, or 3; and at least one occurrence of R$^5$ is —N(R')$_2$, —NR'CH(CH$_2$OH)R', —NR'CH(CH$_2$CH$_2$OH)R', —NR'(CH$_2$)R', —NR'(CH$_2$)$_2$R', NR'(CH$_2$)$_2$R', —NR'(CH$_2$)$_2$N(R')$_2$, —OR', —NR'COR', —NR'COCH$_2$R', or —NR'CO(CH$_2$)$_2$R'; and R' is a C$_1$-C$_6$ aliphatic group optionally substituted with y occurrences of R$^7$, or is a ring selected from (i)-(xLvi) or (xLvii). In yet other embodiments, R$^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In yet other embodiments for compounds described directly above, R$^3$ is an optionally substituted 5- or 6-membered saturated, partially unsaturated, or fully unsaturated ring having 0-3 heteroatoms independently selected from nitrogen, oxygen, or sulfur. In yet other embodiments, R$^3$ is an optionally substituted ring selected from phenyl, pyridyl, pyrimidinyl, thiazolyl, oxazolyl, thienyl, furyl, pyrrolyl, pyrazolyl, triazolyl, pyrazinyl, thiadiazolyl, or oxadiazolyl. As described generally above, R$^3$ is optionally substituted with z occurrences of R$^6$. In certain embodiments, wherein z is 0, 1, 2, or 3, and each occurrence of R$^6$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR"(CH$_2$)$_4$OR".

In still other embodiments, R$^1$, R$^2$, R$^3$ and R$^4$ are each hydrogen, and x is 1, and compounds of formula I-A-vii are provided:

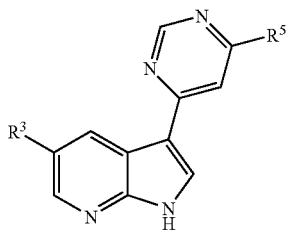

wherein:

R³ is an optionally substituted group selected from a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur;
R⁵ is —N(R')₂, —NR'CH(CH₂OH)R', —NR'CH(CH₂CH₂OH)R', —NR'(CH₂)R', —NR'(CH₂)₂R', NR'(CH₂)N(R')₂, —NR'(CH₂)₂N(R')₂, —OR', —NR'COR', —NR'COCH₂R', or —NR'CO(CH₂)₂R'; and R' is a C₁-C₆aliphatic group optionally substituted with y occurrences of R⁷, or is a ring selected from (i)-(xLvi) or (xLvii). In yet other embodiments, R⁵ is —N(R')₂ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In yet other embodiments for compounds described directly above, R³ is an optionally substituted 5- or 6-membered saturated, partially unsaturated, or fully unsaturated ring having 0-3 heteroatoms independently selected from nitrogen, oxygen, or sulfur. In yet other embodiments, R³ is an optionally substituted ring selected from phenyl, pyridyl, pyrimidinyl, thiazolyl, oxazolyl, thienyl, furyl, pyrrolyl, pyrazolyl, triazolyl, pyrazinyl, thiadiazolyl, or oxadiazolyl. As described generally above, R³ is optionally substituted with z occurrences of R⁶. In certain embodiments, wherein z is 0, 1, 2, or 3, and each occurrence of R⁶ is independently hydrogen, R', —CH₂R'', halogen, CN, NO₂, —N(R'')₂, —CH₂N(R'')₂, —OR'', —CH₂OR'', —SR'', —CH₂SR'', —COOR'', —NR''COR'', —NR''COOR'', —CON(R'')₂, —SO₂N(R'')₂, —CONR''(CH₂)₂N(R'')₂, —CONR(CH₂)₃N(R'')₂, —CONR''(CH₂)₄N(R'')₂, —O(CH₂)₂OR'', O(CH₂)₃OR'', O(CH₂)₄OR'', —O(CH₂)₂N(R'')₂, —O(CH₂)₃N(R'')₂, —O(CH₂)₄N(R'')₂, —NR''CH(CH₂OH)R'', —NR''CH(CH₂CH₂OH)R'', —NR''(CH₂)R'', —NR''(CH₂)₂R'', —NR''(CH₂)₃R'', —NR''(CH₂)₄R'', —NR''(CH₂)N(R'')₂, —NR''(CH₂)₂N(R'')₂, —NR''(CH₂)₃N(R'')₂, —NR''(CH₂)₄N(R'')₂, —NR''(CH₂)OR'', —NR''(CH₂)₂OR'', —NR''(CH₂)₃OR'', or —NR'(CH₂)₄OR''.

In still other embodiments, R¹, R², R³ and R⁴ are each hydrogen, x is 1, and compounds of formula I-A-viii are provided:

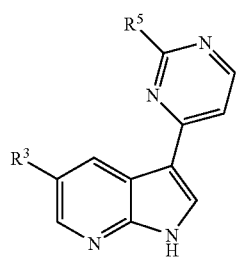

wherein:

R³ is an optionally substituted group selected from a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; R⁵ is —N(R')₂, —NR'CH(CH₂OH)R', —NR'CH(CH₂CH₂OH)R', —NR'(CH₂)R', —NR'(CH₂)₂R', NR'(CH₂)N(R')₂, —NR'(CH₂)₂N(R')₂, —OR', —NR'COR', —NR'COCH₂R', or —NR'CO(CH₂)₂R'; and R' is a C₁-C₆aliphatic group optionally substituted with y occurrences of R¹, or is a ring selected from (i)-(xLvi) or (xLvii). In yet other embodiments, R⁵ is —N(R')₂ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In yet other embodiments for compounds described directly above, R³ is an optionally substituted 5- or 6-membered saturated, partially unsaturated, or fully unsaturated ring having 0-3 heteroatoms independently selected from nitrogen, oxygen, or sulfur. In yet other embodiments, R³ is an optionally substituted ring selected from phenyl, pyridyl, pyrimidinyl, thiazolyl, oxazolyl, thienyl, furyl, pyrrolyl, pyrazolyl, riazolyl, pyrazinyl, thiadiazolyl, or oxadiazolyl. As described generally above, R³ is optionally substituted with z occurrences of R⁶. In certain embodiments, wherein z is 0, 1, 2, or 3, and each occurrence of R⁶ is independently hydrogen, R', —CH₂R'', halogen, CN, NO₂, —N(R'')₂, —CH₂N(R'')₂, —OR'', —CH₂OR'', —SR'', —CH₂SR'', —COOR'', —NR''COR'', —NR''COOR'', —CON(R'')₂, —SO₂N(R'')₂, —CONR''(CH₂)₂N(R'')₂, —CONR(CH₂)₃N(R'')₂, —CONR''(CH₂)₄N(R'')₂, —O(CH₂)₂OR'', O(CH₂)₃OR'', O(CH₂)₄OR'', —O(CH₂)₂N(R'')₂, —O(CH₂)₃N(R'')₂, —O(CH₂)₄N(R'')₂, —NR''CH(CH₂OH)R'', —NR''CH(CH₂CH₂OH)R'', —NR''(CH₂)R'', —NR''(CH₂)₂R'', —NR''(CH₂)₃R'', —NR''(CH₂)₄R'', —NR''(CH₂)N(R'')₂, —NR''(CH₂)₂N(R'')₂, —NR''(CH₂)₃N(R'')₂, —NR''(CH₂)₄N(R'')₂, —NR''(CH₂)OR'', —NR''(CH₂)₂OR'', —NR''(CH₂)₃OR'', or —NR'(CH₂)₄OR''.

Certain additional subsets of compounds of general formula I include:

II. Compounds of formula I-C:

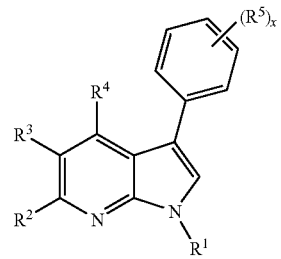

wherein $R^1$, $R^2$, $R^3$, $R^4$, $R^5$ and x are each described generally above and in subsets described above and herein.

In some embodiments, for compounds of formula I-C:
a. $R^1$ is:
  i. T-R', wherein T is a bond or an optionally substituted $C_1$-$C_6$ alkylidene chain wherein up to two methylene units are optionally and independently replaced with —O—, —S—, —NR'—, —OCO—, —COO—, —SO$_2$— or —CO—, and R' is hydrogen, $C_1$-$C_4$-alkyl, or an optionally substituted 5- or 6-membered aryl or heteroaryl group, or
  ii. —Si(R')$_3$, wherein $R^1$ is hydrogen, $C_1$-$C_4$-alkyl, or an optionally substituted 5- or 6-membered saturated, partially unsaturated, or fully unsaturated monocyclic ring having 0-3 heteroatoms independently selected from nitrogen, oxygen, or sulfur;
b. $R^2$, $R^3$, and $R^4$ are each independently hydrogen, R', halogen, CN, NO$_2$, —N(R')$_2$, —CH$_2$N(R')$_2$, —OR', —CH$_2$OR', —SR', —CH$_2$SR', —COOR', —NR'COR', —CON(R')$_2$, —SO$_2$N(R')$_2$, —CONR'(CH$_2$)$_2$N(R')$_2$, —CONR'(CH$_2$)$_3$N(R')$_2$, —CONR'(CH$_2$)$_4$N(R')$_2$, —O(CH$_2$)$_2$OR', —O—(CH$_2$)$_3$OR', O(CH$_2$)$_4$OR', —O(CH$_2$)$_2$N(R')$_2$, —O(CH$_2$)$_3$N(R')$_2$, or —O(CH$_2$)$_4$N(R')$_2$; wherein $R^2$, $R^3$, and $R^4$ are each optionally substituted with z occurrences of $R^6$, wherein z is 0-5 and $R^6$ is =O, =NR', =S, halogen, —CN, —NO$_2$, or Z—R", wherein Z is a bond or an optionally substituted $C_1$-$C_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; and
c. each occurrence of $R^5$ is independently hydrogen, halogen, R', CN, —CH$_2$CN, —(CH$_2$)$_2$CN, NO$_2$, —CH$_2$NO$_2$, —(CH$_2$)$_2$NO$_2$, CON(R')$_2$, —CH$_2$CON(R')$_2$, —(CH$_2$)$_2$CON(R')$_2$, COOR', —CH$_2$COOR', —(CH$_2$)$_2$COOR', —SO$_2$N(R')$_2$, —CH$_2$SO$_2$N(R')$_2$, —(CH$_2$)$_2$SO$_2$N(R')$_2$, —NR'SO$_2$R', —CH$_2$NR'SO$_2$R', —(CH$_2$)$_2$NR'SO$_2$R', NR'CON(R')$_2$, —CH$_2$NR'CON(R')$_2$, —(CH$_2$)$_2$NR'CON(R')$_2$, —NR'SO$_2$N(R')$_2$, —CH$_2$NR'SO$_2$N(R')$_2$, —(CH$_2$)$_2$NR'SO$_2$N(R')$_2$, —COCOR', —CH$_2$COCOR', —(CH$_2$)$_2$COCOR', —N(R')$_2$, —CH$_2$N(R')$_2$, —(CH$_2$)$_2$N(R')$_2$, —OR', —CH$_2$OR', —(CH$_2$)$_2$OR', —NR'COR', —NR'COCH$_2$R', —NR'CO(CH$_2$)$_2$R'; —CH$_2$NR'COR', or —(CH$_2$)$_2$NR'COR', wherein $R^5$ is optionally substituted with y occurrences of $R^7$, wherein y is 0-5 and $R^7$ is =O, =NR', =S, halogen, —CN, —NO$_2$, or W—R', wherein W is a bond or an optionally substituted $C_1$-$C_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In still other embodiments, for compounds of formula I-C:
a. $R^1$ is hydrogen, $C_1$-$C_4$alkyl, —COR', —SO$_2$R', or —Si(R')$_3$;
b. $R^2$, $R^3$, and $R^4$ are each independently Cl, Br, F, —CN, —COOH, —COOMe, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$N(Me)$_2$, or an optionally substituted group selected from $C_1$-$C_4$alkyl, $C_1$-$C_4$alkyloxy, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $R^2$, $R^3$, and $R^4$ are each independently and optionally substituted with z occurrences of $R^6$, wherein z is 0, 1, 2, or 3, and each occurrence of $R^6$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR'(CH$_2$)$_4$OR"; each occurrence of $R^5$ is independently CN, —CH$_2$CN, —(CH$_2$)$_2$CN, —NO$_2$, —CH$_2$NO$_2$, —(CH$_2$)$_2$NO$_2$, OR', —CH$_2$OR', —CON(R')$_2$, —SO$_2$N(R')$_2$, —N(R')$_2$, or R', wherein $R^5$ is optionally substituted y occurrences of $R^7$, wherein y is 0, 1, 2, or 3, and each occurrence of $R^7$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"

(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR"(CH$_2$)$_4$OR".

In other embodiments, for compounds of formula I-C and subsets described directly above, R$^1$ is hydrogen, methyl, ethyl, n-propyl, isopropyl, n-butyl, p-toluenesulfonyl (Ts), t-butyldimethylsilyl (TBS), triisopropylsilyl (TIPS), or triethylsilyl (TES).

In still other embodiments, for compounds of formula I-C and subsets described directly above, R$^2$, R$^3$, and R$^4$ are each hydrogen. In other embodiments, one of R$^2$, R$^3$, or R$^4$ is hydrogen. In yet other embodiments, two of R$^2$, R$^3$, or R$^4$ is hydrogen. In yet other embodiments, R$^2$ and R$^4$ are both hydrogen, and R$^3$ is halogen, CN, NO$_2$, or V—R'. In still other embodiments, R$^2$ and R$^4$ are both hydrogen, and R$^3$ is an optionally substituted group selected from a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur. In yet other embodiments, R$^2$ and R$^4$ are both hydrogen, and R$^3$ is an optionally substituted 5- or 6-membered saturated, partially unsaturated, or fully unsaturated ring having 0-3 heteroatoms independently selected from nitrogen, oxygen, or sulfur. In yet other embodiments, R$^2$ and R$^4$ are both hydrogen, and R$^3$ is an optionally substituted ring selected from phenyl, pyridyl, pyrimidinyl, thiazolyl, oxazolyl, thienyl, furyl, pyrrolyl, pyrazolyl, triazolyl, pyrazinyl, thiadiazolyl, or oxadiazolyl.

In other embodiments, for compounds of formula I-C and subsets described directly above, R$^2$, R$^3$, and R$^4$ are each independently and optionally substituted with z occurrences of R$^6$, wherein z is 1, 2, or 3 and each occurrence of R$^6$ is independently F, Cl, Br, CN, OH, NH$_2$, —CH$_2$OH, C$_1$-C$_6$alkyl, —O(C$_1$-C$_6$alkyl), —CH$_2$O(C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$-phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic.

In certain exemplary embodiments, for compounds of formula I-C and subsets described directly above, x is 1, 2, or 3, and at least one occurrence of R$^5$ is halogen, CN, —CH$_2$CN, —(CH$_2$)$_2$CN, NO$_2$, —CH$_2$NO$_2$, —(CH$_2$)$_2$NO$_2$, —CONH$_2$, —CON(C$_1$-C$_4$alkyl), —SO$_2$NH$_2$, —SO$_2$N(C$_1$-C$_4$alkyl), NH$_2$, —N(C$_1$-C$_4$alkyl), —OH, —O(C$_1$-C$_4$alkyl), —CH$_2$OH, —CH$_2$O(C$_1$-C$_4$alkyl), or an optionally substituted 5- or 6-membered unsaturated ring wherein 0-3 ring carbon atoms is optionally replaced by oxygen, sulfur, or nitrogen. In other embodiments, x is 1, 2, or 3, and at least one occurrence of R$^5$ is —OR'.

In still other embodiments, for compounds of formula I-C and subsets described directly above, R$^5$ is optionally substituted with y occurrences of R$^7$, wherein y is 1, 2, or 3 and each occurrence of R$^7$ is independently F, Cl, Br, CN, OH, NH$_2$, —CH$_2$OH, C$_1$-C$_6$alkyl, —O(C$_1$-C$_6$alkyl), —CH$_2$O(C$_1$-C$_6$alkyl), —CO(C$_1$-C$_6$alkyl), —COO(C$_1$-C$_6$alkyl), —NHSO$_2$(C$_1$-C$_6$alkyl), —SO$_2$NH$_2$, —CONH$_2$, —CON(C$_1$-C$_6$alkyl), —SO$_2$(C$_1$-C$_6$alkyl), —SO$_2$-phenyl, phenyl, benzyl, —N(C$_1$-C$_6$alkyl)$_2$, or —S(C$_1$-C$_6$alkyl), wherein each of the foregoing phenyl, benzyl, and C$_1$-C$_6$alkyl groups is independently and optionally substituted, and wherein each of the foregoing C$_1$-C$_6$alkyl groups is linear, branched, or cyclic.

In yet other embodiments, x is 1 and compounds have general formula I-C-i:

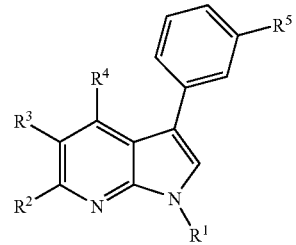

I-C-i wherein R$^1$, R$^2$, R$^3$, and R$^4$ are described generally and in subsets above and herein, and R$^5$ is halogen, R', CN, —CH$_2$CN, —(CH$_2$)$_2$CN, NO$_2$, —CH$_2$NO$_2$, —(CH$_2$)$_2$NO$_2$, CON(R')$_2$, —CH$_2$CON(R')$_2$, —(CH$_2$)$_2$CON(R')$_2$, COOR', —CH$_2$COOR', —(CH$_2$)$_2$COOR', —SO$_2$N(R')$_2$, —CH$_2$SO$_2$N(R')$_2$, —(CH$_2$)$_2$SO$_2$N(R')$_2$, —NR'SO$_2$R', —CH$_2$NR'SO$_2$R', —(CH$_2$)$_2$NR'SO$_2$R', NR'CON(R')$_2$, —CH$_2$NR'CON(R')$_2$, —(CH$_2$)$_2$NR'CON(R')$_2$, —NR'SO$_2$N(R')$_2$, —CH$_2$NR'SO$_2$N(R')$_2$, —(CH$_2$)$_2$NR'SO$_2$N(R')$_2$, —COCOR', —CH$_2$COCOR', —(CH$_2$)$_2$COCOR', —N(R')$_2$, —CH$_2$N(R')$_2$, —(CH$_2$)$_2$N(R')$_2$, —OR', —CH$_2$OR', —(CH$_2$)$_2$ OR', —NR'COR', —CH$_2$NR'COR', or —(CH$_2$)$_2$NR'COR', and R' is a C$_1$-C$_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R$^7$. In some embodiments, R$^5$ is CN, —CH$_2$CN, —(CH$_2$)$_2$CN, —NO$_2$, —CH$_2$NO$_2$, —(CH$_2$)$_2$NO$_2$, OR', —CH$_2$OR', —CON(R')$_2$, —SO$_2$N(R')$_2$, —N(R')$_2$, or R'. In certain embodiments, R' is hydrogen, C$_1$-C$_6$alkyl optionally substituted with 1-3 occurrences of R$^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R$^7$. In other embodiments, R' is hydrogen, C$_1$-C$_6$alkyl optionally substituted with 1-3 occurrences of R$^7$, or is a ring selected from (i)-(xLvi) or (xLvii).

In yet other embodiments, x is 1 and compounds have general formula I-C-ii:

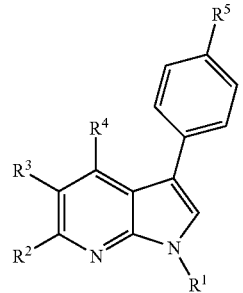

I-C-ii wherein $R^1$, $R^2$, $R^3$, and $R^4$ are described generally and in subsets above and herein, and $R^5$ is halogen, R', CN, —$CH_2CN$, —$(CH_2)_2CN$, $NO_2$, —$CH_2NO_2$, —$(CH_2)_2NO_2$, $CON(R')_2$, —$CH_2CON(R')_2$, —$(CH_2)_2CON(R')_2$, COOR', —$CH_2COOR'$, —$(CH_2)_2COOR'$, —$SO_2N(R')_2$, —$CH_2SO_2N(R')_2$, —$(CH_2)_2SO_2N(R')_2$, —$NR'SO_2R'$, —$CH_2NR'SO_2R'$, —$(CH_2)_2NR'SO_2R'$, $NR'CON(R')_2$, —$CH_2NR'CON(R')_2$, —$(CH_2)_2NR'CON(R')_2$, —$NR'SO_2N(R')_2$, —$CH_2NR'SO_2N(R')_2$, —$(CH_2)_2NR'SO_2N(R')_2$, —COCOR', —$CH_2COCOR'$, —$(CH_2)_2COCOR'$, —$N(R')_2$, —$CH_2N(R')_2$, —$(CH_2)_2N(R')_2$, —OR', —$CH_2OR'$, —$(CH_2)_2$ OR', —NR'COR', —$CH_2NR'COR'$, or —$(CH_2)_2NR'COR'$, and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In some embodiments, $R^5$ is CN, —$CH_2CN$, —$(CH_2)_2CN$, —$NO_2$, —$CH_2NO_2$, —$(CH_2)_2NO_2$, OR', —$CH_2OR'$, —$CON(R')_2$, —$SO_2N(R^{12}$, —$N(R')_2$, or R'. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii).

In still other embodiments, each occurrence of $R^5$ is independently CN, —$CH_2CN$, —$(CH_2)_2CN$, —$NO_2$, —$CH_2NO_2$, —$(CH_2)_2NO_2$, OR', —$CH_2OR'$, —$CON(R')_2$, —$SO_2N(R')_2$, —$N(R')_2$, or R'. In still other embodiments, each occurrence of $R^5$ is independently hydrogen, halogen, CN, —$CH_2CN$, —$(CH_2)_2CN$, $NO_2$, —$CH_2NO_2$, —$(CH_2)_2NO_2$, —$CONH_2$, —$CON(C_1$-$C_4alkyl)$, —$SO_2NH_2$, —$SO_2N(C_1$-$C_4alkyl)$, $NH_2$, —$N(C_1$-$C_4alkyl)$, —OH, —$O(C_1$-$C_4alkyl)$, —$CH_2OH$, —$CH_2O(C_1$-$C_4alkyl)$, or an optionally substituted 5- or 6-membered unsaturated ring wherein 0-3 ring carbon atoms is optionally replaced by oxygen, sulfur, or nitrogen, wherein $R^5$ is optionally substituted by 0-3 occurrences of $R^7$.

In yet other embodiments, x is 2 and compounds have general formula I-C-iii:

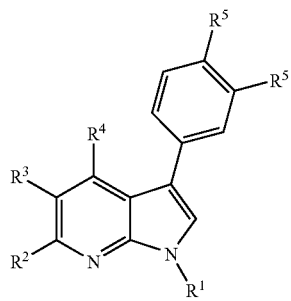

I-C-iii wherein $R^1$, $R^2$, $R^3$, and $R^4$ are described generally and in subsets above and herein, and each occurrence of $R^5$ is independently halogen, R', CN, —$CH_2CN$, —$(CH_2)_2CN$, $NO_2$, —$CH_2NO_2$, —$(CH_2)_2NO_2$, $CON(R')_2$, —$CH_2CON(R')_2$, —$(CH_2)_2CON(R')_2$, COOR', —$CH_2COOR'$, —$(CH_2)_2COOR'$, —$SO_2N(R')_2$, —$CH_2SO_2N(R')_2$, —$(CH_2)_2SO_2N(R')_2$, —$NR'SO_2R'$, —$CH_2NR'SO_2R'$, —$(CH_2)_2NR'SO_2R'$, $NR'CON(R')_2$, —$CH_2NR'CON(R')_2$, —$(CH_2)_2NR'CON(R')_2$, —$NR'SO_2N(R')_2$, —$CH_2NR'SO_2N(R')_2$, —$(CH_2)_2NR'SO_2N(R')_2$, —COCOR', —$CH_2COCOR'$, —$(CH_2)_2COCOR'$, —$N(R')_2$, —$CH_2N(R')_2$, —$(CH_2)_2N(R')_2$, —OR', —$CH_2OR'$, —$(CH_2)_2OR'$, —NR'COR'-$CH_2NR'COR'$, or —$(CH_2)_2NR'COR'$, and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In some embodiments, $R^5$ is CN, —$CH_2CN$, —$(CH_2)_2CN$, —$NO_2$, —$CH_2NO_2$, —$(CH_2)_2NO_2$, OR', —$CH_2OR'$, —$CON(R')_2$, —$SO_2N(R')_2$, —$N(R')_2$, or R'. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii).

In still other embodiments, each occurrence of $R^5$ is independently CN, —$CH_2CN$, —$(CH_2)_2CN$, —$NO_2$, —$CH_2NO_2$, —$(CH_2)_2NO_2$, OR', —$CH_2OR'$, —$CON(R')_2$, —$SO_2N(R')_2$, —$N(R')_2$, or R'. In still other embodiments, each occurrence of $R^5$ is independently hydrogen, halogen, CN, —$CH_2CN$, —$(CH_2)_2CN$, $NO_2$, —$CH_2NO_2$, —$(CH_2)_2NO_2$, —$CONH_2$, —$CON(C_1$-$C_4alkyl)$, —$SO_2NH_2$, —$SO_2N(C_1$-$C_4alkyl)$, $NH_2$, —$N(C_1$-$C_4alkyl)$, —OH, —$O(C_1$-$C_4alkyl)$, —$CH_2OH$, —$CH_2O(C_1$-$C_4alkyl)$, or an optionally substituted 5- or 6-membered unsaturated ring wherein 0-3 ring carbon atoms is optionally replaced by oxygen, sulfur, or nitrogen, wherein $R^5$ is optionally substituted by 0-3 occurrences of $R^7$.

In still other embodiments, $R^1$, $R^2$, $R^3$ and $R^4$ are each hydrogen, and x is 1, and compounds of formula I-C-iv are provided:

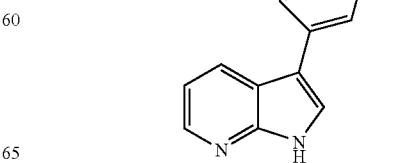

I-C-iv wherein R⁵ is halogen, R', CN, —CH₂CN, —(CH₂)₂CN, NO₂, —CH₂NO₂, —(CH₂)₂NO₂, CON(R')₂, —CH₂CON (R')₂, —(CH₂)₂CON(R')₂, COOR', —CH₂COOR', —(CH₂)₂COOR', —SO₂N(R')₂, —CH₂SO₂N(R')₂, —(CH₂)₂SO₂N (R')₂, —NR'SO₂R', —CH₂NR'SO₂R', —(CH₂)₂NR'SO₂R', NR'CON(R')₂, —CH₂NR'CON(R')₂, —(CH₂)₂NR'CON (R')₂, —NR'SO₂N(R')₂, —CH₂NR'SO₂N(R')₂, —(CH₂)₂ NR'SO₂N(R')₂, —COCOR', —CH₂COCOR', —(CH₂)₂CO-COR', —N(R')₂, —CH₂N(R')₂, —(CH₂)₂N(R')₂, —OR', —CH₂OR', —(CH₂)₂OR', —NR'COR', —CH₂NR'COR', or —(CH₂)₂NR'COR', and R' is a C₁-C₆aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R⁷. In some embodiments, R⁵ is CN, —CH₂CN, —(CH₂)₂CN, —NO₂, —CH₂NO₂, —(CH₂)₂ NO₂, OR', —CH₂OR', —CON(R')₂, —SO₂N(R')₂, —N(R')₂, or R'. In certain embodiments, R' is hydrogen, C₁-C₆alkyl optionally substituted with 1-3 occurrences of R⁷, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R⁷. In other embodiments, R' is hydrogen, C₁-C₄alkyl optionally substituted with 1-3 occurrences of R⁷, or is a ring selected from (i)-(xLvi) or (xLvii).

In still other embodiments, each occurrence of R⁵ is independently CN, —CH₂CN, —(CH₂)₂CN, —NO₂, —CH₂NO₂, —(CH₂)₂NO₂, OR', —CH₂OR', —CON(R')₂, —SO₂N(R')₂, —N(R')₂, or R'. In still other embodiments, each occurrence of R⁵ is independently hydrogen, halogen, CN, —CH₂CN, —(CH₂)₂CN, NO₂, —CH₂NO₂, —(CH₂)₂NO₂, —CONH₂, —CON(C₁-C₄alkyl), —SO₂NH₂, —SO₂N (C₁-C₄alkyl), NH₂, —N(C₁-C₄alkyl), —OH, —O(C₁-C₄alkyl), —CH₂OH, —CH₂O(C₁-C₄alkyl), or an optionally substituted 5- or 6-membered unsaturated ring wherein 0-3 ring carbon atoms is optionally replaced by oxygen, sulfur, or nitrogen, wherein R⁵ is optionally substituted by 0-3 occurrences of R⁷.

In yet other embodiments, R¹, R², R³ and R⁴ are each hydrogen, x is 1 and compounds have general formula I-C-v:

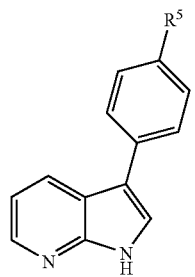

I-C-v wherein R⁵ is halogen, R', CN, —CH₂CN, —(CH₂)₂CN, NO₂, —CH₂NO₂, —(CH₂)₂NO₂, CON(R')₂, —CH₂CON (R')₂, —(CH₂)₂CON(R')₂, COOR', —CH₂COOR', —(CH₂)₂ COOR', —SO₂N(R')₂, —CH₂SO₂N(R')₂, —(CH₂)₂SO₂N (R')₂, —NR'SO₂R', —CH₂NR'SO₂R', —(CH₂)₂NR'SO₂R', NR'CON(R')₂, —CH₂NR'CON(R')₂, —(CH₂)₂NR'CON (R')₂, —NR'SO₂N(R')₂, —CH₂NR'SO₂N(R')₂, —(CH₂)₂ NR'SO₂N(R')₂, —COCOR', —CH₂COCOR', —(CH₂)₂CO-COR', —N(R')₂, —CH₂N(R')₂, —(CH₂)₂N(R')₂, —OR', —CH₂OR', —(CH₂)₂OR', —NR'COR', —CH₂NR'COR', or —(CH₂)₂NR'COR', and R' is a C₁-C₆aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R⁷. In some embodiments, R⁵ is CN, —CH₂CN, —(CH₂)₂CN, —NO₂, —CH₂NO₂, —(CH₂)₂ NO₂, OR', —CH₂OR', —CON(R')₂, —SO₂N(R')₂, —N(R')₂, or R'. In certain embodiments, R' is hydrogen, C₁-C₆alkyl optionally substituted with 1-3 occurrences of R⁷, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R⁷. In other embodiments, R' is hydrogen, C₁-C₄alkyl optionally substituted with 1-3 occurrences of R⁷, or is a ring selected from (i)-(xLvi) or (xLvii).

In still other embodiments, each occurrence of R⁵ is independently CN, —CH₂CN, —(CH₂)₂CN, —NO₂, —CH₂NO₂, —(CH₂)₂NO₂, OR', —CH₂OR', —CON(R')₂, —SO₂N(R')₂, —N(R')₂, or R'. In still other embodiments, each occurrence of R⁵ is independently hydrogen, halogen, CN, —CH₂CN, —(CH₂)₂CN, NO₂, —CH₂NO₂, —(CH₂)₂ NO₂, —CONH₂, —CON(C₁-C₄alkyl), —SO₂NH₂, —SO₂N (C₁-C₄alkyl), NH₂, —N(C₁-C₄alkyl), —OH, —O(C₁-C₄alkyl), —CH₂OH, —CH₂O(C₁-C₄alkyl), or an optionally substituted 5- or 6-membered unsaturated ring wherein 0-3 ring carbon atoms is optionally replaced by oxygen, sulfur, or nitrogen, wherein R⁵ is optionally substituted by 0-3 occurrences of R⁷.

In yet other embodiments, R¹, R², R³ and R⁴ are each hydrogen, x is 2 and compounds have general formula I-C-vi:

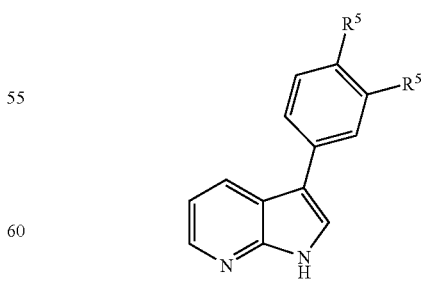

I-C-vi wherein each occurrence of R⁵ is independently halogen, R', CN, —CH₂CN, —(CH₂)₂CN, NO₂, —CH₂NO₂, —(CH₂)₂ NO₂, CON(R')₂, —CH₂CON(R')₂, —(CH₂)₂CON(R')₂, COOR', —CH₂COOR', —(CH₂)₂COOR', —SO₂N(R')₂, —CH₂SO₂N(R')₂, —(CH₂)₂SO₂N(R')₂, —NR'SO₂R', —CH₂NR'SO₂R', —(CH₂)₂NR'SO₂R', NR'CON(R')₂, —CH₂NR'CON(R')₂, —(CH₂)₂NR'CON(R')₂, —NR'SO₂N(R')₂, —CH₂NR'SO₂N(K)₂, —(CH₂)₂NR'SO₂N(R')₂, —COCOR', —CH₂COCOR', —(CH₂)₂COCOR', —N(R')₂, —CH₂N(R')₂, —(CH₂)₂N(R')₂, —OR', —CH₂OR', —(CH₂)₂ OR', —CH₂NR'COR', or —(CH₂)₂NR'COR', and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In some embodiments, $R^5$ is CN, —CH₂CN, —(CH₂)₂CN, —NO₂, —CH₂NO₂, —(CH₂)₂NO₂, OR', —CH₂OR', —CON(R')₂, —SO₂N(R')₂, —N(R')₂, or R'. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii).

In still other embodiments, each occurrence of $R^5$ is independently CN, —CH₂CN, —(CH₂)₂CN, —NO₂, —CH₂NO₂, —(CH₂)₂NO₂, OR', —CH₂OR', —CON(R')₂, —SO₂N(R')₂, —N(R')₂, or R'. In still other embodiments, each occurrence of $R^5$ is independently hydrogen, halogen, CN, —CH₂CN, —(CH₂)₂CN, NO₂, —CH₂NO₂, —(CH₂)₂NO₂, —CONH₂, —CON($C_1$-$C_4$alkyl), —SO₂NH₂, —SO₂N($C_1$-$C_4$alkyl), NH₂, —N($C_1$-$C_4$alkyl), —OH, —O($C_1$-$C_4$alkyl), —CH₂OH, —CH₂O($C_1$-$C_4$alkyl), or an optionally substituted 5- or 6-membered unsaturated ring wherein 0-3 ring carbon atoms is optionally replaced by oxygen, sulfur, or nitrogen, wherein $R^5$ is optionally substituted by 0-3 occurrences of $R^7$.

Representative examples of compounds of formula I are set forth below in Table 1.

TABLE 1

Examples of Compounds of Formula I:

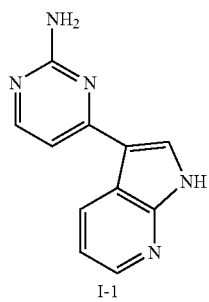

I-1

TABLE 1-continued

Examples of Compounds of Formula I:

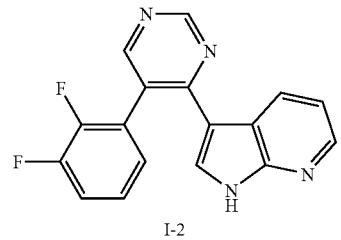

I-2

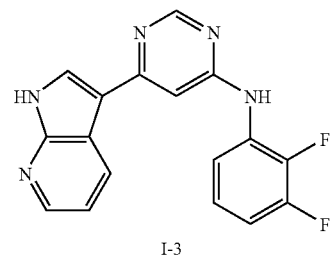

I-3

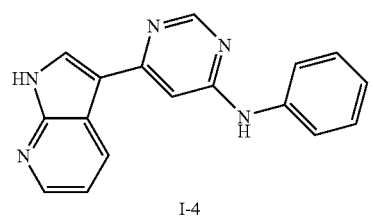

I-4

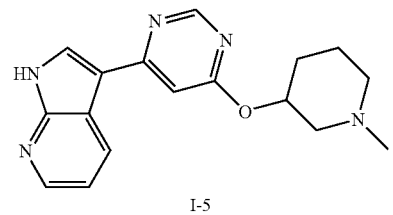

I-5

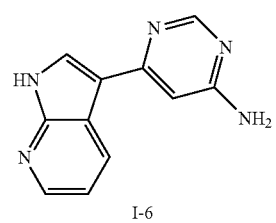

I-6

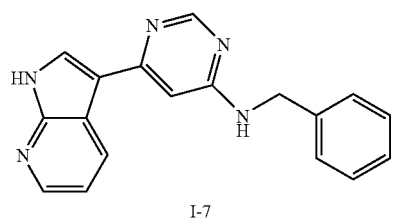

I-7

TABLE 1-continued
Examples of Compounds of Formula I:
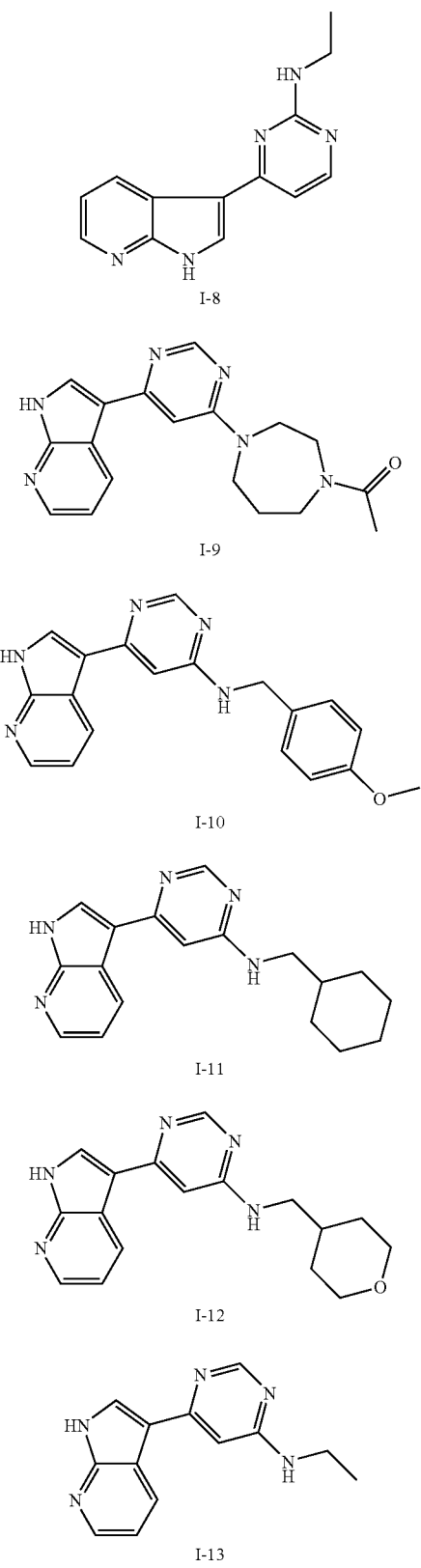
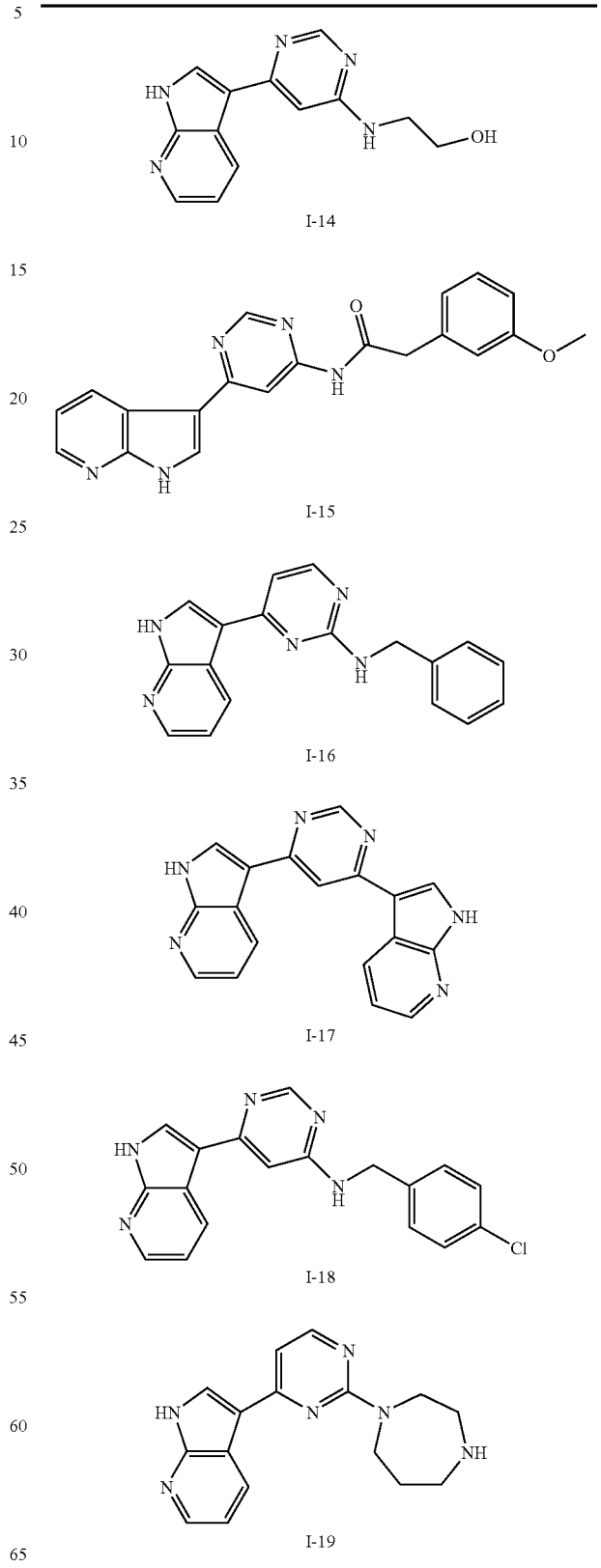

TABLE 1-continued
Examples of Compounds of Formula I:
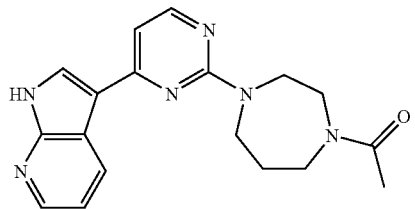
I-20
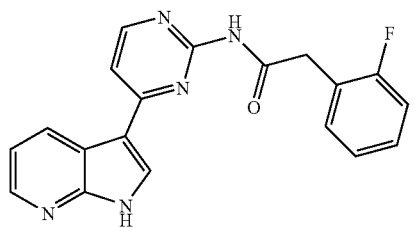
I-21
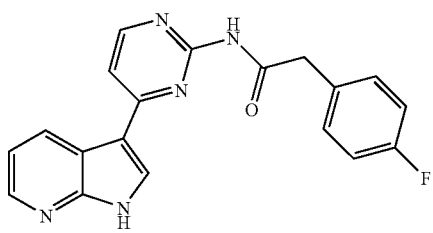
I-22
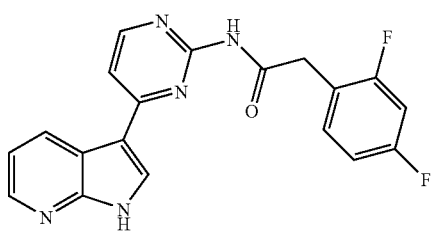
I-23
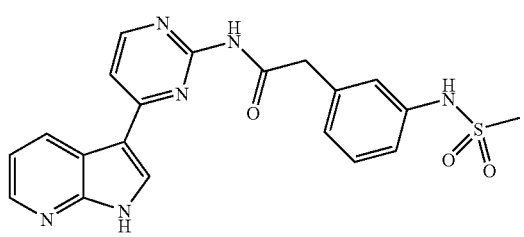
I-24
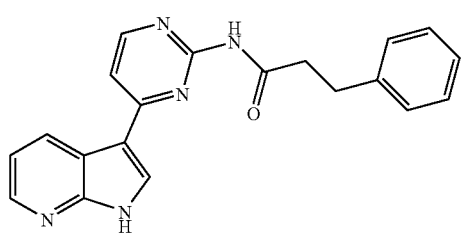
I-25
TABLE 1-continued
Examples of Compounds of Formula I:
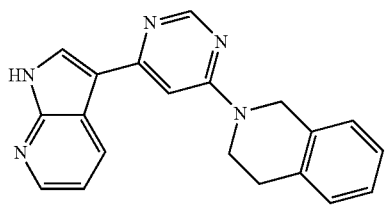
I-26
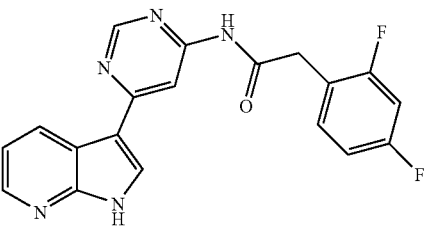
I-27
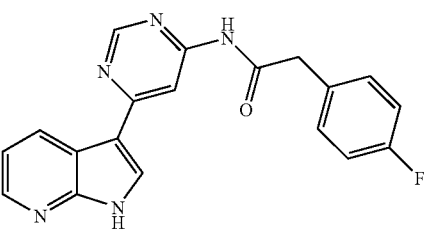
I-28
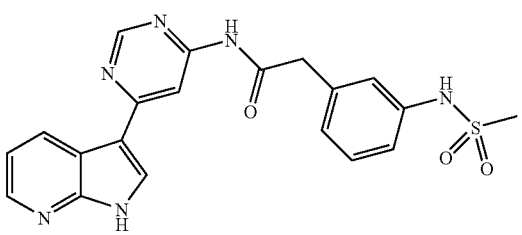
I-29
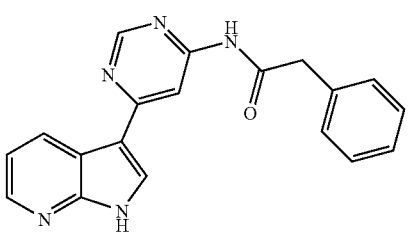
I-30
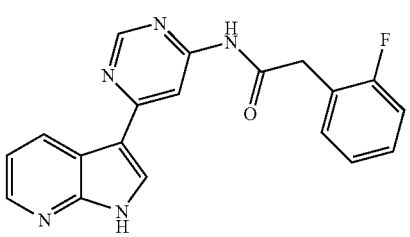
I-31

TABLE 1-continued
Examples of Compounds of Formula I:
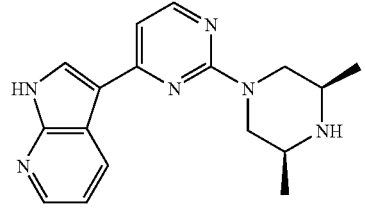
I-32
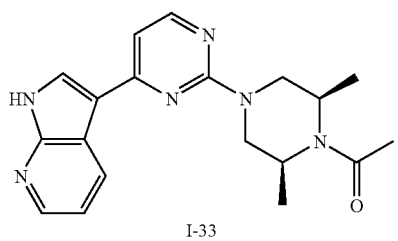
I-33
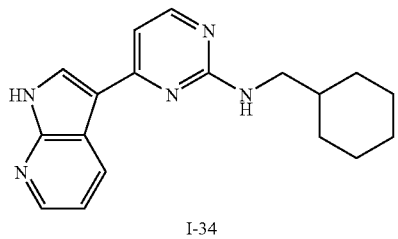
I-34
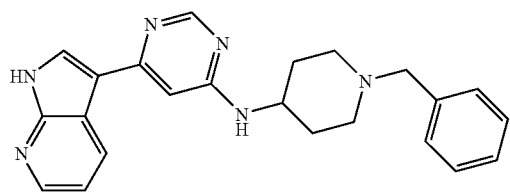
I-35
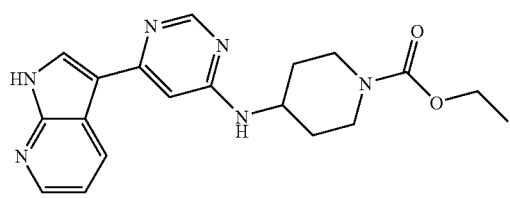
I-36
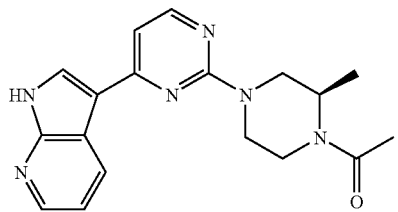
I-37
TABLE 1-continued
Examples of Compounds of Formula I:
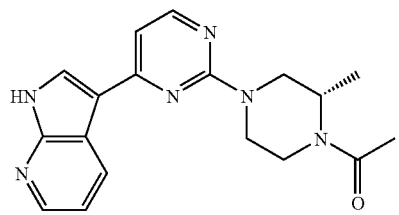
I-38
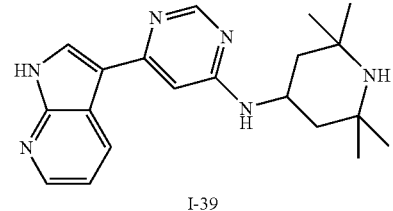
I-39
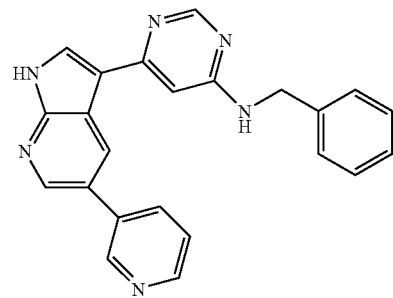
I-40
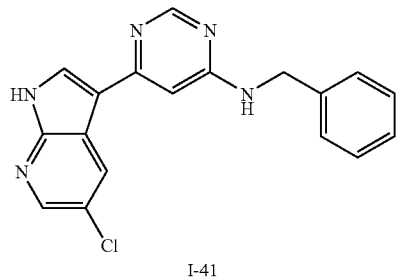
I-41
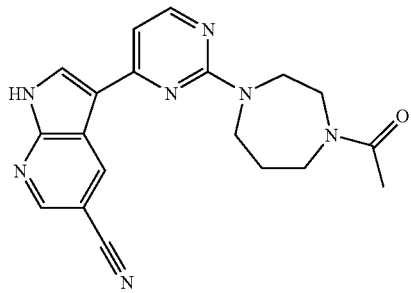
I-42

TABLE 1-continued
Examples of Compounds of Formula I:
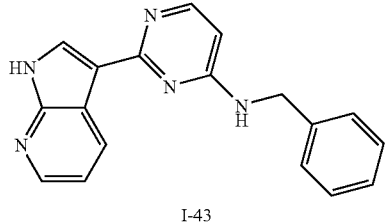
I-43
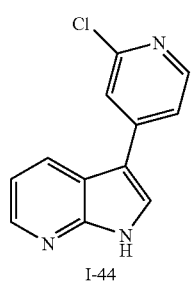
I-44
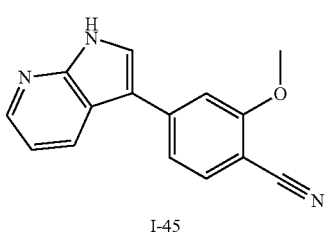
I-45
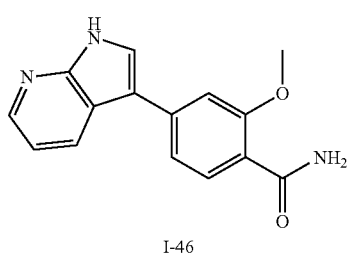
I-46
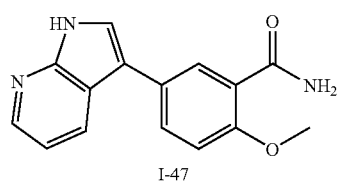
I-47
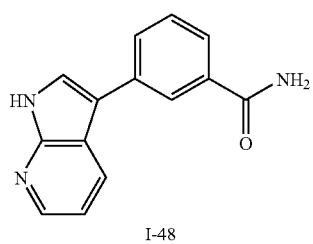
I-48
TABLE 1-continued
Examples of Compounds of Formula I:
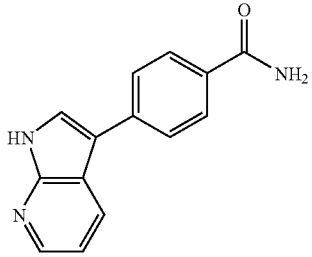
I-49
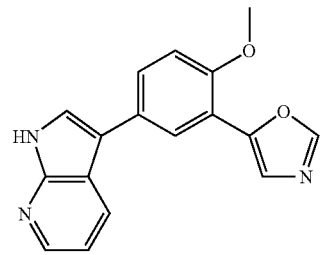
I-50
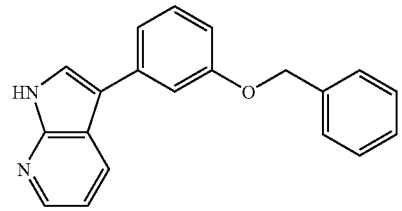
I-51
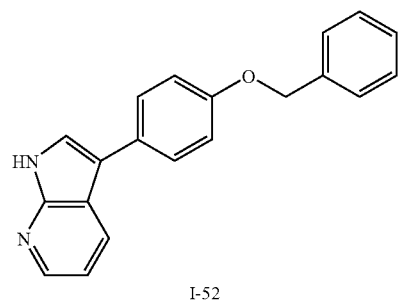
I-52
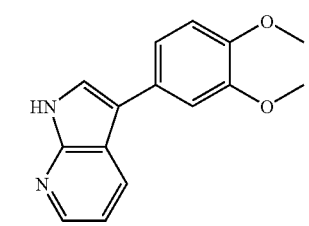
I-53

TABLE 1-continued

Examples of Compounds of Formula I:

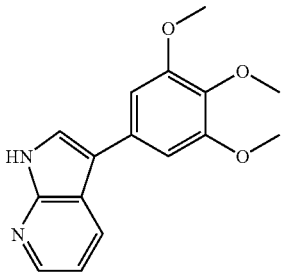

I-54

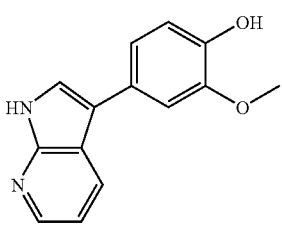

I-55

Certain additional subsets of compounds of general formula I include:

Compounds of formula I-B:

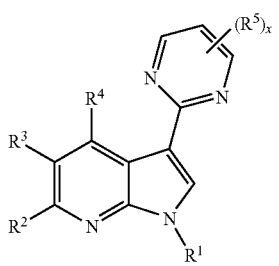

I-B wherein $R^1$, $R^2$, $R^3$, $R^4$, $R^5$ and x are each described generally above and in subsets described above and herein.

In some embodiments, for compounds of formula I-B:

a. $R^1$ is:
  i. T-R', wherein T is a bond or an optionally substituted $C_1$-$C_6$ alkylidene chain wherein up to two methylene units are optionally and independently replaced with —O—, —S—, —NR'—, —OCO—, —COO—, —SO$_2$— or —CO—, and R' is hydrogen, $C_1$-$C_4$-alkyl, or an optionally substituted 5- or 6-membered aryl or heteroaryl group, or
  ii. —Si(R')$_3$, wherein $R^1$ is hydrogen, $C_1$-$C_4$-alkyl, or an optionally substituted 5- or 6-membered saturated, partially unsaturated, or fully unsaturated monocyclic ring having 0-3 heteroatoms independently selected from nitrogen, oxygen, or sulfur;

b. $R^2$, $R^3$, and $R^4$ are each independently hydrogen, R', halogen, CN, NO$_2$, —N(R')$_2$, —CH$_2$N(R')$_2$, —OR', —CH$_2$OR', —SR', —CH$_2$SR', —COOR', —NR'COR', —NR'C(O)OR', —NR'COCH$_2$R', —NR'CO(CH$_2$)$_2$R', —CON(R')$_2$, —SO$_2$N(R')$_2$, —CONR'(CH$_2$)$_2$N(R')$_2$, —CONR'(CH$_2$)$_3$N(R')$_2$, —CONR'(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, or —O(CH$_2$)$_4$N(R')$_2$; wherein R', R', and $R^4$ are each optionally substituted with z occurrences of $R^6$, wherein z is 0-5 and $R^6$ is =O, =NR', =S, halogen, —CN, —NO$_2$, or Z—R", wherein Z is a bond or an optionally substituted $C_1$-$C_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; and c. each occurrence of $R^5$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COCH$_2$R', —NR'CO(CH$_2$)$_2$R', —NR'COOR', —CON(R')$_2$, —SO$_2$N(R')$_2$, —CONR'(CH$_2$)$_2$N(R')$_2$, —CONR(CH$_2$)$_3$N(R')$_2$, —CONR'(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, —O—(CH$_2$)$_4$N(R')$_2$, —NR'CH(CH$_2$OH)R', —NR'CH(CH$_2$CH$_2$OH)R', —NR'(CH$_2$)R', —NR'CH$_2$(CH$_3$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$N(R')$_2$, —NR'(CH$_2$)OR', —NR'(CH$_2$)$_2$OR', —NR'(CH$_2$)$_3$OR', or —NR'(CH$_2$)$_4$OR', wherein $R^5$ is optionally substituted with y occurrences of $R^7$, wherein y is 0-5 and $R^7$ is =O, =NR', =S, halogen, —CN, —NO$_2$, or W—R', wherein W is a bond or an optionally substituted $C_1$-$C_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In still other embodiments, for compounds of formula I-B:
a. $R^1$ is hydrogen, $C_1$-$C_4$alkyl, —COR', —SO$_2$R', or —Si(R')$_3$;
b. $R^2$ and $R^4$ are each independently Cl, Br, F, —CN, —COOH, —COOMe, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$N(Me)$_2$, or an optionally substituted group selected from $C_1$-$C_4$alkyl, $C_1$-$C_4$alkyloxy, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $R^2$ and $R^4$ are each independently and optionally substituted with z occurrences of $R^6$, wherein z is 0, 1, 2, or 3, and each occurrence of $R^6$ is independently hydrogen, R', —CH$_2$R'', halogen, CN, NO$_2$, —N(R'')$_2$, —CH$_2$N(R'')$_2$, —OR'', —CH$_2$OR'', —SR'', —CH$_2$SR'', —COOR'', —NR''COR'', —NR''COOR'', —CON(R'')$_2$, —SO$_2$N(R'')$_2$, —CONR''(CH$_2$)$_2$N(R'')$_2$, —CONR(CH$_2$)$_3$N(R'')$_2$, —CONR''(CH$_2$)$_4$N(R'')$_2$, —O(CH$_2$)$_2$OR'', O(CH$_2$)$_3$OR'', O(CH$_2$)$_4$OR'', —O(CH$_2$)$_2$N(R'')$_2$, —O(CH$_2$)$_3$N(R'')$_2$, —O(CH$_2$)$_4$N(R'')$_2$, —NR''CH(CH$_2$OH)R'', —NR''CH(CH$_2$CH$_2$OH)R'', —NR''(CH$_2$)R'', —NR''(CH$_2$)$_2$R'', —NR''(CH$_2$)$_3$R'', —NR''(CH$_2$)$_4$R'', —NR''(CH$_2$)N(R'')$_2$, —NR''(CH$_2$)$_2$N(R'')$_2$, —NR''(CH$_2$)$_3$N(R'')$_2$, —NR''(CH$_2$)$_4$N(R'')$_2$, —NR''(CH$_2$)OR'', —NR''(CH$_2$)$_2$OR'', —NR''(CH$_2$)$_3$OR'', or —NR'(CH$_2$)$_4$OR'';
c. $R^3$ is independently Cl, Br, F, —CN, —COOH, —COOMe, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$N(Me)$_2$, or an optionally substituted group selected from $C_1$-$C_4$alkyl, $C_1$-$C_4$alkyloxy, wherein $R^3$ is independently and optionally substituted with z occurrences of $R^6$, wherein z is 0 or 1, and each occurrence of $R^6$ is independently hydrogen, R', —CH$_2$R'', halogen, CN, NO$_2$, —N(R'')$_2$, —CH$_2$N(R'')$_2$, —OR'', —CH$_2$OR'', —SR'', —CH$_2$SR'', —COOR'', —NR''COR'', —NR''COOR'', —CON(R'')$_2$, —SO$_2$N(R'')$_2$, —CONR''(CH$_2$)$_2$N(R'')$_2$, —CONR''(CH$_2$)$_3$N(R'')$_2$, —O(CH$_2$)$_2$OR'', O(CH$_2$)$_3$OR'', O(CH$_2$)$_4$ OR'', —O(CH$_2$)$_2$N(R'')$_2$, —O(CH$_2$)$_3$N(R'')$_2$, —O(CH$_2$)$_4$N(R'')$_2$, —NR''CH(CH$_2$OH)R'', —NR''CH(CH$_2$CH$_2$OH)R'', —NR''(CH$_2$)R'', —NR''(CH$_2$)$_2$R'', —NR''(CH$_2$)$_3$R'', —NR''(CH$_2$)$_4$R'', —NR''(CH$_2$)N(R'')$_2$, —NR''(CH$_2$)$_2$N(R'')$_2$, —NR''(CH$_2$)$_3$N(R'')$_2$, —NR''(CH$_2$)$_4$N(R'')$_2$, —NR''(CH$_2$)OR'', —NR''(CH$_2$)$_2$OR'', —NR''(CH$_2$)$_3$OR'', or —NR'(CH$_2$)$_4$OR'';
d. each occurrence of $R^5$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COCH$_2$R', —NR'CO(CH$_2$)$_2$R', —NR'COOR', —CON(R')$_2$, —SO$_2$N(R')$_2$, —CONR'(CH$_2$)$_2$N(R')$_2$, —CONR(CH$_2$)$_3$N(R')$_2$, —CONR'(CH$_2$)$_4$ N(R')$_2$, —O(CH$_2$)$_2$OR', O(CH$_2$)$_3$OR', O(CH$_2$)$_4$ OR', —O(CH$_2$)$_2$N(R')$_2$, —O(CH$_2$)$_3$N(R')$_2$, —O(CH$_2$)$_4$N(R')$_2$, —NR'CH(CH$_2$OH)R', —NR'CH(CH$_2$CH$_2$OH)R', —NR'(CH$_2$)R', —NR'CH$_2$(CH$_3$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$N(R')$_2$, —NR'(CH$_2$)OR', —NR'(CH$_2$)$_2$OR', —NR'(CH$_2$)$_3$OR', or —NR'(CH$_2$)$_4$OR', wherein $R^5$ is optionally substituted with y occurrences of $R^7$, wherein y is 0, 1, 2, or 3, and each occurrence of $R^7$ is independently hydrogen, R', —CH$_2$R'', halogen, CN, NO$_2$, —N(R'')$_2$, —CH$_2$N(R'')$_2$, —OR'', —CH$_2$OR'', —SR'', —CH$_2$SR'', —COOR'', —NR''COR'', —NR''COOR'', —CON(R'')$_2$, —SO$_2$N(R'')$_2$, —CONR''(CH$_2$)$_2$N(R'')$_2$, —CONR(CH$_2$)$_3$N(R'')$_2$, —CONR''(CH$_2$)$_4$N(R'')$_2$, —O(CH$_2$)$_2$OR'', O(CH$_2$)$_3$OR'', O(CH$_2$)$_4$OR'', —O(CH$_2$)$_2$N(R'')$_2$, —O(CH$_2$)$_3$N(R'')$_2$, —O(CH$_2$)$_4$N(R'')$_2$, —NR''CH(CH$_2$OH)R'', —NR''CH(CH$_2$CH$_2$OH)R'', —NR''(CH$_2$)R'', —NR''(CH$_2$)$_2$R'', —NR''(CH$_2$)$_3$R'', —NR''(CH$_2$)$_4$R'', —NR''(CH$_2$)N(R'')$_2$, —NR''(CH$_2$)$_2$N(R'')$_2$, —NR''(CH$_2$)$_3$N(R'')$_2$, —NR''(CH$_2$)$_4$N(R'')$_2$, —NR''(CH$_2$)OR'', —NR''(CH$_2$)$_2$OR'', —NR''(CH$_2$)$_3$OR'', or —NR''(CH$_2$)$_4$OR''.

In other embodiments, for compounds of formula I-B and subsets described directly above, $R^1$ is hydrogen, methyl, ethyl, n-propyl, isopropyl, n-butyl, p-toluenesulfonyl (Ts), t-butyldimethylsilyl (TBS), triisopropylsilyl (TIPS), or triethylsilyl (TES).

In still other embodiments, for compounds of formula I-B and subsets described directly above, $R^2$, $R^3$, and $R^4$ are each hydrogen. In other embodiments, one of $R^2$, $R^3$, or $R^4$ is hydrogen. In yet other embodiments, two of $R^2$, $R^3$, or $R^4$ is hydrogen. In yet other embodiments, $R^2$ and $R^4$ are both hydrogen, and $R^3$ is halogen, CN, NO$_2$, or V—R'. In still further embodiments, $R^2$ and $R^4$ are both hydrogen and $R^3$ is halogen. In yet further embodiments, $R^2$ and $R^4$ are both hydrogen and $R^3$ is Cl.

In other embodiments, for compounds of formula I-B and subsets described directly above, $R^2$, $R^3$, and $R^4$ are each independently and optionally substituted with z occurrences of $R^6$, wherein z is 1, 2, or 3 and each occurrence of $R^6$ is independently F, Cl, Br, CN, OH, NH$_2$, —CH$_2$OH, $C_1$-$C_6$alkyl, —O($C_1$-$C_6$alkyl), CH$_2$O($C_1$-$C_6$alkyl), —CO($C_1$-$C_6$alkyl), —COO($C_1$-$C_6$alkyl), —NHSO$_2$($C_1$-$C_6$alkyl), —SO$_2$NH$_2$, —CONH$_2$, —CON($C_1$-$C_6$alkyl), —SO$_2$($C_1$-$C_6$alkyl), —SO$_2$-phenyl, phenyl, benzyl, —N($C_1$-$C_6$alkyl)$_2$, or —S($C_1$-$C_6$alkyl), wherein each of the foregoing phenyl, benzyl, and $C_1$-$C_6$alkyl groups is independently and optionally substituted, and wherein each of the foregoing $C_1$-$C_6$alkyl groups is linear, branched, or cyclic with the proviso that $R^3$ is not phenyl.

In certain exemplary embodiments, for compounds of formula I-B and subsets described directly above, x is 1, 2, or 3, and at least one occurrence of $R^5$ is —N(R')$_2$, —NR'CH(CH$_2$OH)R', —NR'CH(CH$_2$CH$_2$OH)R', —NR'(CH$_2$)R', —NR'CH$_2$(CH$_3$)R', —NR'(CH$_2$)$_2$R', NR'(CH$_2$)N(R')$_2$, or —NR'(CH$_2$)$_2$N(R')$_2$. In other embodiments, x is 1, 2, or 3, and at least one occurrence of $R^5$ is —OR'. In yet other embodiments, x is 1, 2, or 3, and at least one occurrence of $R^5$ is —NR'COR', —NR'COCH$_2$R', or —NR'CO(CH$_2$)$_2$R'. In still other embodiments, x is 1, 2, or 3, and at least one occurrence of $R^5$ is an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur.

In still other embodiments, for compounds of formula I-B and subsets described directly above, $R^5$ is optionally substituted with y occurrences of $R^7$, wherein y is 1, 2, or 3 and each occurrence of $R^7$ is independently F, Cl, Br, CN, OH, NH$_2$, —CH$_2$OH, $C_1$-$C_6$alkyl, —O($C_1$-$C_6$alkyl), —CH$_2$O($C_1$-$C_6$alkyl), —CO($C_1$-$C_6$alkyl), —COO($C_1$-$C_6$alkyl), —NHSO$_2$($C_1$-$C_6$alkyl), —SO$_2$NH$_2$, —CONH$_2$, —CON($C_1$-$C_6$alkyl), —SO$_2$($C_1$-$C_6$alkyl), —SO$_2$-phenyl, phenyl, benzyl, —N(C₁-C₆alkyl)₂, or —S(C₁-C₆alkyl), wherein each of the foregoing phenyl, benzyl, and C₁-C₆alkyl groups is independently and optionally substituted, and wherein each of the foregoing C₁-C₆alkyl groups is linear, branched, or cyclic.

In yet other embodiments, for compounds of formula I-B and subsets described directly above, x is 1, 2, or 3; at least one occurrence of R⁵ is —N(R')₂, —NR'CH(CH₂OH)R¹, —NR'CH(CH₂CH₂OH)R', —NR'(CH₂)R', —NR'CH₂(CH₃) R', —NR'(CH₂)₂R', NR'(CH₂)N(R')₂, —NR'(CH₂)₂N(R')₂, —OR', —NR'COR', —NR'COCH₂R', or —NR'CO(CH₂)₂ R'; and R' is a C₁-C₆aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R⁷. In certain embodiments, R' is hydrogen, C₁-C₆alkyl optionally substituted with 1-3 occurrences of R⁷, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R⁷. In other embodiments, R' is hydrogen, C₁-C₆alkyl optionally substituted with 1-3 occurrences of R⁷, or is a ring selected from (i)-(xLvi) or (xLvii). In yet other embodiments, R⁵ is —N(R')₂ and the two occurrences of R' are taken together with the nitrogen atom to which they are bound to form an optionally substituted 3-10-membered monocyclic or bicyclic heterocyclic ring. In certain embodiments, the ring is selected from (a)-(o).

wherein y and R⁷ are described generally and in subsets above.

In yet other embodiments, x is 1 and compounds have general formula I-B-i:

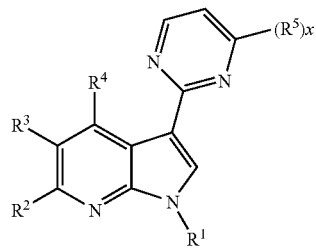

I-B-i wherein R¹, R², R³, and R⁴ are described generally and in subsets above and herein, and R⁵ is —N(R')₂, —NR'CH (CH₂OH)R', —NR'CH(CH₂CH₂OH)R', —NR'(CH₂)R', —NR'CH₂(CH₃)R'—NR'(CH₂)₂R', NR'(CH₂)N(R')₂, —NR' (CH₂)₂N(R')₂, —OR', —NR'COR', —NR'COCH₂R', or —NR'CO(CH₂)₂R'; and R' is a C₁-C₆aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R⁷. In some embodiments, R⁵ is N(R')₂. In certain embodiments, R' is hydrogen, C₁-C₆alkyl optionally substituted with 1-3 occurrences of R⁷, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R⁷. In other embodiments, R' is hydrogen, C₁-C₄alkyl optionally substituted with 1-3 occurrences of R⁷, or is a ring selected from (i)-(xLvi) or (xLvii). In yet other embodiments, R⁵ is —N(R')₂ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In yet other embodiments, x is 0-3 and compounds have general formula I-B-ii:

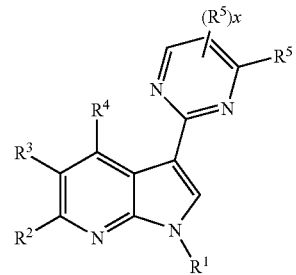

I-B-ii wherein R¹, R², R³, and R⁴ are described generally and in subsets above and herein, and each R⁵ is independently selected from halogen, optionally substituted C₁-C₆ alkyl, —SR', —CN, —COON, —CO₂R', —CON((R')₂, —N(R')₂, —NR'CH(CH₂OH)R', —NR'CH(CH₂CH₂OH)R', —NR' (CH₂)R', —NR'CH(CH₃)R'—NR'(CH₂)₂R', NR'(CH₂)N (R')₂, —NR'(CH₂)₂N(R')₂, —OR', —NR'COR', —NR'COCH₂R', or —NR'CO(CH₂)₂R'; and R' is a C₁-C₆ aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of R⁷. In some embodiments, R⁵ is N(R')₂. In certain embodiments, R' is hydrogen, C₁-C₆ alkyl optionally substituted with 1-3 occurrences of R⁷, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of R⁷. In other embodiments, R' is hydrogen, C₁-C₄ alkyl optionally substituted with 1-3 occurrences of R⁷, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In yet other embodiments, x is 1-4 and compounds have general formula I-B-iii:

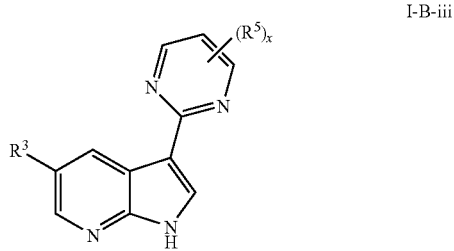

I-B-iii wherein:
$R^3$ is an optionally substituted group selected from halogen, optionally substituted $C_{1-6}$ alkyl, CN, N(R')$_2$, CO$_2$R', NR'COR', CON(R')$_2$, CH$_2$N(R')$_2$, OR', SR', CH$_2$OR'; x is 1, 2, or 3; and at least one occurrence of $R^5$ is selected from halogen, optionally substituted $C_1$-$C_6$ aliphatic group, —SR', —CN, —COOH, —CONOR')$_2$, —N(R')$_2$, —NR'CH(CH$_2$OH)R', —NR'CH(CH$_2$CH$_2$OH)R', —NR'(CH$_2$)R', —NR'CH(CH$_3$)R'—NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is selected from hydrogen, a $C_1$-$C_6$aliphatic group optionally substituted with y occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$ and $R^4$ are each hydrogen, and x is 0-3, and compounds of formula I-B-iv are provided:

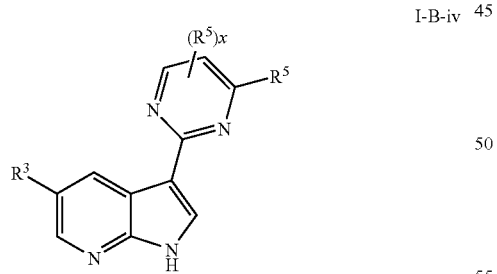

I-B-iv wherein:
$R^3$ is an optionally substituted group selected from halogen, optionally substituted C1-6 aliphatic, CN, N(R')$_2$, CO$_2$R', NR'COR', CON(R')$_2$, CH$_2$N(R')$_2$, OR', SR', CH$_2$OR'; $R^5$ is selected from halogen, optionally substituted C1-C6 aliphatic group, —SR', —CN, —COOH, —CO$_2$R', —CON((R')$_2$, —N(R')$_2$, —NR'CH(CH$_2$OH)R', —NR'CH(CH$_2$CH$_2$OH)R', —NR'(CH$_2$)R', —NR'CH(CH$_3$)R$^1$—NR' (CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is selected from hydrogen, a $C_1$-$C_6$aliphatic group optionally substituted with y occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$ and $R^4$ are each hydrogen, and x is 2, and compounds of formula I-B-v are provided:

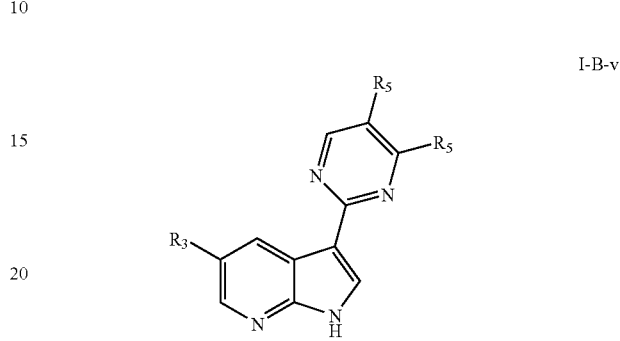

I-B-v wherein:
$R^3$ is an optionally substituted group selected from halogen, optionally substituted $C_{1-6}$ aliphatic, CN, N(R')$_2$, CO$_2$R', NR'COR', CON(R')$_2$, CH$_2$N(R')$_2$, OR', SR', CH$_2$OR'; $R^5$ is selected from halogen, optionally substituted $C_1$-$C_6$ aliphatic group, —SR', —CN, —COOH, —CO$_2$R', —CON((R')$_2$, —N(R')$_2$, —NR'CH(CH$_2$OH)R', —NR'CH(CH$_2$CH$_2$OH)R', —NR'(CH$_2$)R', —NR'CH(CH$_3$)R'—NR'(CH$_2$)$_2$R', NR(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is selected from hydrogen, a $C_1$-$C_6$aliphatic group optionally substituted with y occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$ and $R^4$ are each hydrogen, and x is 2, and compounds of formula I-B-vi are provided:

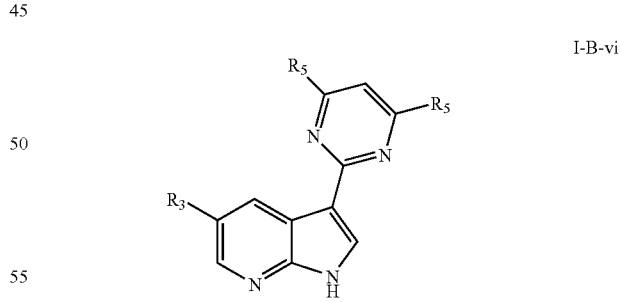

I-B-vi wherein:
$R^3$ is an optionally substituted group selected from halogen, optionally substituted C1-6 aliphatic, CN, N(R')$_2$, CO$_2$R', NR'COR', CON(R')$_2$, CH$_2$N(R')$_2$, OR', SR', CH$_2$OR'; $R^5$ is selected from halogen, optionally substituted $C_1$-$C_6$ aliphatic group, —SR', —CN, —COOH, —CO$_2$R', —CON((R')$_2$, —N(R')$_2$, —NR'CH(CH$_2$OH)R', —NR'CH (CH$_2$CH$_2$OH)R', —NR'(CH$_2$)R', —NR'CH(CH$_3$)R'—NR' (CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is selected from hydrogen, a $C_1$-$C_6$aliphatic group optionally substituted with y occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

Certain additional subsets of compounds of general formula I include:

Compounds of Formula I-E:

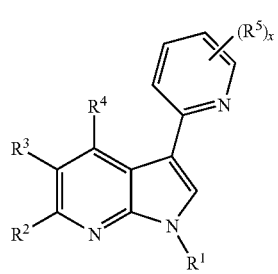

I-E wherein $R^1$, $R^2$, $R^3$, $R^4$, $R^5$ and x are each described generally above and in subsets described above and herein.

In some embodiments, for compounds of formula I-E:
a. $R^1$ is:
  i. T-R', wherein T is a bond or an optionally substituted $C_1$-$C_6$alkylidene chain wherein up to two methylene units are optionally and independently replaced with —O—, —S—, —NR'—, —OCO—, —COO—, —SO$_2$— or —CO—, and R' is hydrogen, $C_1$-$C_4$-alkyl, or an optionally substituted 5- or 6-membered aryl or heteroaryl group, or
  ii. —Si(R')$_3$, wherein $R^1$ is hydrogen, $C_1$-$C_4$-alkyl, or an optionally substituted 5- or 6-membered saturated, partially unsaturated, or fully unsaturated monocyclic ring having 0-3 heteroatoms independently selected from nitrogen, oxygen, or sulfur;
b. $R^2$, $R^3$, and $R^4$ are each independently hydrogen, R', halogen, CN, NO$_2$, —N(R')$_2$, —CH$_2$N(R')$_2$, —OR', —CH$_2$OR', —SR', —CH$_2$SR', —COOR', —NR'COR', —NR'C(O)OR', —NR'COCH$_2$R', —NR'CO(CH$_2$)$_2$R', —CON(R')$_2$, —SO$_2$N(R')$_2$, —CONR'(CH$_2$)$_2$N(R')$_2$, —CONR'(CH$_2$)$_3$N(R')$_2$, —CONR'(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, or —O(CH$_2$)$_4$N(R')$_2$; wherein $R^2$, $R^3$, and $R^4$ are each optionally substituted with z occurrences of $R^6$, wherein z is 0-5 and $R^6$ is =O, =NR', =S, halogen, —CN, —NO$_2$, or Z—R", wherein Z is a bond or an optionally substituted $C_1$-$C_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

c. each occurrence of $R^5$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COCH$_2$R', —NR'CO(CH$_2$)$_2$R', —NR'COOR', —CON(R')$_2$, —SO$_2$N(R')$_2$, —CONR'(CH$_2$)$_2$N(R')$_2$, —CONR(CH$_2$)$_3$N(R')$_2$, —CONR'(CH$_2$)$_4$ N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, —O(CH$_2$)$_4$ N(R')$_2$, —NR'CH(CH$_2$OH)R', —NR'CH(CH$_2$CH$_2$OH) R', —NR'(CH$_2$)R', —NR'CH(CH$_3$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$ N(R')$_2$, —NR'(CH$_2$)OR', —NR'(CH$_2$)$_2$OR', —NR'(CH$_2$)$_3$OR', or —NR'(CH$_2$)$_4$OR', wherein $R^5$ is optionally substituted with y occurrences of $R^7$, wherein y is 0-5 and $R^7$ is =O, =NR', =S, halogen, —CN, —NO$_2$, or W—R', wherein W is a bond or an optionally substituted $C_1$-$C_6$ alkylidene chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$—, or —POR"—, and each occurrence of R" is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R" are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In still other embodiments, for compounds of formula I-E:
a. $R^1$ is hydrogen, $C_1$-$C_4$alkyl, —COR', —SO$_2$R', or —Si (R')$_3$;
b. $R^2$ and $R^4$ are each independently Cl, Br, F, —CN, —COOH, —COOMe, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$N (Me)$_2$, or an optionally substituted group selected from $C_1$-$C_4$alkyl, $C_1$-$C_4$alkyloxy, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $R^2$, $R^3$, and $R^4$ are each independently and optionally substituted with z occurrences of $R^6$, wherein z is 0, 1, 2, or 3, and each occurrence of $R^6$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR'(CH$_2$)$_4$OR";

c. $R^3$ is independently Cl, Br, F, —CN, —COOH, —COOMe, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$N(Me)$_2$, or an optionally substituted group selected from $C_1$-$C_4$alkyl, $C_1$-$C_4$alkyloxy, wherein $R^3$ is independently and optionally substituted with z occurrences of $R^6$, wherein z is 0 or 1, and each occurrence of $R^6$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$ OR", —O(CH$_2$)$_2$N(R")$_2$, —O(CH$_2$)$_3$N(R")$_2$, —O(CH$_2$)$_4$N(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR'(CH$_2$)$_4$OR";

d. each occurrence of $R^5$ is independently hydrogen, R', —CH$_2$R', halogen, CN, NO$_2$, —N(R')$_2$, —CH$_2$N(R')$_2$, —OR', —CH$_2$OR', —SR', —CH$_2$SR', —COOR', —NR'COR', —NR'COCH$_2$R', —NR'CO(CH$_2$)$_2$R', —NR'COOR', —CON(R')$_2$, —SO$_2$N(R')$_2$, —CONR'(CH$_2$)$_2$N(R')$_2$, —CONR(CH$_2$)$_3$N(R')$_2$, —CONR'(CH$_2$)$_4$ N(R')$_2$, —O(CH$_2$)$_2$OR', O(CH$_2$)$_3$OR', O(CH$_2$)$_4$ OR', —O(CH$_2$)$_2$N(R')$_2$, —O(CH$_2$)$_3$N(R')$_2$, —O(CH$_2$)$_4$N(R')$_2$, —NR'CH(CH$_2$OH)R', —NR'CH(CH$_2$CH$_2$OH)R', —NR'(CH$_2$)R', —NR'CH(CH$_3$)R', —NR'(CH$_2$)$_2$R', —NR'(CH$_2$)$_3$R', —NR'(CH$_2$)$_4$R', —NR'(CH$_2$)N(R')$_2$, —NR'(CH$_2$)$_2$N(R')$_2$, —NR'(CH$_2$)$_3$N(R')$_2$, —NR'(CH$_2$)$_4$ N(R')$_2$, —NR'(CH$_2$)OR', —NR'(CH$_2$)$_2$OR', —NR'(CH$_2$)$_3$OR', or —NR'(CH$_2$)$_4$OR', wherein $R^5$ is optionally substituted with y occurrences of $R^7$, wherein y is 0, 1, 2, or 3, and each occurrence of $R^7$ is independently hydrogen, R', —CH$_2$R", halogen, CN, NO$_2$, —N(R")$_2$, —CH$_2$N(R")$_2$, —OR", —CH$_2$OR", —SR", —CH$_2$SR", —COOR", —NR"COR", —NR"COOR", —CON(R")$_2$, —SO$_2$N(R")$_2$, —CONR"(CH$_2$)$_2$N(R")$_2$, —CONR(CH$_2$)$_3$N(R")$_2$, —CONR"(CH$_2$)$_4$N(R")$_2$, —O(CH$_2$)$_2$OR", O(CH$_2$)$_3$OR", O(CH$_2$)$_4$OR", —O(CH$_2$)$_2$N(R")$_2$, —O(CH$_2$)$_3$N(R")$_2$, —O(CH$_2$)$_4$(R")$_2$, —NR"CH(CH$_2$OH)R", —NR"CH(CH$_2$CH$_2$OH)R", —NR"(CH$_2$)R", —NR"(CH$_2$)$_2$R", —NR"(CH$_2$)$_3$R", —NR"(CH$_2$)$_4$R", —NR"(CH$_2$)N(R")$_2$, —NR"(CH$_2$)$_2$N(R")$_2$, —NR"(CH$_2$)$_3$N(R")$_2$, —NR"(CH$_2$)$_4$N(R")$_2$, —NR"(CH$_2$)OR", —NR"(CH$_2$)$_2$OR", —NR"(CH$_2$)$_3$OR", or —NR"(CH$_2$)$_4$OR".

In other embodiments, for compounds of formula I-E and subsets described directly above, $R^1$ is hydrogen, methyl, ethyl, n-propyl, isopropyl, n-butyl, p-toluenesulfonyl (Ts), t-butyldimethylsilyl (TBS), triisopropylsilyl (TIPS), or triethylsilyl (TES).

In still other embodiments, for compounds of formula I-E and subsets described directly above, $R^2$, $R^3$, and $R^4$ are each hydrogen. In other embodiments, one of $R^2$, $R^3$, or $R^4$ is hydrogen. In yet other embodiments, two of $R^2$, R', or $R^4$ is hydrogen. In yet other embodiments, $R^2$ and $R^4$ are both hydrogen, and $R^3$ is halogen, CN, NO$_2$, or V—R'. In still further embodiments $R^2$ and $R^4$ are both hydrogen and $R^3$ is halogen. In yet further embodiments $R^2$ and $R^4$ are both hydrogen and $R^3$ is Cl.

In other embodiments, for compounds of formula I-E and subsets described directly above, $R^2$, $R^3$, and $R^4$ are each independently and optionally substituted with z occurrences of $R^6$, wherein z is 1, 2, or 3 and each occurrence of $R^6$ is independently F, Cl, Br, CN, OH, NH$_2$, —CH$_2$OH, $C_1$-$C_6$alkyl, —O($C_1$-$C_6$alkyl), —CH$_2$O($C_1$-$C_6$alkyl), —CO($C_1$-$C_6$alkyl), —COO($C_1$-$C_6$alkyl), —NHSO$_2$($C_1$-$C_6$alkyl), —SO$_2$NH$_2$, —CONH$_2$, —CON($C_1$-$C_6$alkyl), —SO$_2$($C_1$-$C_6$alkyl), —SO$_2$-phenyl, phenyl, benzyl, —N($C_1$-$C_6$alkyl)$_2$, or —S($C_1$-$C_6$alkyl), wherein each of the foregoing phenyl, benzyl, and $C_1$-$C_6$alkyl groups is independently and optionally substituted, and wherein each of the foregoing $C_1$-$C_6$alkyl groups is linear, branched, or cyclic.

In certain exemplary embodiments, for compounds of formula I-E and subsets described directly above, x is 1, 2, or 3, and at least one occurrence of $R^5$ is —N(R')$_2$, —NR'CH(CH$_2$OH)R', —NR'CH(CH$_2$CH$_2$OH)R', —NR'(CH$_2$)R', —NR'CH(CH$_3$)R', —NR'(CH$_2$)$_2$R', NR'(CH$_2$)N(R')$_2$, or —NR'(CH$_2$)$_2$N(R')$_2$. In other embodiments, x is 1, 2, or 3, and at least one occurrence of $R^5$ is —OR'. In yet other embodiments, x is 1, 2, or 3, and at least one occurrence of $R^5$ is —NR'COR', —NR'COCH$_2$R', or —NR'CO(CH$_2$)$_2$R'. In still other embodiments, x is 1, 2, or 3, and at least one occurrence of $R^5$ is an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur.

In still other embodiments, for compounds of formula I-E and subsets described directly above, $R^5$ is optionally substituted with y occurrences of $R^7$, wherein y is 1, 2, or 3 and each occurrence of $R^7$ is independently F, Cl, Br, CN, OH, NH$_2$, —CH$_2$OH, $C_1$-$C_6$alkyl, —O($C_1$-$C_6$alkyl), —CH$_2$O($C_1$-$C_6$alkyl), —CO($C_1$-$C_6$alkyl), —COO($C_1$-$C_6$alkyl), —NHSO$_2$($C_1$-$C_6$alkyl), —SO$_2$NH$_2$, —CONH$_2$, —CON($C_1$-$C_6$alkyl), —SO$_2$($C_1$-$C_6$alkyl), —SO$_2$-phenyl, phenyl, benzyl, —N($C_1$-$C_6$alkyl)$_2$, or —S($C_1$-$C_6$alkyl), wherein each of the foregoing phenyl, benzyl, and $C_1$-$C_6$alkyl groups is independently and optionally substituted, and wherein each of the foregoing $C_1$-$C_6$alkyl groups is linear, branched, or cyclic.

In yet other embodiments, for compounds of formula I-E and subsets described directly above, x is 1, 2, or 3; at least one occurrence of $R^5$ is —N(R')$_2$, —NR'CH(CH$_2$OH)R', —NR'CH(CH$_2$CH$_2$OH)R', —NR'(CH$_2$)R', —NR'CH(CH$_3$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

wherein y and $R^7$ are described generally and in subsets above.

In yet other embodiments, x is 1 and compounds have general formula I-E-i:

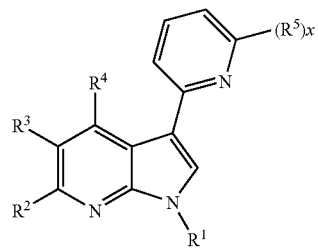

I-E-i wherein $R^1$, $R^2$, $R^3$, and $R^4$ are described generally and in subsets above and herein, and $R^5$ is —N(R')$_2$, —NR'CH(CH$_2$OH)R', —NR'CH(CH$_2$CH$_2$OH)R', —NR'(CH$_2$)R', —NR'CH$_2$(CH$_3$)R'—NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a $C_1$-$C_6$aliphatic group or a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein each occurrence of R' is optionally substituted with y occurrences of $R^7$. In some embodiments, $R^5$ is N(R')$_2$. In certain embodiments, R' is hydrogen, $C_1$-$C_6$alkyl optionally substituted with 1-3 occurrences of $R^7$, or is a 5-10-membered monocyclic or bicyclic saturated, partially unsaturated or fully unsaturated ring having 0-4 heteroatoms independently selected from nitrogen, oxygen, or sulfur, wherein the ring is optionally substituted with 1-3 occurrences of $R^7$. In other embodiments, R' is hydrogen, $C_1$-$C_4$alkyl optionally substituted with 1-3 occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$, and $R^4$ are each hydrogen, and compounds of formula I-E-ii are provided:

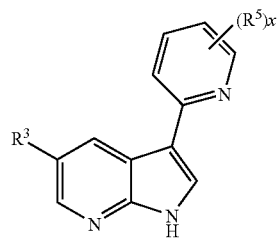

I-E-ii wherein:
$R^3$ is an optionally substituted group selected from halogen, optionally substituted C1-6 alkyl, CN, N(R')2, CO2R', NR'COR', CON(R')2, CH2N(R')2, OR', SR', CH2OR';

x is 1, 2, or 3; and at least one occurrence of $R^5$ is —N(R')$_2$, —NR'CH(CH$_2$OH)R', —NR'CH(CH$_2$CH$_2$OH)R', —NR'(CH$_2$)R', —NR'CH$_2$(CH$_3$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a $C_1$-$C_6$aliphatic group optionally substituted with y occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$ and $R^4$ are each hydrogen, and x is 0-3, and compounds of formula I-E-iii are provided:

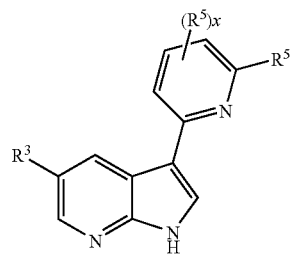

I-E-iii wherein:
$R^3$ is an optionally substituted group selected from halogen, optionally substituted C1-6 alkyl, CN, N(R')$_2$, CO$_2$R', NR'COR', CON(R')$_2$, CH$_2$N(R')$_2$, OR', SR', CH$_2$OR'; $R^5$ is —N(R')$_2$, —NR'CH(CH$_2$OH)R', —NR'CH(CH$_2$CH$_2$OH)R', —NR'(CH$_2$)R', —NR'CH$_2$(CH$_3$)R', —NR'(CH$_2$)$_2$R', NR'(CH$_2$)N(R')$_2$, —NR'(CH$_2$)$_2$N(R')$_2$, —OR', —NR'COR', —NR'COCH$_2$R', or —NR'CO(CH$_2$)$_2$R'; and R' is a $C_1$-$C_6$aliphatic group optionally substituted with y occurrences of $R^7$, or is a ring selected from (i)-(xLvi) or (xLvii). In yet other embodiments, $R^5$ is —N(R')$_2$ and the two occurrences of R' are taken together with the nitrogen atom to which they are bound to form an optionally substituted 3-10-membered monocyclic or bicyclic heterocyclic ring. In certain embodiments, the ring is selected from (a)-(o).

In still other embodiments, $R^1$, $R^2$ and $R^4$ are each hydrogen, and x is 1, and compounds of formula I-E-iv are provided:

I-E-iv

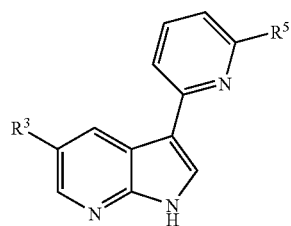

wherein:

R³ is an optionally substituted group selected from halogen, optionally substituted C₁₋₆ alkyl, CN, N(R')₂, CO₂R', NR'COR', CON(R')₂, CH₂N(R')₂, OR', SR', CH₂OR'; R⁵ is —N(R')₂, —NR'CH(CH₂OH)R', —NR'CH(CH₂CH₂OH)R', —NR'(CH₂)R', —NR'CH₂(CH₃)R', —NR'(CH₂)₂R', NR'(CH₂)N(R')₂, —NR'(CH₂)₂N(R')₂, —NR'COR', —NR'COCH₂R', or —NR'CO(CH₂)₂R'; and R' is a C₁-C₆aliphatic group optionally substituted with y occurrences of R⁷, or is a ring selected from (i)-(xLvi) or (xLvii). In yet other embodiments, R⁵ is —N(R')₂ and the two occurrences of R' are taken together with the nitrogen atom to which they are bound to form an optionally substituted 3-10-membered monocyclic or bicyclic heterocyclic ring. In certain embodiments, the ring is selected from (a)-(o).

Representative examples of compounds of formula I are set forth below in Table 2. Compounds of Table 2 may also be represented by II-x, where x is the compound number indicated in Table 2.

TABLE 2

Examples of Compounds of Formula I:

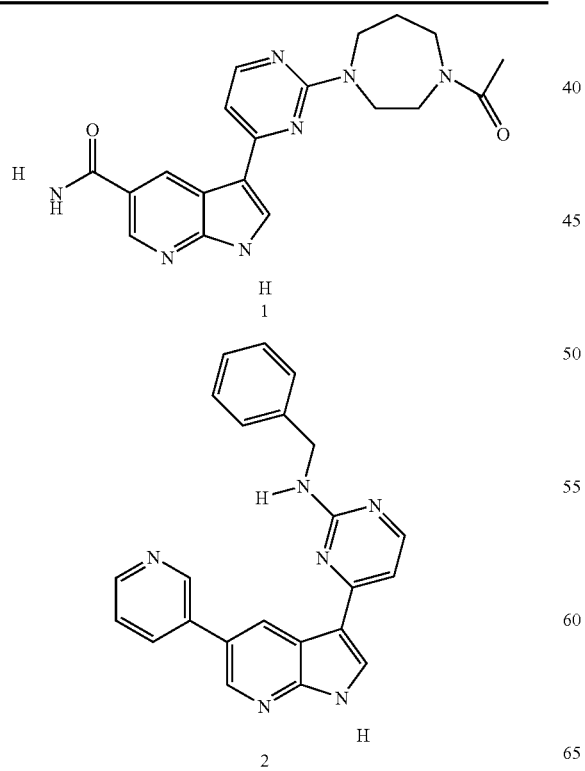

TABLE 2-continued

Examples of Compounds of Formula I:

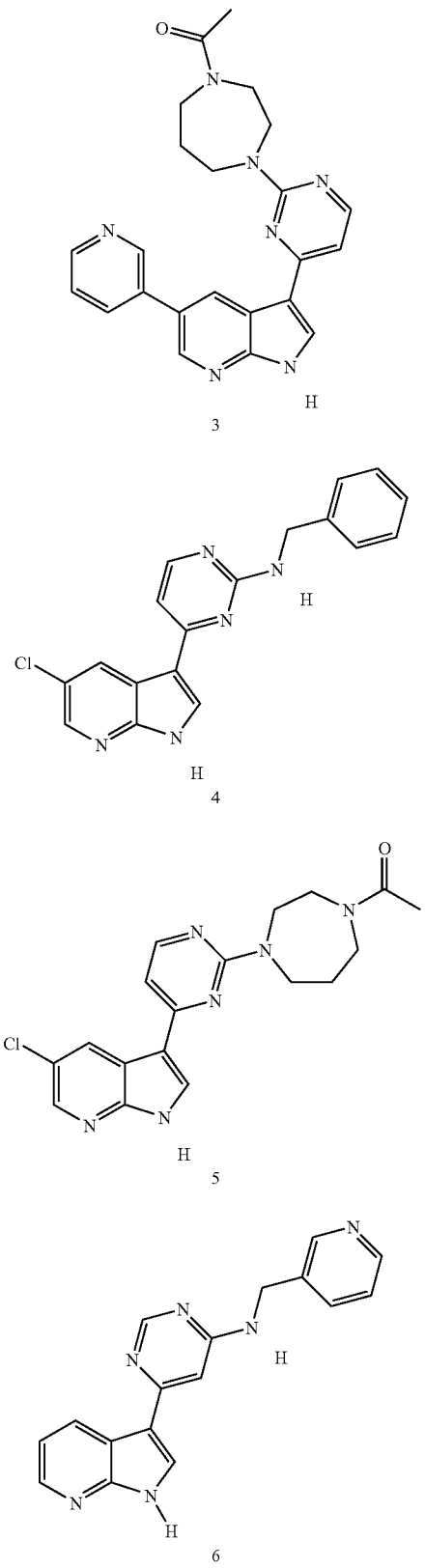

TABLE 2-continued
Examples of Compounds of Formula I:
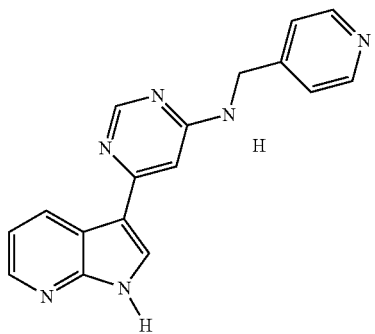
7
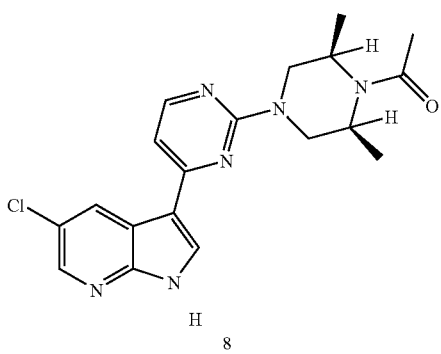
8
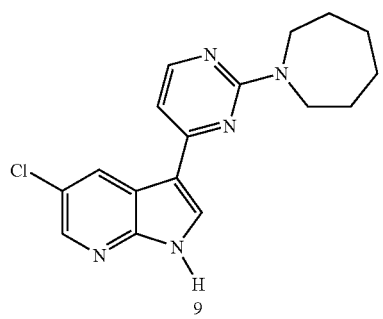
9
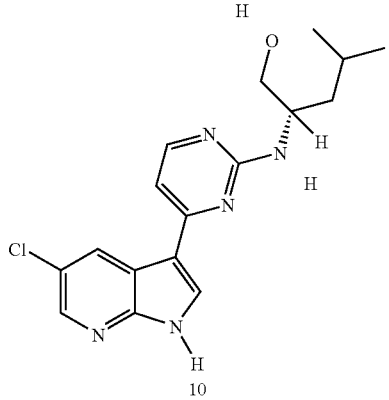
10
TABLE 2-continued
Examples of Compounds of Formula I:
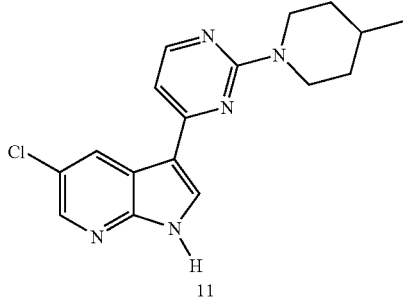
11
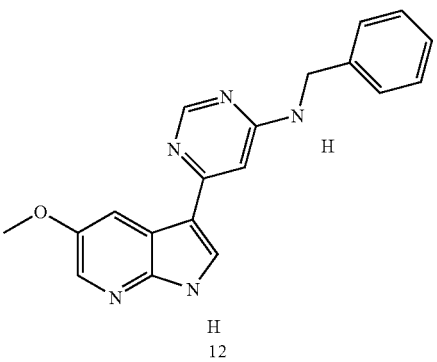
12
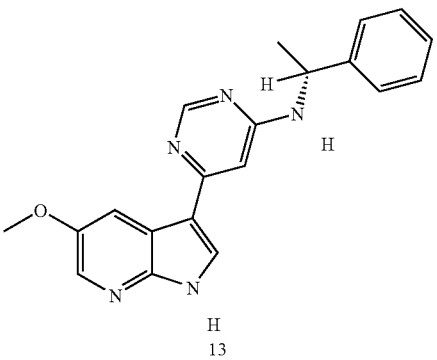
13
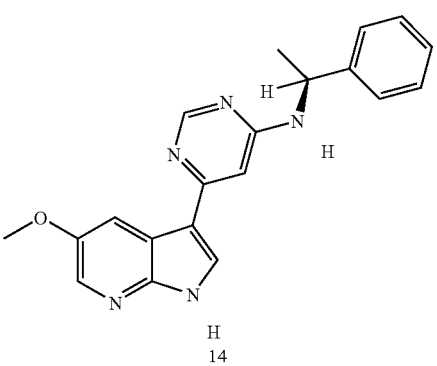
14

TABLE 2-continued
Examples of Compounds of Formula I:
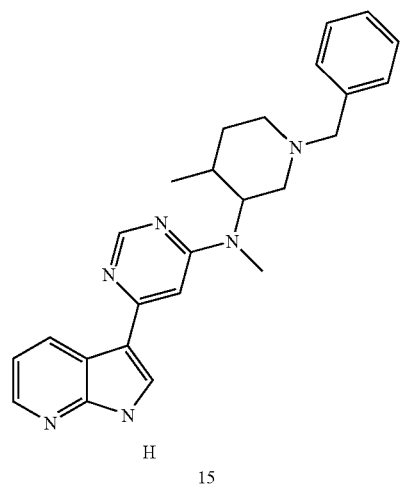
15
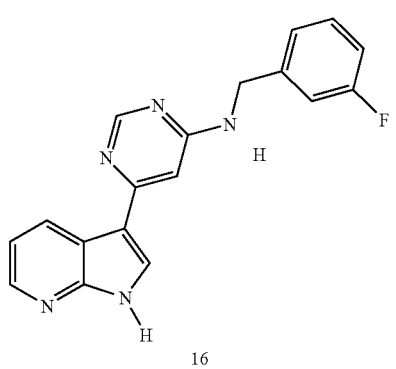
16
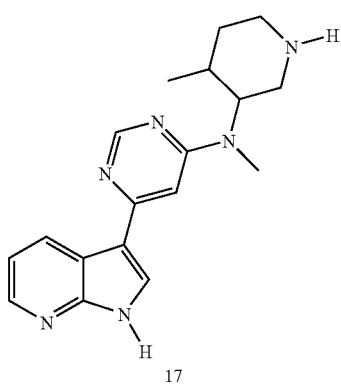
17
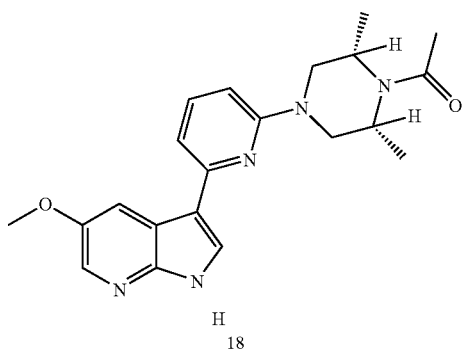
18
TABLE 2-continued
Examples of Compounds of Formula I:
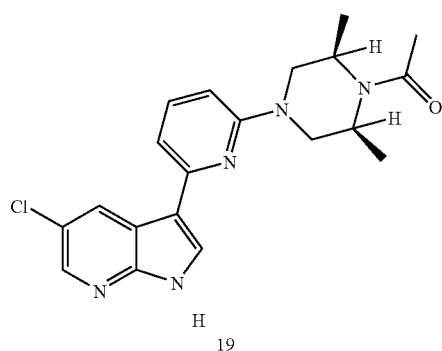
19
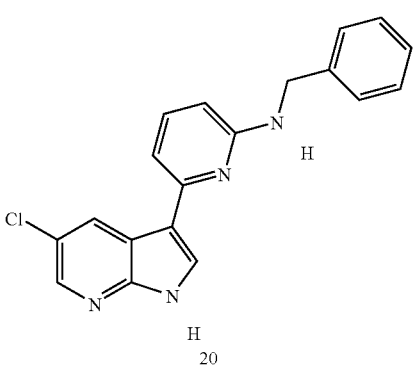
20
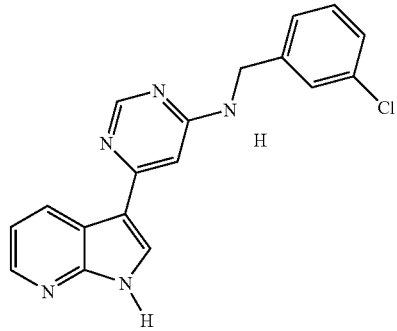
21
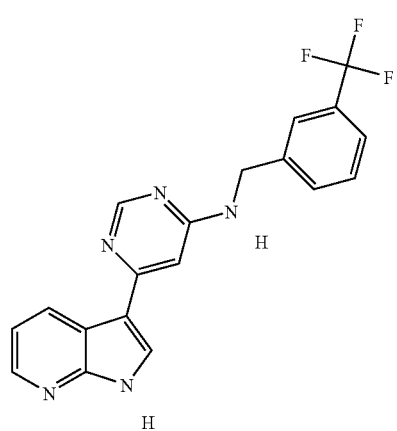
22

TABLE 2-continued
Examples of Compounds of Formula I:
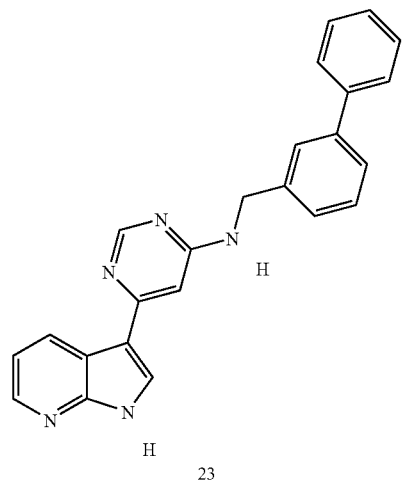
23
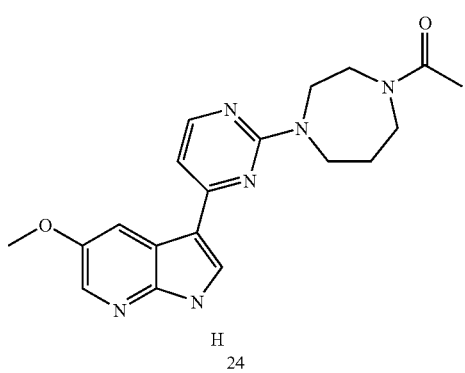
24
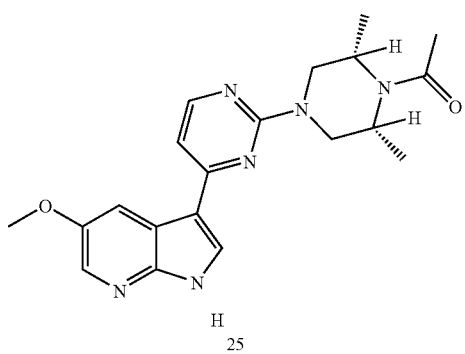
25
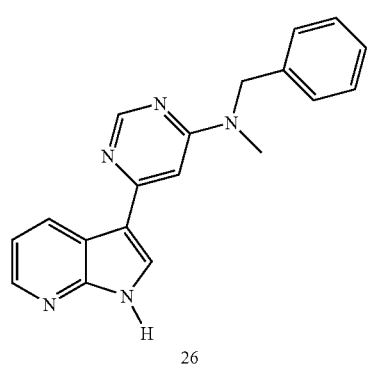
26
TABLE 2-continued
Examples of Compounds of Formula I:
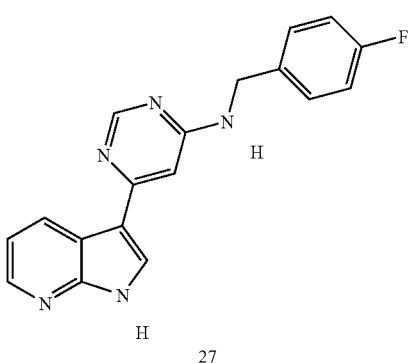
27
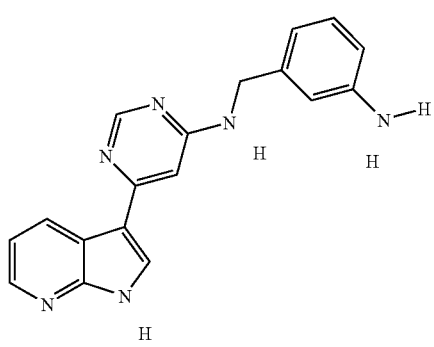
28
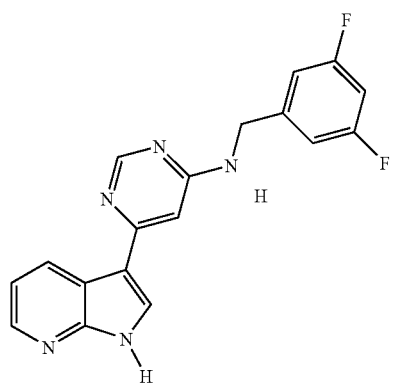
29
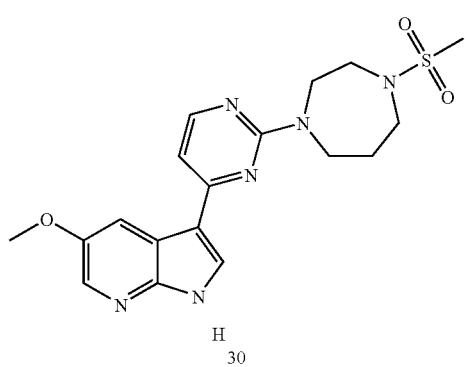
30

TABLE 2-continued
Examples of Compounds of Formula I:
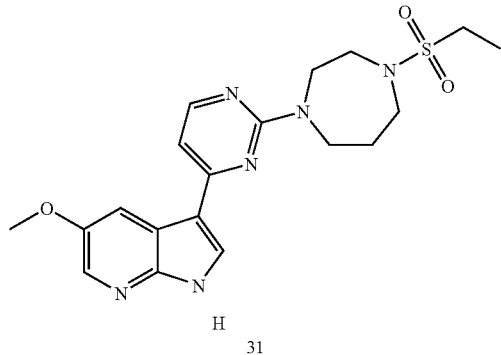
31
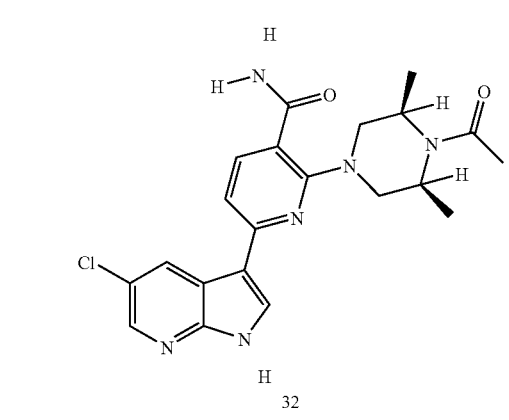
32
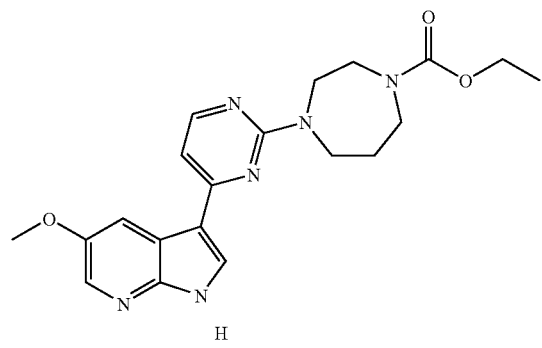
33
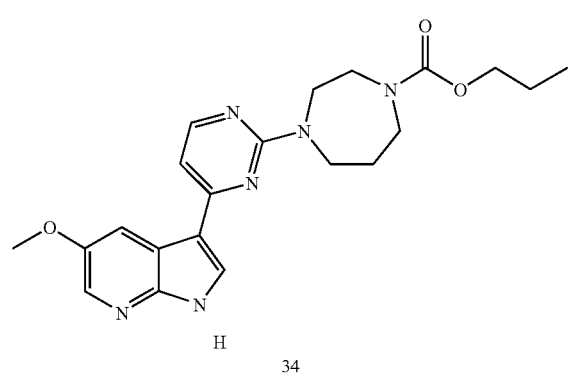
34
TABLE 2-continued
Examples of Compounds of Formula I:
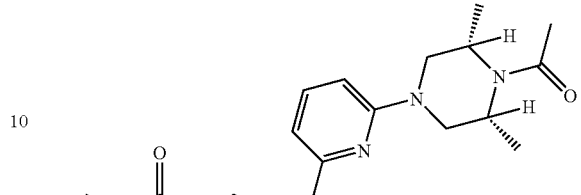
35
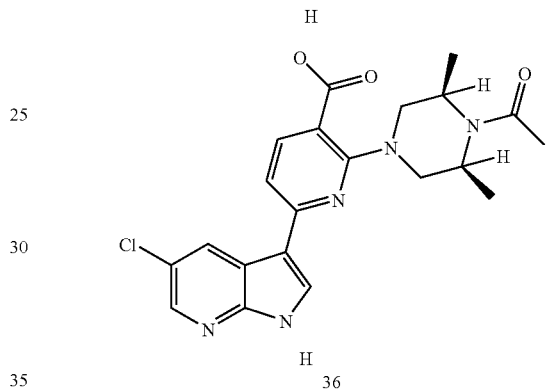
36
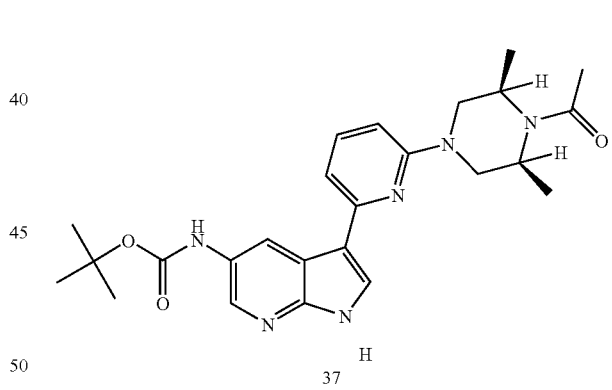
37
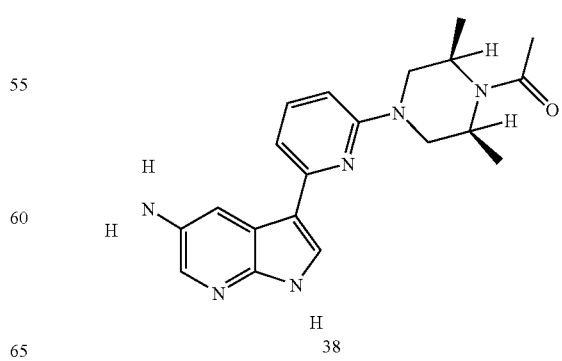
38

TABLE 2-continued
Examples of Compounds of Formula I:
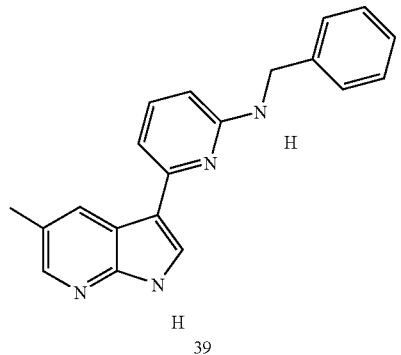
39
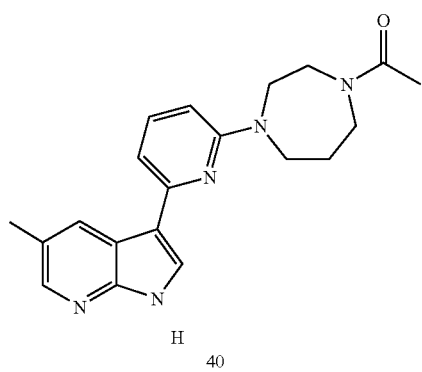
40
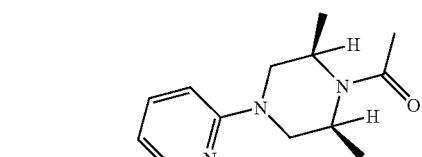
41
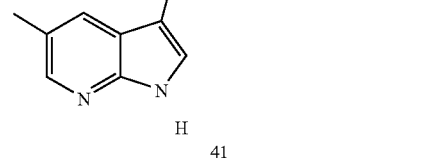
42
TABLE 2-continued
Examples of Compounds of Formula I:
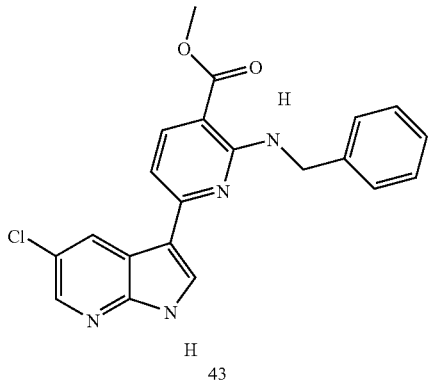
43
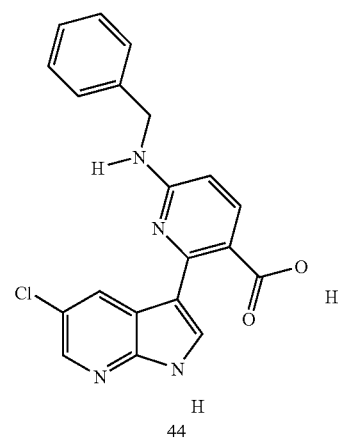
44
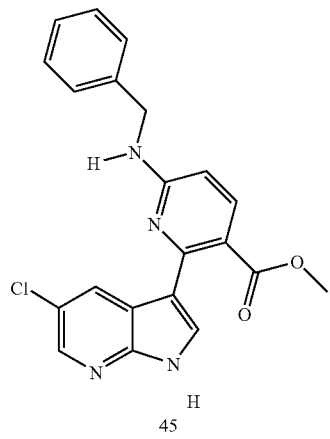
45

TABLE 2-continued
Examples of Compounds of Formula I:
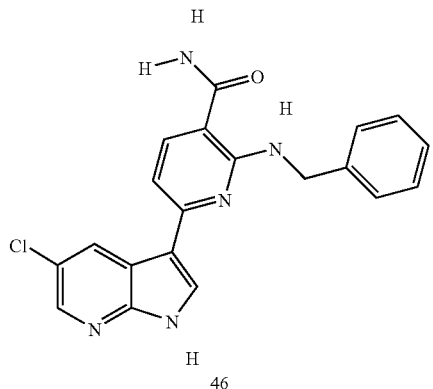
46
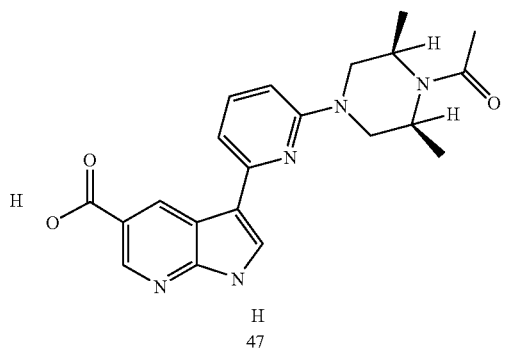
47
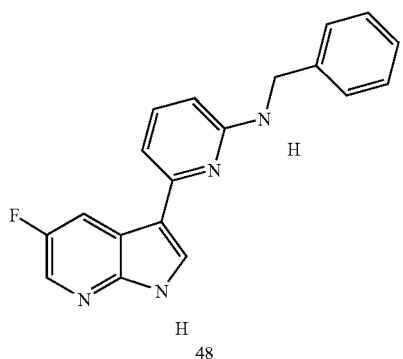
48
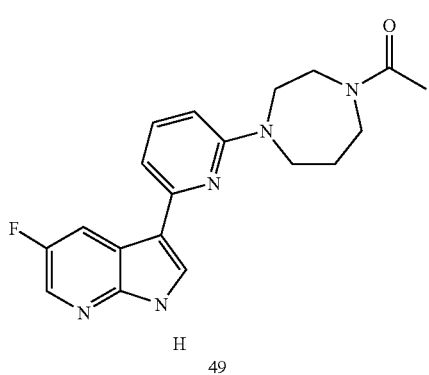
49
TABLE 2-continued
Examples of Compounds of Formula I:
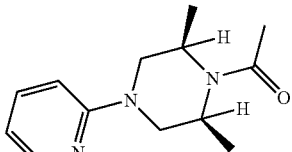
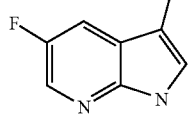
50
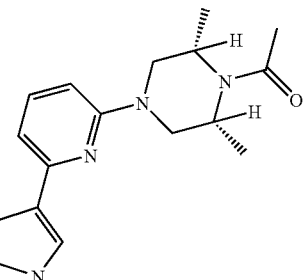
51
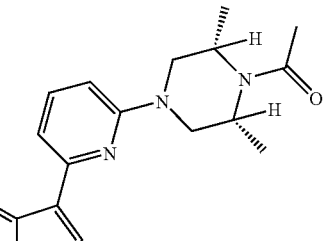
52
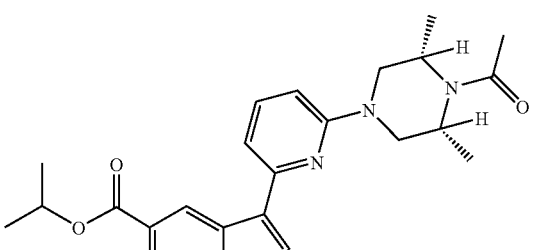
53

TABLE 2-continued
Examples of Compounds of Formula I:
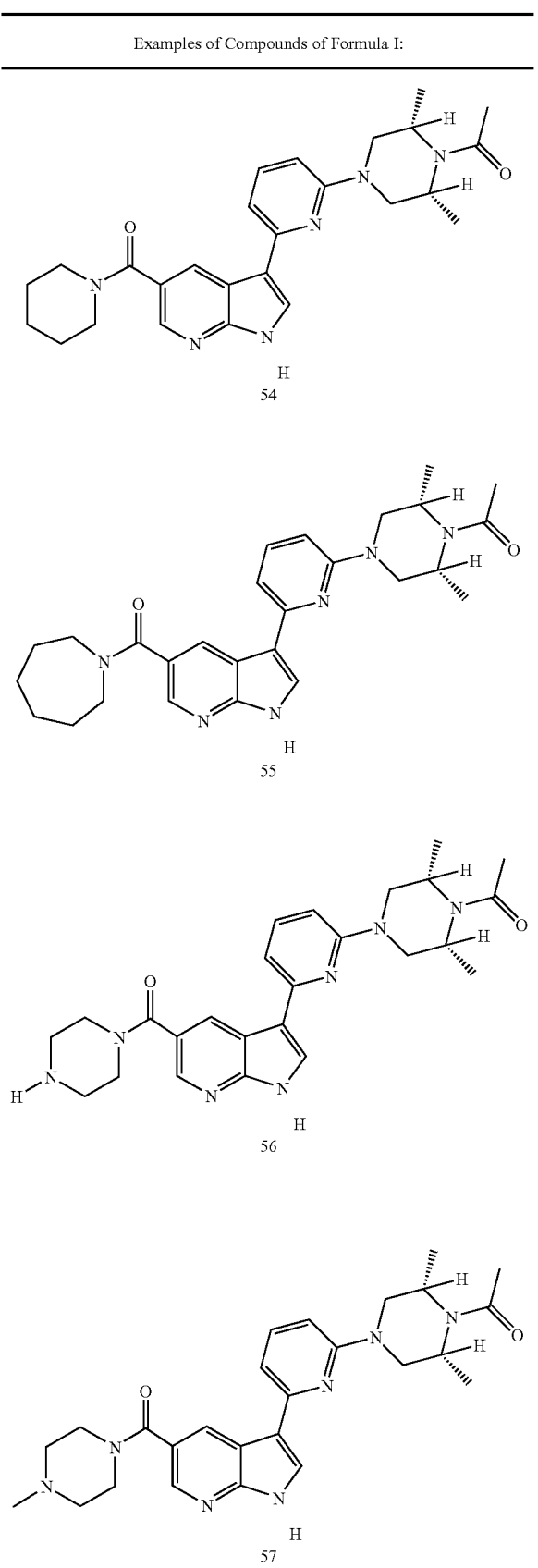
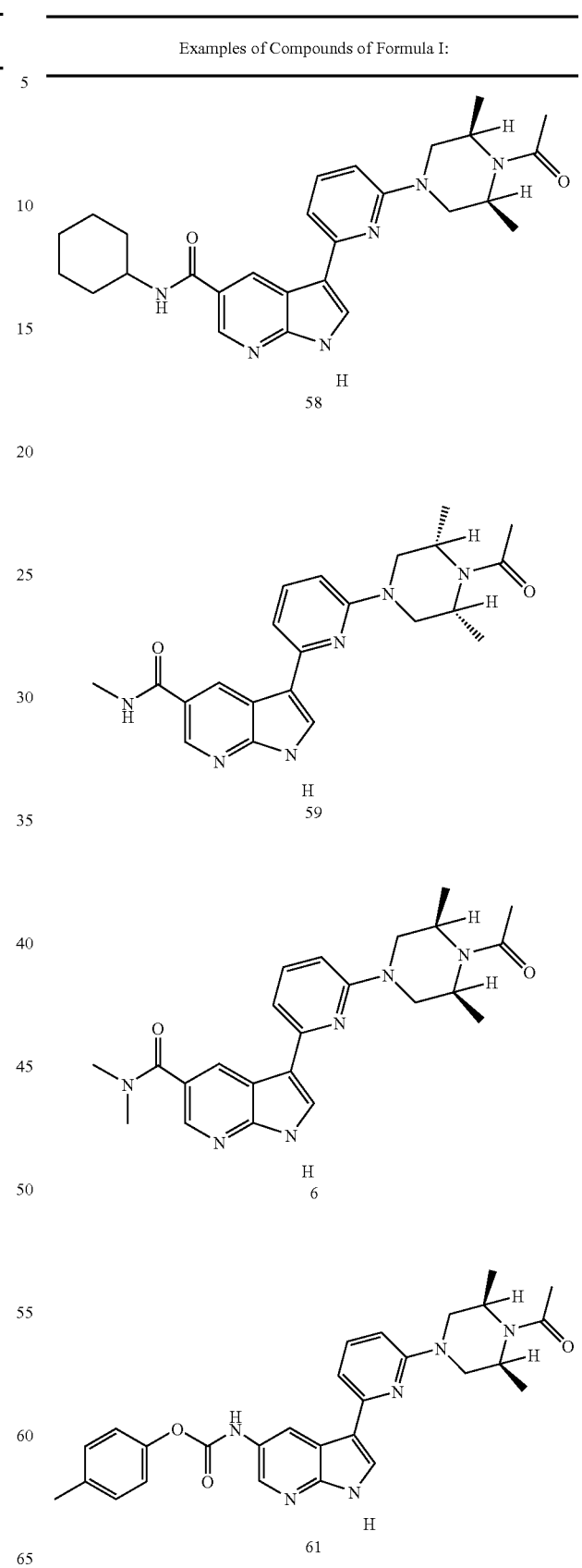

TABLE 2-continued
Examples of Compounds of Formula I:
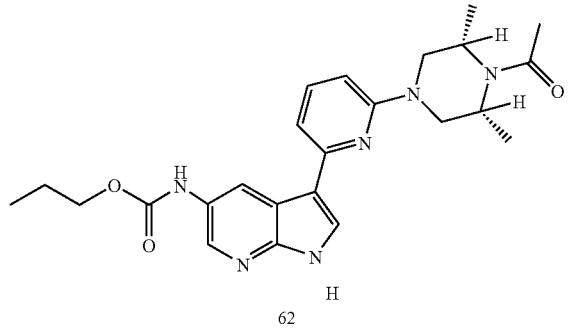
62
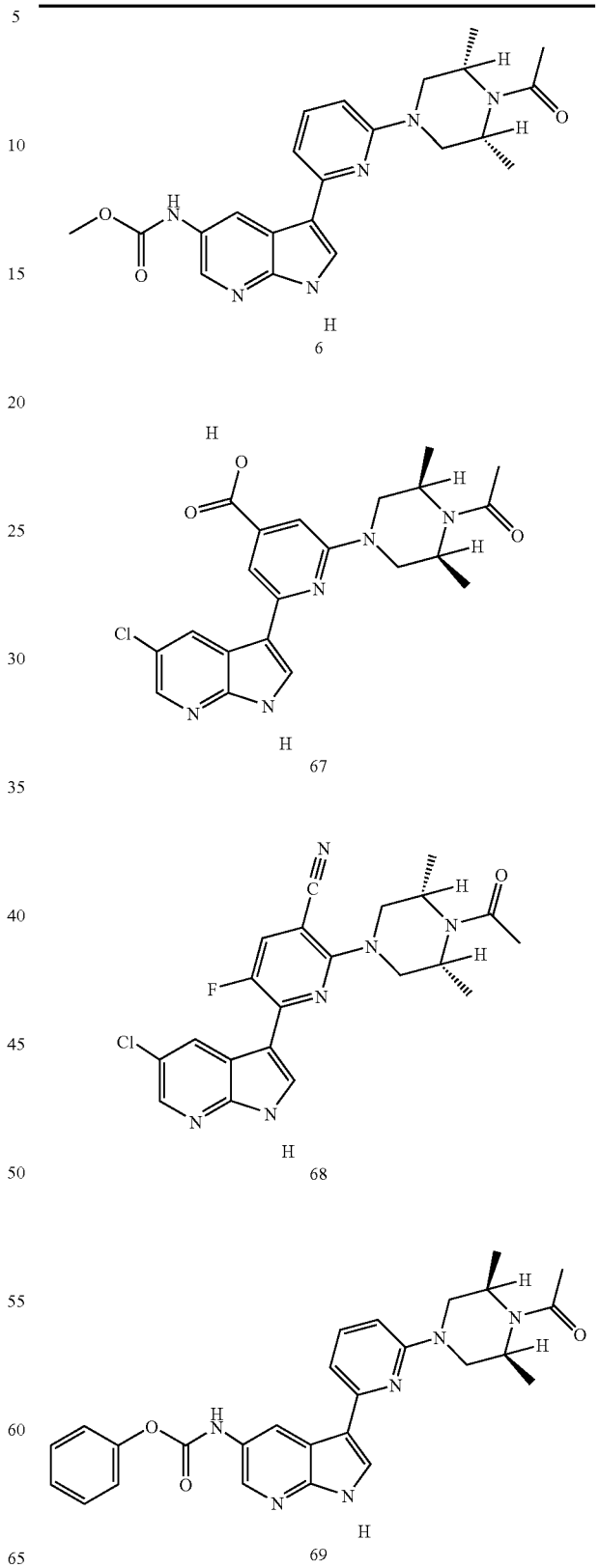

TABLE 2-continued
Examples of Compounds of Formula I:
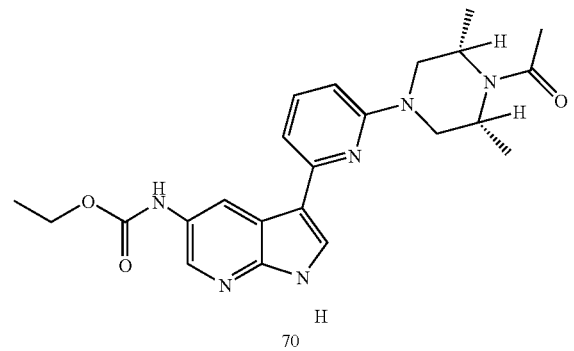
70
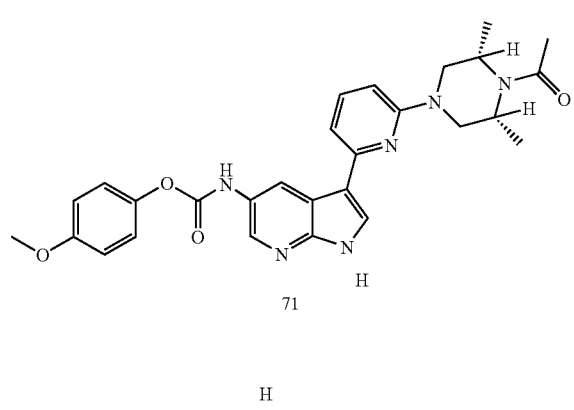
71
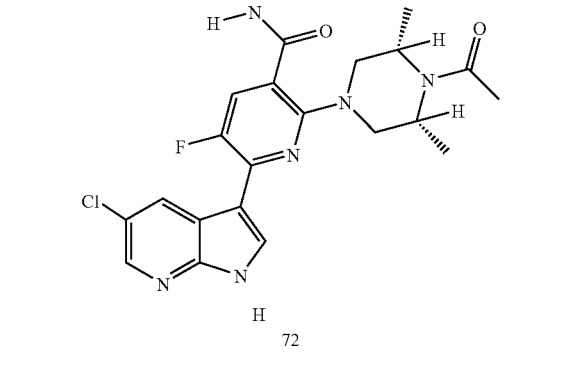
72
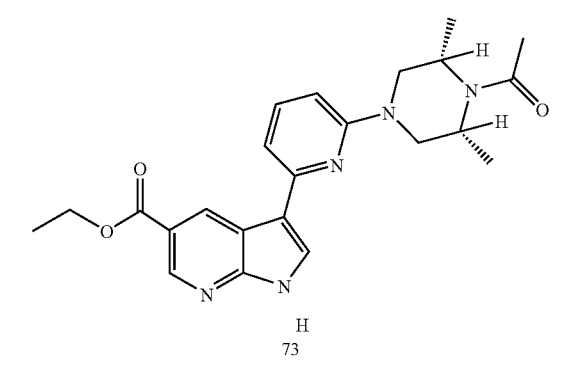
73
TABLE 2-continued
Examples of Compounds of Formula I:
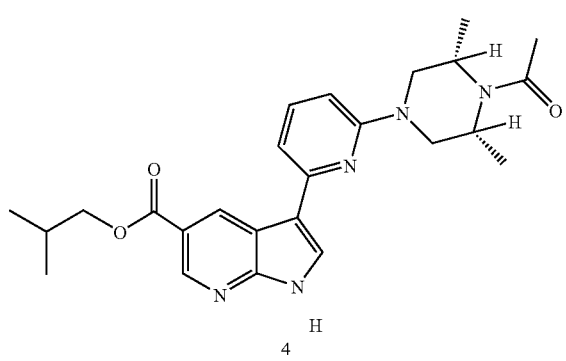
74
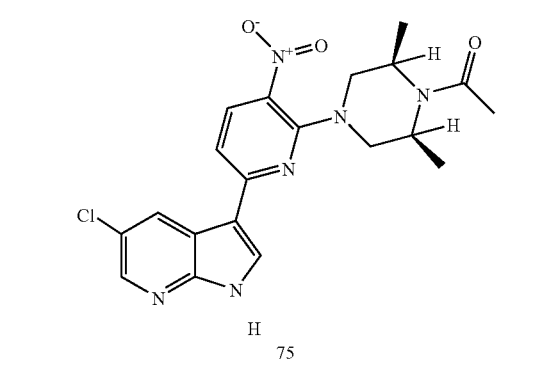
75
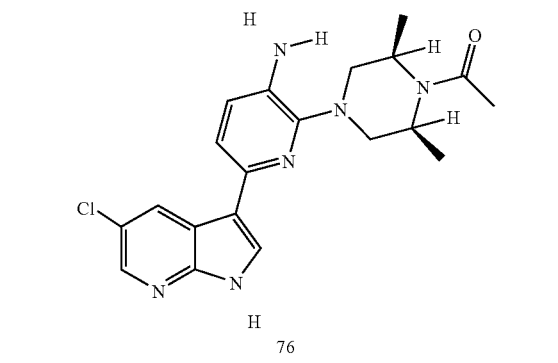
76
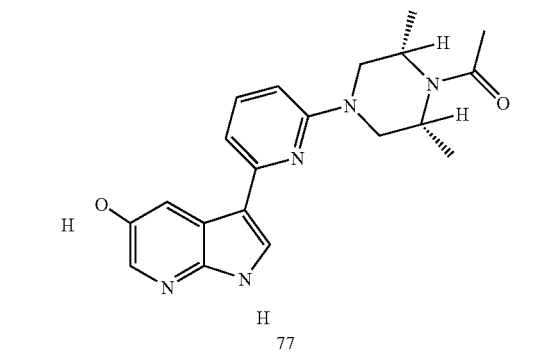
77

TABLE 2-continued
Examples of Compounds of Formula I:
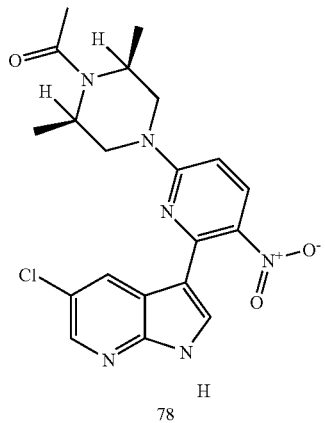
78
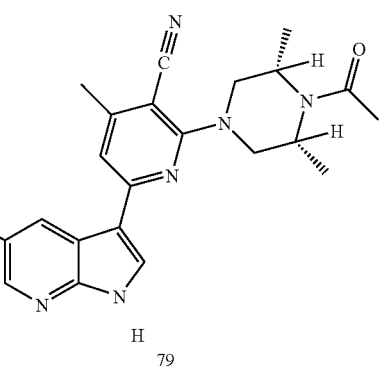
79
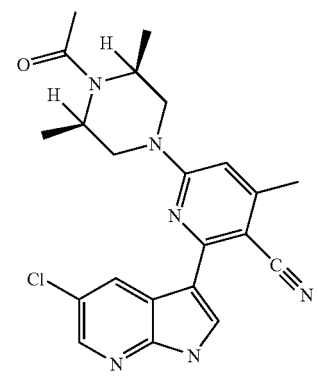
80
TABLE 2-continued
Examples of Compounds of Formula I:
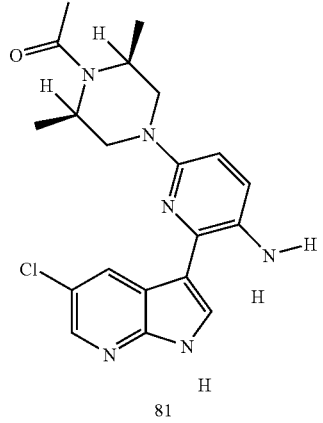
81
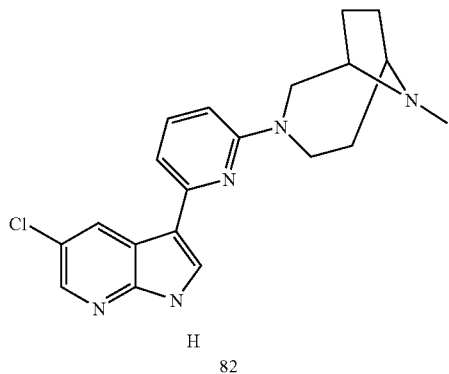
82
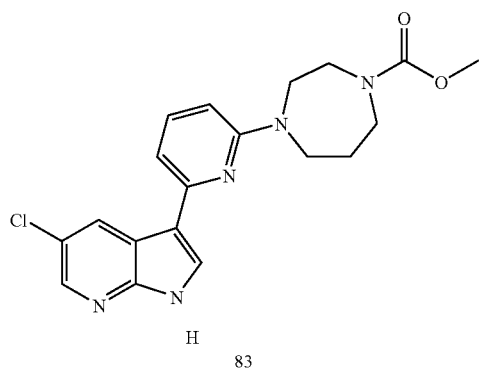
83
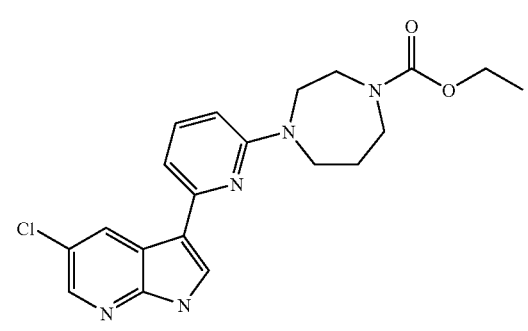
84

TABLE 2-continued
Examples of Compounds of Formula I:
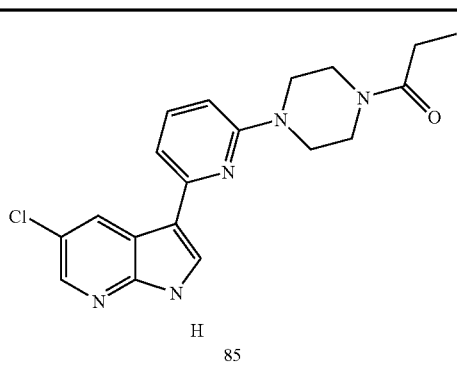
85
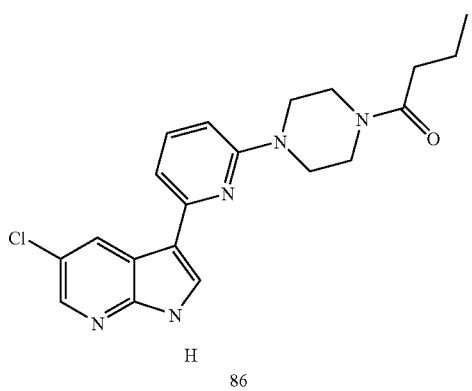
86
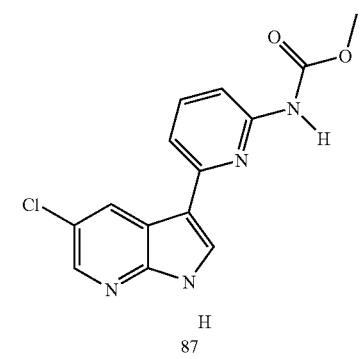
87
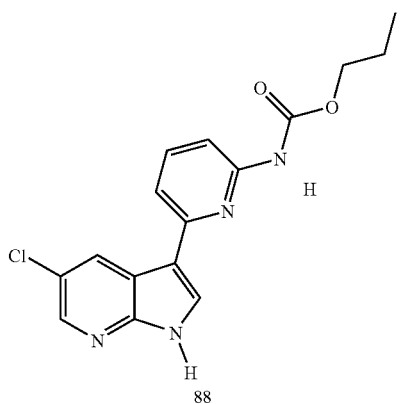
88
TABLE 2-continued
Examples of Compounds of Formula I:
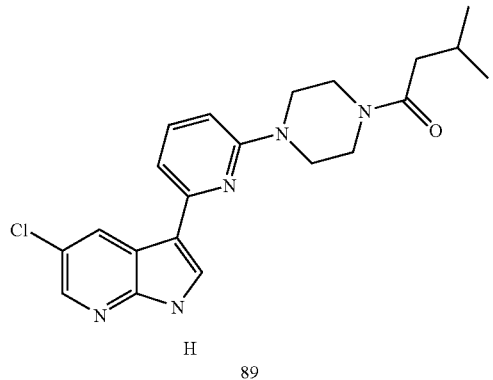
89
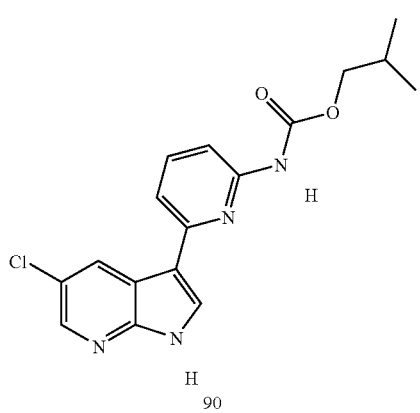
90
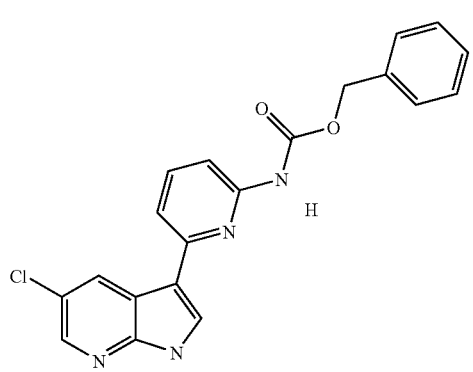
91
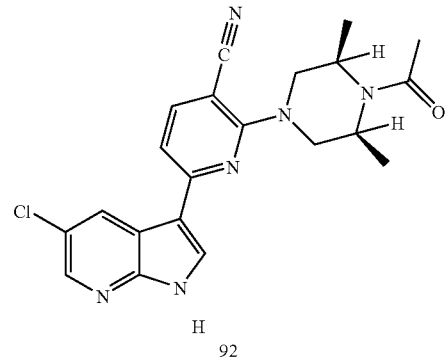
92

TABLE 2-continued
Examples of Compounds of Formula I:
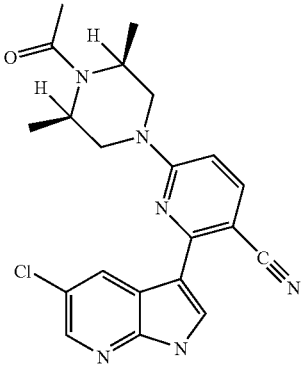
93
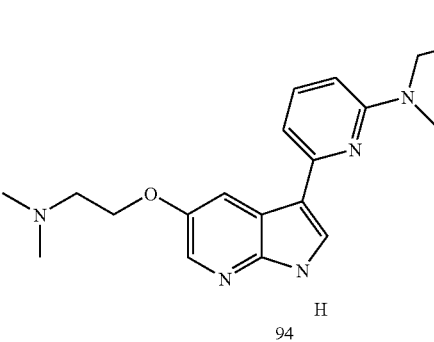
94
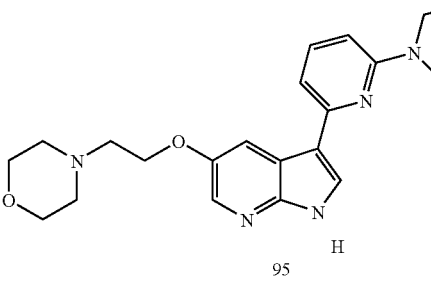
95
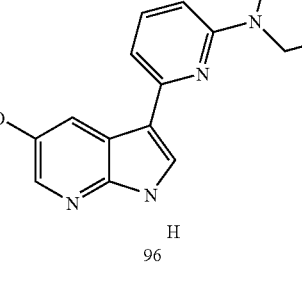
96
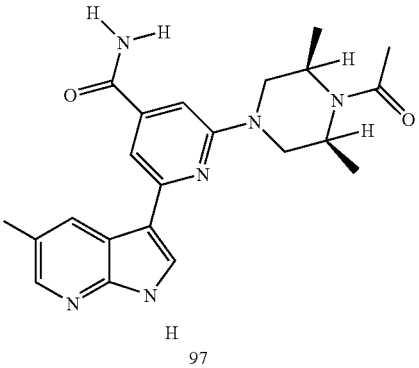
97
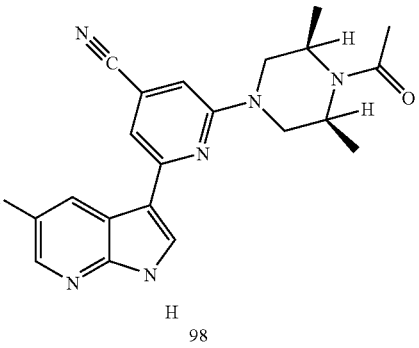
98
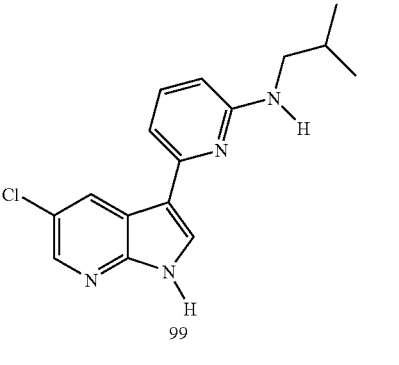
99
100

TABLE 2-continued
Examples of Compounds of Formula I:
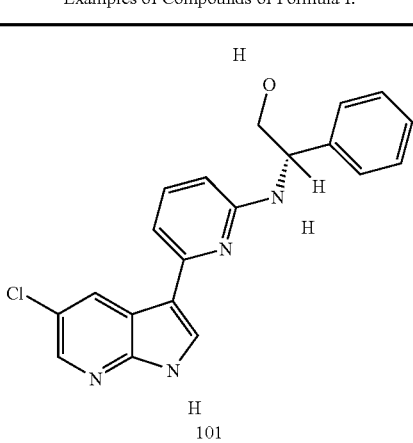
101
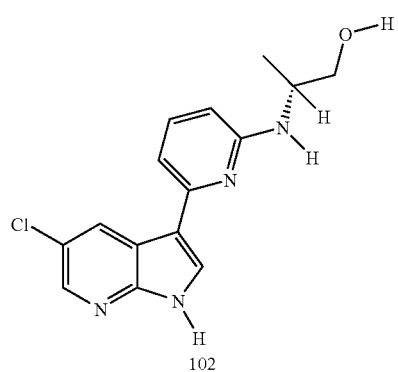
102
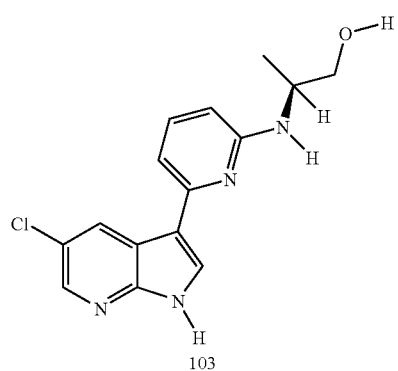
103
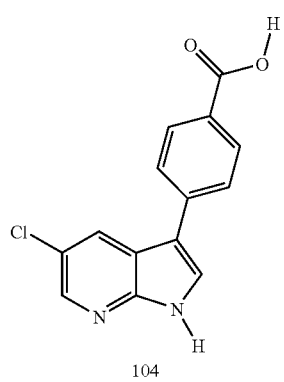
104
TABLE 2-continued
Examples of Compounds of Formula I:
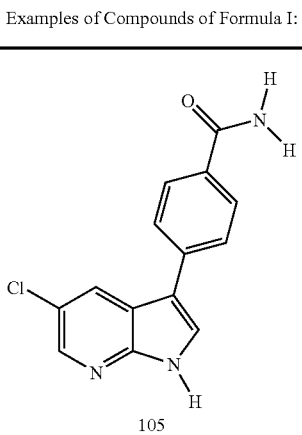
105
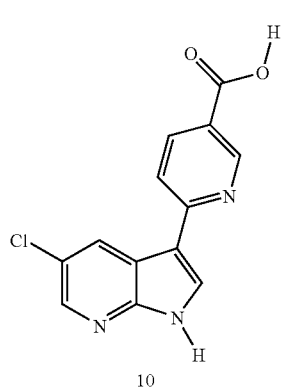
106
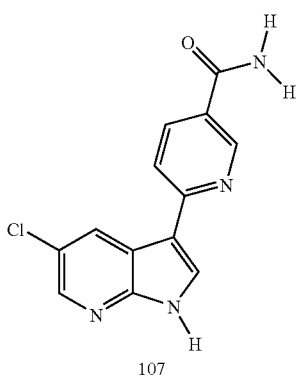
107
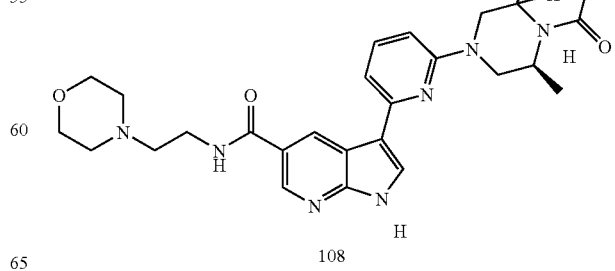
108

TABLE 2-continued
Examples of Compounds of Formula I:
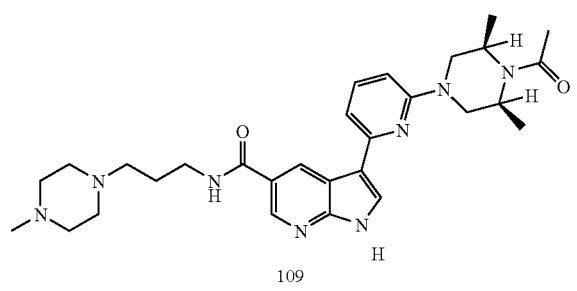
109
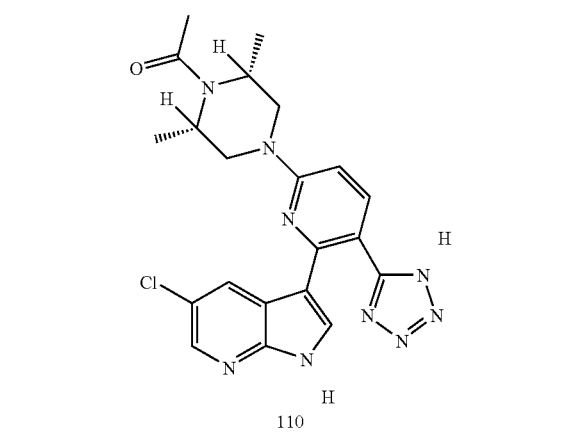
110
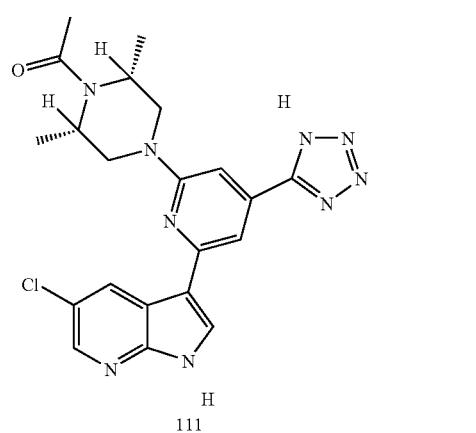
111
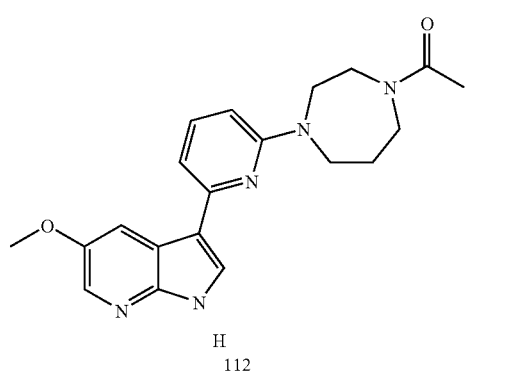
112
TABLE 2-continued
Examples of Compounds of Formula I:
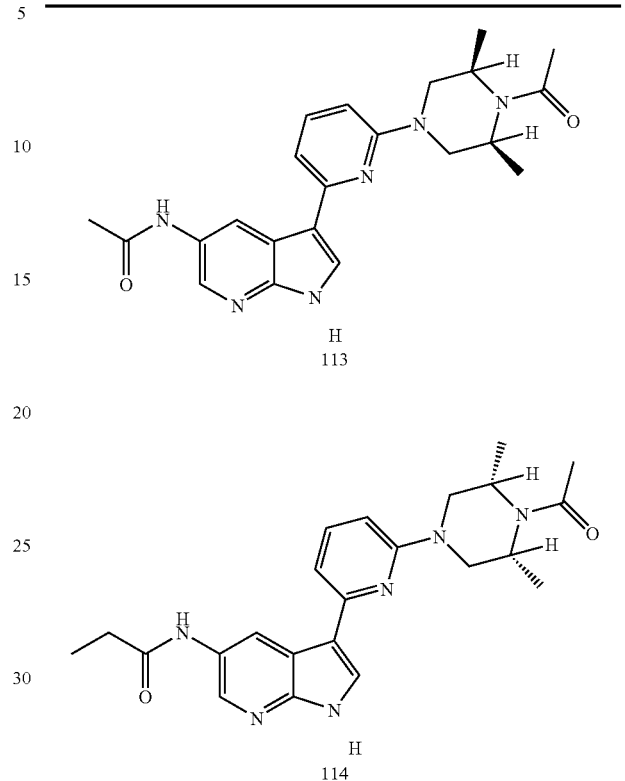
113
114
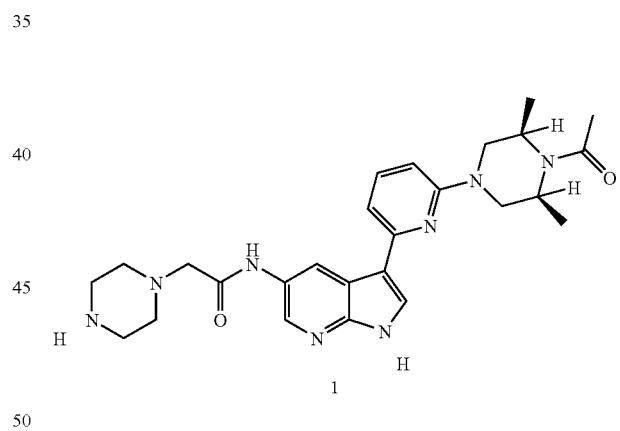
1
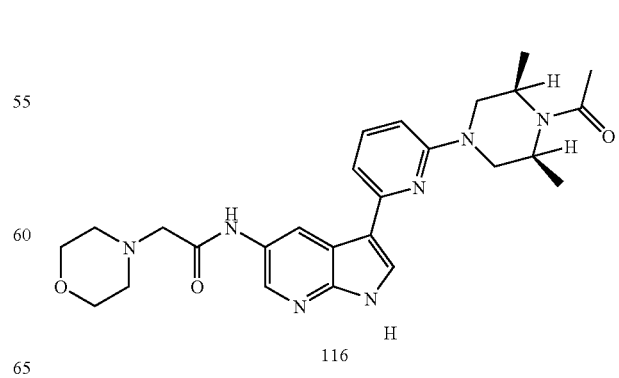
116

TABLE 2-continued
Examples of Compounds of Formula I:
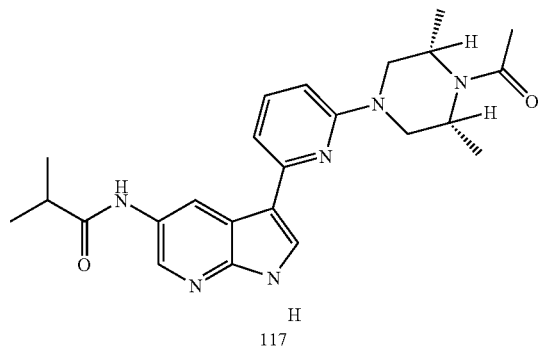
117
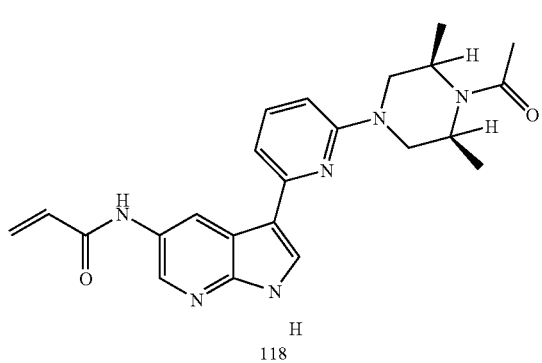
118
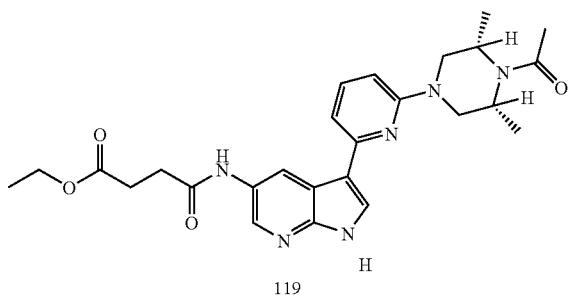
119
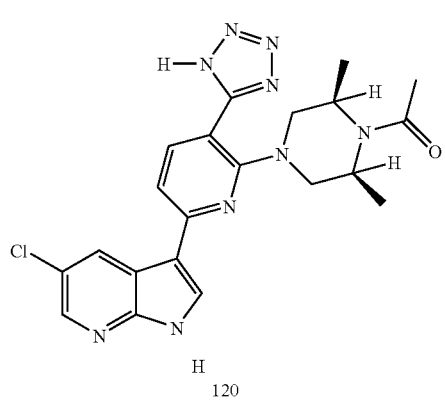
120
TABLE 2-continued
Examples of Compounds of Formula I:
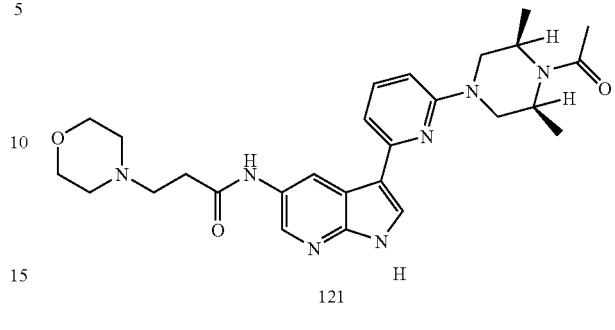
121
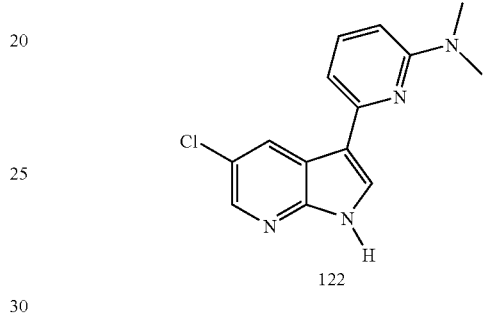
122
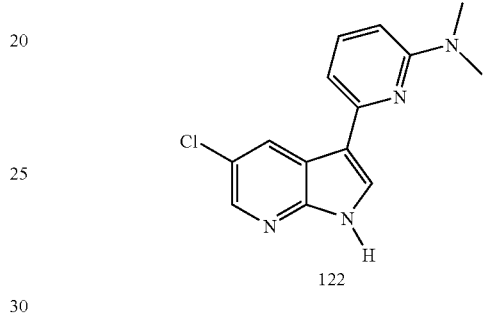
123
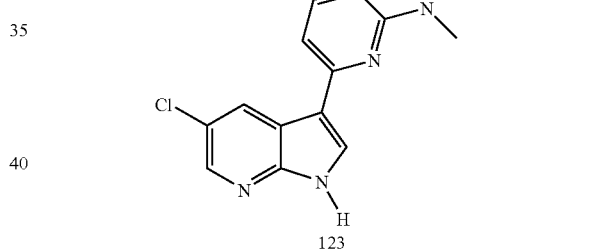
124
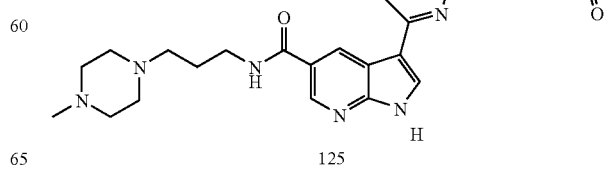
125

TABLE 2-continued
Examples of Compounds of Formula I:
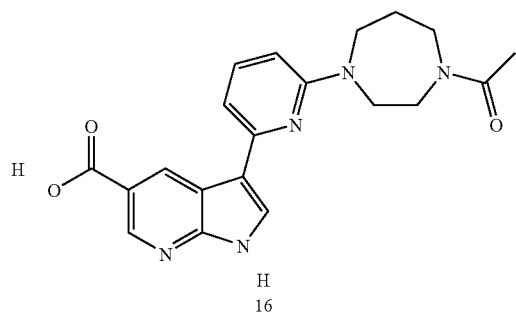
16
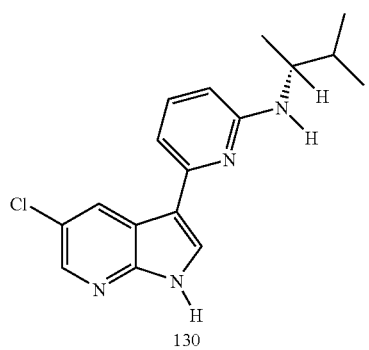
130
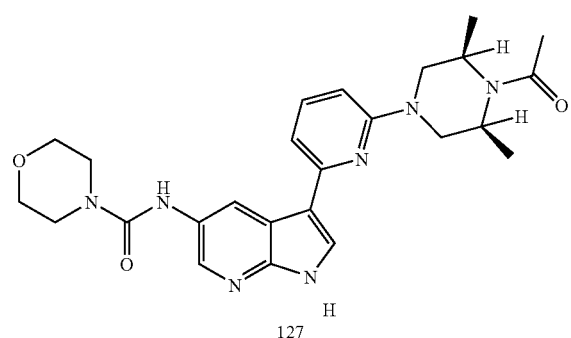
127
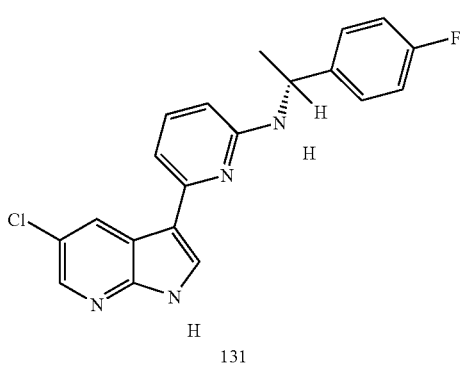
131
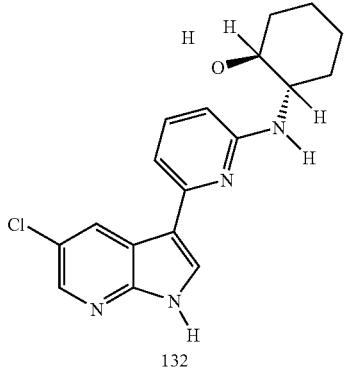
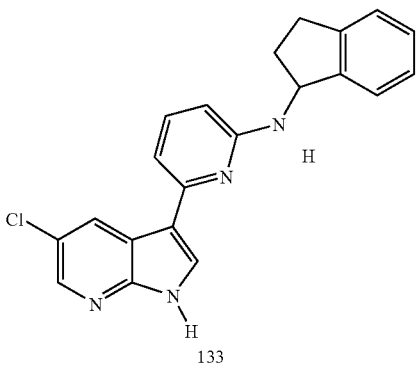

TABLE 2-continued
Examples of Compounds of Formula I:
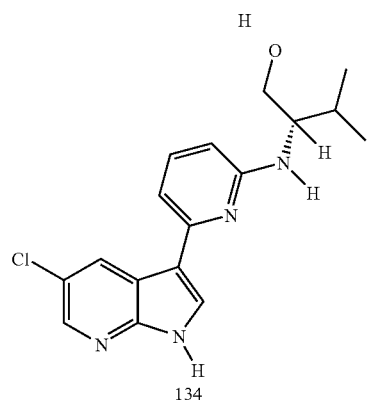
134
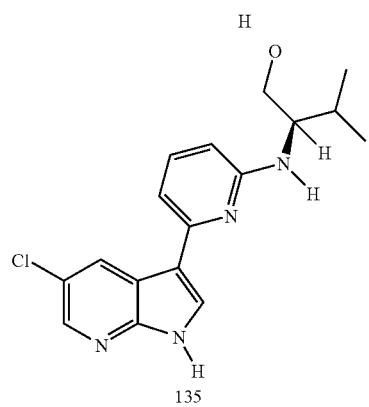
135
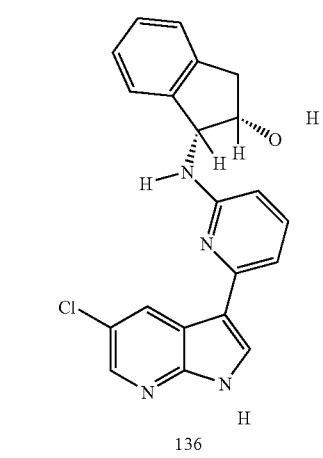
136
TABLE 2-continued
Examples of Compounds of Formula I:
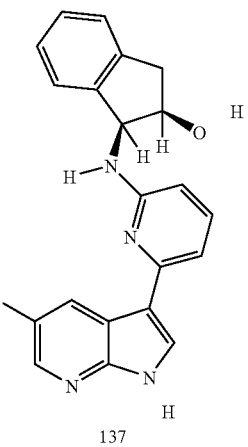
137
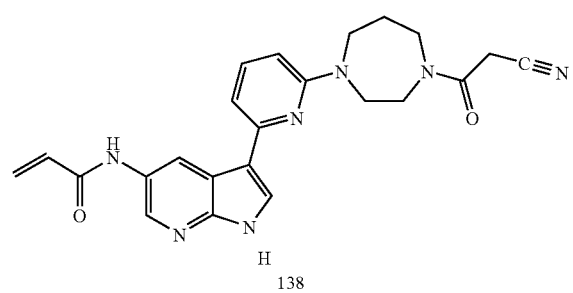
138
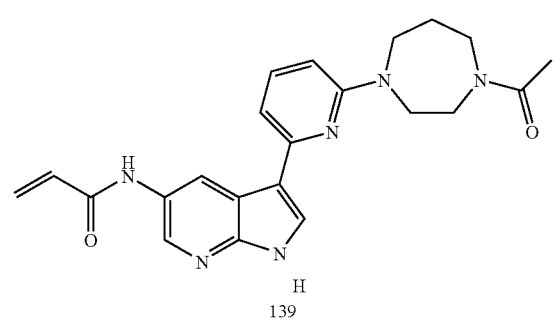
139
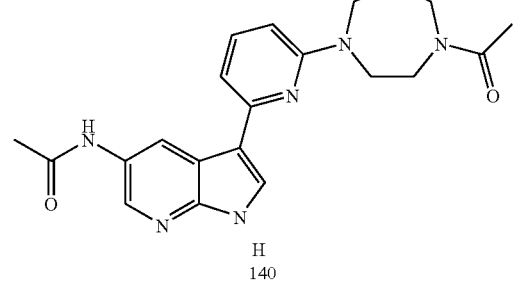
140

TABLE 2-continued
Examples of Compounds of Formula I:
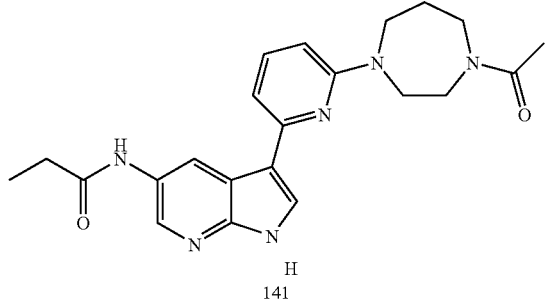
141
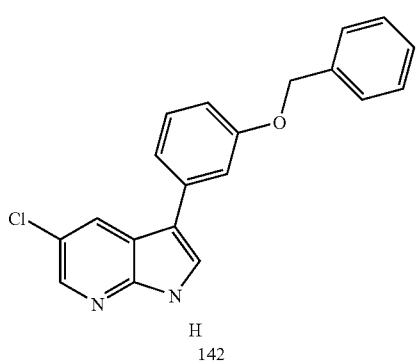
142
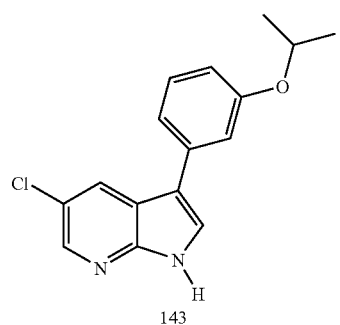
143
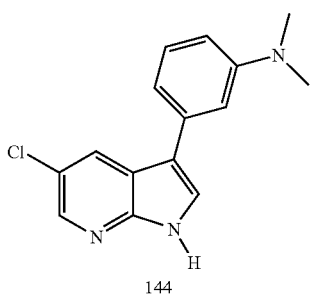
144
TABLE 2-continued
Examples of Compounds of Formula I:
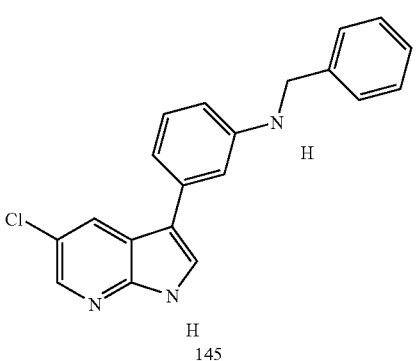
145
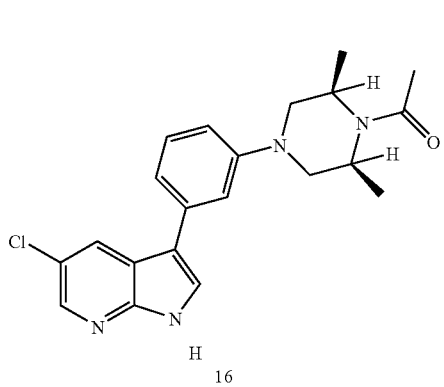
16
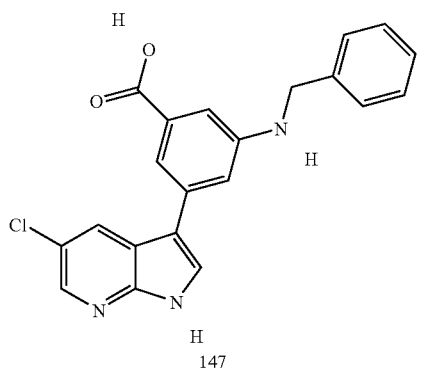
147
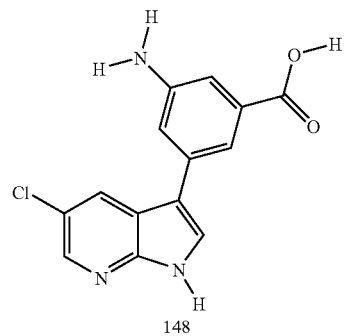
148

TABLE 2-continued
Examples of Compounds of Formula I:
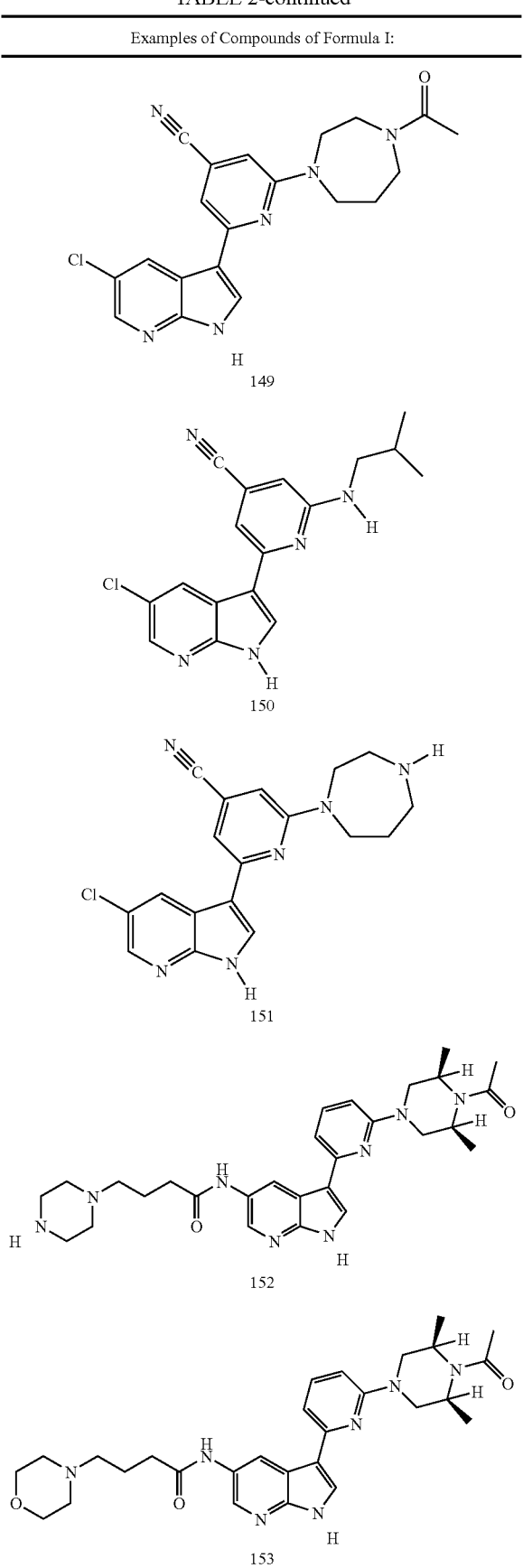
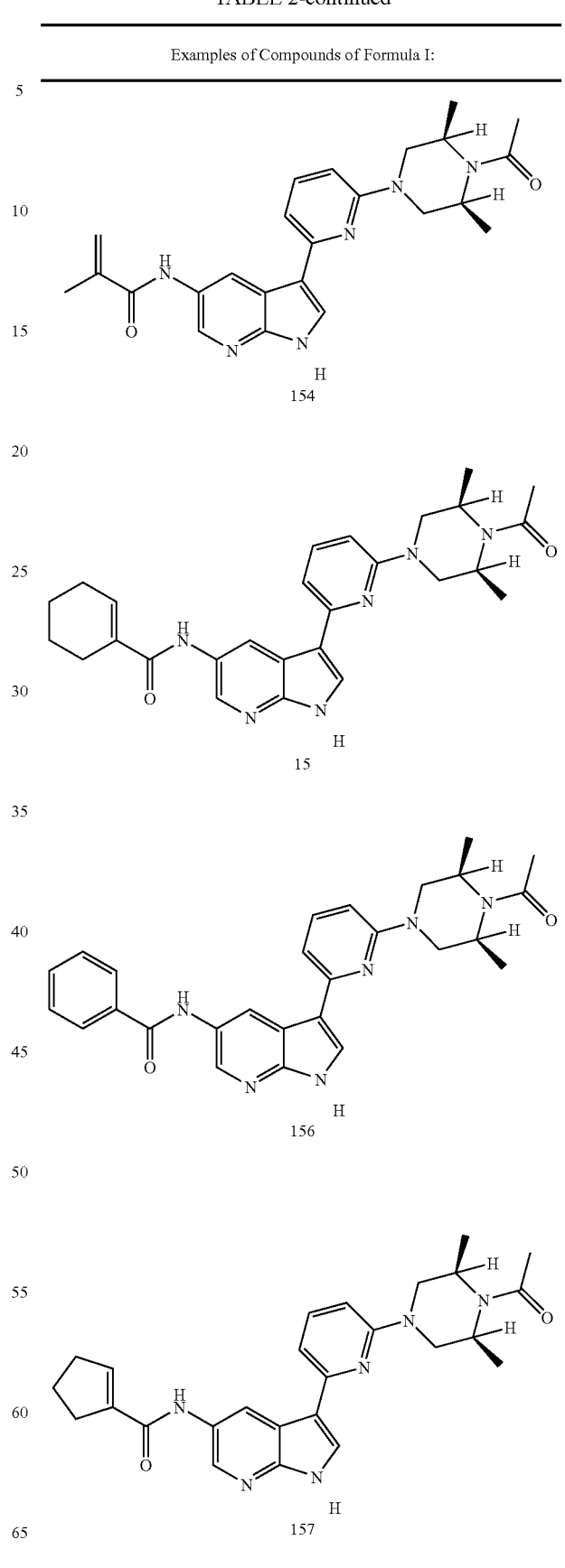

TABLE 2-continued
Examples of Compounds of Formula I:
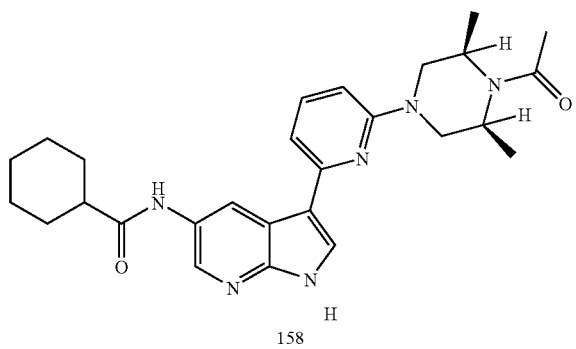
158
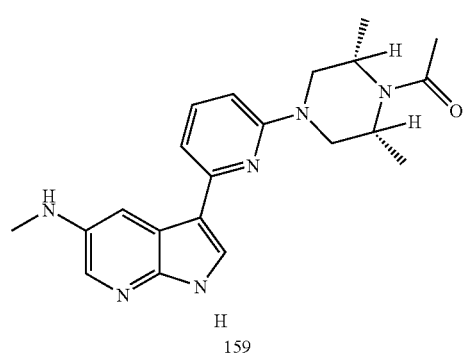
159
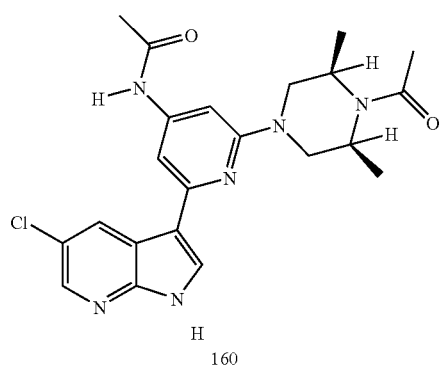
160
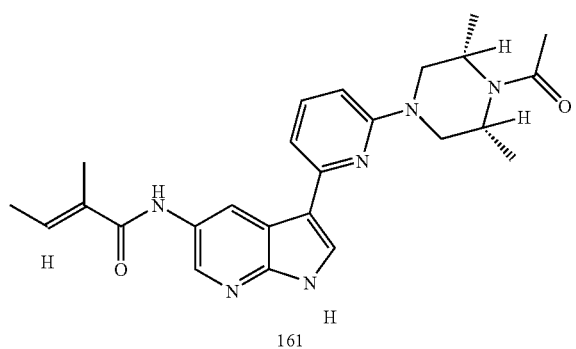
161
TABLE 2-continued
Examples of Compounds of Formula I:
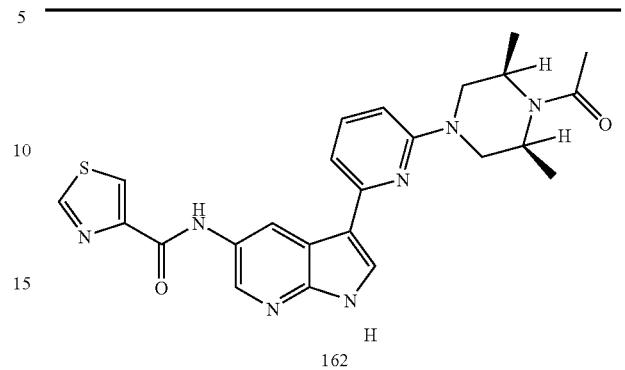
162
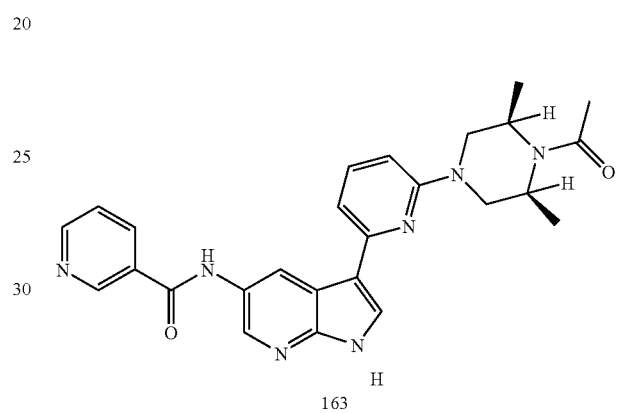
163
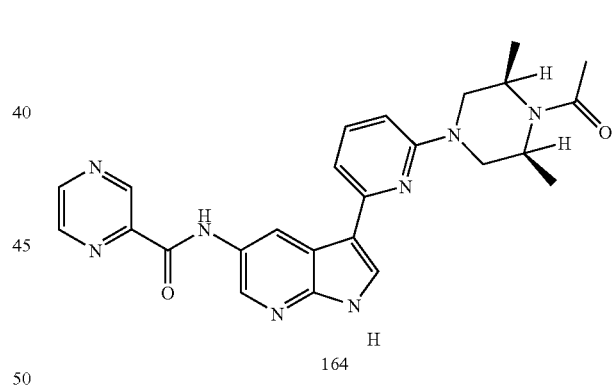
164
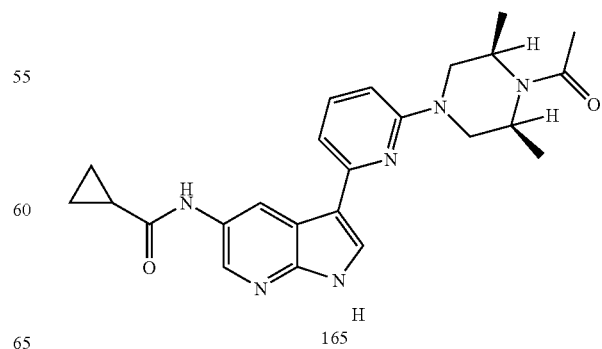
165

TABLE 2-continued
Examples of Compounds of Formula I:
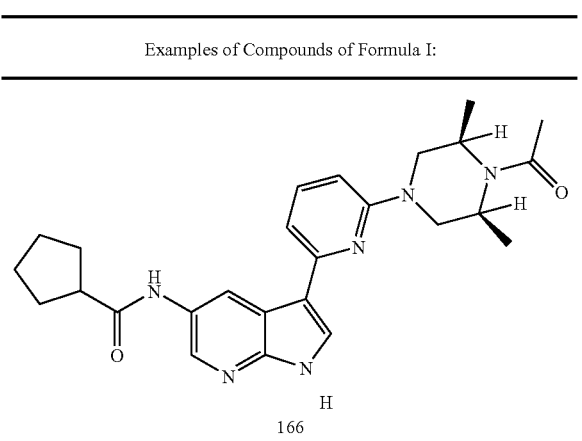
166
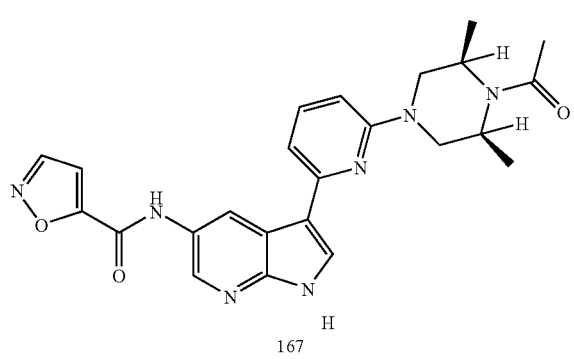
167
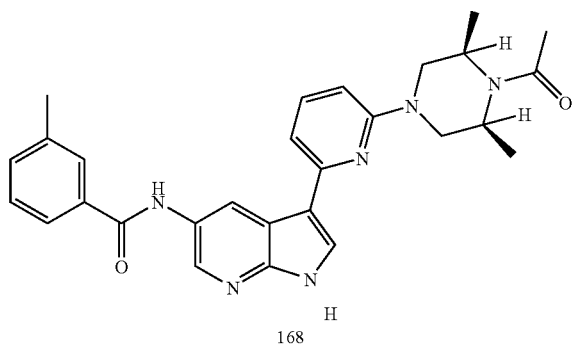
168
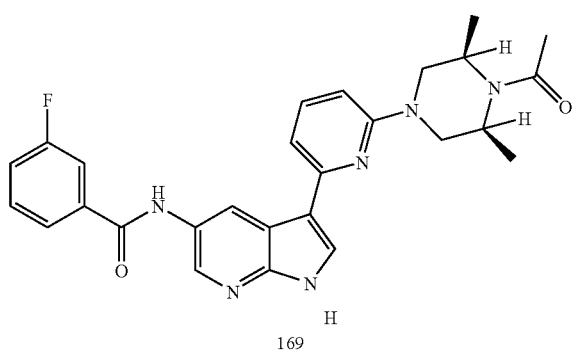
169
TABLE 2-continued
Examples of Compounds of Formula I:
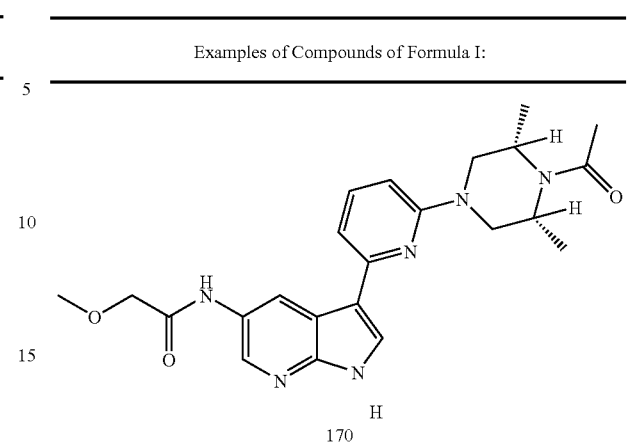
170
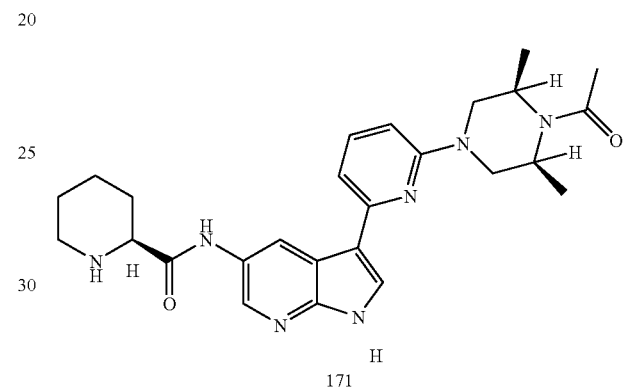
171
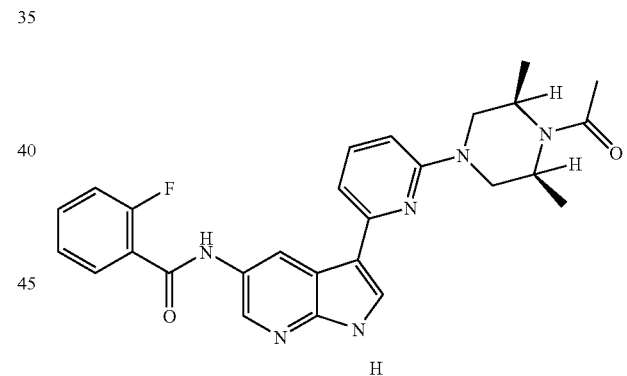
12
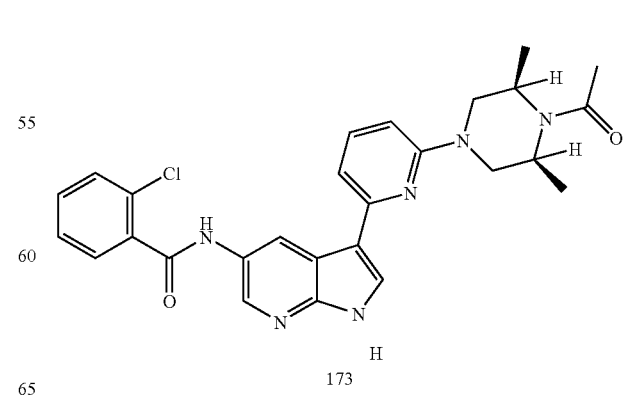
173

TABLE 2-continued
Examples of Compounds of Formula I:
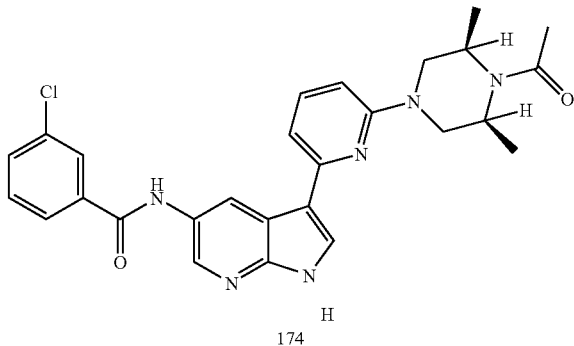
174
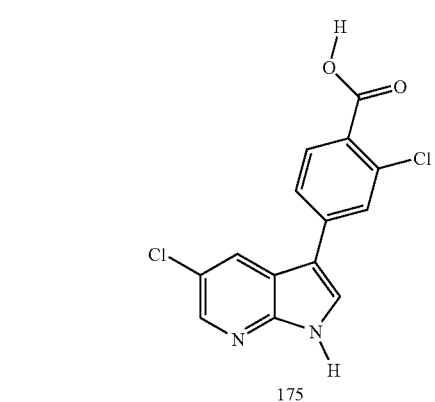
175
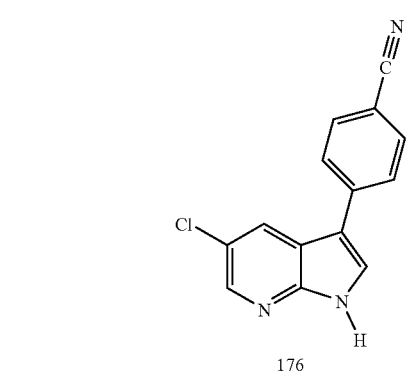
176
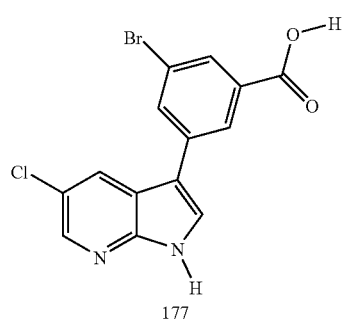
177
TABLE 2-continued
Examples of Compounds of Formula I:
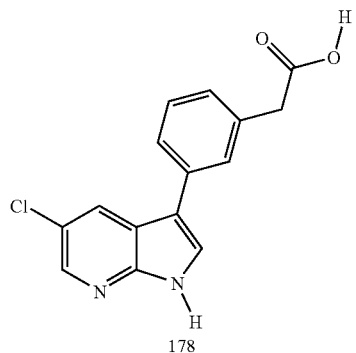
178
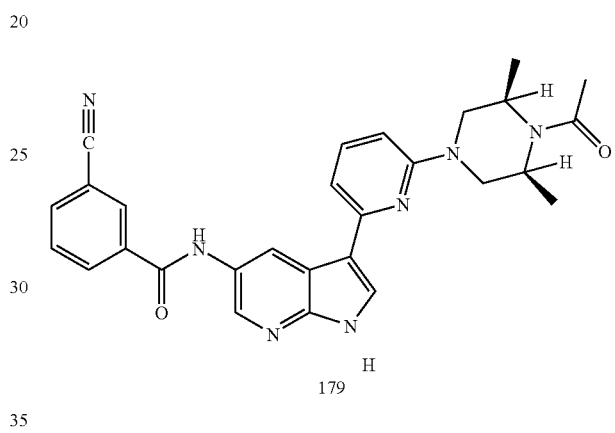
179
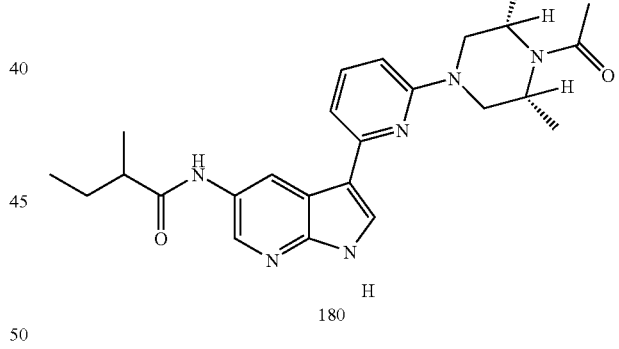
180
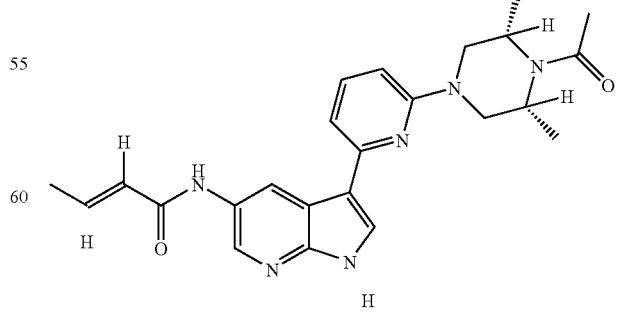
181

TABLE 2-continued
Examples of Compounds of Formula I:
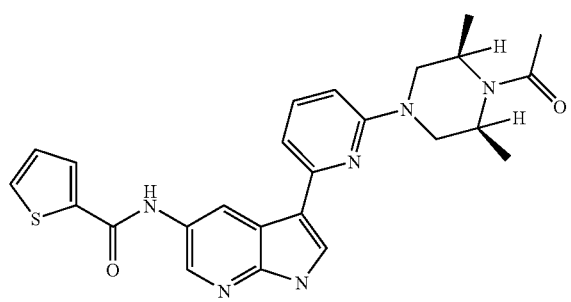
182
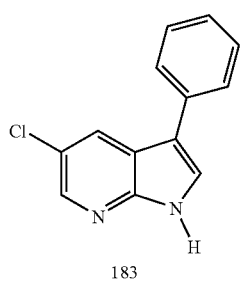
183
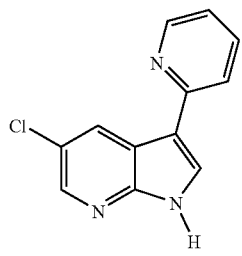
184
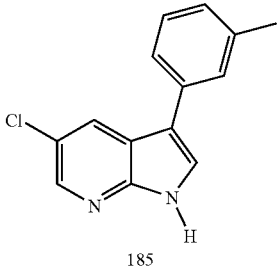
185
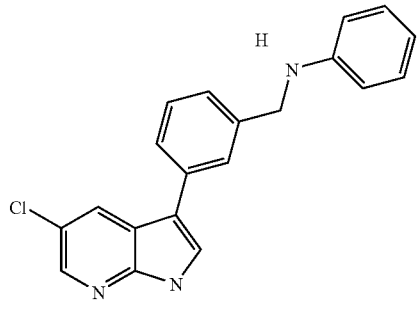
186
TABLE 2-continued
Examples of Compounds of Formula I:
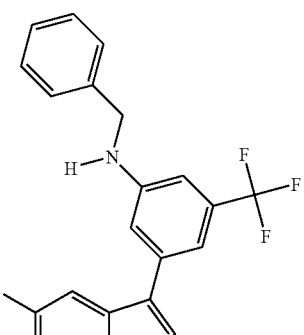
187
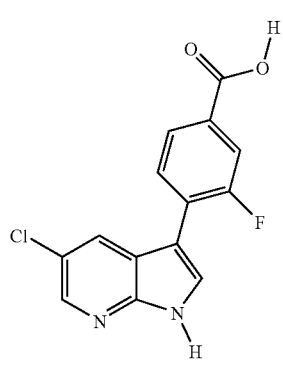
188
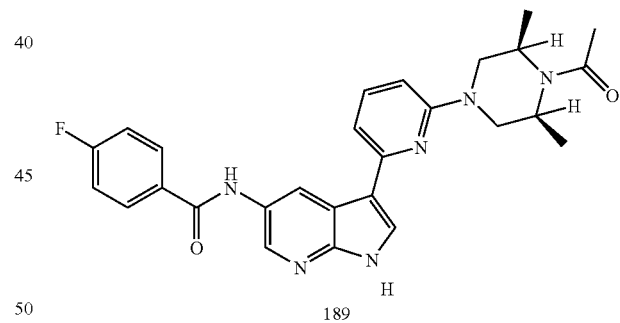
189
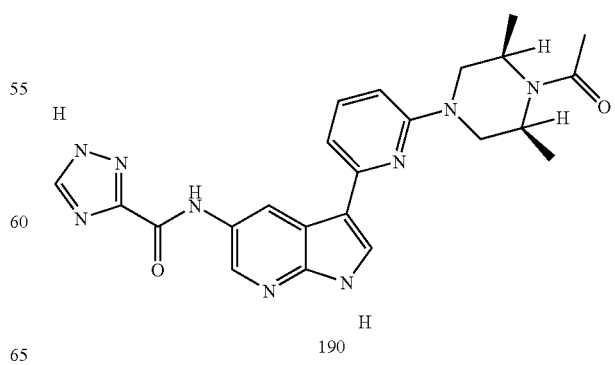
190

TABLE 2-continued
Examples of Compounds of Formula I:
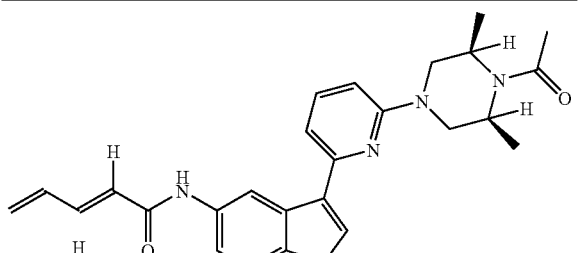
191
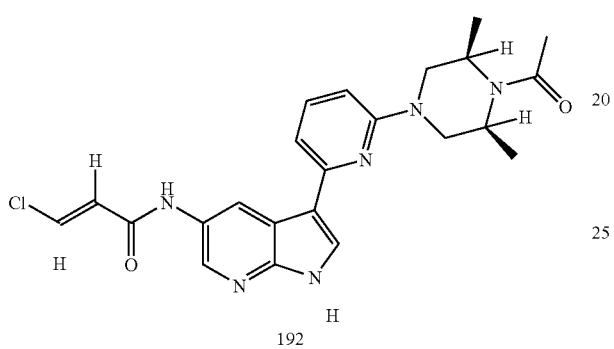
192
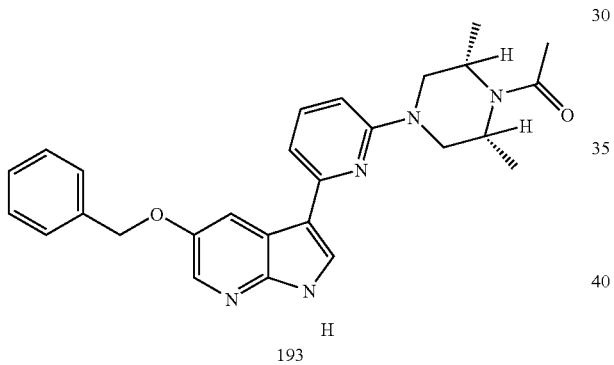
193
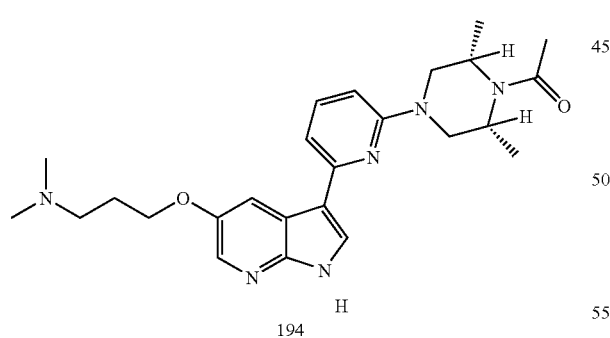
194
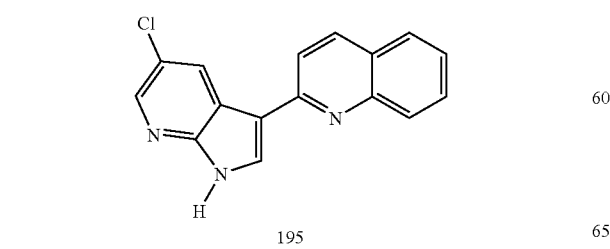
195
TABLE 2-continued
Examples of Compounds of Formula I:
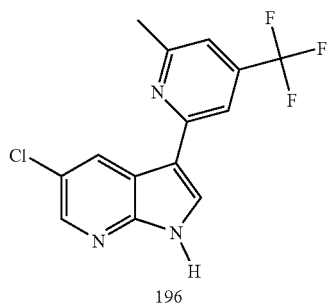
196
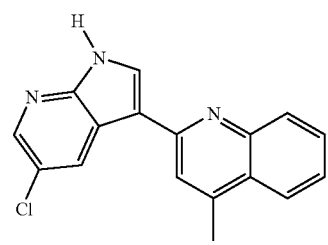
197
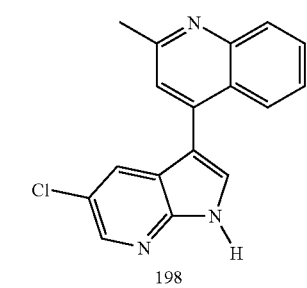
198
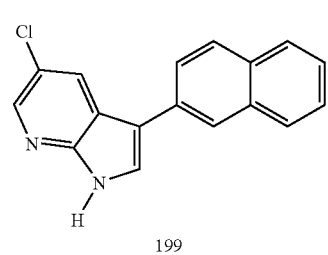
199
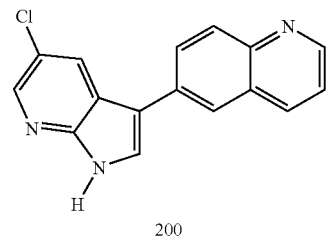
200

TABLE 2-continued
Examples of Compounds of Formula I:
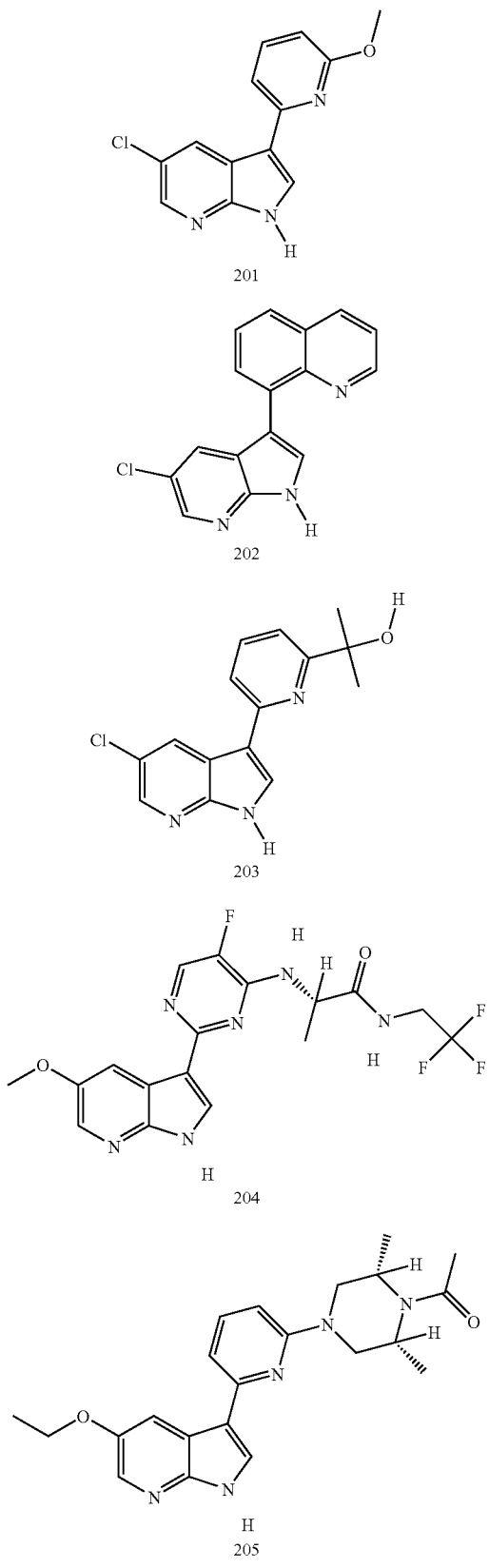
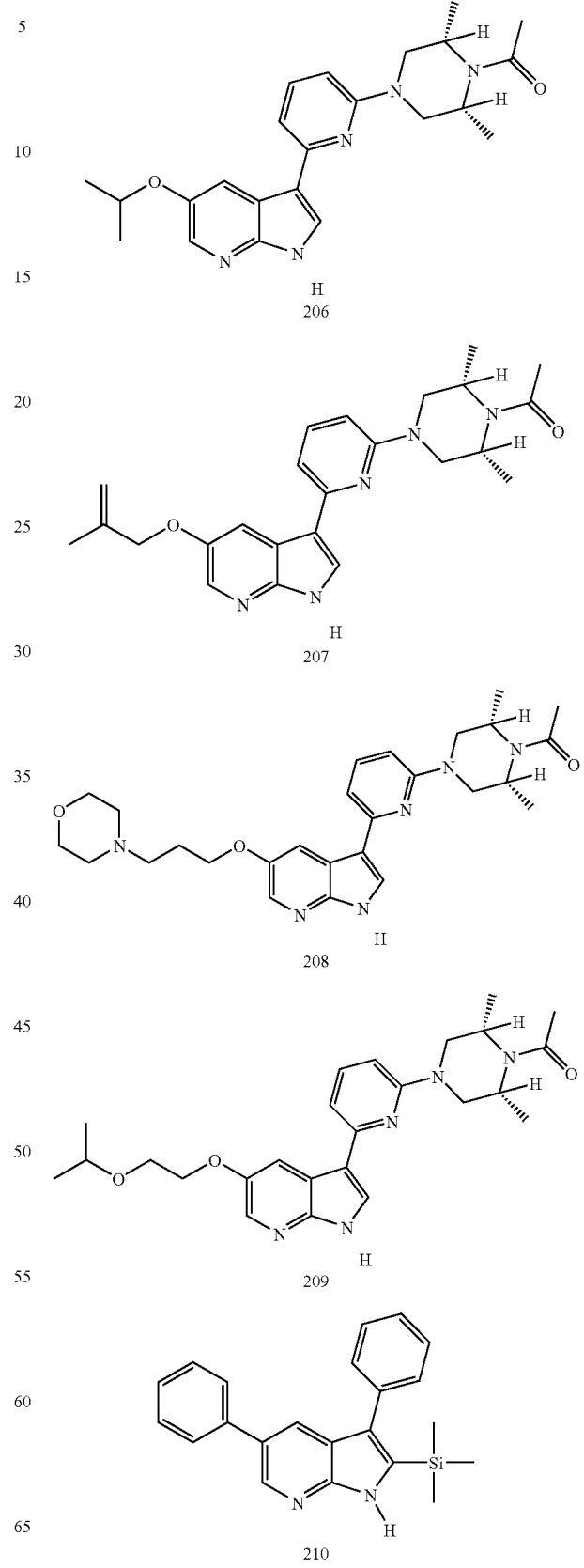

TABLE 2-continued
Examples of Compounds of Formula I:
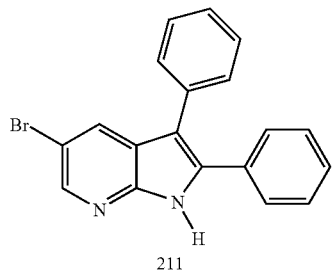
211
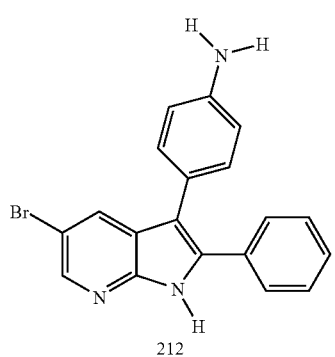
212
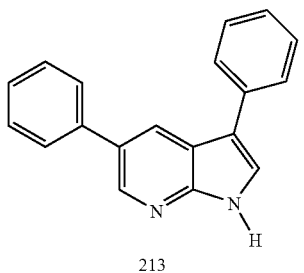
213
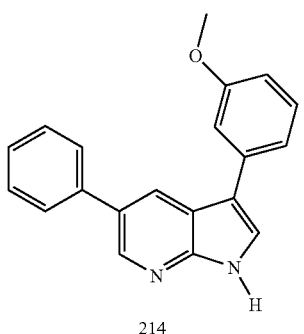
214
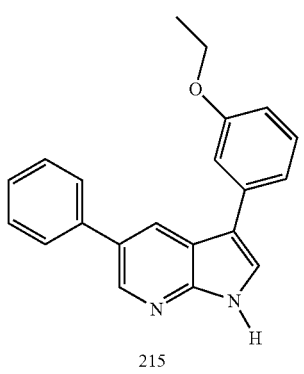
215
TABLE 2-continued
Examples of Compounds of Formula I:
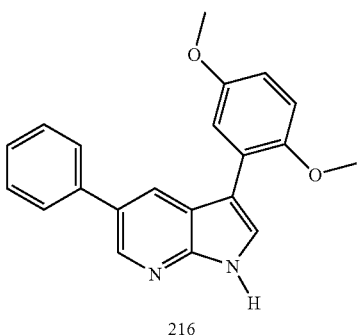
216
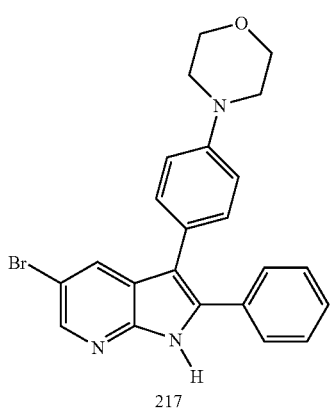
217
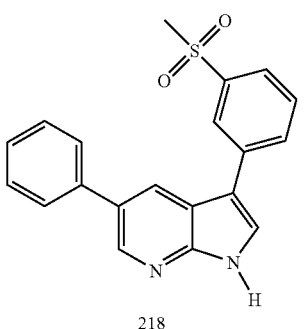
218
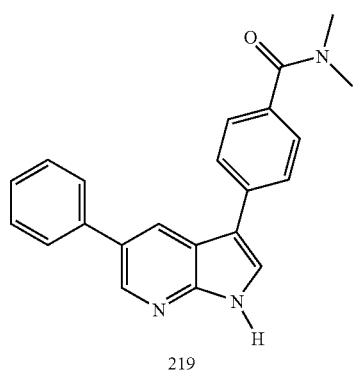
219

TABLE 2-continued
Examples of Compounds of Formula I:
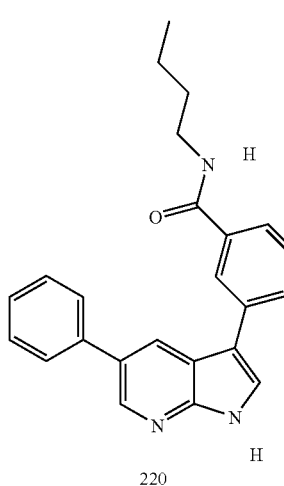
220
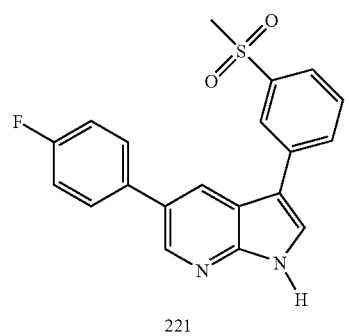
221
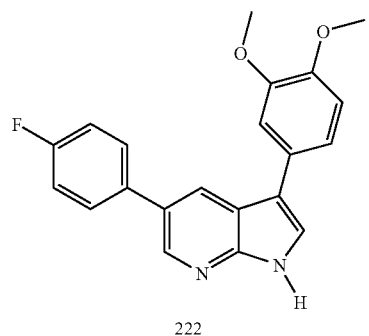
222
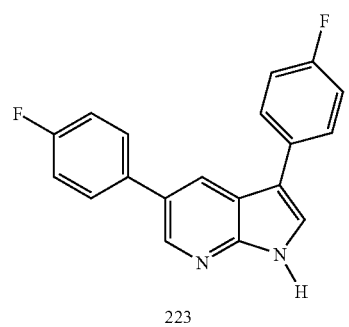
223
TABLE 2-continued
Examples of Compounds of Formula I:
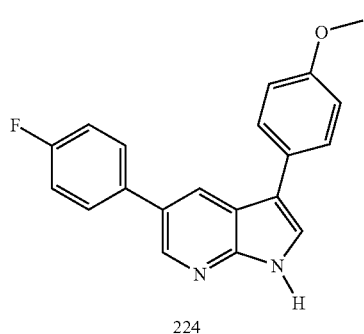
224
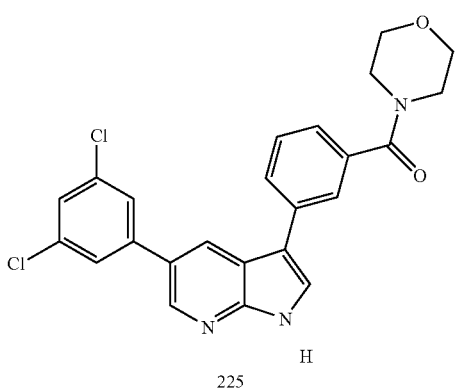
225
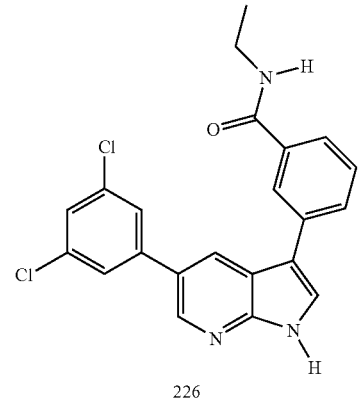
226
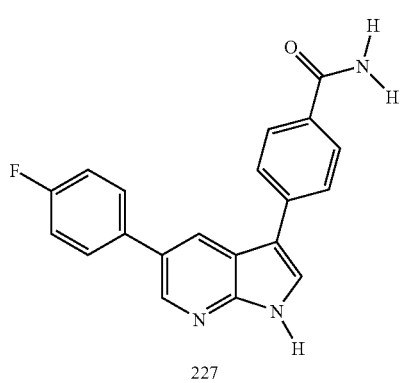
227

TABLE 2-continued
Examples of Compounds of Formula I:
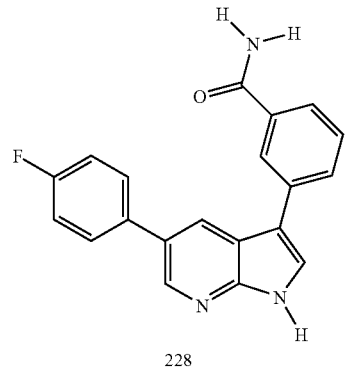
228
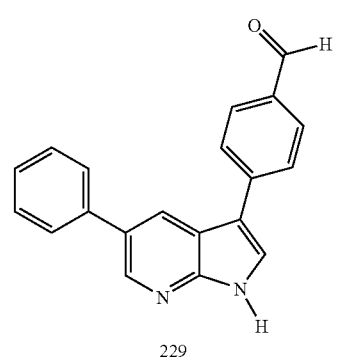
229
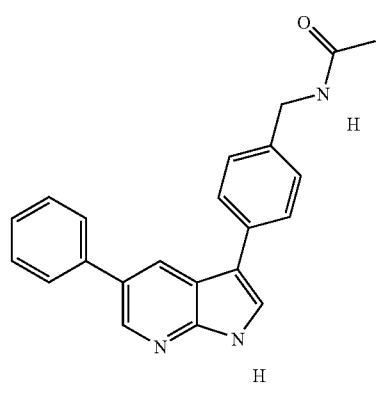
230
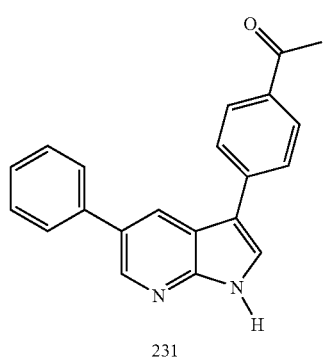
231
TABLE 2-continued
Examples of Compounds of Formula I:
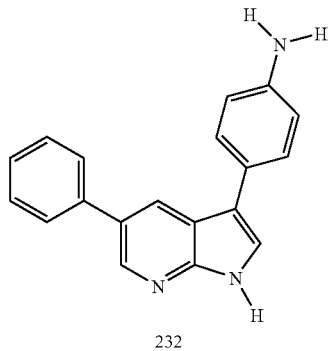
232
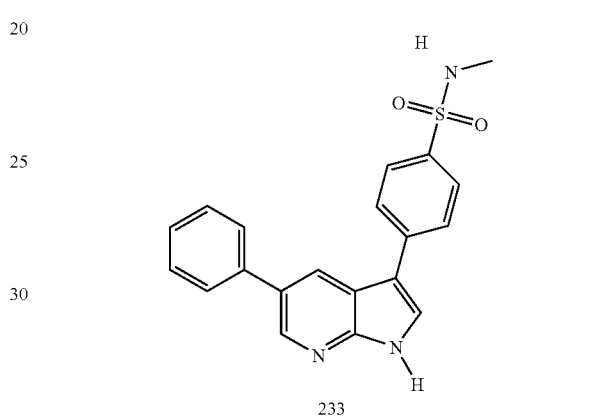
233
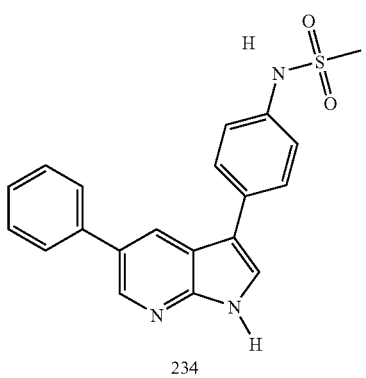
234
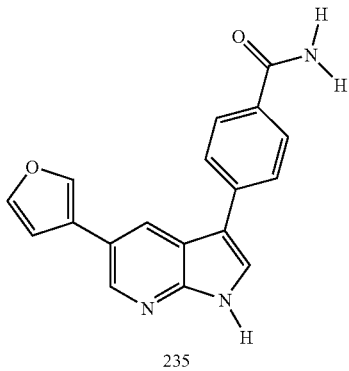
235

TABLE 2-continued
Examples of Compounds of Formula I:
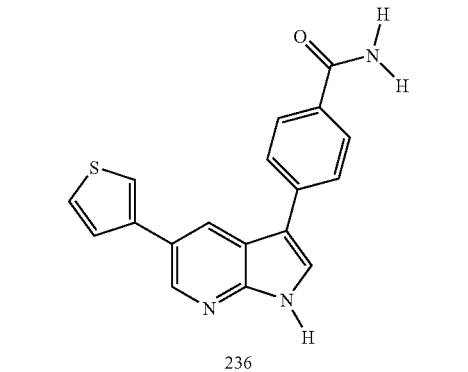
236
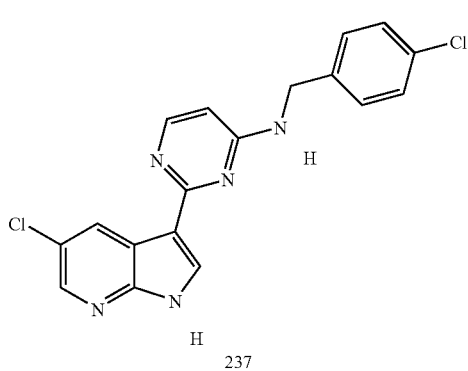
237
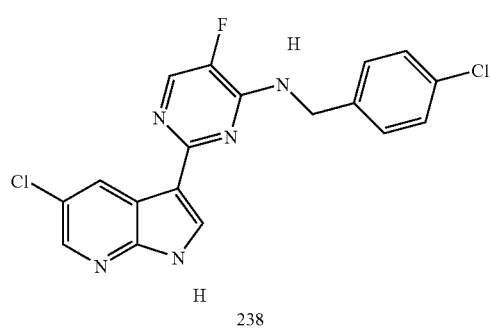
238
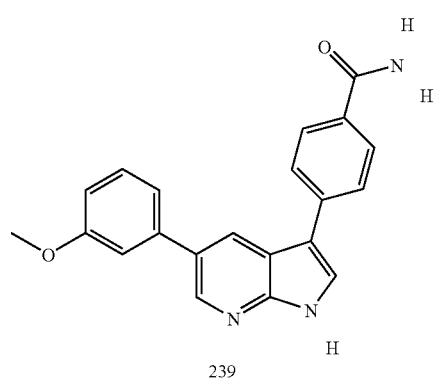
239
TABLE 2-continued
Examples of Compounds of Formula I:
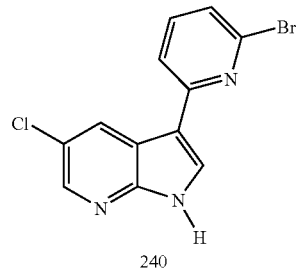
240
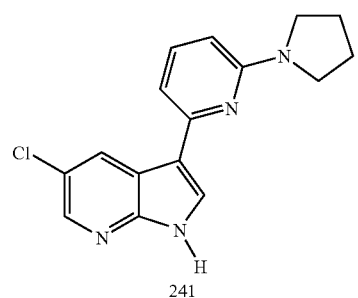
241
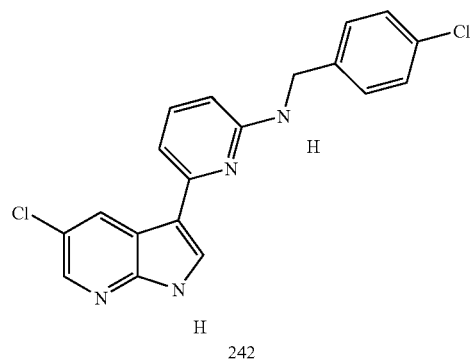
242
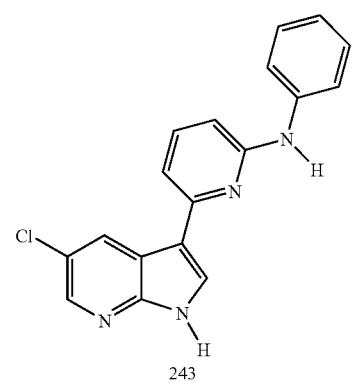
243

TABLE 2-continued
Examples of Compounds of Formula I:
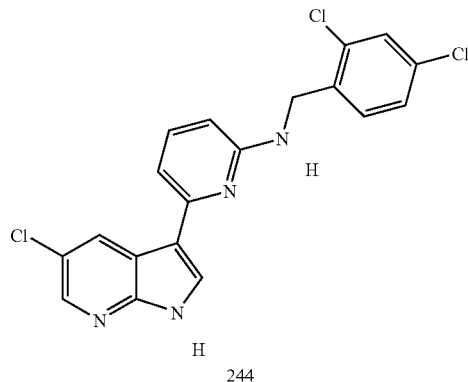
244
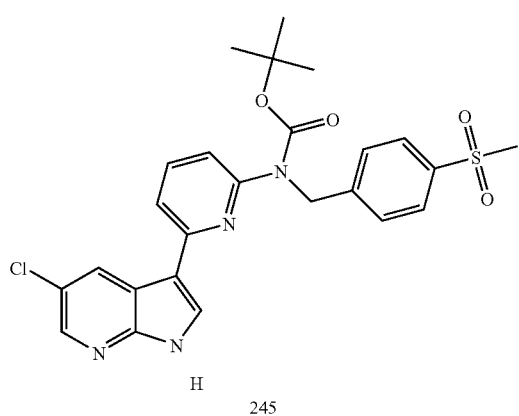
245
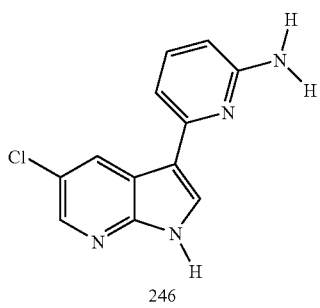
246
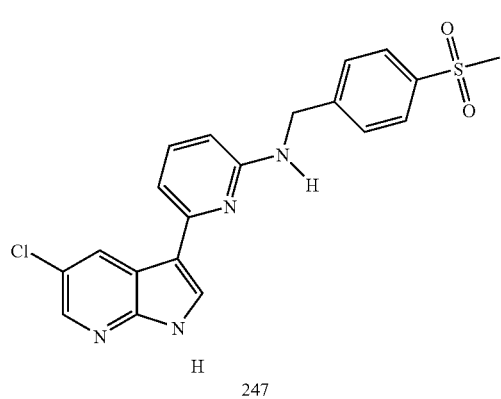
247
TABLE 2-continued
Examples of Compounds of Formula I:
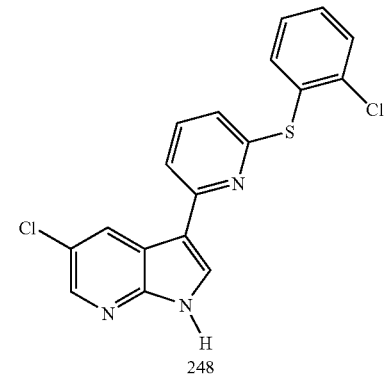
248
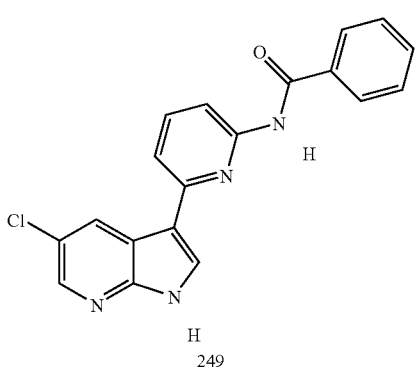
249
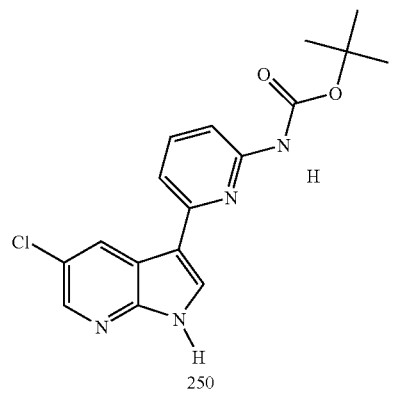
250
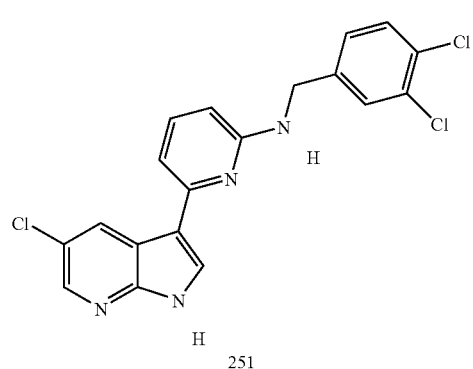
251

TABLE 2-continued
Examples of Compounds of Formula I:
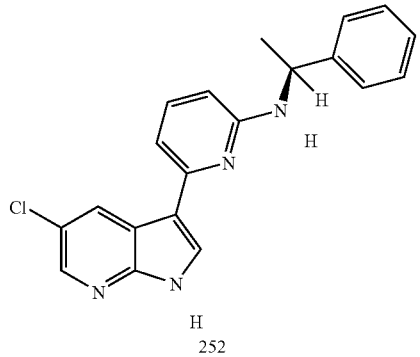
252
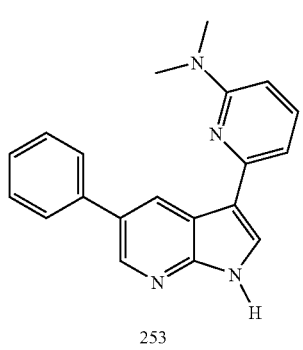
253
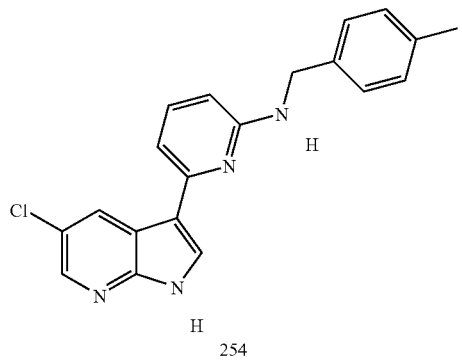
254
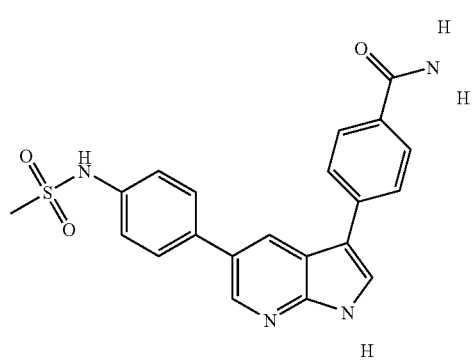
255
TABLE 2-continued
Examples of Compounds of Formula I:
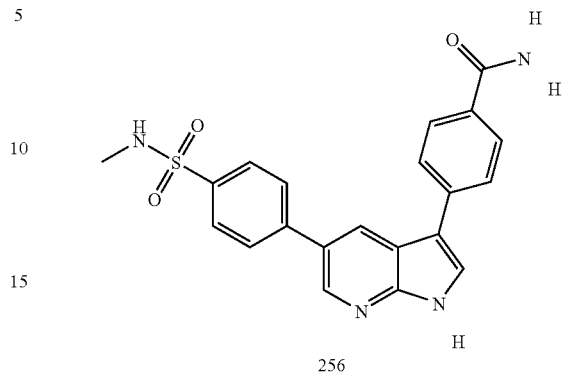
256
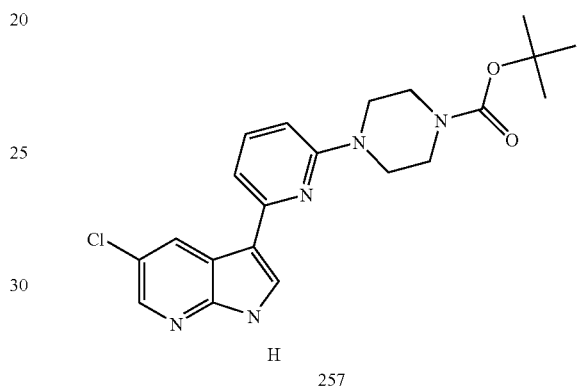
257
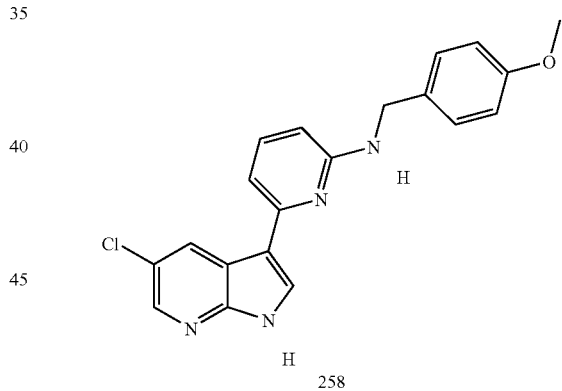
258
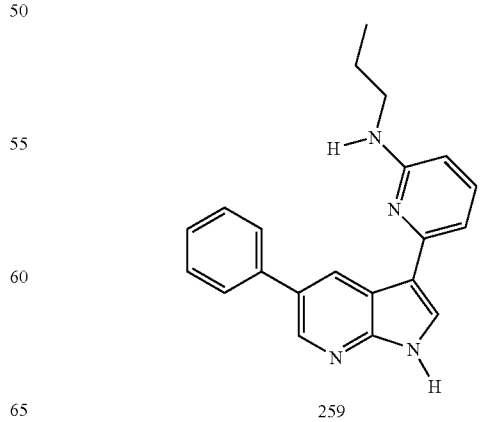
259

TABLE 2-continued
Examples of Compounds of Formula I:
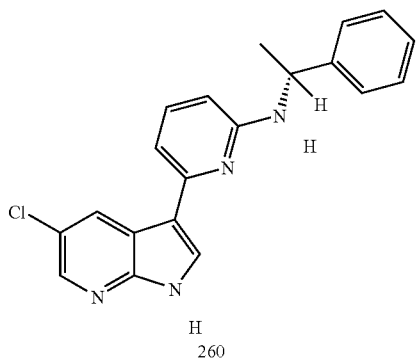
260
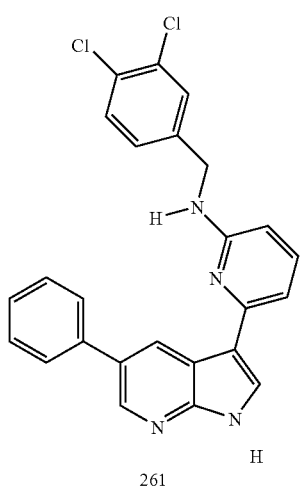
261
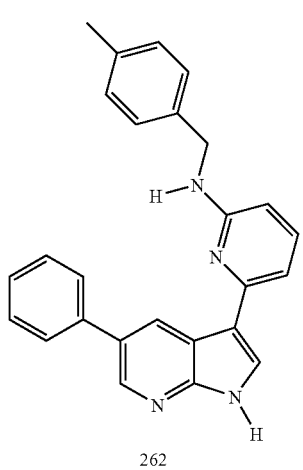
262
TABLE 2-continued
Examples of Compounds of Formula I:
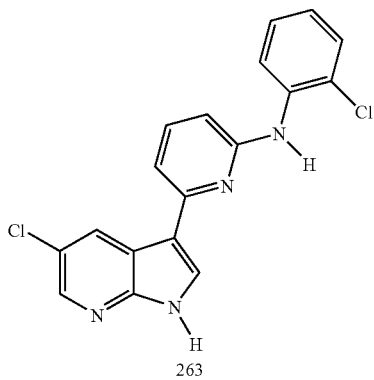
263
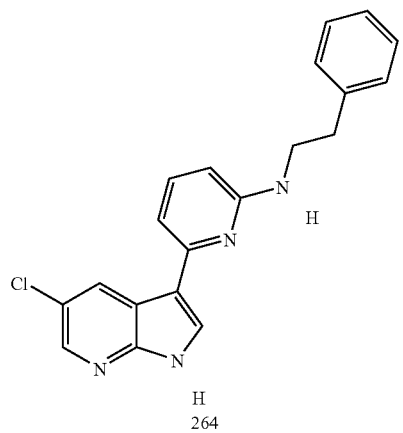
264
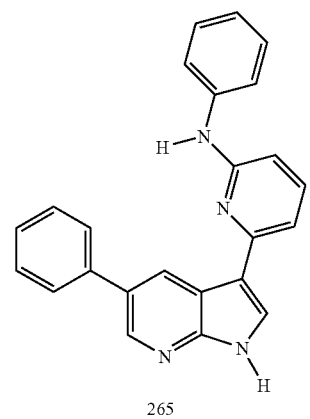
265

TABLE 2-continued
Examples of Compounds of Formula I:
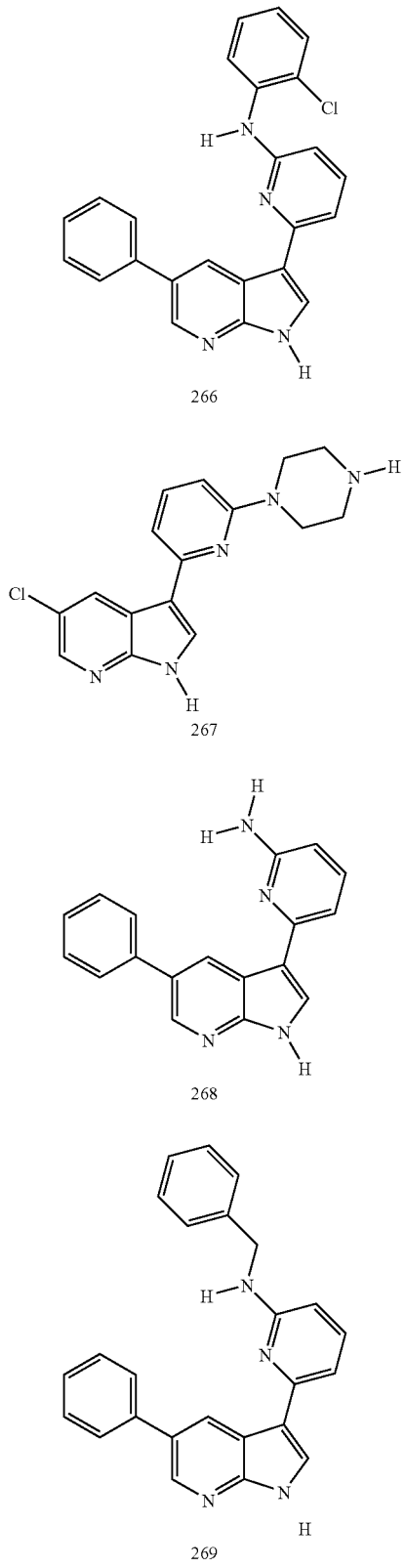
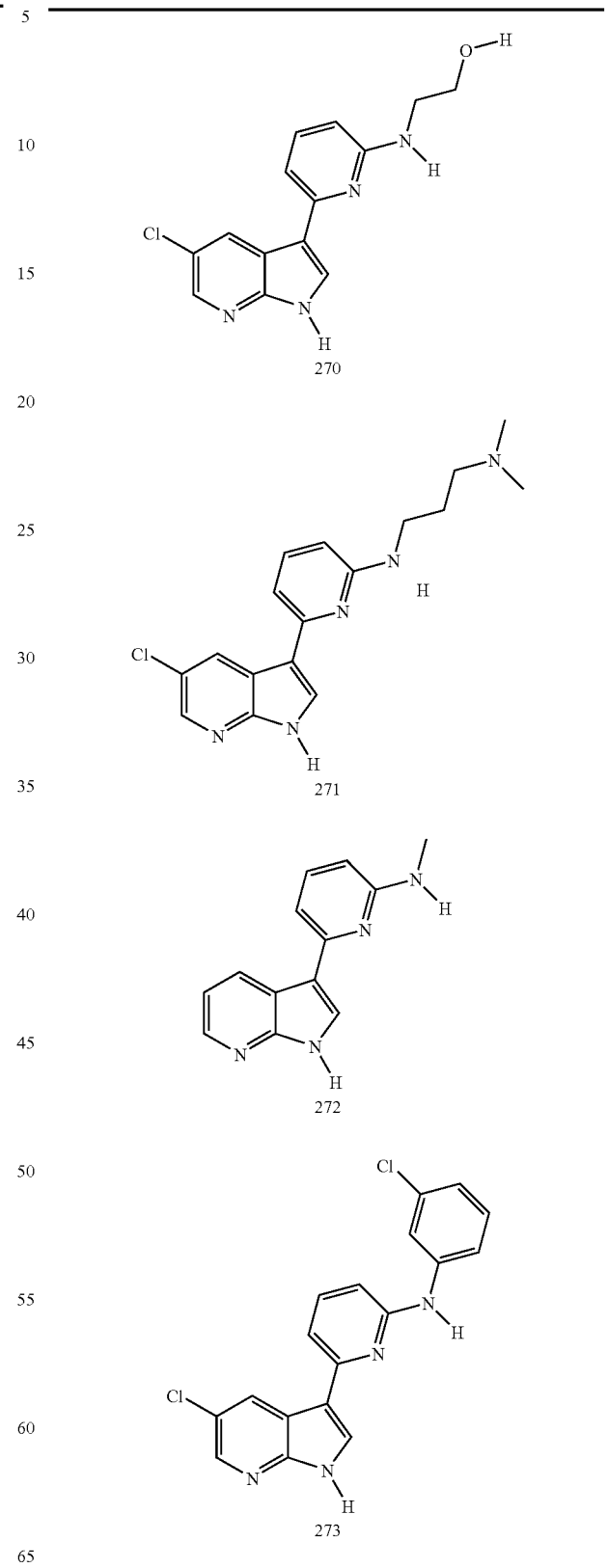

TABLE 2-continued
Examples of Compounds of Formula I:
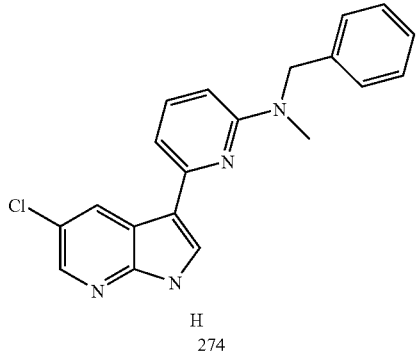
274
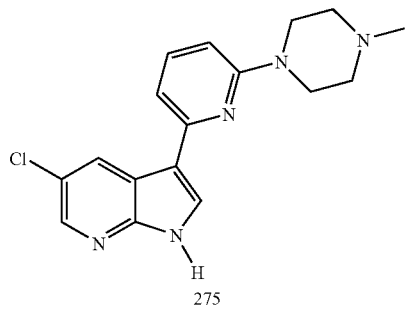
275
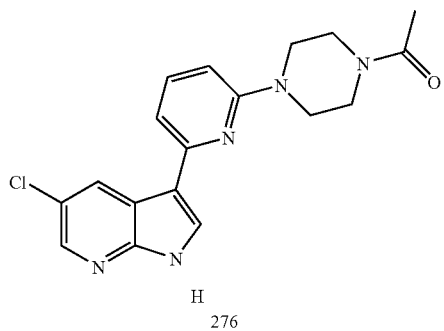
276
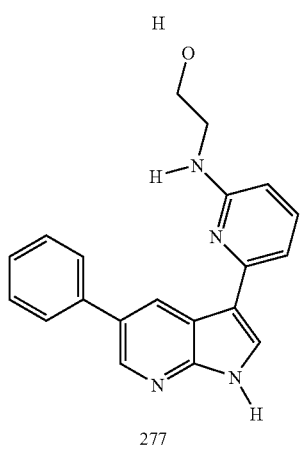
277
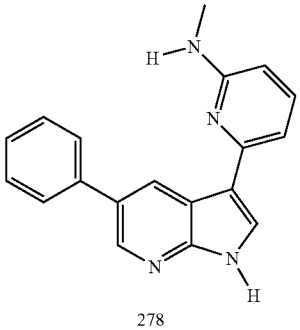
278
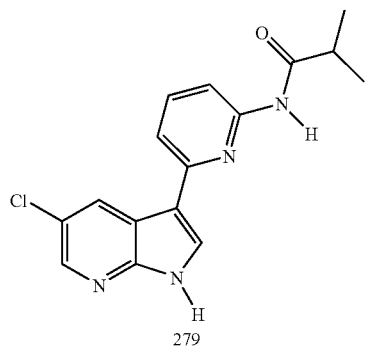
279
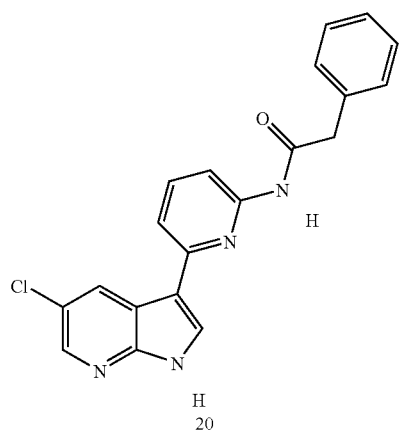
20
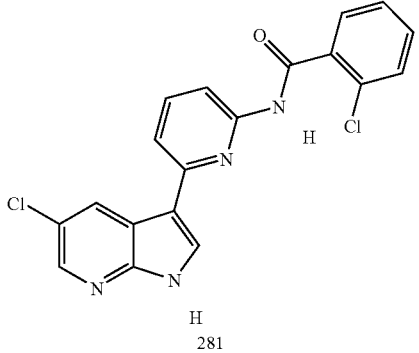
281

TABLE 2-continued
Examples of Compounds of Formula I:
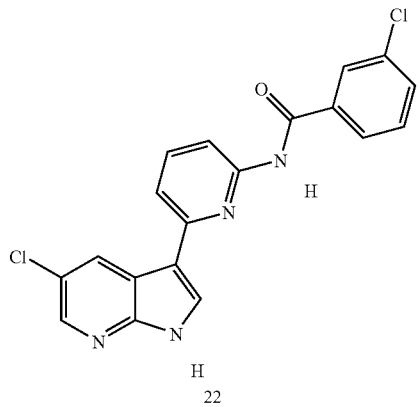
22
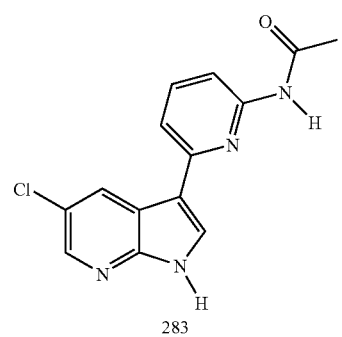
283
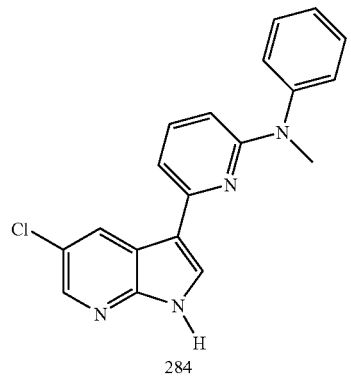
284
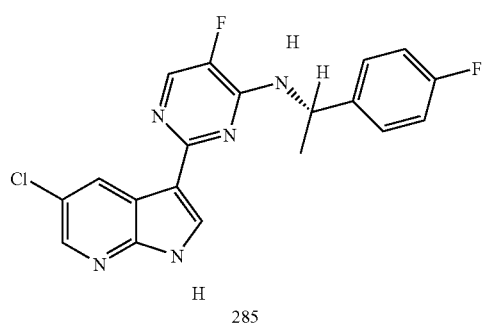
285
TABLE 2-continued
Examples of Compounds of Formula I:
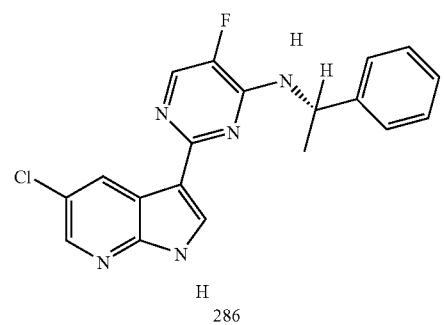
286
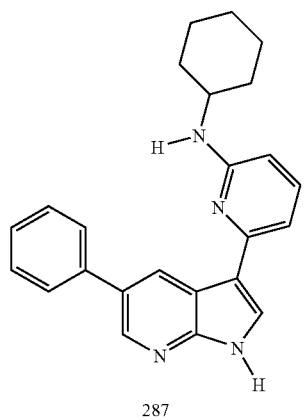
287
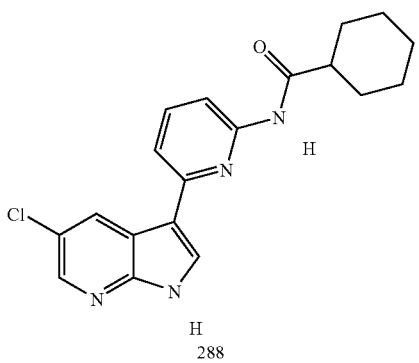
288
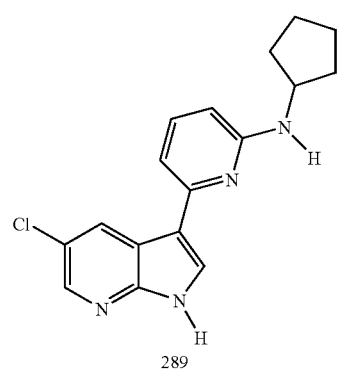
289

TABLE 2-continued
Examples of Compounds of Formula I:
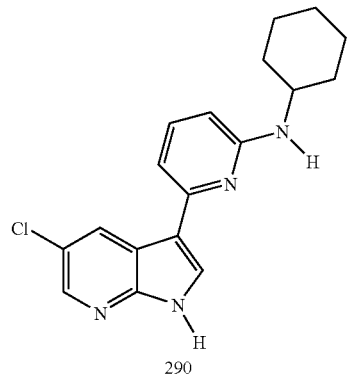
290
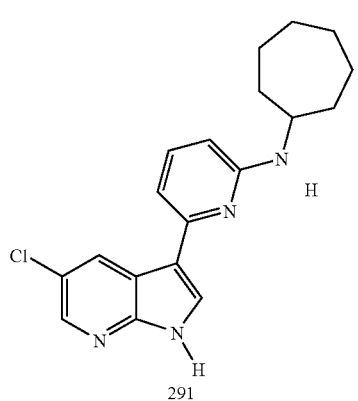
291
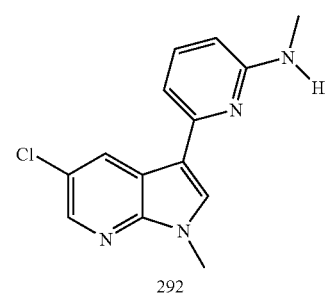
292
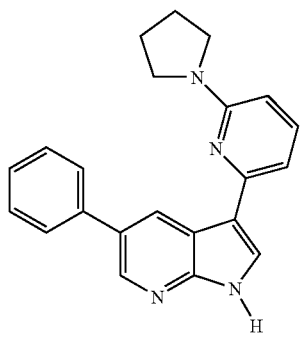
293
TABLE 2-continued
Examples of Compounds of Formula I:
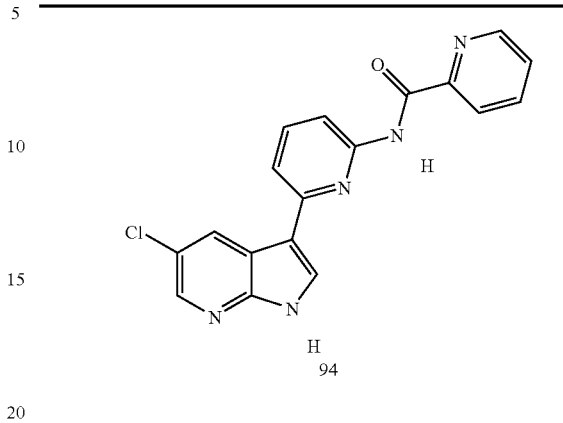
94
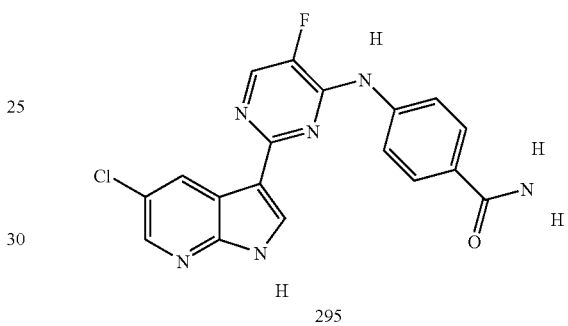
295
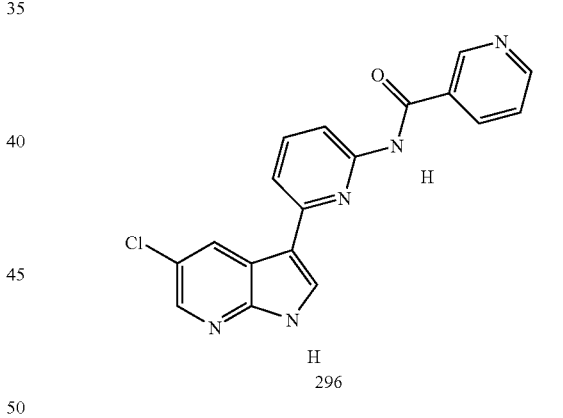
296
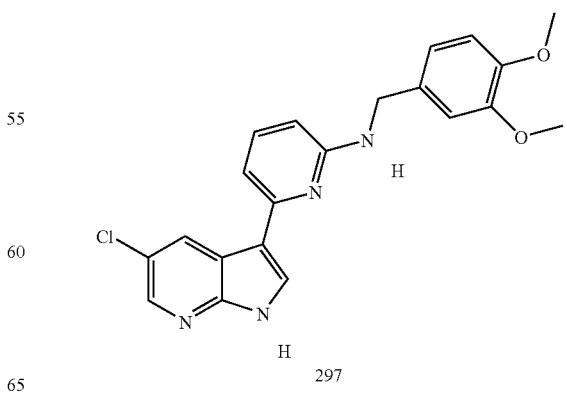
297

TABLE 2-continued
Examples of Compounds of Formula I:
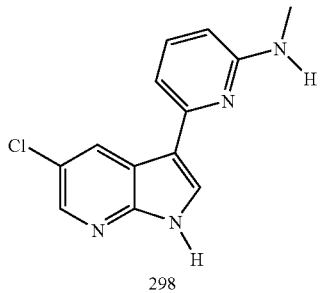
298
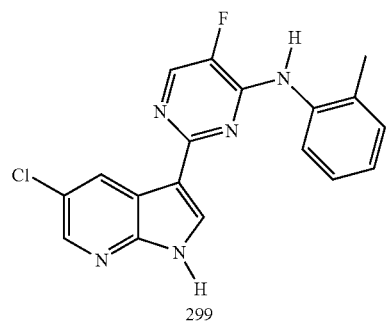
299
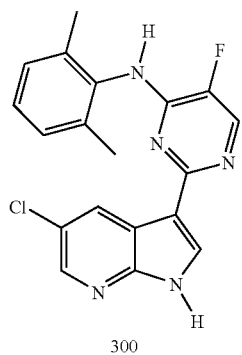
300
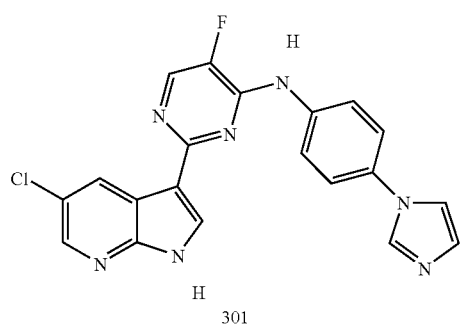
301
TABLE 2-continued
Examples of Compounds of Formula I:
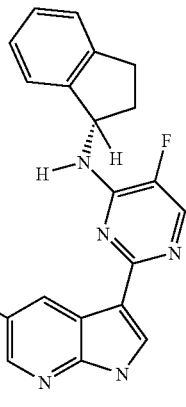
302
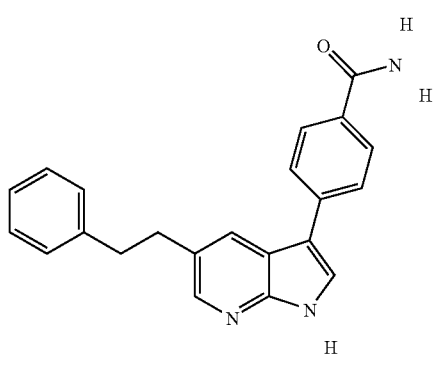
303
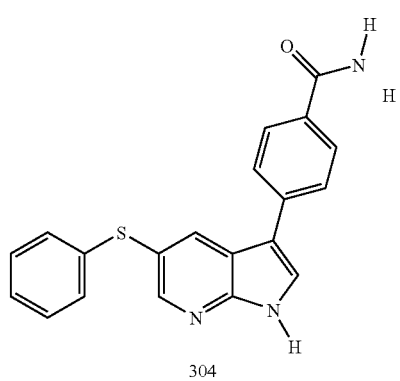
304
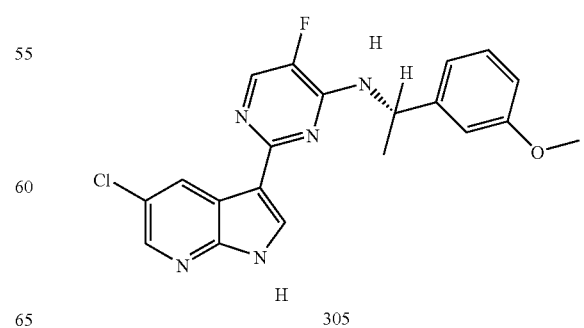
305

TABLE 2-continued
Examples of Compounds of Formula I:
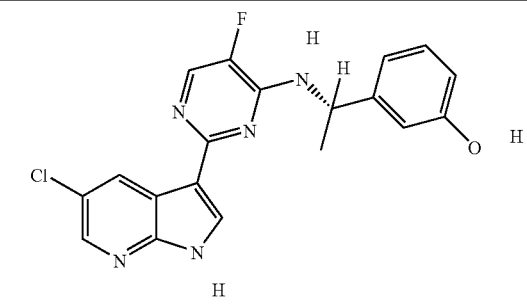
306
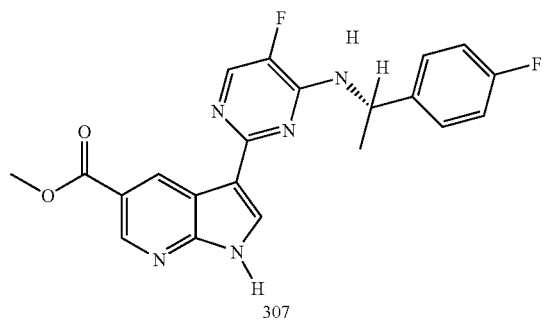
307
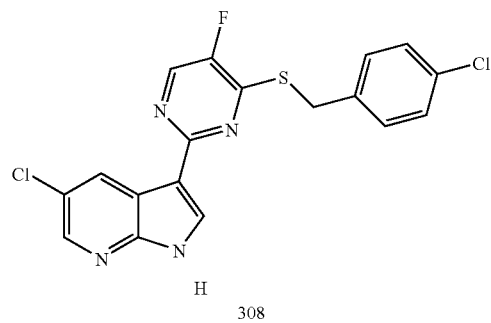
308
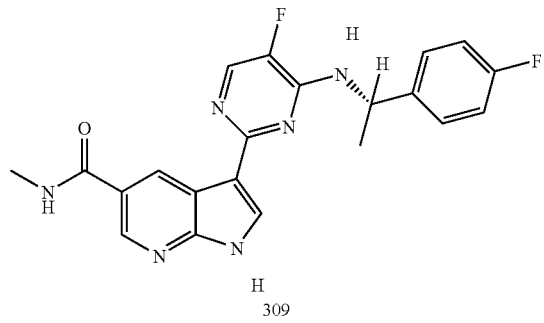
309
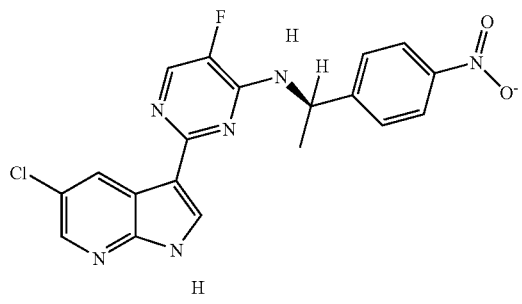
310
TABLE 2-continued
Examples of Compounds of Formula I:
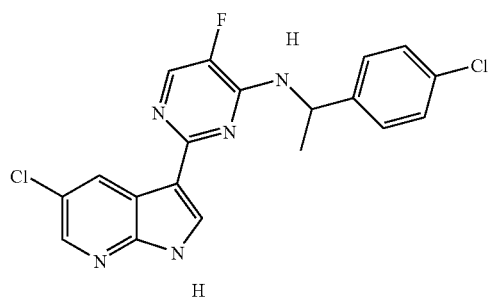
311
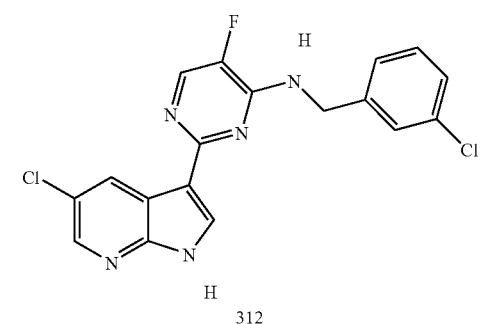
312
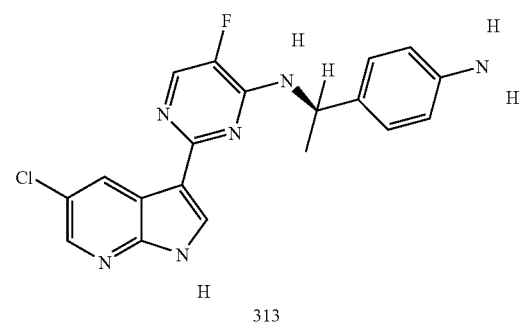
313
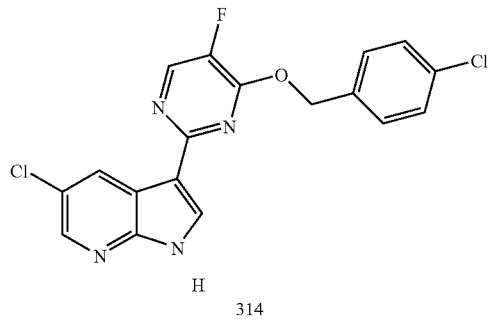
314

TABLE 2-continued
Examples of Compounds of Formula I:
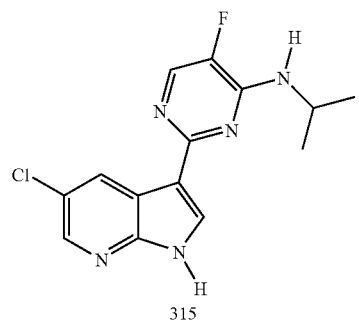
315
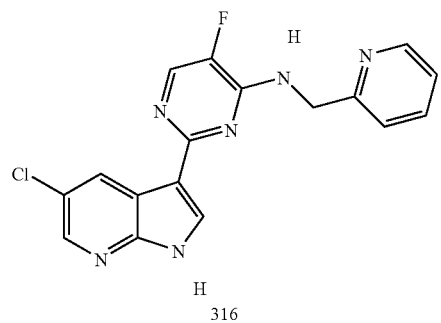
316
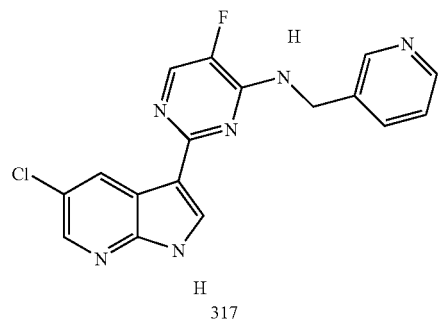
317
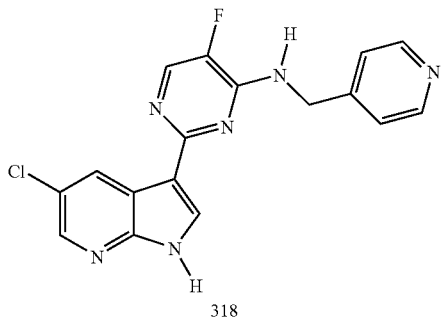
318
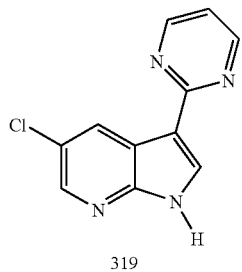
319
TABLE 2-continued
Examples of Compounds of Formula I:
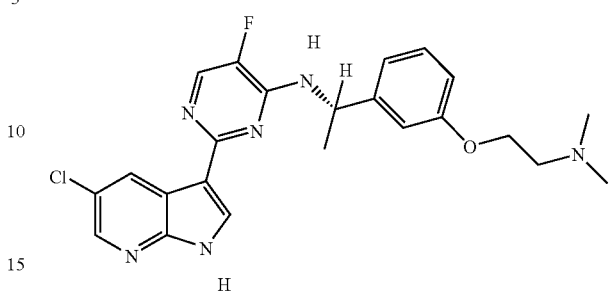
320
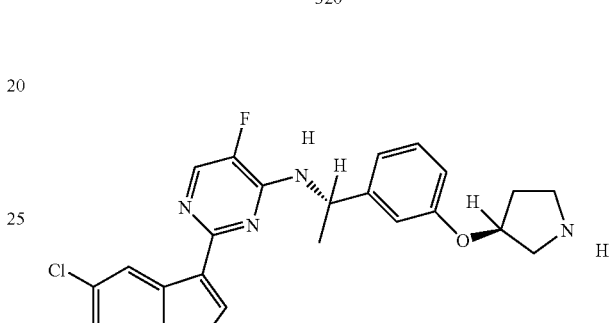
321
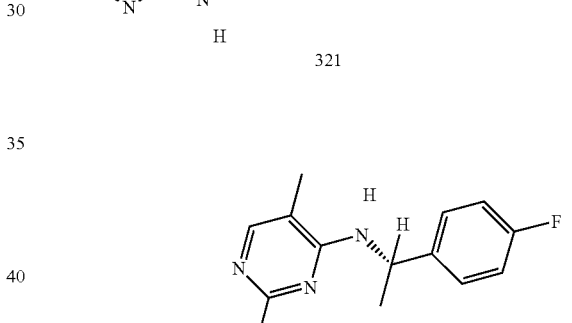
322
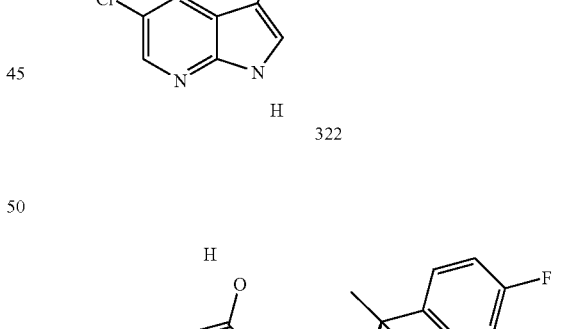
323

TABLE 2-continued
Examples of Compounds of Formula I:
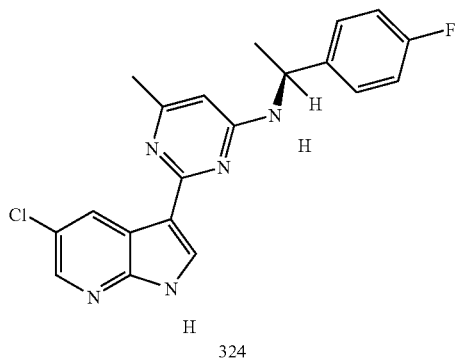
324
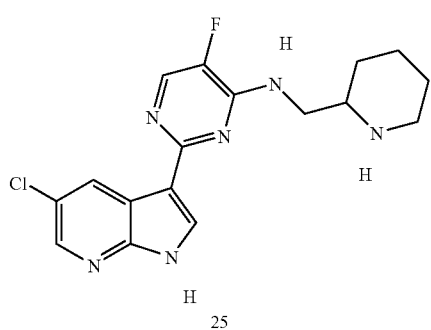
25
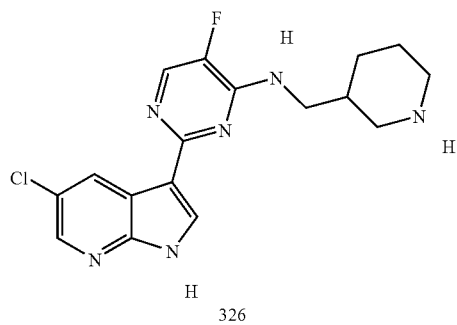
326
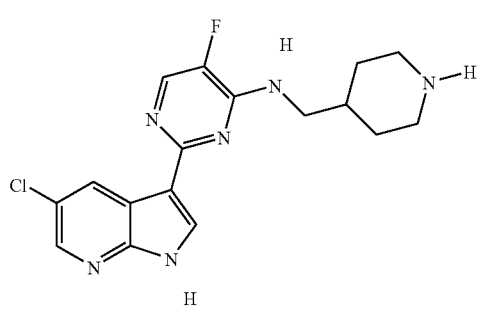
327
TABLE 2-continued
Examples of Compounds of Formula I:
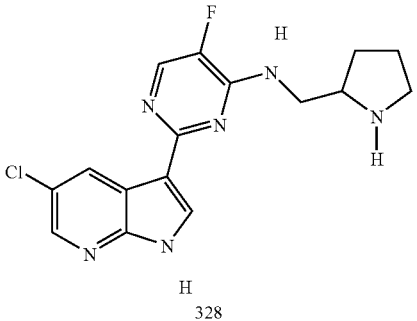
328
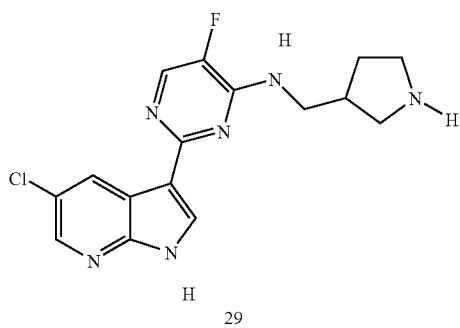
29
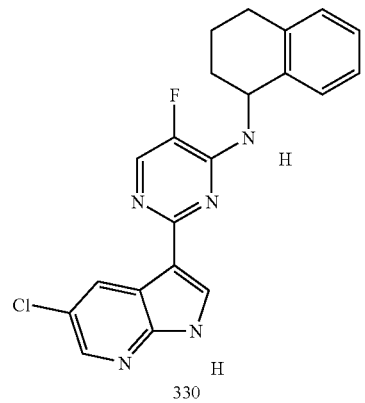
330
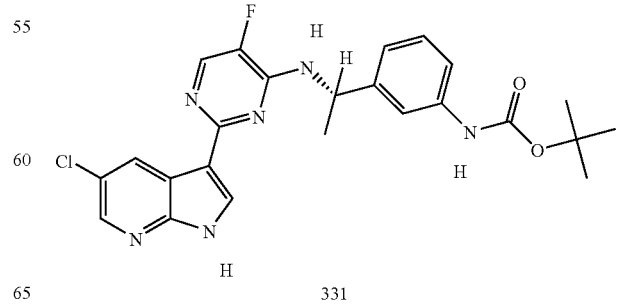
331

TABLE 2-continued
Examples of Compounds of Formula I:
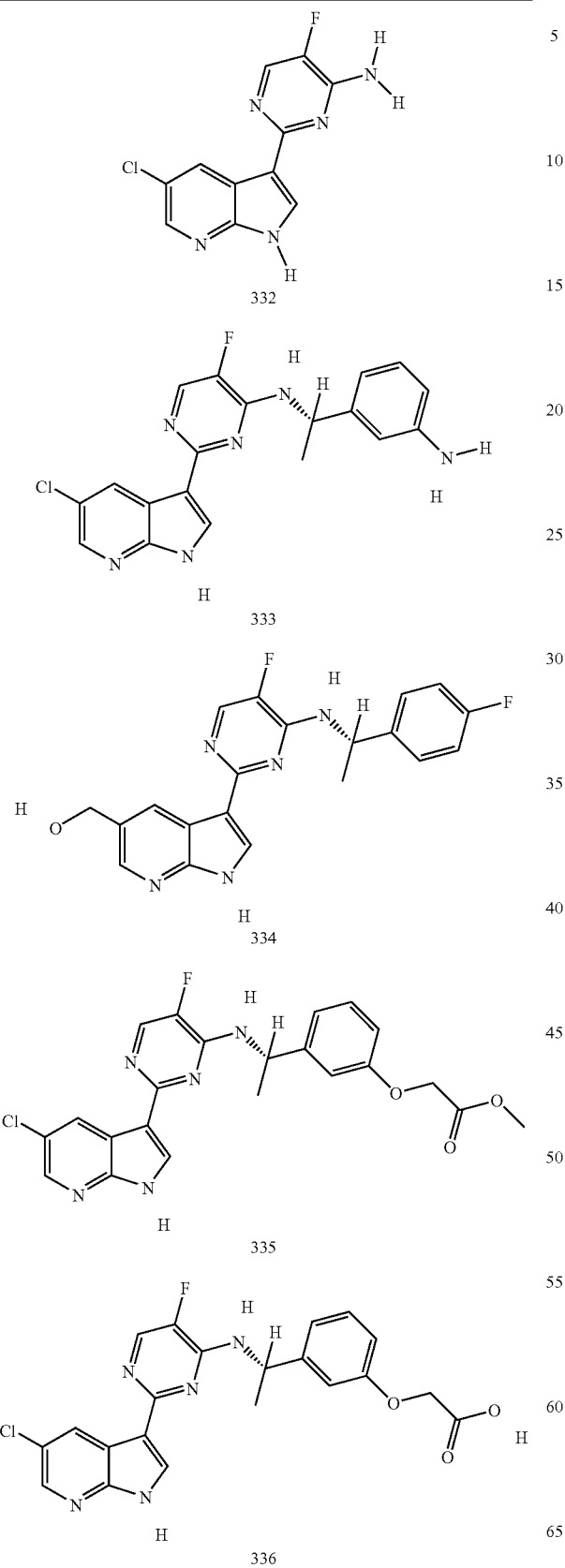
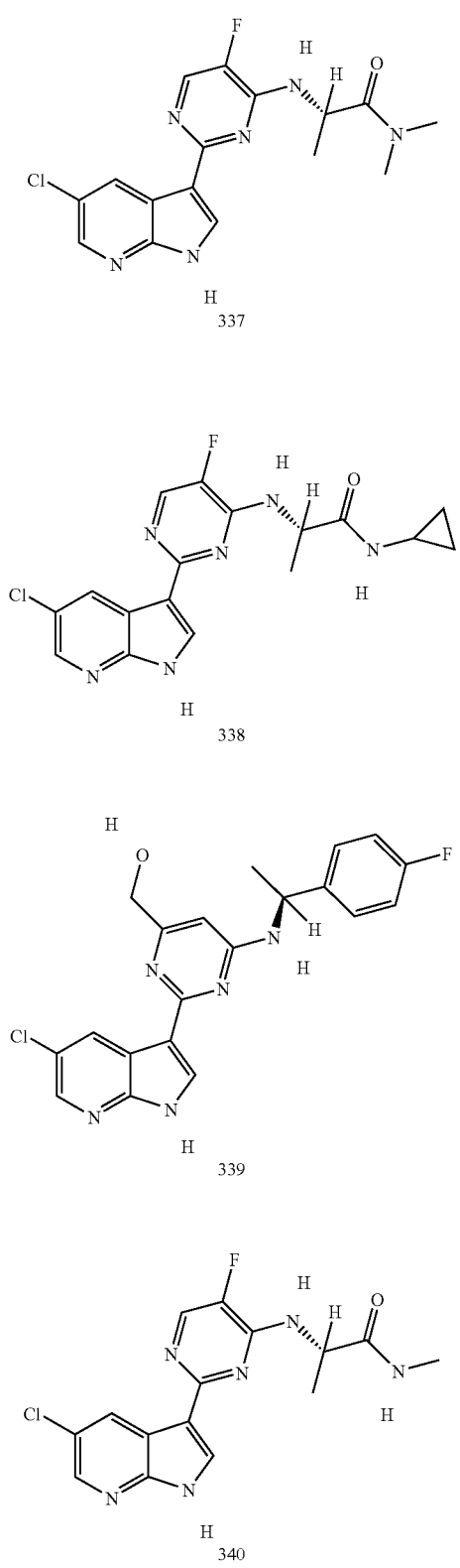

TABLE 2-continued
Examples of Compounds of Formula I:
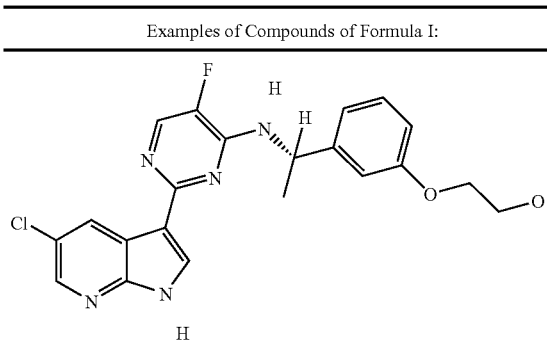
341
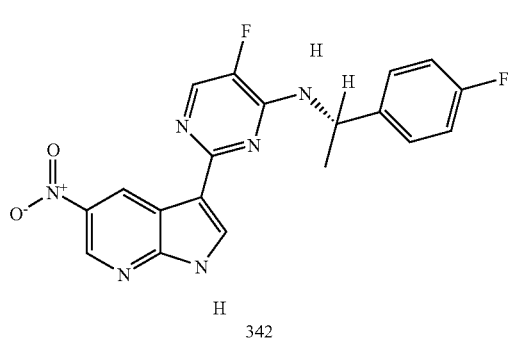
342
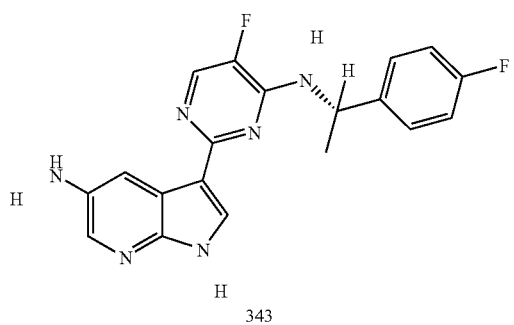
343
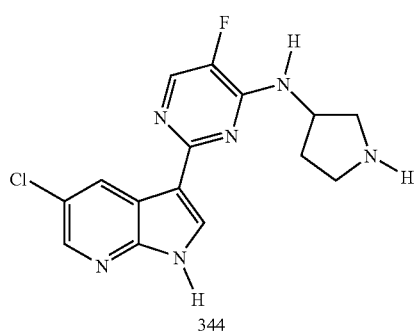
344
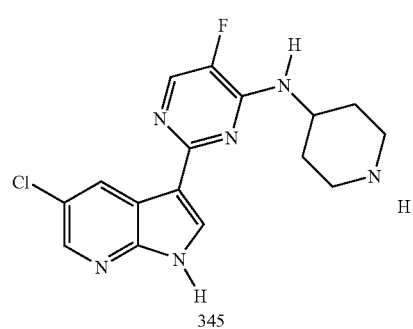
345
TABLE 2-continued
Examples of Compounds of Formula I:
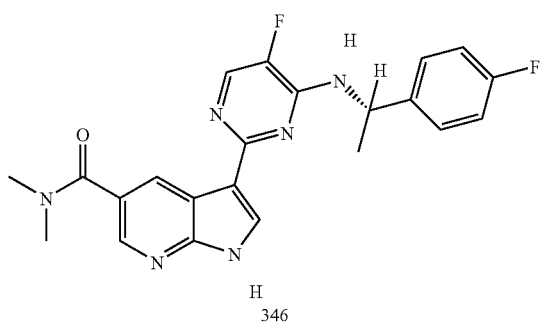
346
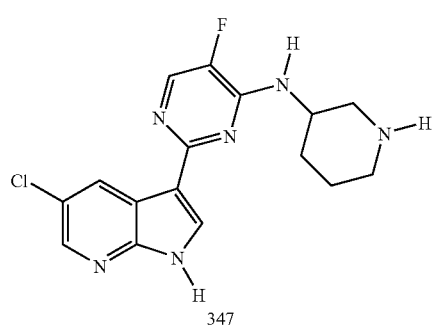
347
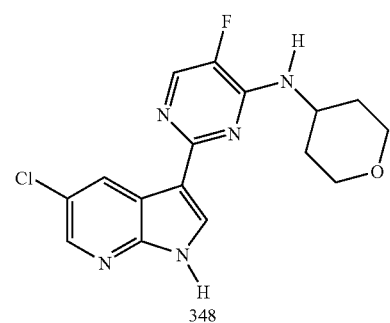
348
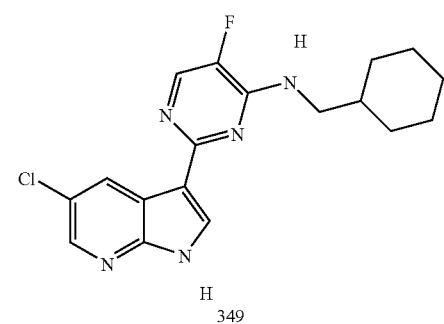
349

TABLE 2-continued
Examples of Compounds of Formula I:
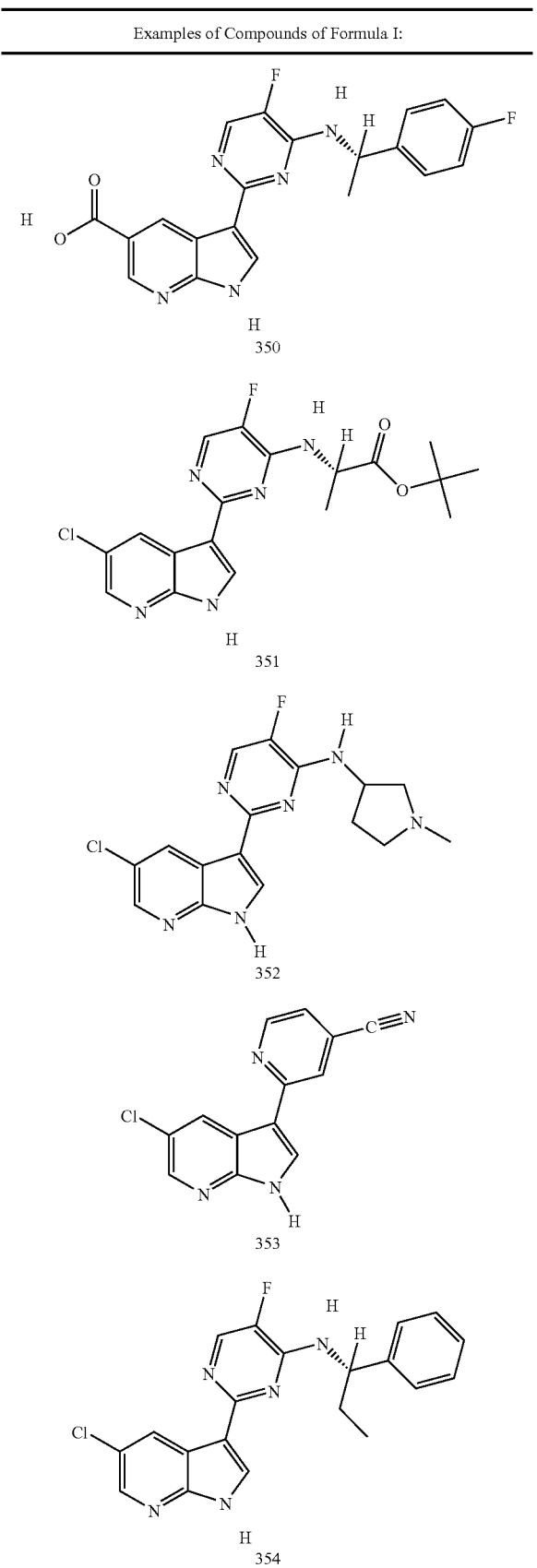
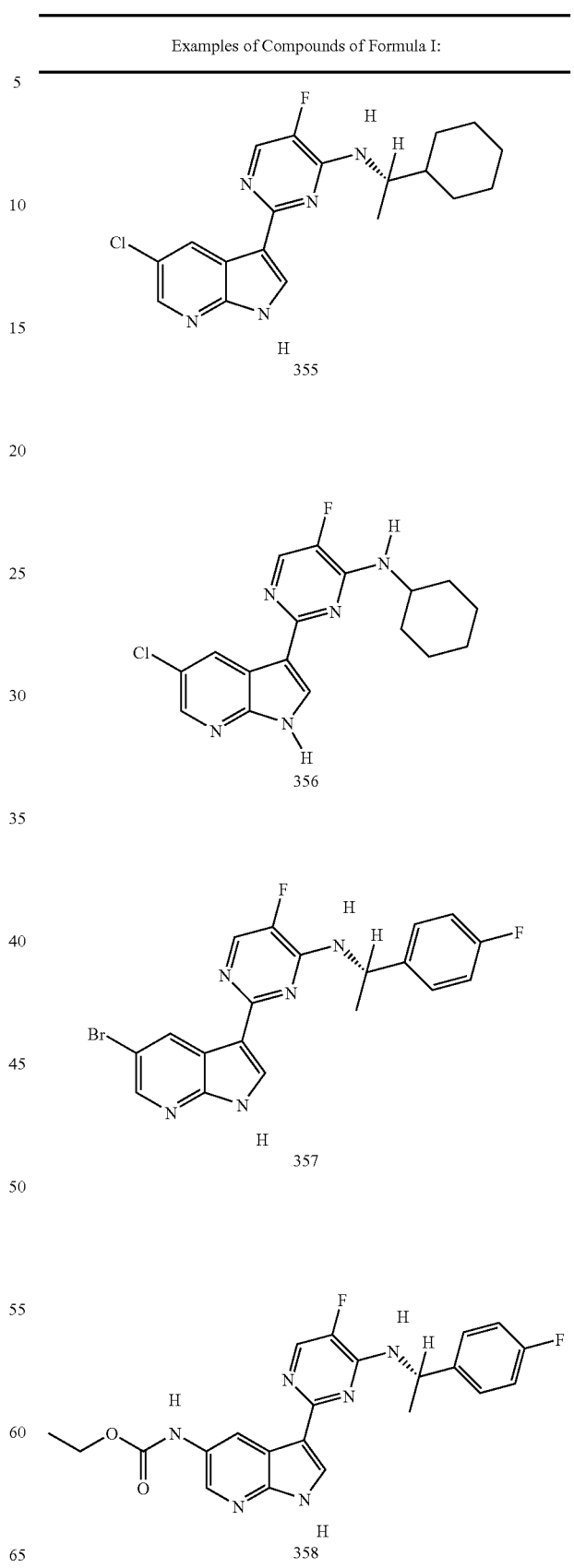

TABLE 2-continued
Examples of Compounds of Formula I:
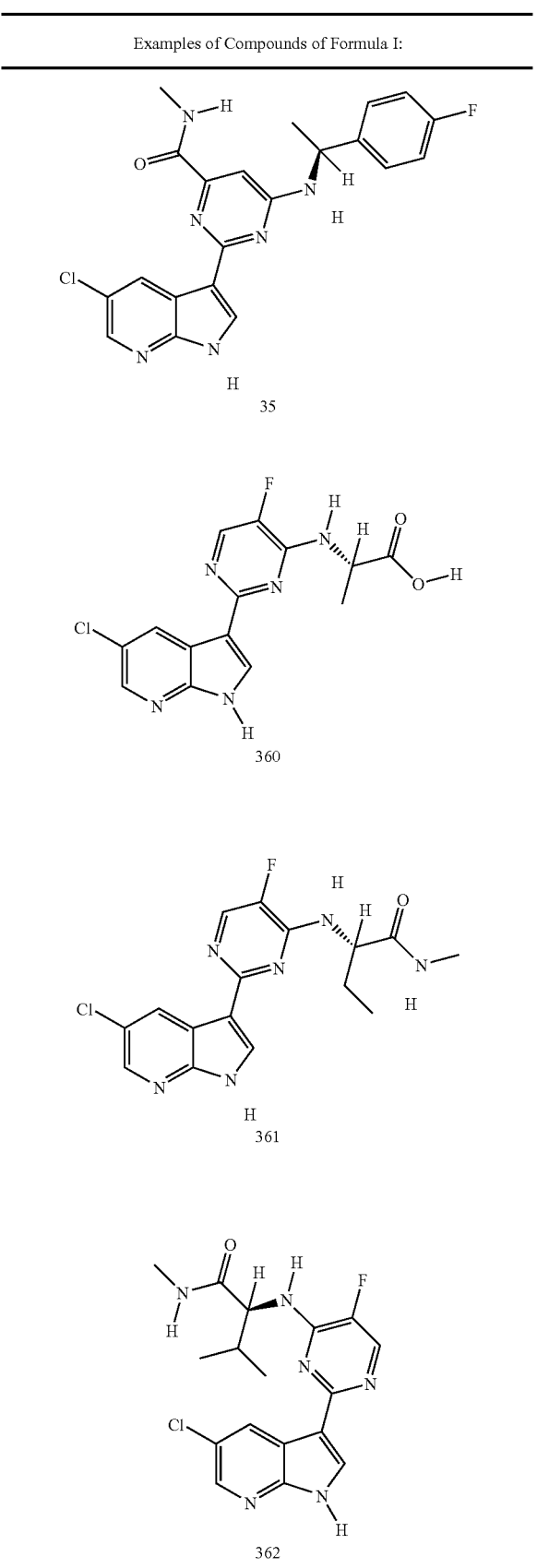
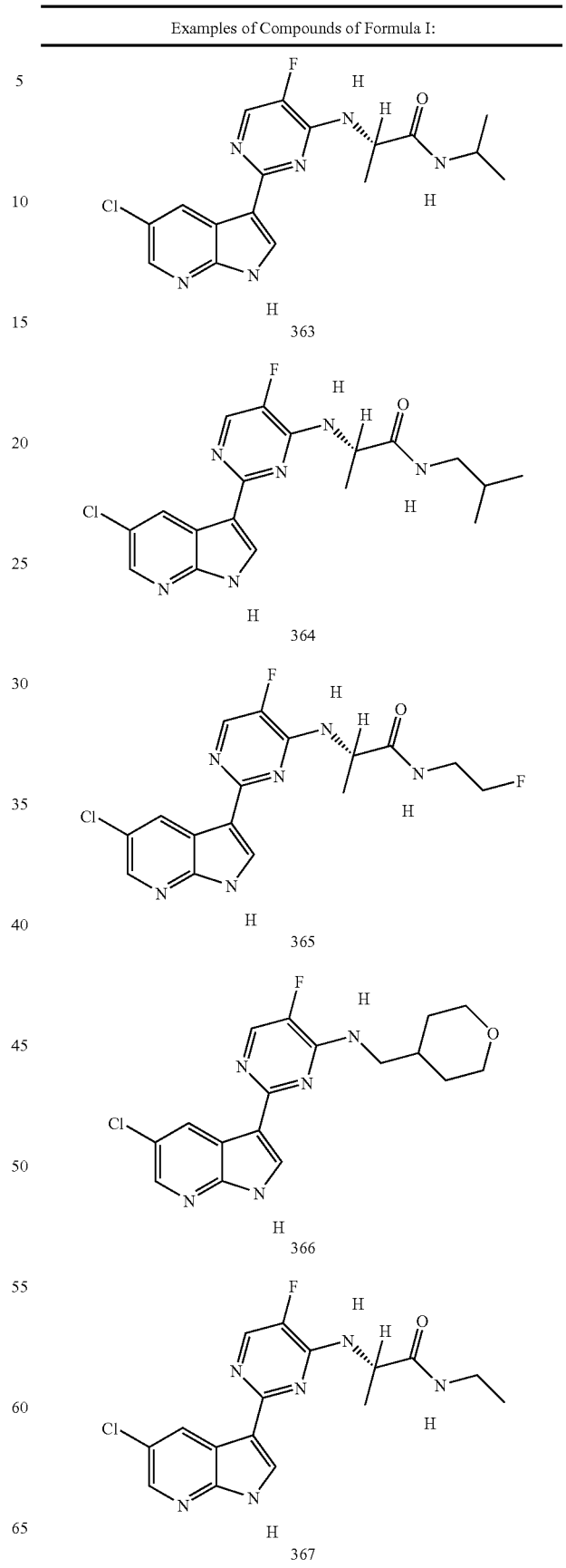

TABLE 2-continued
Examples of Compounds of Formula I:
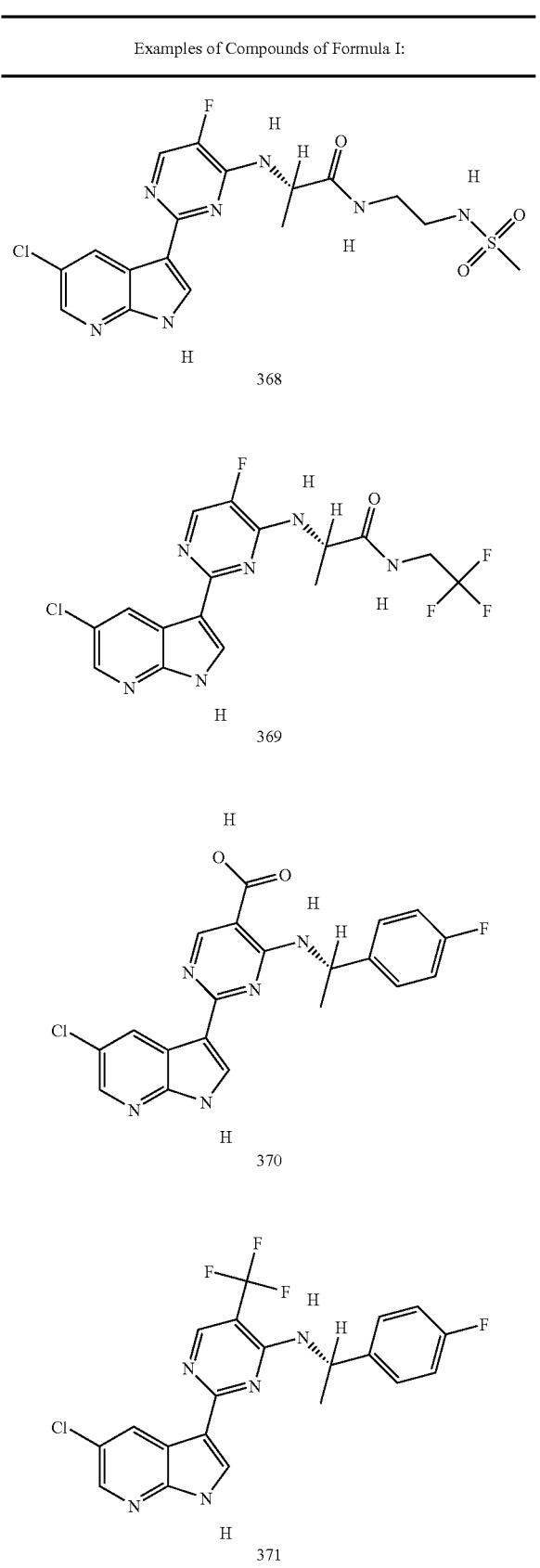
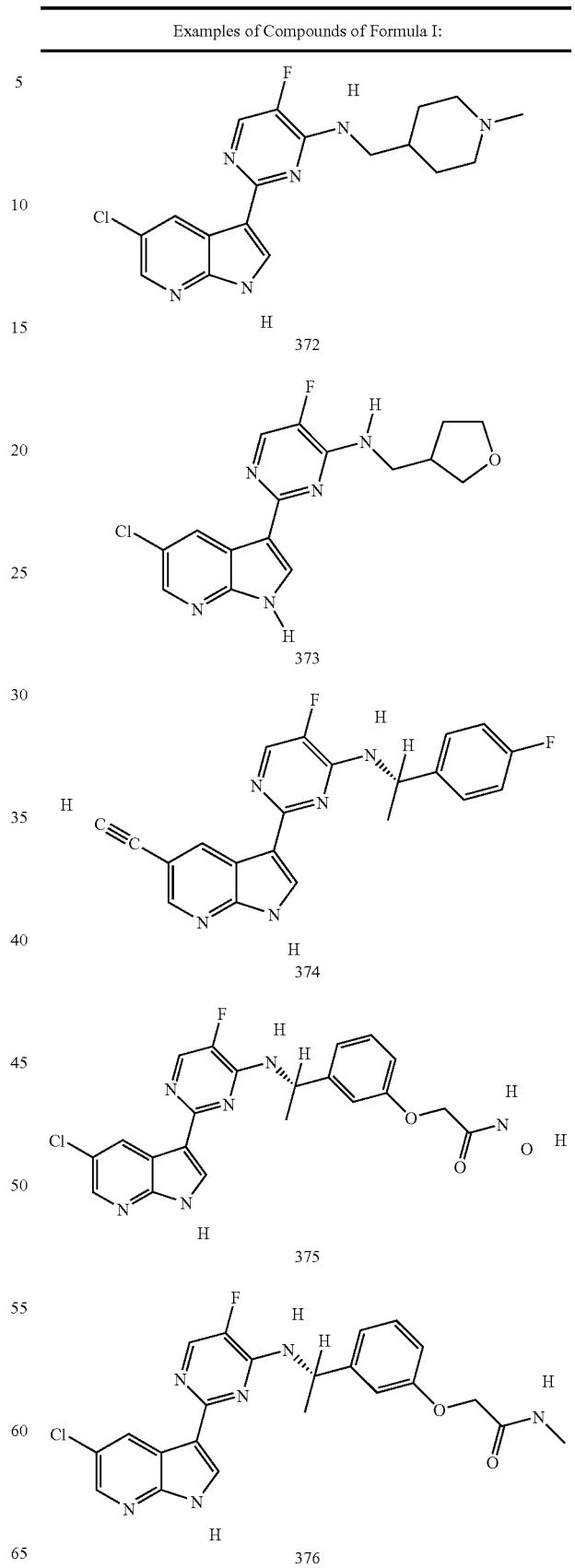

TABLE 2-continued
Examples of Compounds of Formula I:
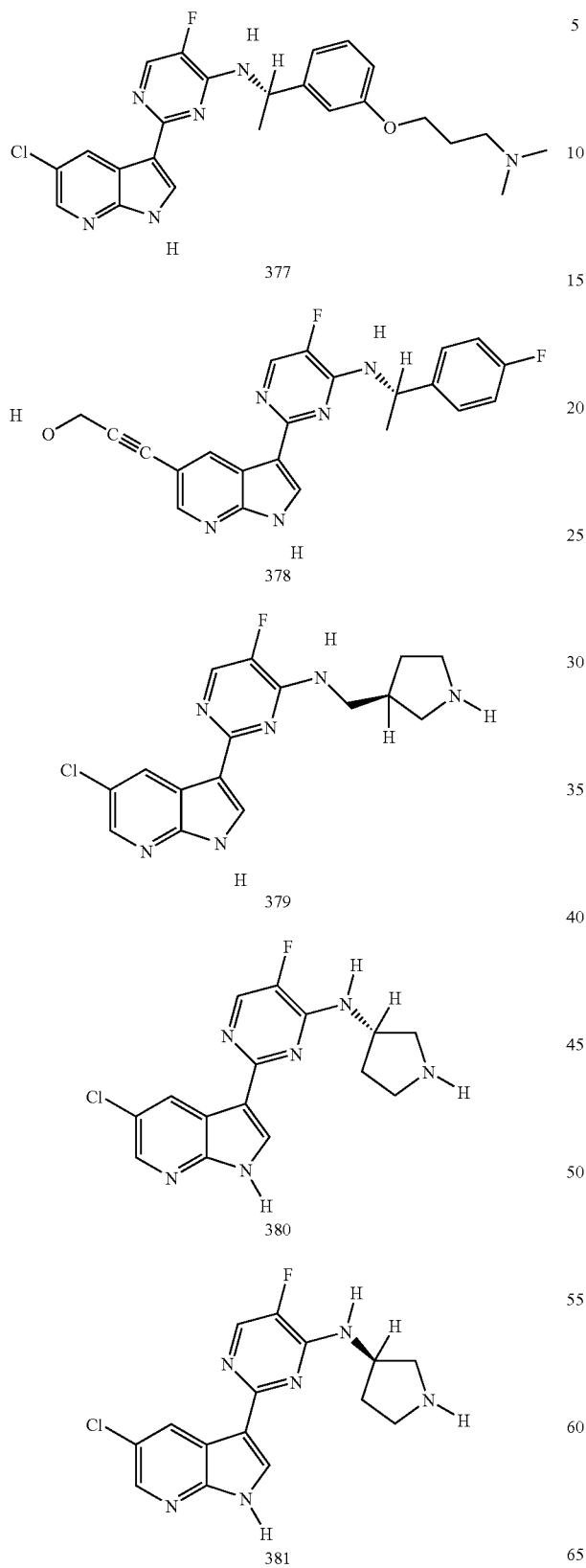
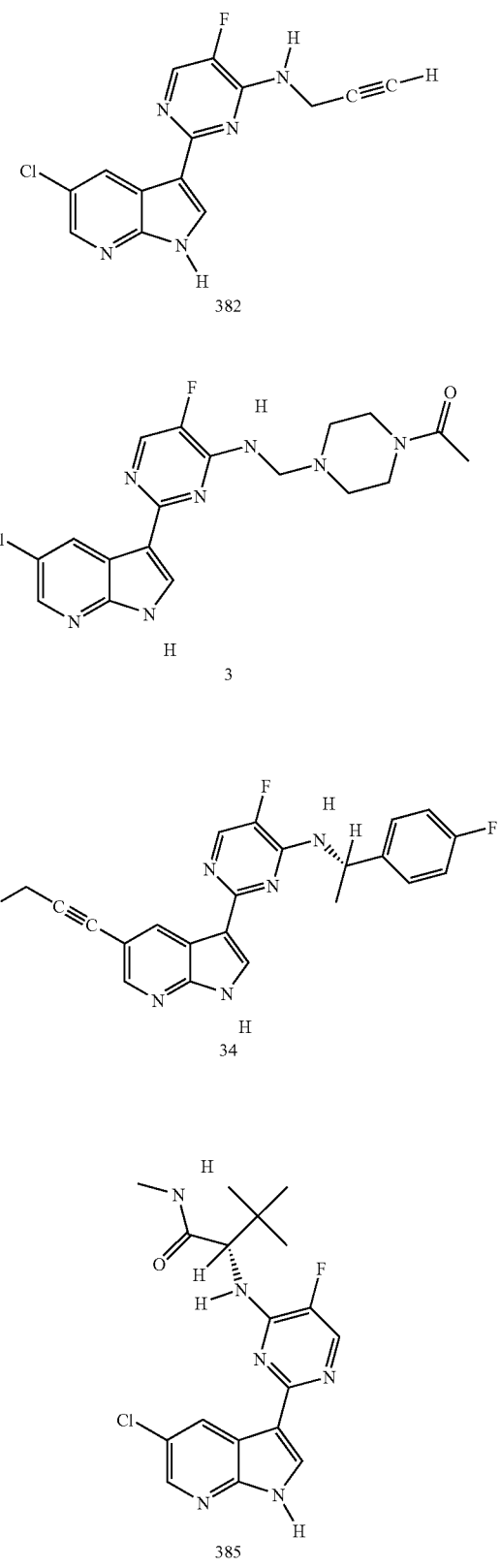

TABLE 2-continued
Examples of Compounds of Formula I:
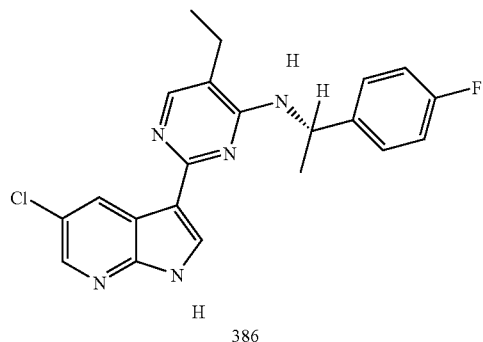
386
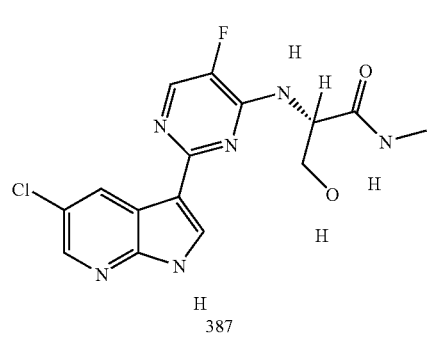
387
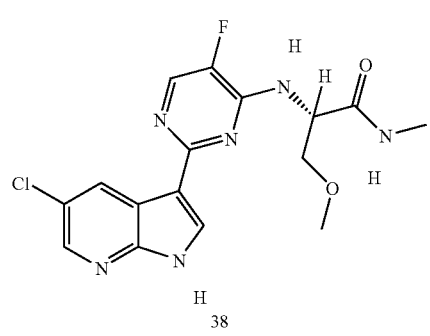
38
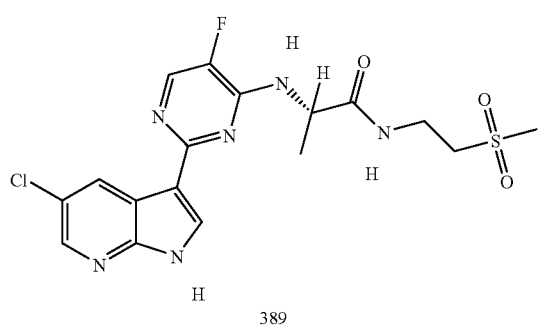
389
TABLE 2-continued
Examples of Compounds of Formula I:
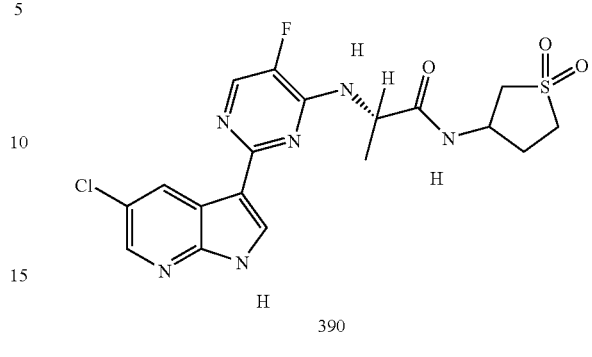
390
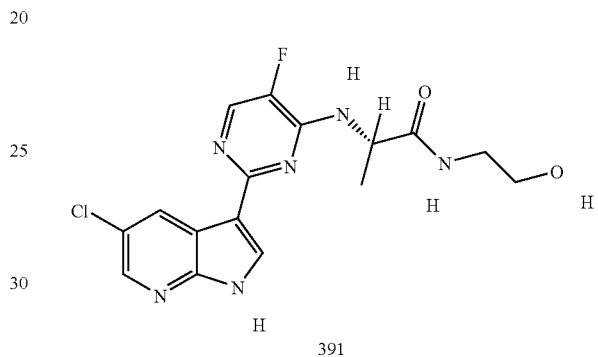
391
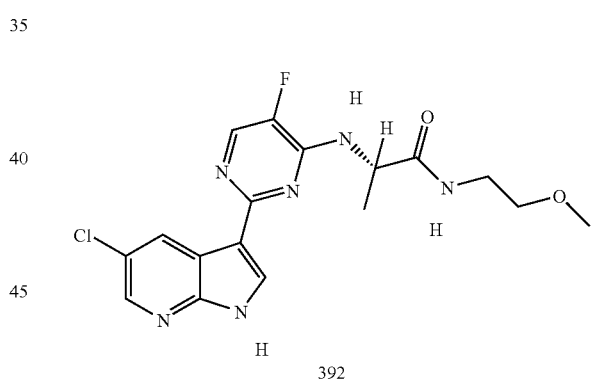
392
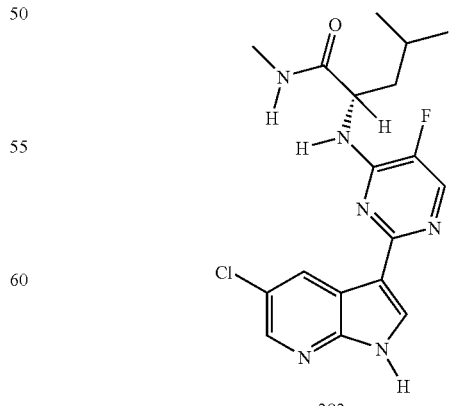
393

TABLE 2-continued
Examples of Compounds of Formula I:
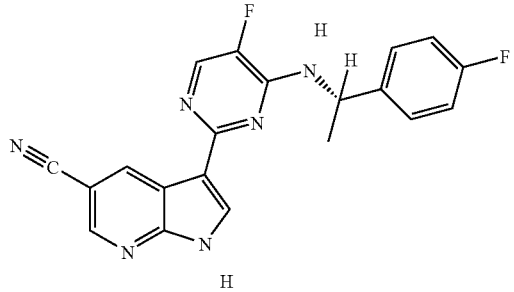
394
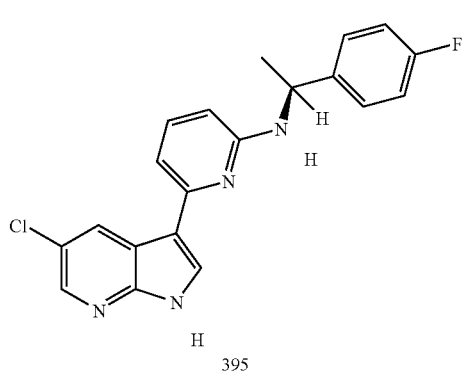
395
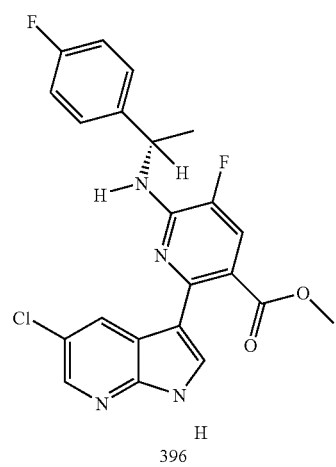
396
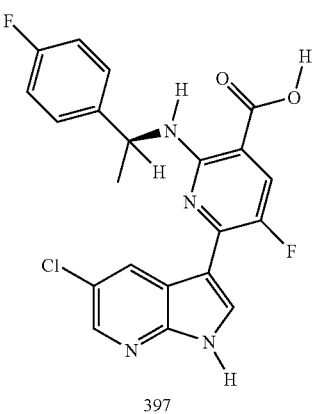
397
TABLE 2-continued
Examples of Compounds of Formula I:
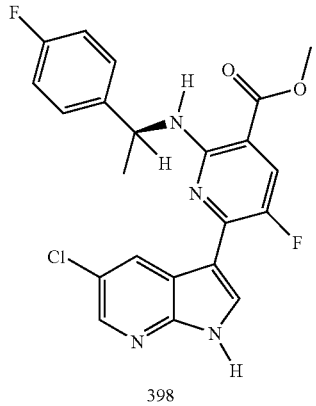
398
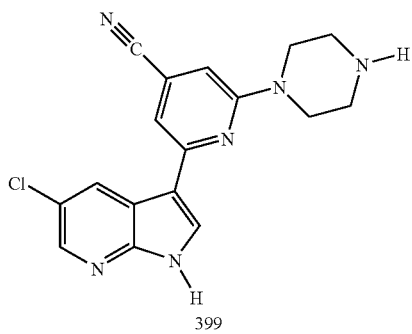
399
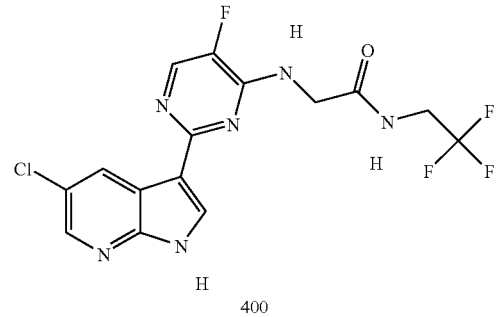
400
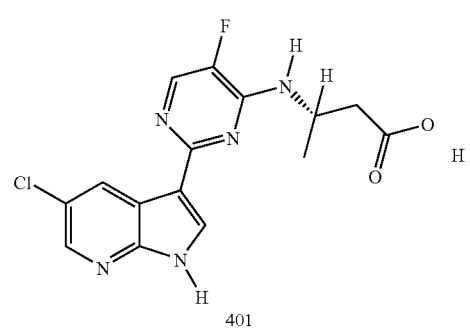
401

TABLE 2-continued
Examples of Compounds of Formula I:
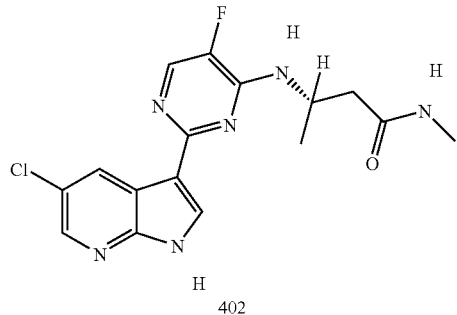
402
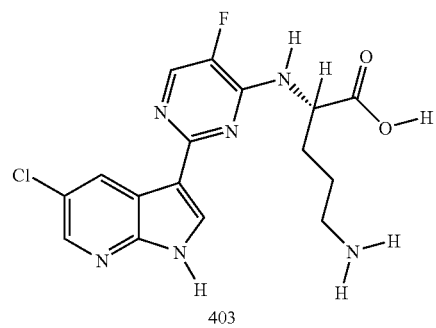
403
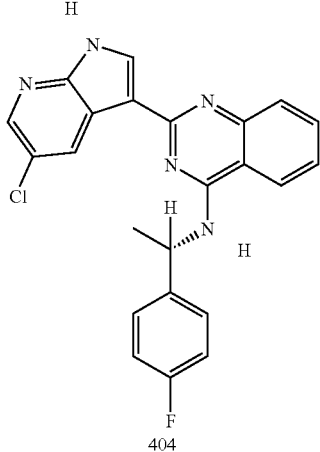
404
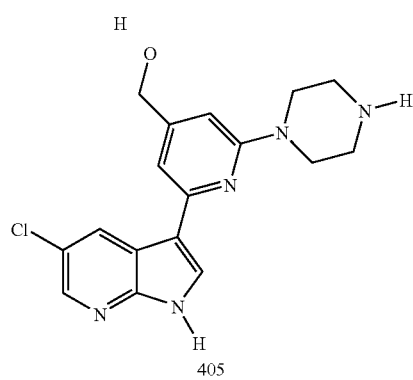
405
TABLE 2-continued
Examples of Compounds of Formula I:
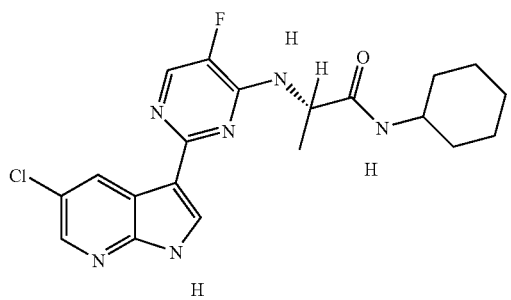
406
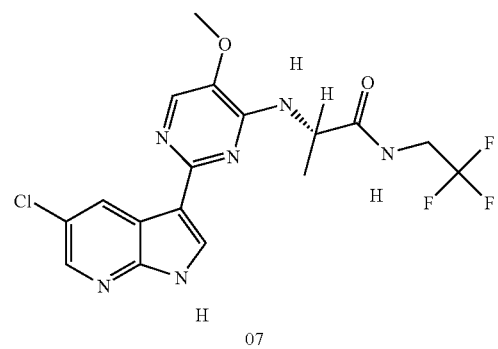
407
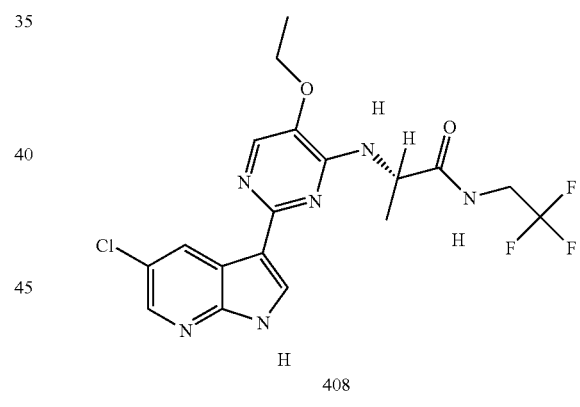
408
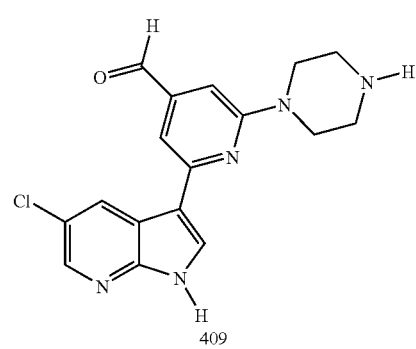
409

TABLE 2-continued
Examples of Compounds of Formula I:
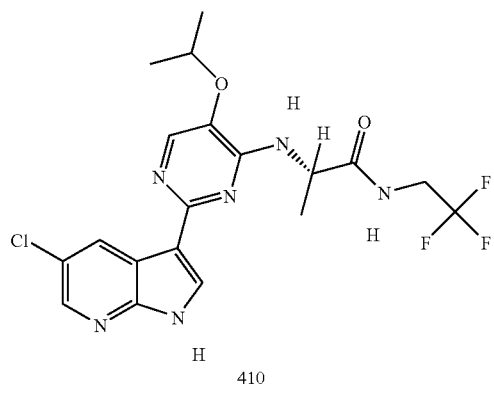
410
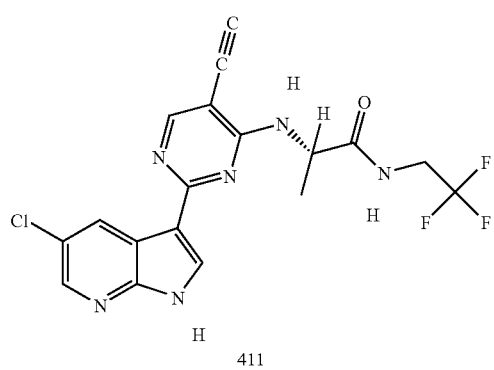
411
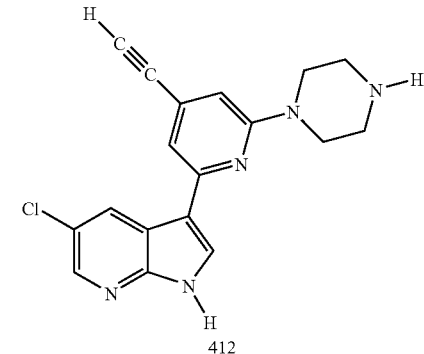
412
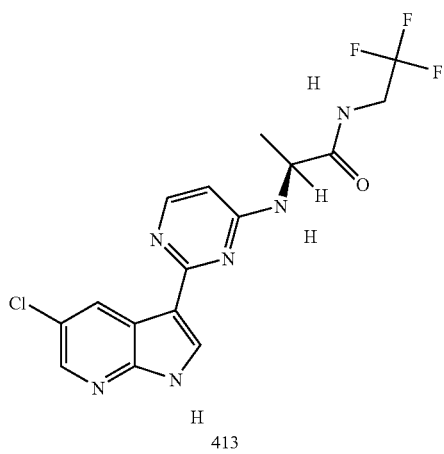
413
TABLE 2-continued
Examples of Compounds of Formula I:
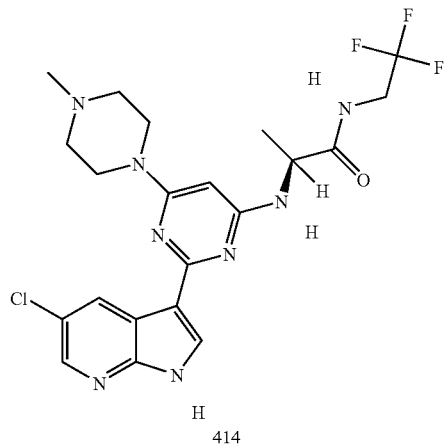
414
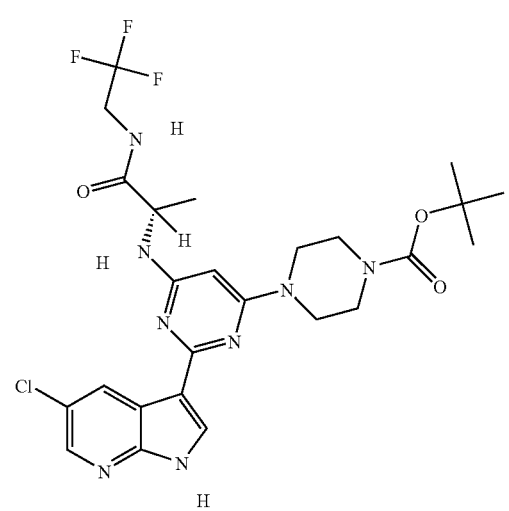
415
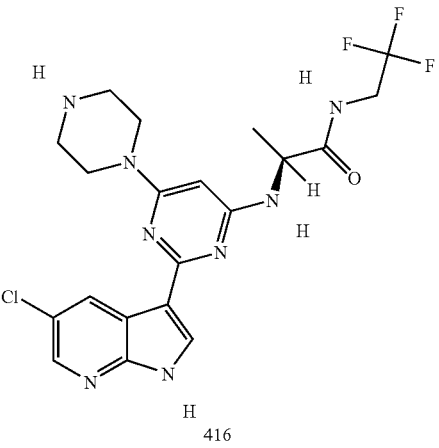
416

TABLE 2-continued
Examples of Compounds of Formula I:
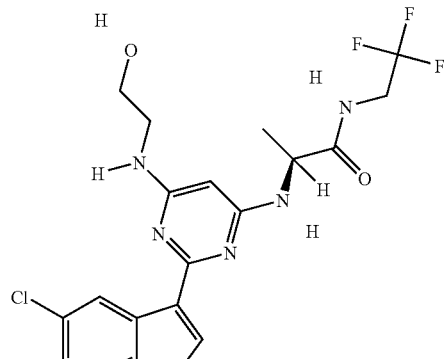
417
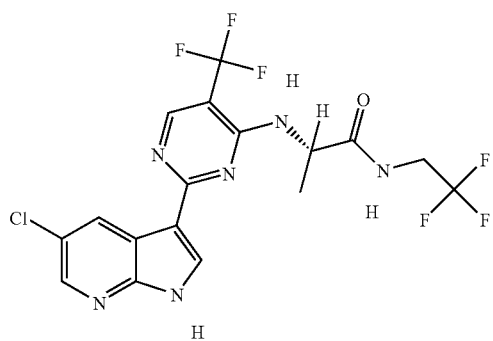
418
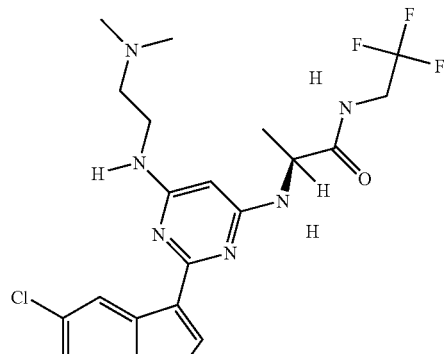
419
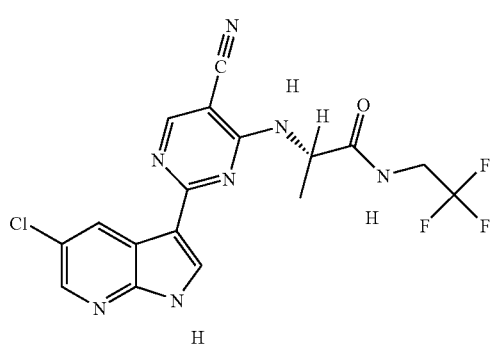
420
TABLE 2-continued
Examples of Compounds of Formula I:
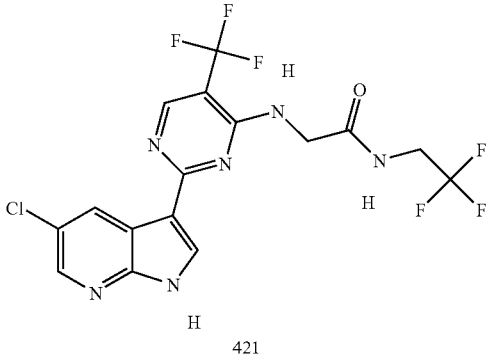
421
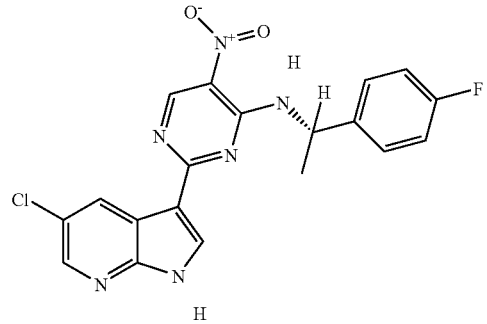
422
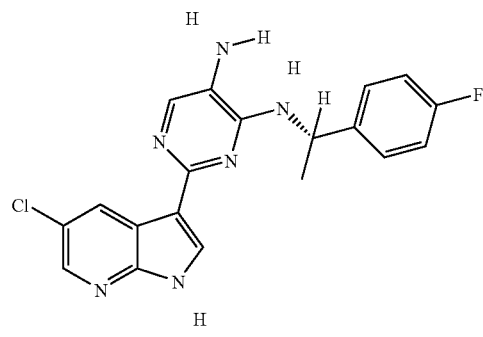
423
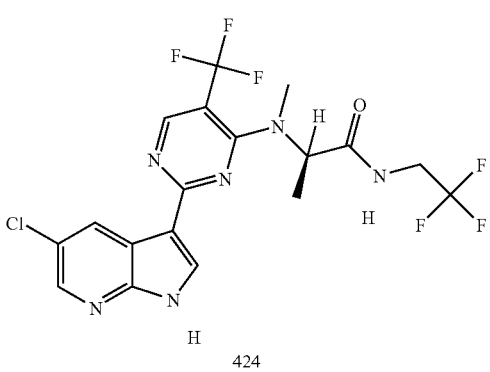
424

TABLE 2-continued
Examples of Compounds of Formula I:
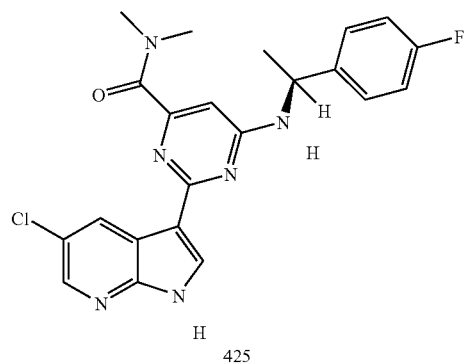
425
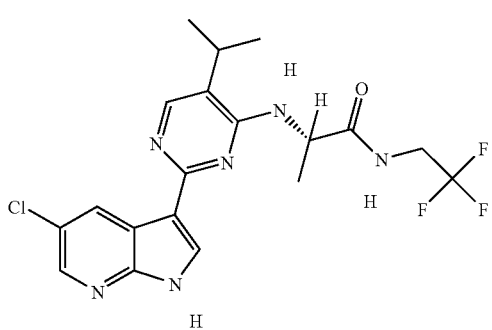
429
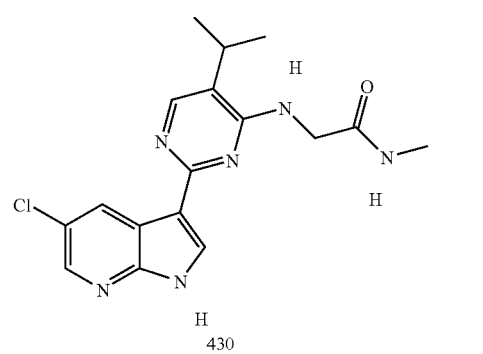
426
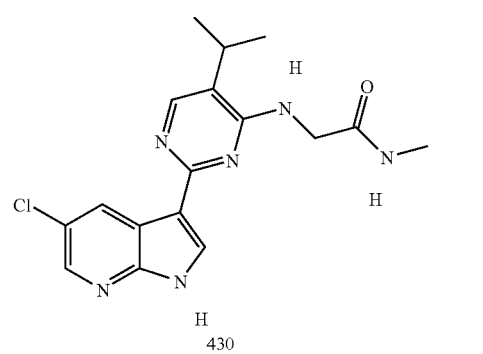
430
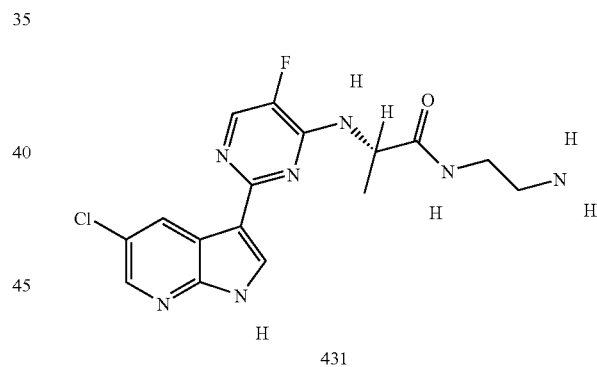
427
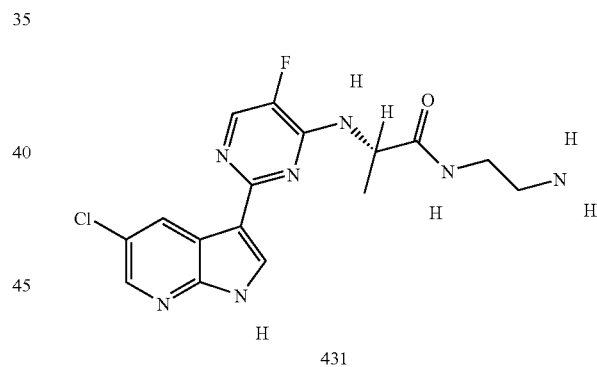
431
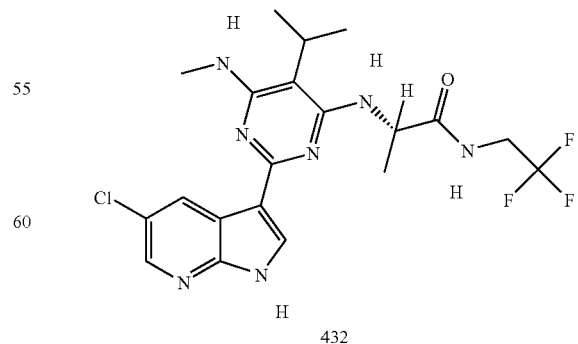
428
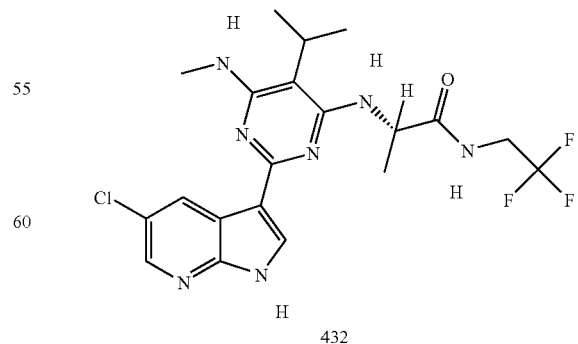
432

TABLE 2-continued
Examples of Compounds of Formula I:
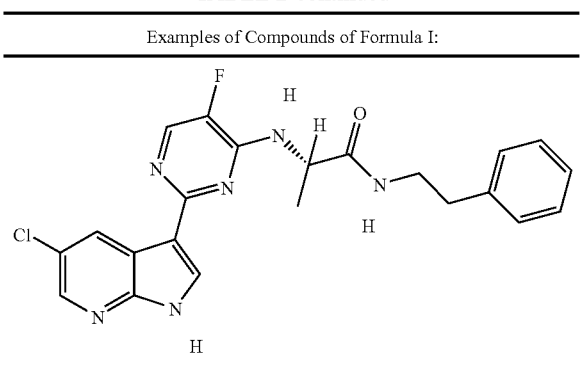
433
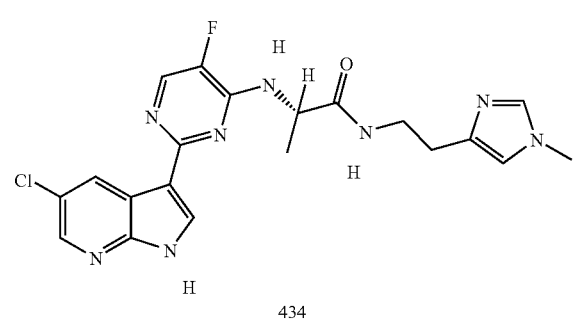
434
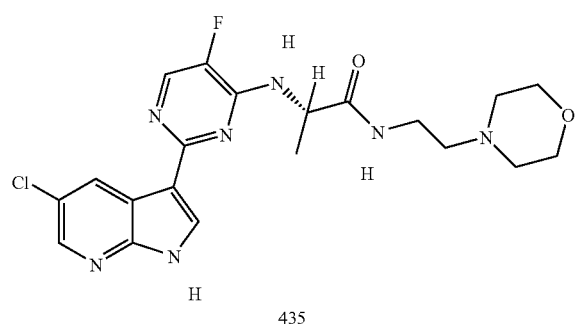
435
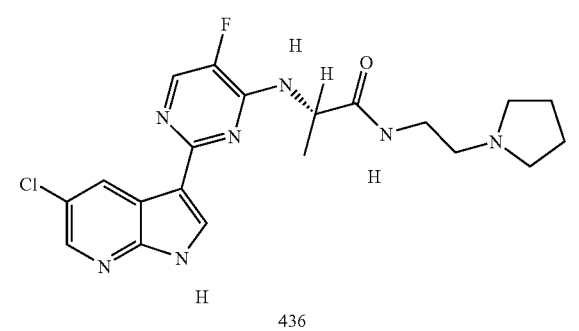
436
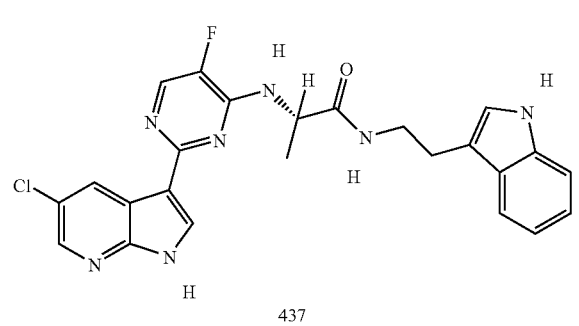
437
TABLE 2-continued
Examples of Compounds of Formula I:
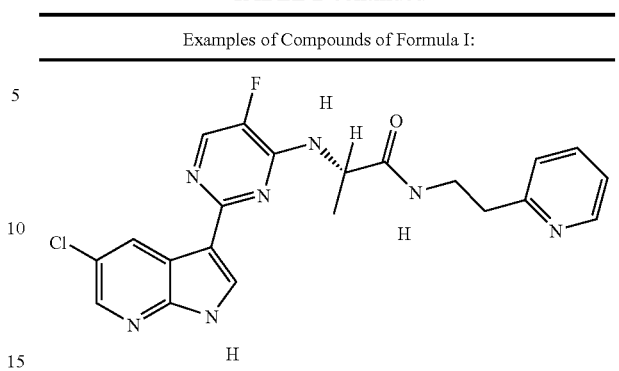
438
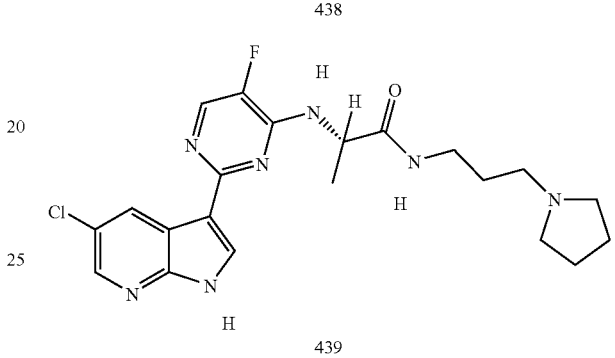
439
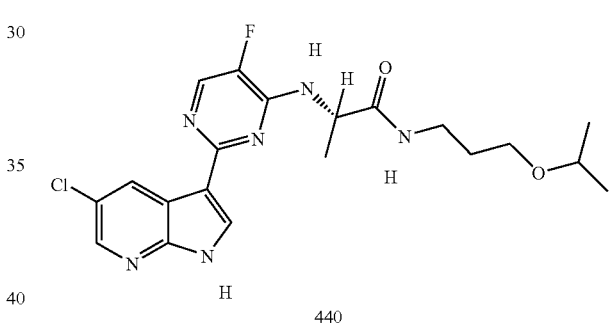
440
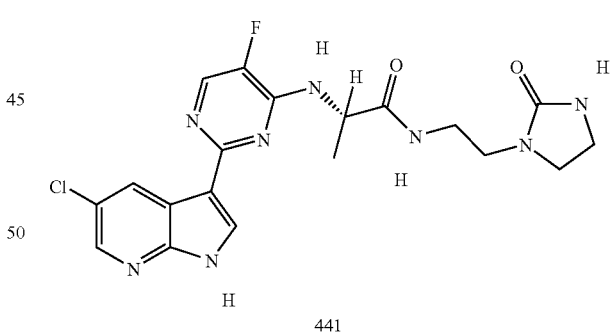
441
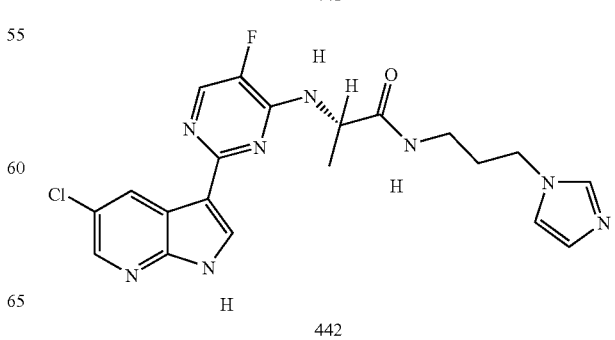
442

TABLE 2-continued
Examples of Compounds of Formula I:
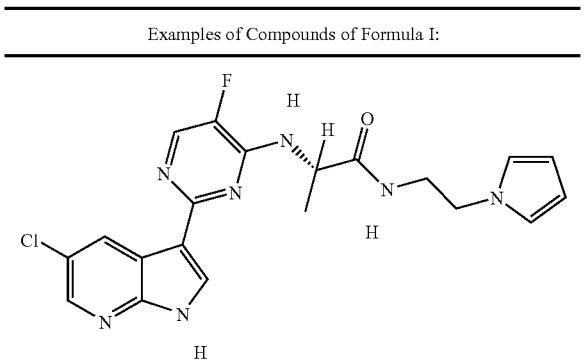
443
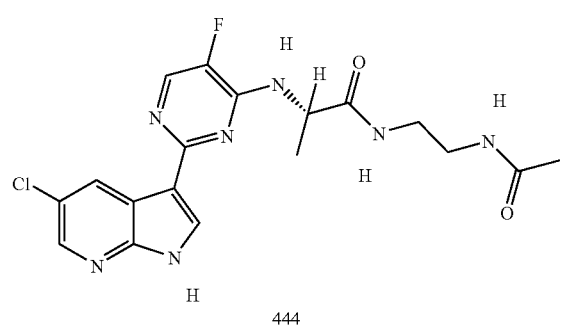
444
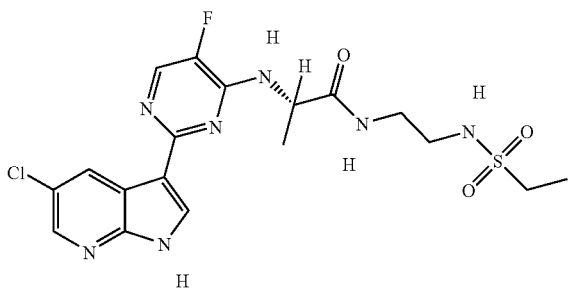
445
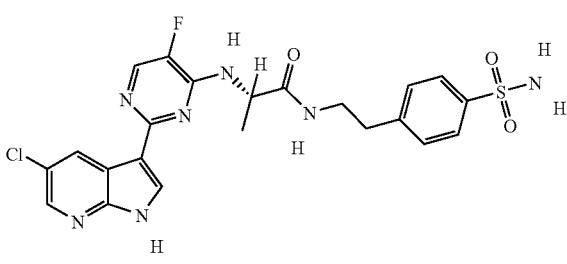
446
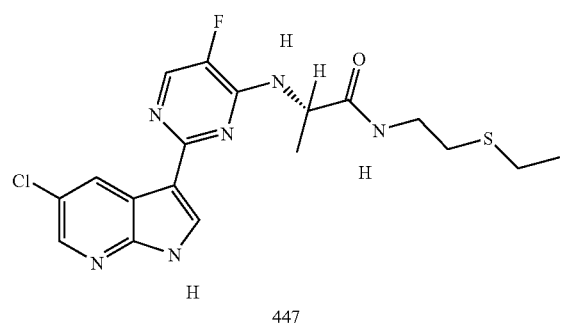
447
TABLE 2-continued
Examples of Compounds of Formula I:
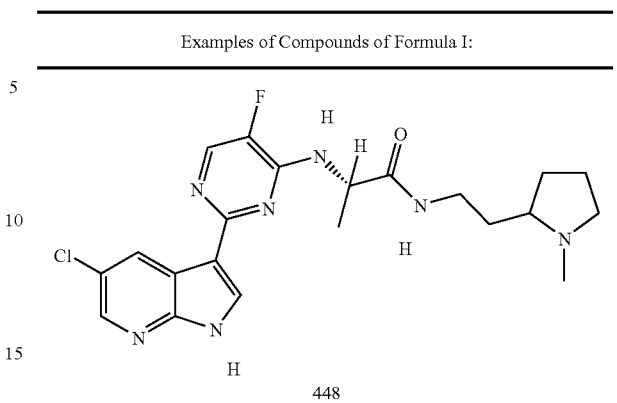
448
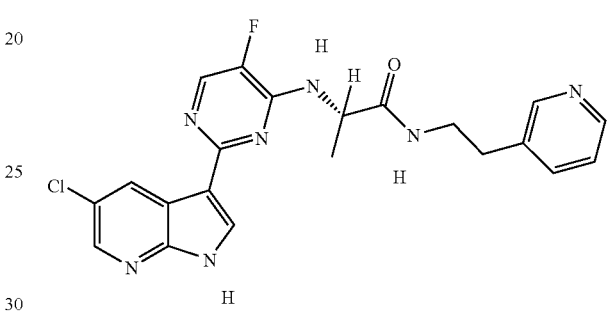
449
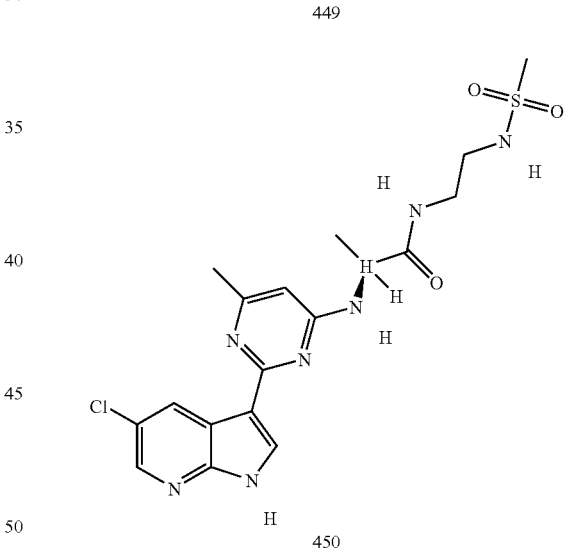
450
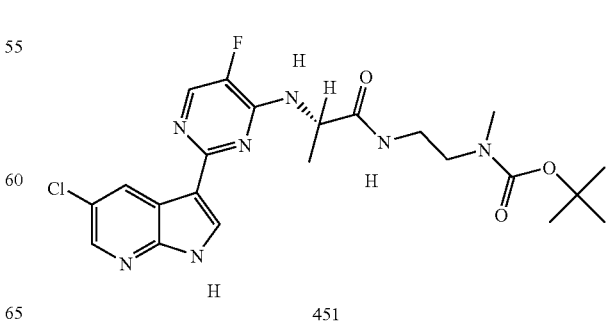
451

TABLE 2-continued
Examples of Compounds of Formula I:
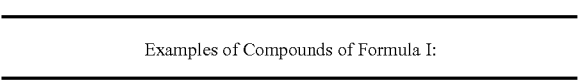
452
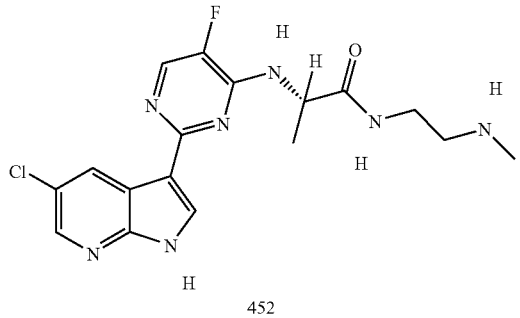
453
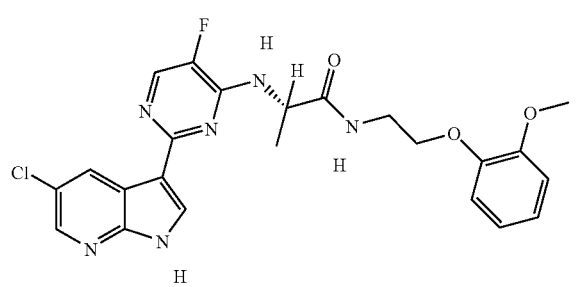
454
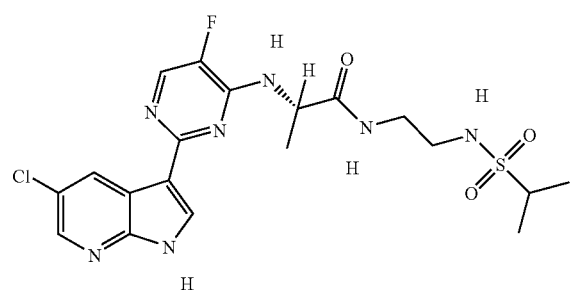
455
TABLE 2-continued
Examples of Compounds of Formula I:
456
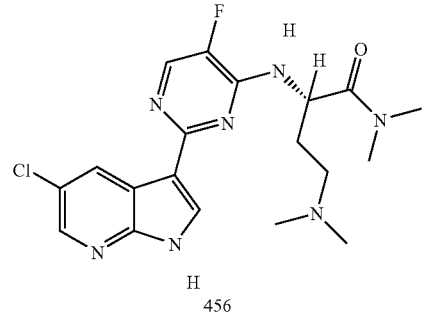
457
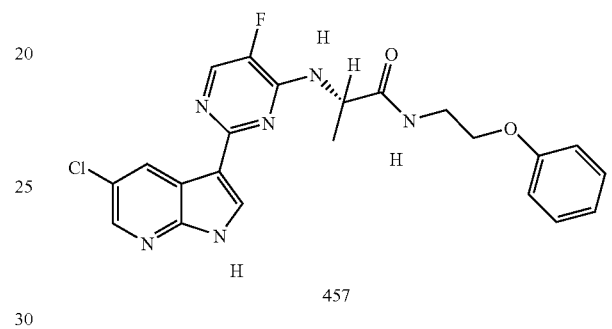
458
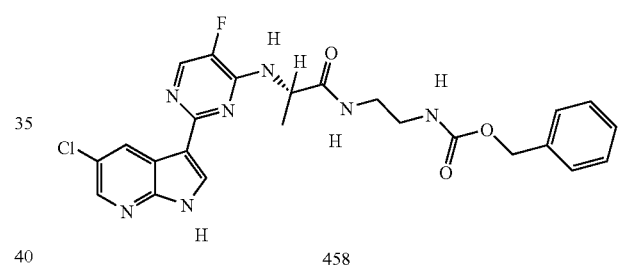
459
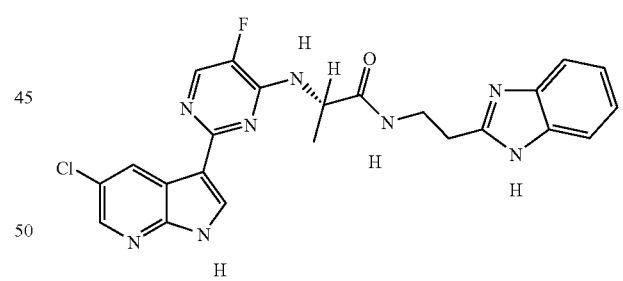
460

TABLE 2-continued

Examples of Compounds of Formula I:

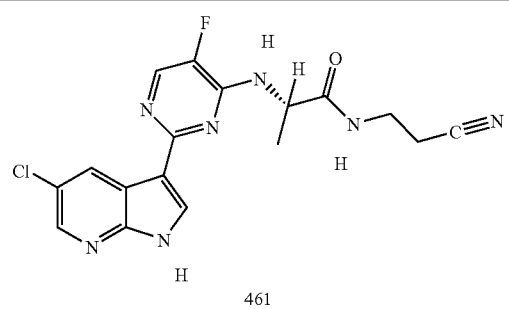

461

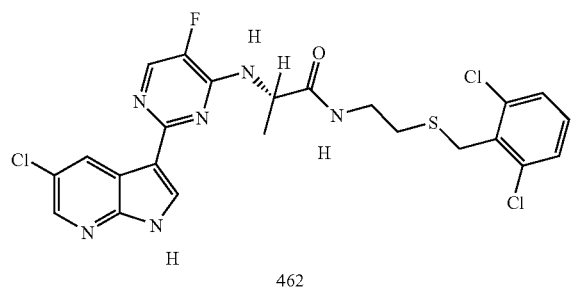

462

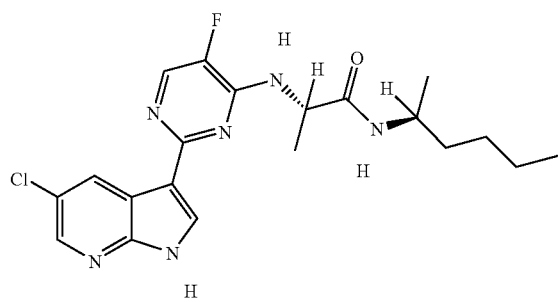

463

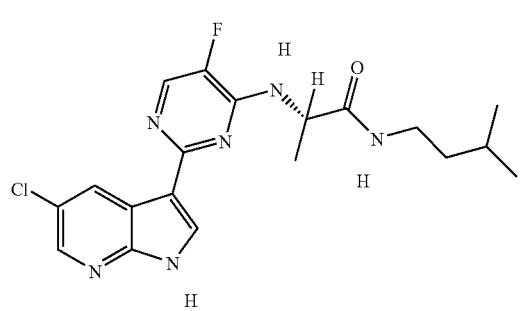

464

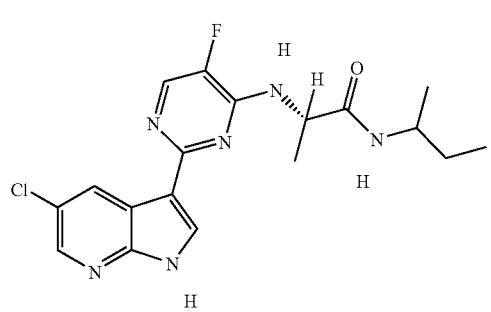

465

TABLE 2-continued

Examples of Compounds of Formula I:

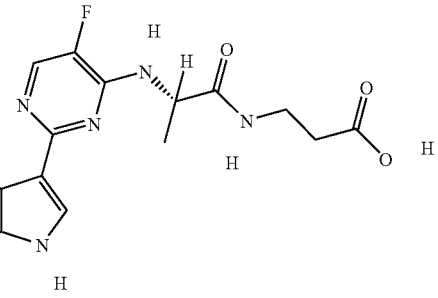

466

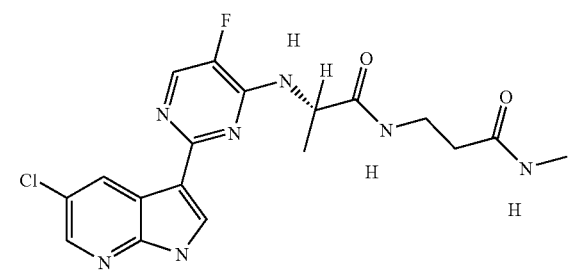

467

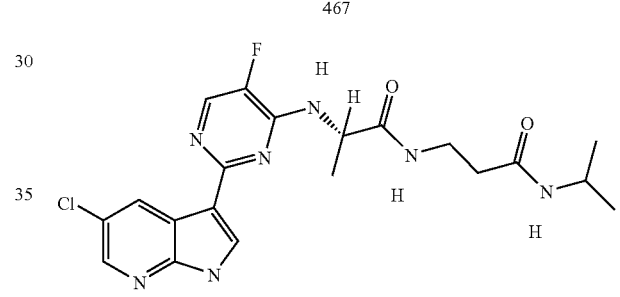

468

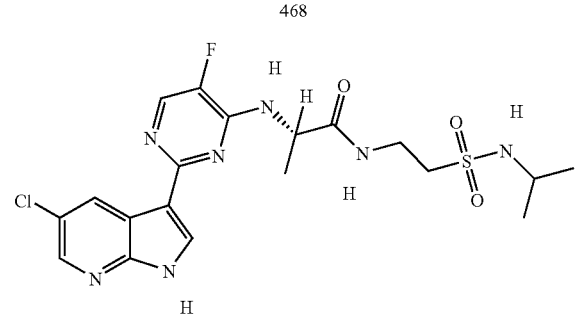

469

4. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In certain embodiments, the compounds are useful for the treatment of immune responses such as allergic or type I hypersensitivity reactions or asthma; autoimmune diseases such as transplant rejection, graft versus host disease, rheumatoid arthritis, amyotrophic lateral sclerosis, and multiple sclerosis; neurodegenerative disorders such as Familial amyotrophic lateral sclerosis (FALS); and solid and hematologic malignancies such as leukemias and lymphomas.

These compounds and pharmaceutical compositions thereof are also useful for treating or preventing a variety of disorders, including, but not limited to, heart disease, diabetes, Alzheimer's disease, immunodeficiency disorders, inflammatory diseases, hypertension, allergic diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, ovarian cancer, breast cancer and endometrial cancer), liver disease including hepatic ischemia, heart disease such as myocardial infarction and congestive heart failure, pathologic immune conditions involving T cell activation, and neurodegenerative disorders.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a JAK-3, ROCK and Aurora.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder.

In other aspects, the invention comprises a method for treating or lessening the severity of a variety of disorders, including, but not limited to, heart disease, diabetes, Alzheimer's disease, immunodeficiency disorders, inflammatory diseases, hypertension, allergic diseases, autoimmune diseases, destructive bone disorders such as osteoporosis, proliferative disorders, infectious diseases, immunologically-mediated diseases, and viral diseases. In other aspects, the invention comprises methods for preventing cell death and hyperplasia and therefore may be used to treat or prevent reperfusion/ischemia in stroke, heart attacks, and organ hypoxia. In other embodiments, the invention comprises methods for preventing thrombin-induced platelet aggregation. The invention also comprises methods for treating, lessening the severity or preventing disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, ovarian cancer, breast cancer and endometrial cancer), liver disease including hepatic ischemia, heart disease such as myocardial infarction and congestive heart failure, pathologic immune conditions involving T cell activation, and neurodegenerative disorders.

The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection.

This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of JAK-3, ROCK and Aurora isoforms, and thus, without wishing to be bound by any particular theory, the compounds and compositions are particularly useful for treating or lessening the severity of a disease, condition, or disorder where activation of JAK-3, ROCK or Aurora is implicated in the disease, condition, or disorder. When activation of JAK-3, ROCK or Aurora is implicated in a particular disease, condition, or disorder, the disease, condition, or disorder may also be referred to as a "JAK-3-mediated disease", "ROCK-mediated disease", "Aurora-mediated disease" or disease symptom. Accordingly, in another aspect, the present invention provides a method for treating or lessening the severity of a disease, condition, or disorder where activation or one or more of JAK-3, ROCK or Aurora isoforms is implicated in the disease state.

The activity of a compound utilized in this invention as an inhibitor of JAK-3, ROCK or Aurora may be assayed in vitro, in vivo or in a cell line. In vitro assays include assays that determine inhibition of either the phosphorylation activity or ATPase activity of activated JAK-3, ROCK or Aurora. Alternate in vitro assays quantitate the ability of the inhibitor to bind to JAK-3, ROCK or Aurora. Inhibitor binding may be measured by radiolabelling the inhibitor prior to binding, isolating the inhibitor/JAK-3, inhibitor/ROCK or inhibitor/Aurora complex and determining the amount of radiolabel bound. Alternatively, inhibitor binding may be determined by running a competition experiment where new inhibitors are incubated with JAK-3, ROCK or Aurora bound to known radioligands.

The term "measurably inhibit", as used herein means a measurable change in JAK-3, ROCK or Aurora activity between a sample comprising said composition and a JAK-3, ROCK or Aurora kinase and an equivalent sample comprising JAK-3, ROCK or Aurora kinase in the absence of said composition.

The term "JAK-mediated disease", as used herein means any disease or other deleterious condition in which a JAK family kinase is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction.

The term "Aurora-mediated condition" or "disease", as used herein, means any disease or other deleterious condition in which Aurora is known to play a role. The term "Aurora-mediated condition" or "disease" also means those diseases or conditions that are alleviated by treatment with a Aurora inhibitor. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

Examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting JAK-3, ROCK or Aurora activity in a biological sample or a patient, which method comprises administering to the patient, or contacting said biological sample with a compound of formula I or a composition comprising said compound. The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of JAK-3, ROCK or Aurora kinase activity in a biological sample is useful for a variety of purposes that are known to one of skill in the art. Examples of such purposes include, but are not limited to, blood transfusion, organ-transplantation, biological specimen storage, and biological assays.

EXAMPLES
Although certain exemplary embodiments are described in detail below, it will be appreciated that additional compounds of general formula I can be prepared according to the methods described generally herein using appropriate starting materials by methods generally available to one of ordinary skill in the art.
Scheme 1
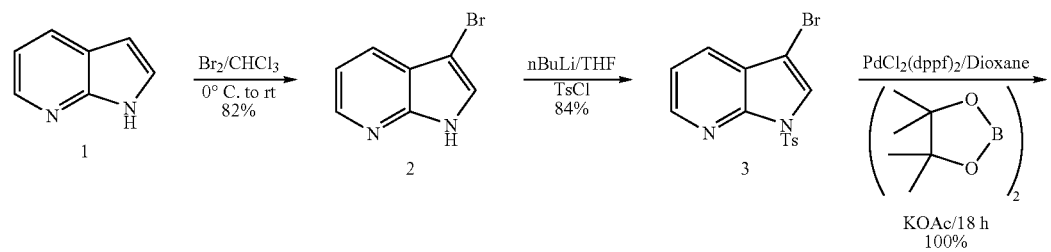
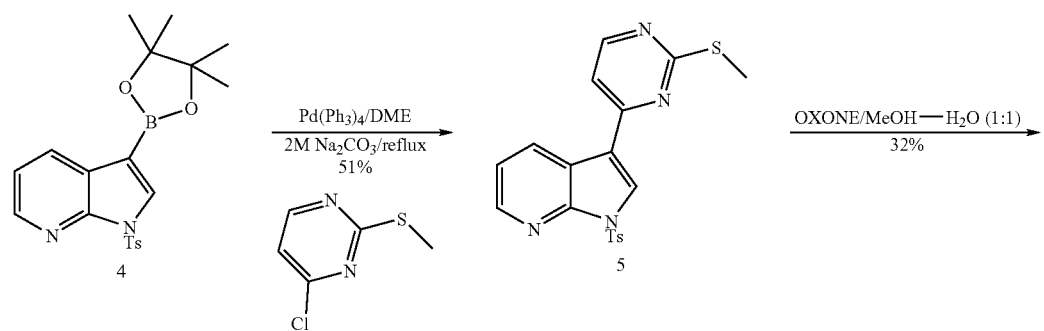
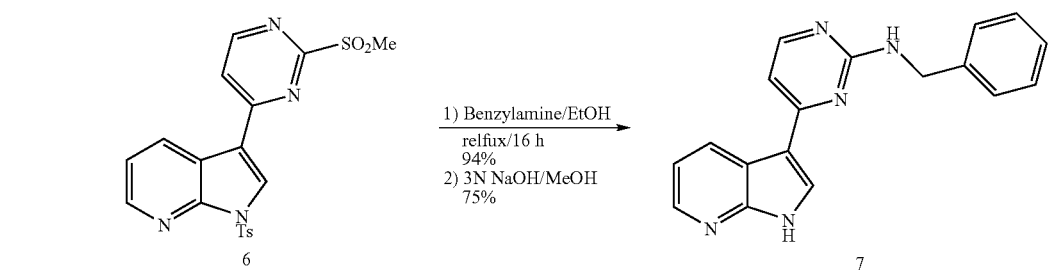
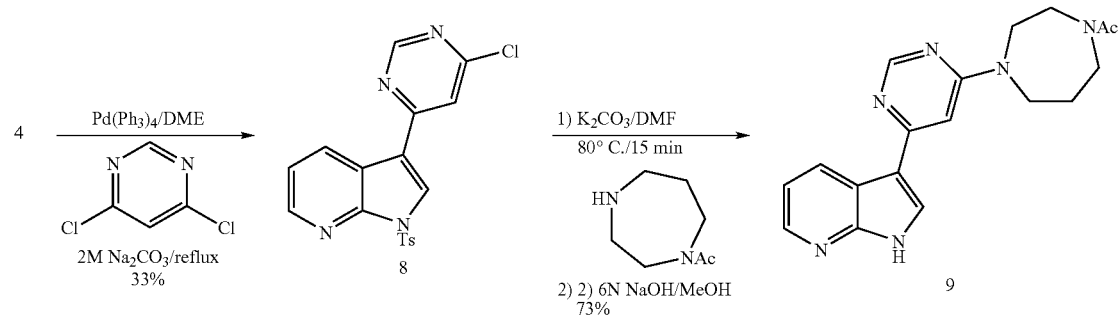

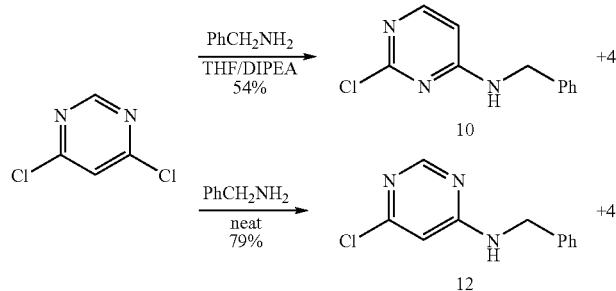
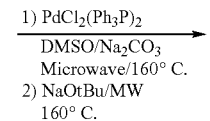
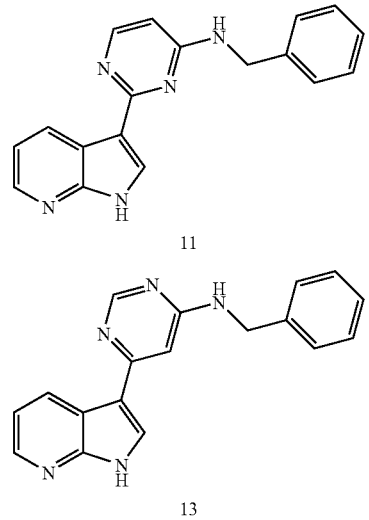

3-Bromo-1H-pyrrolo[2,3-b]pyridine (2)

Azaindole 1 (4 g, 0.025 mol) in 100 mL of chloroform was cooled to 0° C. Bromine in 20 mL of chloroform was added dropwise the resulting mixture was stirred at 0° C. for 1 h. The resulting suspension was diluted with 0.5N HCl and the aqueous layer was made basic with 0.5 N NaOH and the solid filtered to provide 4 g (82%) of crude product 2 that was used directly for the next step.

3-Bromo-1-(toluene-4-sulfonyl)-1H-pyrrolo[2,3-b]pyridine (3)

3 g (0.015 mol) of 2 in 20 mL of anhydrous THF was cooled to −78° C. and n-BuLi 2.5 M in hexanes (6.7 mL, 0.167 mol) was added dropwise. After 15 minutes of stirring, tosyl chloride in 5 mL of THF was added dropwise. The cooling bath was removed and the reaction mixture stirred at rt for 1 h. Extracted with ether and the organic phase washed with brine, dried with magnesium sulfate and concentrated in vacuo to give a white solid that was passed through a pad of silica (70% EtOAc; 30% Hexanes) to give 4.65 g (84%) of 3. $^1$H NMR CDCl$_3$ 8.4 (s, 1H), 8.1 (d, 2H), 7.8 (s, 2H), 7.2 (m, 3H), 2.3 (s, 3H).

3-(4,4,5,5-Tetramethyl-[1,3,2]dioxaborolan-2-yl)-1-(toluene-4-sulfonyl)-1H-pyrrolo[2,3-b]pyridine(4)

3 (850 mg, 0.0024 mol) was dissolved in 20 mL of DME and pinnacol borane (921 mg, 0.0036 mol), Pd$_2$Cl$_2$ (dppf)$_2$ (197 mg, 0.24 mmol) and KOAc (713 mg, 0.00726 mol) were added and the mixture was stirred and refluxed at 90° C. for 18 h. Diluted with ethyl acetate and the organic phase washed with water and brine then dried (Na$_2$SO$_4$) and concentrated in vacuo. The residue was subjected to flash chromatography (20% EtOAc/80% hexanes) to give 900 mg (99%) of the desired product 4.

3-(2-Methylsulfanyl-pyrimidin-4-yl)-1-(toluene-4-sulfonyl)-1H-pyrrolo[2,3b]pyridine (5)

A mixture of boronic ester 4 (900 mg, 0.0023 mol), 4-chloro-2-thiomethyl pyrimidine (341 mg, 0.0029 mol), Pd(Ph$_3$P)$_4$ (260 mg, 0.23 mmol) and 2 M sodium carbonate (3.4 mL, 0.0068 mol) in 20 mL of DME was refluxed under nitrogen for 18 h. Diluted with ethyl acetate and the organic phase washed with water and brine then dried (Na$_2$SO$_4$) and concentrated in vacuo. The residue was subjected to flash chromatography (40% EtOAc/60% hexanes) to give 460 mg (51%) of the desired product 5. $^1$H NMR CDCl$_3$ 8.8 (d, 1H), 8.7 (m, 2H), 8.4 (s, 1H), 8.1 (d, 2H), 7.2 (m, 4H), 2.6 (s, 3H), 2.3 (s, 3H).

3-(2-Methanesulfonyl-pyrimidin-4-yl)-1-(toluene-4-sulfonyl)-1H-pyrrolo[2,3-b]pyridine (6)

Pyrimidine 5 (460 mg, 0.0012 mol) was dissolved in 20 mL of methanol-water (1:1) then oxone (2.14 g, 0.0035 mol) was added and the reaction was refluxed for 18 h. The methanol was removed in vacuo and the aqueous was extracted with ethyl acetate. The organic phase washed with water and brine then dried (Na$_2$SO$_4$) and concentrated in vacuo. The residue was subjected to flash chromatography (40% EtOAc/60% hexanes) to give 160 mg (32%) of the desired product 6. LCMS ES$^+$=428.9.

Benzyl-[4-(1H-pyrrolo[2,3-b]pyridin-3-yl)-pyrimidin-2-yl]-amine (7)

A solution of 6 (20 mg, 0.047 mmol) and benzylamine (0.007 mL, 0.061 mmol) in 1 mL of ethanol was heated in a seal tube at 80° C. for 18 h. The solvent was evaporated and the crude product was purified by preparative TLC (50% EtOAc/50% hexanes) to give 20 mg of product which was deprotected with 2 mL of 3N NaOH in methanol for 4 h. Added 2 mL of 3N HCl and evaporated to dryness. Reverse phase HPLC (20-70% MeCN-water with 0.1% TFA (20 mL/min) gave 10 mg (75%) of 7.
$^1$H NMR DMSOD$_6$ 8.7 (s, 1H), 8.4 (s, 1H), 8.25 (d, 1H), 8.1 (d, 1H), 7.4 (m, 2H), 7.25 (m, 3H), 7.2 (s, 1H), 7.15 (dd, 1H), 7.1 (s, 1H), 4.8 (s, 2H). LCMS ES$^+$=302.0.

3-(6-Chloro-pyrimidin-4-yl)-1-(toluene-4-sulfonyl)-1H-pyrrolo[2,3-b]pyridine (8)

A solution of boronate 4 (0.11 g, 0.276 mmol), 4,6-dichloropyrimidine (0.049 g, 0.331 mmol), catalytic Pd(PPh$_3$)$_4$ and excess potassium carbonate in DMF was heated in the microwave at 160° C. for 5 minutes resulting in conversion to product by TLC (20% EtOAc:hexanes). The reaction was partitioned between EtOAc/H₂O, extracted, stripped down in vacuo and purified by silica column (eluent:5% EtOAc:hexanes) giving 8 (0.035 g) as a white solid in 33% yield.

1-{4-[6-(1H-Pyrrolo[2,3-b]pyridin-3-yl)-pyrimidin-4-yl]-[1,4]diazepan-1-yl}-ethanone (9)

A solution of 8 (0.035 g, 0.091 mmol), N-acetyl-homopiperizine (0.025 g, 0.18 μmol), excess potassium carbonate in DMF was heated at 80° C. resulting in a color change after 5 minutes. LC/MS and TLC indicated conversion to tosyl protected product after 15 minutes. 1 ml of 6N NaOH and 1 ml of methanol were added to the reaction resulting in the immediate removal the tosyl group by LC/MS (M+1=337). The reaction was partitioned between EtOAc/H₂O and extracted. The crude product was purified by preparative HPLC giving 9 (0.022 g) as a clear oil in 73% yield.

NMR: MeOD 2.0 bs(2H), 2.1 s(3H), 3.6 m(2H), 3.8-4.3 bm(6H), 7.1 d(1H), 7.3 m(1H), 8.2 d(1H), 8.35 m(2H), 8.65 d(1H). LC/MS (M+1)=337

Benzyl-(2-chloro-pyrimidin-4-yl)-amine (10)

To a solution of 2,4-dichloropyrimidine (0.15 g, 1.0 mmol), benzylamine (0.109 ml, 1.0 mmol) in THF was added DIPEA (0.526 ml, 3.0 mmol) and the reaction was heated at reflux for 2 hours resulting in formation of a 4:1 mixture of regioisomers (desired versus undesired) by TLC (5% Methanol:methylene chloride). The reaction was stripped down in vacuo and purified by silica column (eluent: 2% methanol: methylene chloride) giving 0.12 g (0.548 mmol) of desired product 10 in 54% yield. LC/MS (M+1)=220

Benzyl-(6-chloro-pyrimidin-4-yl)-amine (12)

Benzyl amine (0.697 ml, 6.76 mmol) was added to 4,6-dichloropyrimidine (1.0 g, 6.76 mmol) neat causing a vigorous reaction and color change. The reaction was slowly diluted with methylene chloride resulting in a white precipitate. 1 ml of triethyl amine was added and TLC indicated conversion to product (5% MeOH:methylene chloride). The reaction was loaded directly onto a silica and purified (eluent: 2% MeOH:methylene chloride) giving 1.17 g (5.32 mmol) of 12 as a yellow wax in 79% yield.

Benzyl-[2-(1H-pyrrolo[2,3-b]pyridin-3-yl)-pyrimidin-4-yl]-amine (11)

A solution of 4 (0.36 g, 0.09 mmol), 10 (0.028 g, 0.108 mmol), 2.0M Na₂CO₃ (0.108 ml, 0.271 mmol) and catalytic PdCl₂(PPh₃)₂ in 1 ml of DMSO was heated in the microwave at 160° C. for 5 minutes resulting in conversion to tosyl protected product by LC/MS (M+1)=456. NaOtBu (0.026 g, 0.271 mmol) was added to the reaction and it was heated in the microwave for 5 minutes at 160° C. resulting in complete conversion to product 11. The reaction was filtered and purified by preparative HPLC giving 0.0032 g of 11 as a white solid in 11% yield.

NMR: MeOD 4.95 bs(2H), 6.6 d(1H), 7.2 m(1H), 7.3-7.5 mm(5H), 8.0 d(1H), 8.3 d(1H), 8.4 s(1H), 8.55 d(1H). LC/MS (M+1)=302

Final product 13 was formed as described for 11 giving 0.012 g (0.039 mmol) of 13 as a white solid. NMR: MeOD 4.8 s(2H), 7.05 s(1H), 7.2-7.6 m (6H), 8.2 s(1H), 8.4 m (2H), 8.55 s(1H). LC/MS (M+1)=302

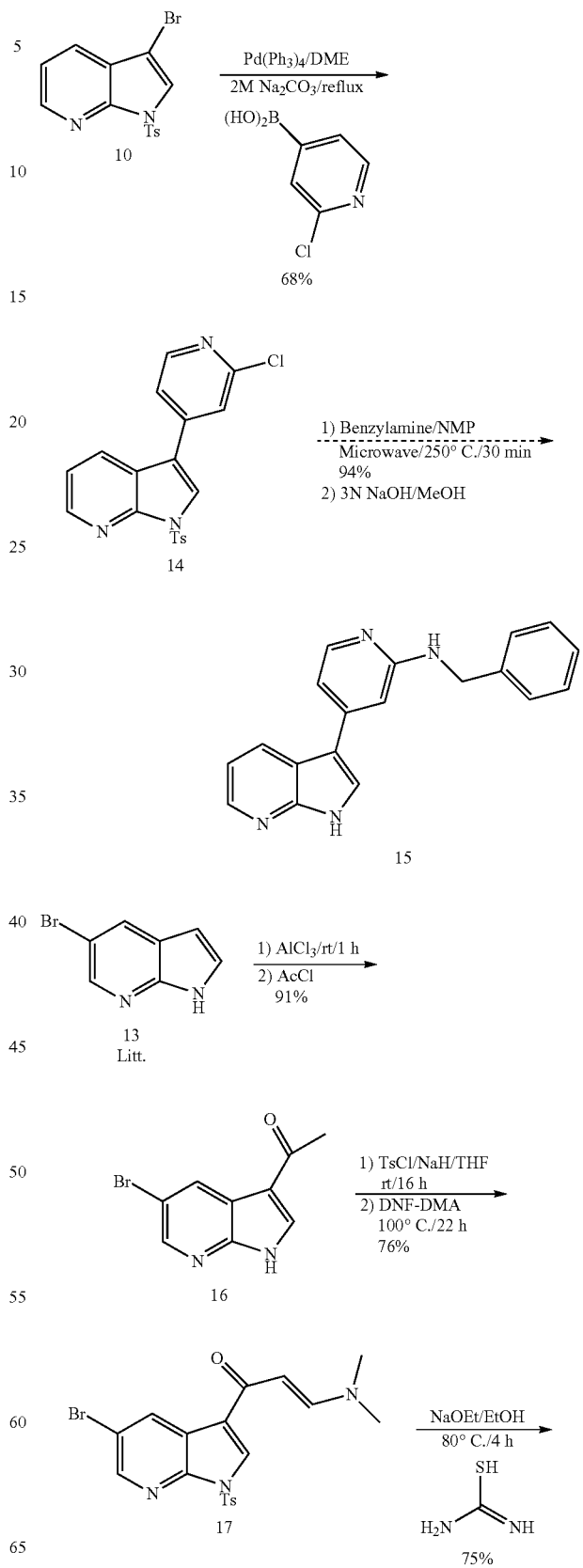

Scheme 2 Synthesis of 5-H-azaindole pyrimidine and pyridine analogues

-continued

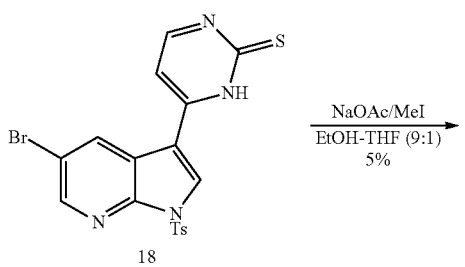

18

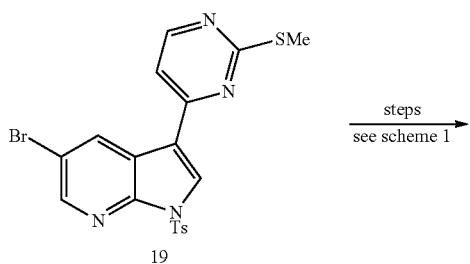

19

3-(2-Chloro-pyridin-4-yl)-1-(toluene-4-sulfonyl)-1H-pyrrolo[2,3-b]pyridine (14)

A mixture of azaindole 3 (80 mg, 0.23 mmol), 2-chloropyridine-4-boronic acid (41 mg, 0.27 mmol), Pd(Ph$_3$P)$_4$ (20 mg, 0.11 mmol) and 2 M sodium carbonate (0.34 mL, 0.68 mmol) in 2 mL of DME was microwaved on high at 160° C. for under nitrogen for 15 minutes. Diluted with ethyl acetate and the organic phase washed with water and brine then dried (Na$_2$SO$_4$) and concentrated in vacuo. The residue was subjected to flash chromatography (40% EtOAc/60% hexanes) to give 60 mg (68%) of the desired product 14. $^1$H NMR CDCl$_3$ 8.6 (d, 2H), 8.1 (m, 4H), 7.25 (m, 5H), 2.5 (s, 3H). The 2-chloropyridine could be displaced, for example, with benzylamine in a microwave reaction at 250° C. for 30 min followed by deprotection to give compound 15.

1-(5-Bromo-1H-pyrrolo[2,3-b]pyridin-3-yl)-ethanone (16)

7-Azaindole 13 (2.16 g, 0.011 mol) was dissolved in 75 mL of dry DCM. Aluminium trichloride (4.36 g, 0.0327 mol) was added to the solution and the reaction mixture was stirred for 1 h at rt. Acetyl chloride (1.16 mL, 0.0164 mol) was added dropwise to the mixture and stirred at rt for 18 h. 20 mL of methanol was added and the reaction for 1 h. Concentrated in vacuo and suspended in water-EtOAc mixture. Extraction with EtOAc and drying of the organic gave, after concentration in vacuo, 2.37 g (91%) of compound 14. $^1$H NMR CDCl$_3$ 9.5 (bs, 1H), 8.8 (s, 1H), 8.5 (s, 1H), 7.9 (s, 1H), 2.4 (s, 3H).

1-[5-Bromo-1-(toluene-4-sulfonyl)-1H-pyrrolo[2,3-b]pyridin-3-yl]-3-dimethylamino-propenone (17)

To a suspension of NaH (263 mg, 0.0104 mol) in dry THF at 0° C. was slowly added 16 (2.37 g, 0.01 mol) in THF. Stirred for 0° C. for 15 min then p-toluensulfonyl chloride (2.27 g, 0.012 mol) in THF was added and the reaction mixture stirred for 18 h at rt. Quenched with water and extracted with ethyl acetate. The organic layer was dried and concentrated in vacuo to 3.37 g of a solid residue that was used directly for the next step. The above intermediate was mixed with DMF-DMA (5.7 mL, 0.0428 mol) and heated at 100° C. for 22 h. Concentrated in vacuo and subjected to flash chromatography (60% EtOAc/40% hexanes) to give 3.37 g (76% from 17) of the desired product 15. $^1$H NMR CDCl$_3$ 8.8 (s, 1H), 8.3 (s, 1H), 8.1 (s, 1H), 8.05 (d, 2H), 7.8 (d, 1H), 7.2 (s, 2H), 5.7 (d, 1H), 3.0 (bs, 6H), 2.2 (s, 3H).

6-(5-Bromo-1H-pyrrolo[2,3-b]pyridin-3-yl)-1H-pyrimidine-2-thione (18)

To a freshly prepared solution of sodium (175 mg, 0.0076 mol) in ethanol (18 mL) were consecutively added compound 17 (1.0 g, 0.0022 mol) and thiourea (187 mg, 0.0025 mol). The mixture was heated to reflux for 4 h. The solvent was removed and the residue was dissolved in 8 mL of water. The solution was neutralized with 1 n HCl and extracted with ethyl acetate. The organic phase was dried and concentrated in vacuo to provide 570 mg (75%) of technically clean 18. $^1$H NMR CDCl$_3$ 12.2 (s, 1H), 8.6 (s, 1H), 8.3 (s, 1H), 8.2 (s, 1H), 7.6 (d, 1H), 5.8 (d, 1H).

5-Bromo-3-(2-methylsulfanyl-pyrimidin-4-yl)-1-(toluene-4-sulfonyl)-1H-pyrrolo[2,3-b]pyridine (19)

A suspension of 18 (565 mg, 0.0018 mol), sodium acetate (526 mg, 0.0039 mol), methyl iodide (0.126 mL, 0.0020 mol) in 15 mL of ethanol-THF (9:1) was heated to reflux for 2 h. Cooled to rt and filtered. Chromatography (70% EtOAc-30% hexane) provided 48 mg (9%) of the thiomethyl intermediate. Tosylation provided 49 mg (70%) of the desired compound 19. $^1$H NMR CDCl$_3$ 8.8 (d, 1H), 8.5 (m, 2H), 8.35 (s, 1H), 8.1 (d, 2H), 7.25 (m, 3H), 2.7 (s, 3H), 2.3 (s, 3H).

Benzyl-[4-(5-bromo-1H-pyrrolo[2,3-b]pyridin-3-yl)-pyrimidin-2-yl]-amine (20).

This compound could be prepared from 19 via oxone oxidation and benzylamine displacement following Scheme 1.

Scheme 3 Synthesis of 5-Substituted-azaindole pyrimidine and pyridine analogues
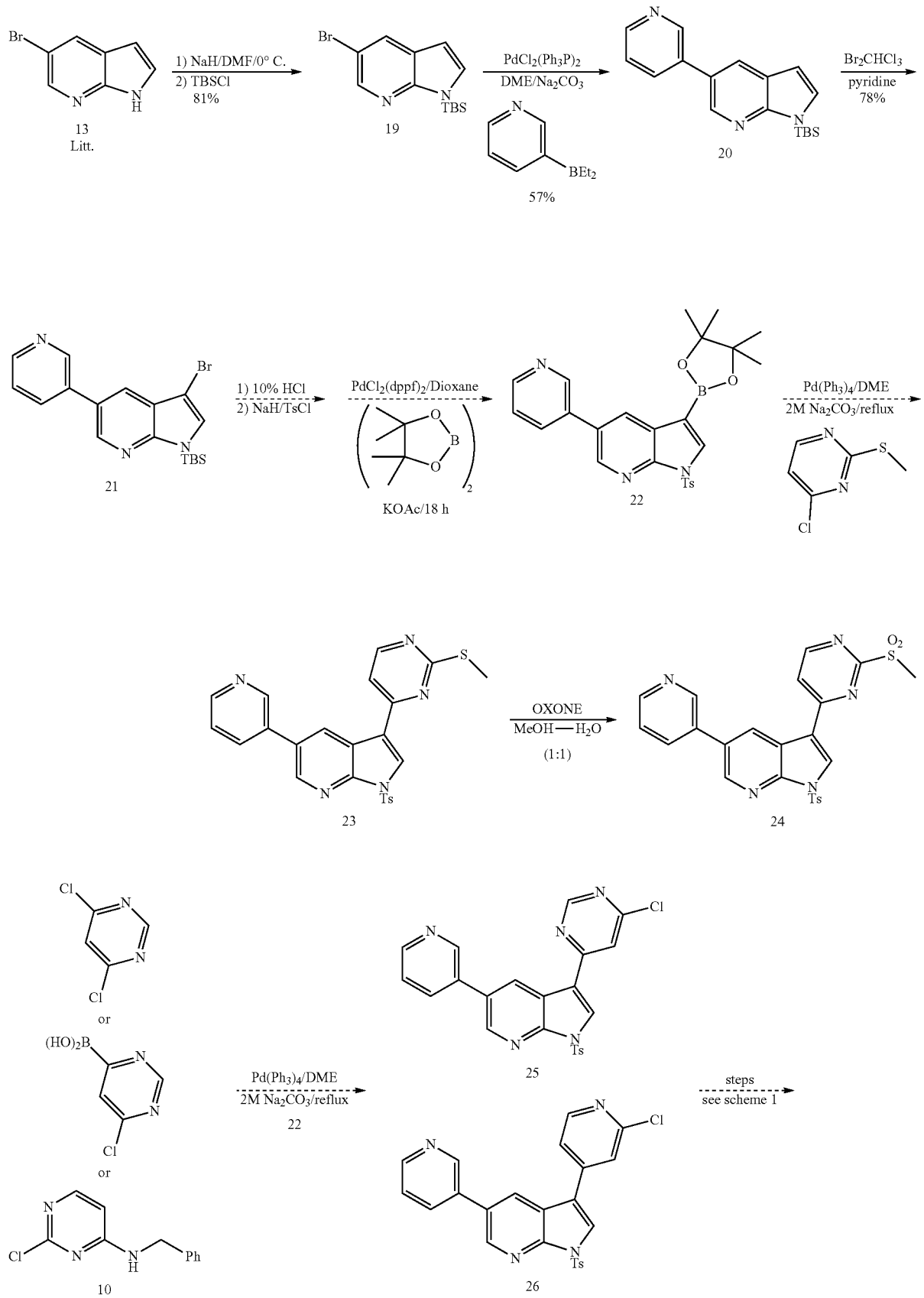

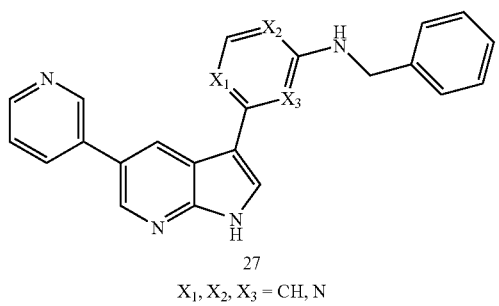

27

$X_1, X_2, X_3 = CH, N$

5-Bromo-1-(tert-butyl-dimethyl-silanyl)-1H-pyrrolo[2,3-b]pyridine (19)

To a suspension of NaH (200 mg, 0.0078 mol) in 15 mL of dry DMF at 0° C. was added azaindole 13 (1.36 g, 0.007 mol) in 5 mL of DMF. Stirred at 0° C. for 10 min. and TBDMSCl in 3 mL of DMF was added and the resulting mixture stirred O.N. Taken in EtOAc and washed with water, brine. The organic layer was dried and concentrated in vacuo to an oil that was used directly for the next step without further purification. $^1$H NMR CDCl$_3$ 8.3 (d, 1H), 7.9 (d, 1H), 7.2 (d, 1H), 6.4 (d, 1H), 0.85 (s, (H), 0.5 (s, 6H).

1-(tert-Butyl-dimethyl-silanyl)-5-pyridin-3-yl-1H-pyrrolo[2,3-b]pyridine (20)

To a solution of 19 (1.77 g, 0.0057 mol), 3-diethylpyridyl borane (1.0 g, 0.0068 mol) in 80 mL of DME, was added PdCl$_2$(Ph$_3$P)$_2$ (320 mg, 0.455 mmol) and aqueous 2M sodium carbonate (8.5 mL, 0.017 mol) under nitrogen. The reaction mixture was refluxed for 3 h. Cooled to rt and diluted with ethyl acetate and washed with brine. The organic layer was dried and concentrated to an oil that was subjected to flash chromatography (30% EtOAc-70% hexanes) to give 1 g (57%) of the desired material 20. $^1$H NMR CDCl$_3$ 8.9 (s, 1H), 8.5 (d, 1H), 8.4 (d, 1H), 8.0 (d, 1H), 7.9 (d, 1H), 7.5 (d, 1H), 7.2 (d, 1H), 6.5 (d, 1H), 0.85 (s, 9H), 0.55 (s, 6H).

3-Bromo-1-(tert-butyl-dimethyl-silanyl)-5-pyridin-3-yl-1H-pyrrolo[2,3-b]pyridine (21)

A solution of bromine (0.166 mL, 0.0032 mol) in 1 mL of CCl$_4$ was added dropwise to a stirred solution of 20 (1.0 g, 0.0032 mol) and pyridine (0.314 mL, 0.0039 mol) in dry CHCl$_3$ (30 mL) at 0° C. The reaction mixture was stirred at 0° C. for 1 h and then neutralized with 10 mL of a mixture of sodium bicarbonate-sodium:thiosulfate (1:1). The organic layer was separated and further extracted with dichloromethane (3×10 mL) and the combined organics dried and concentrated in vacuo. The residue was subjected to flash chromatography (30% EtOAc-70% hexanes) to give 0.97 g (78%) of the desired material 21. $^1$H NMR CDCl$_3$ 8.9 (s, 1H), 8.55 (d, 1H), 8.4 (d, 1H), 8.0 (d, 1H), 7.9 (d, 1H), 7.4 (dd, 1H), 7.2 (s, 1H), 0.9 (s, 9H), 0.5 (s, 6H).

5-Pyridin-3-yl-3-(4,4,5,5-tetramethyl-[1,3,2]dioxaborolan-2-yl)-1-(toluene-4-sulfonyl)-1H-pyrrolo[2,3-b]pyridine (22)

Compound 21 could be desilylated with, for example, 10% HCl and tosylated with, for example, NaH and p-toluenesulfonyl chloride. Compound 22 could be prepared using the same protocol as for compound 4 in Scheme 1.

3-(2-Methanesulfonyl-pyrimidin-4-yl)-5-pyridin-3-yl-1-(toluene-4-sulfonyl)-1H-pyrrolo[2,3-b]pyridine (24)

Compound 24 could be prepared using the same protocol as for compound 6 in Scheme 1.

3-(6-Chloro-pyrimidin-4-yl)-5-pyridin-3-yl-1-(toluene-4-sulfonyl)-1H-pyrrolo[2,3-b]pyridine (25)

Compound 25 could be prepared using the same protocol as for compound 8 in Scheme 1.

3-(2-Chloro-pyridin-4-yl)-5-pyridin-3-yl-1-(toluene-4-sulfonyl)-1H-pyrrolo[2,3-b]pyridine (26)

Compound 26 could be prepared using the same protocol as for compound 14 in Scheme 2.

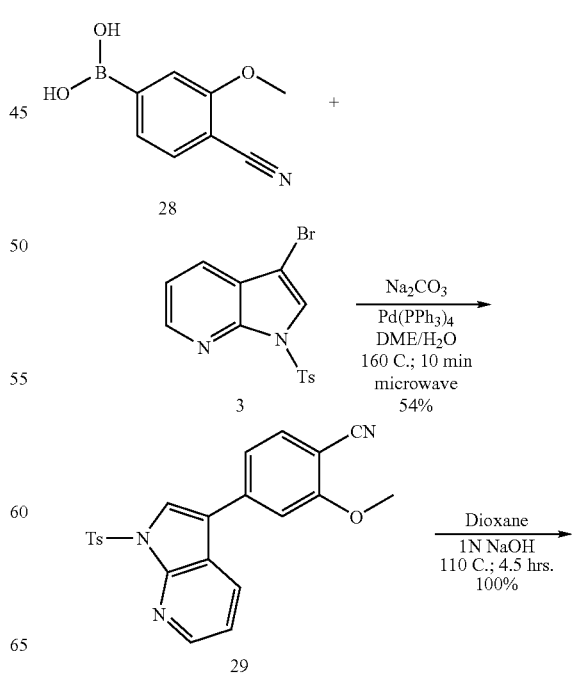

Scheme 4

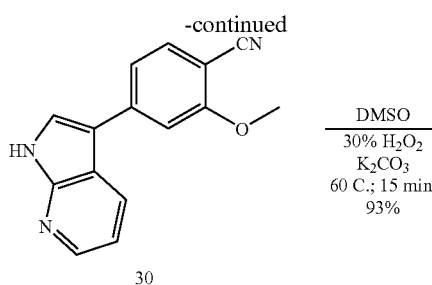

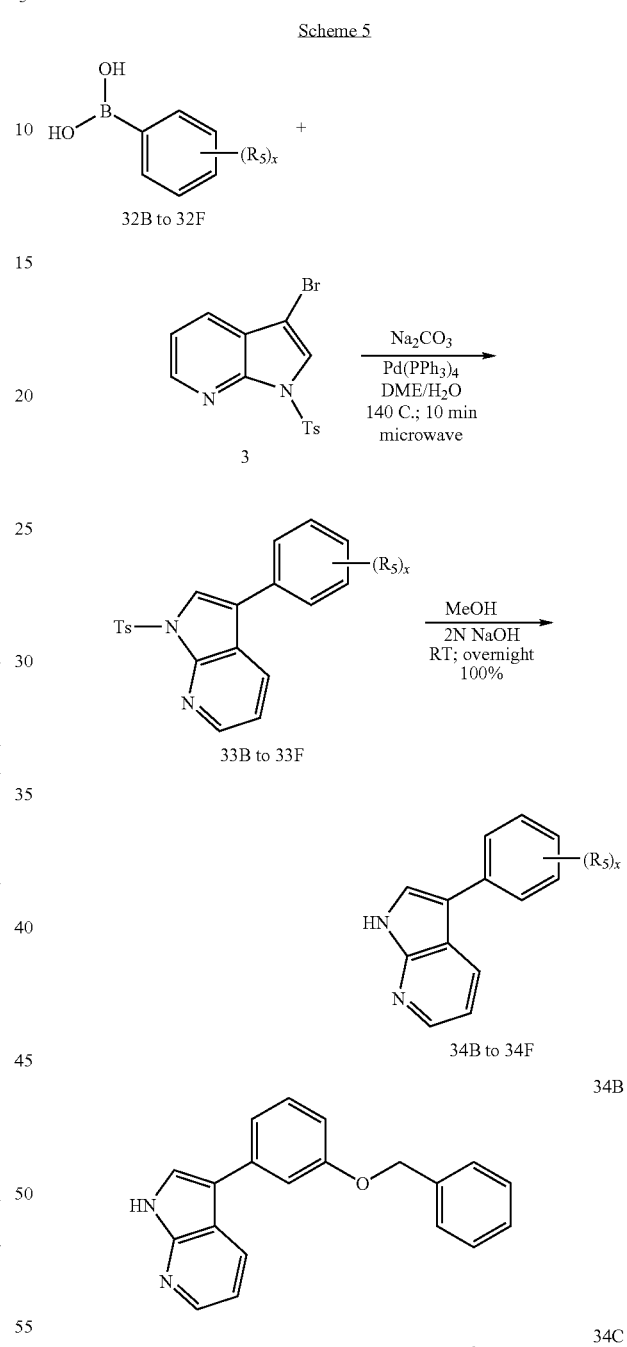

1H), 8.32 (d, 1H), 8.24 (m, 1H), 8.01 (m, 1H), 7.88 (d, 1H), 7.59 (s, 1H), 7.40 (s, 1H), 7.37 (m, 2H), 7.15 (dd, 1H), 4.00 (s, 3H). LC/MS (M+1)=268.

2-Methoxy-4-[1-(toluene-4-sulfonyl)-1H-pyrrolo[2,3-b]pyridin-3-yl]-benzonitrile (29)

In a tube was placed boronic acid 28 (35.4 mg, 200 μmol), and tosyl protected azaindole 3 (65.5 mg, 194 μmol), with sodium carbonate (61.8 mg, 583 μmol) and tetrakis(triphenylphosphine)palladium(0) (8.3 mg, 7.2 μmol). Water (323 mg) and Ethylene glycol dimethyl ether (848 mg) were added and the mixture was deoxygenated. The tube was sealed and heated to 16° C. for 10 minutes with magnetic stirring, utilizing microwave irradiation. The crude product was extracted with ethyl acetate and water. The organics were washed with brine, dried over sodium sulfate, filtered and concentrated to give crude product (83 mg). The crude was purified via flash chromatography and eluted with a gradient from 1:1 ethyl acetate/hexane to 100% ethyl acetate to 4/4/1 ethyl acetate/hexane/7N ammonia in methanol to give 29 (42 mg, 54%) and 30 (7.7 mg, 15%).

2-Methoxy-4-(1H-pyrrolo[2,3-b]pyridin-3-yl)-benzonitrile (30)

The tosyl protecting group was removed from 29 by refluxing in dioxane (5 ml) with 1N sodium hydroxide (200 μl, 2 eq.) for 4.5 hours. The reaction was concentrated and extracted with ethyl acetate and saturated aqueous sodium bicarbonate. The organics were washed with brine, dried over sodium sulfate, filtered and concentrated to give 30 (30 mg, 100%). $^1$H NMR CD$_3$CN 10.00 (s, 1H), 8.32 (m, 2H), 7.83 (s, 1H), 7.65 (d, 1H), 7.40 (m, 2H), 7.20 (dd, 1H), 4.02 (s, 3H). LC/MS (M+1)=250

2-Methoxy-4-(1H-pyrrolo[2,3-b]pyridin-3-yl)-benzamide (31)

The nitrile 30 (10 mg, 40 μmol) was dissolved in dimethyl sulfoxide (0.5 ml). To this was added potassium carbonate (20 mg) and 30% hydrogen peroxide in water (100 μl). The reaction was warmed to approximately 60 C for 15 minutes. The reaction was concentrated to dryness and triturated in water. The resulting precipitate was filtered and dried in-vacuo overnight to give 31 (10 mg, 93%). $^1$H NMR DMSO-d6 11.99 (s, -continued

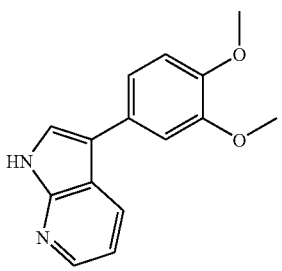
34D

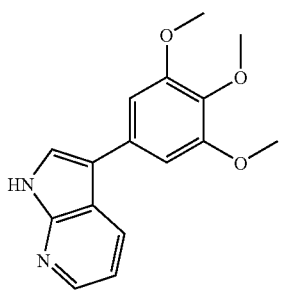
34E

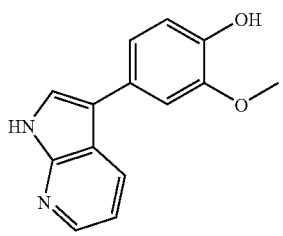
34F

Boronic acids 32B through 32F (500 μmol) were placed in tubes with azaindole 3 (87 mg, 250 μmol). In each vial was placed sodium carbonate (53 mg, 500 μmol) and tetrakis (triphenylphosphine)palladium(0) (15 mg, 13 μmol). Water (1 ml) and Ethylene glycol dimethyl ether (2 ml) were added and the tubes were deoxygenated and sealed. The tubes were heated to 140 C via microwave, for 10 minutes. The reactions were cooled to 0 C and quenched with 2N hydrochloric acid in water (1 ml). The reactions were extracted with ethyl acetate. The organics were washed with brine, dried over sodium sulfate, filtered and concentrated. The products were purified on silica (50% ethyl acetate/hexane to 100% ethyl acetate gradient) to give 33B to 33F.

The compounds 33B to 33F were dissolved in methanol (20 ml) and treated with 2N sodium hydroxide in water (1 ml) at room temperature, overnight. The reactions were neutralized with 2N hydrochloric acid (1 ml) and concentrated to dryness. The products were purified via chromatography on silica gel (50% ethyl acetate/hexane to 100% ethyl acetate gradient) or mass directed reverse phase chromatography on C18 (15% acetonitrile/water with 0.09% trifluoroacetic acid to 35% acetonitrile/water with 0.09% trifluoroacetic acid over 15 minutes) to give products 34B to 34F.

3-(3-Benzyloxy-phenyl)-1H-pyrrolo[2,3-b]pyridine (34B)

$^1$H NMR DMSO-d6 11.95 (s, 1H), 8.29 (m, 1H), 8.20 (d, 1H), 7.89 (s, 1H), 7.49 (d, 2H), 7.41 (t, 2H), 7.34 (m, 2H), 7.29 (m, 2H), 7.13 (dd, 1H), 6.90 (m, 1H), 5.20 (s, 2H). LC/MS (M+1)=301.

3-(4-Benzyloxy-phenyl)-1H-pyrrolo[2,3-b]pyridine (34C)

$^1$H NMR DMSO-d6 11.84 (s, 1H), 8.28 (m, 2H), 7.76 (s, 1H), 7.61 (d, 2H), 7.48 (d, 2H), 7.39 (t, 2H), 7.32 (t, 1H), 7.15 (dd, 1H), 7.09 (d, 2H), 5.13 (s, 2H). LC/MS (M+1)=301.

3-(3,4-Dimethoxy-phenyl)-1H-pyrrolo[2,3-b]pyridine (34D)

$^1$H NMR DMSO-d6 11.90 (s, 1H), 8.31 (d, 1H), 8.28 (d, 1H), 7.80 (s, 1H), 7.21 (m, 2H), 7.19 (dd, 1H), 7.02 (d, 1H), 3.86 (s, 3H), 3.78 (s, 3H). LC/MS (M+1)=255.

3-(3,4,5-Trimethoxy-phenyl)-1H-pyrrolo[2,3-b]pyridine (34E)

$^1$H NMR DMSO-d6 11.85 (s, 1H), 8.29 (d, 1H), 8.27 (d, 1H), 7.83 (s, 1H), 7.15 (d, 1H), 6.92 (s, 2H), 3.86 (s, 6H), 3.69 (s, 3H). LC/MS (M+1)=285.

2-Methoxy-4-(1H-pyrrolo[2,3-b]pyridin-3-yl)-phenol (34F)

$^1$H NMR DMSO-d6/D$_2$O 8.25-8.30 (m, 2H), 7.74 (s, 1H), 7.20 (d, 1H), 7.17 (dd, 1H), 7.10 (dd, 1H), 6.86 (d, 1H), 3.88 (s, 3H). LC/MS (M+1)=241.

Scheme 6

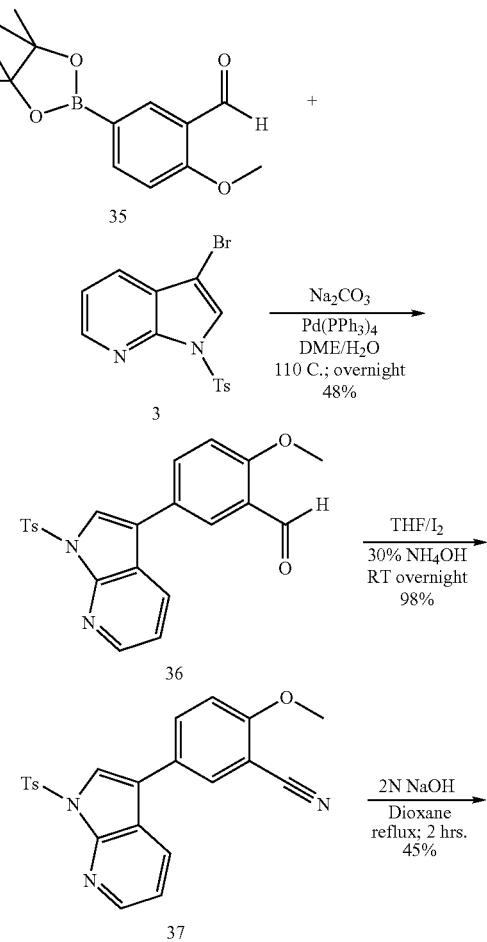

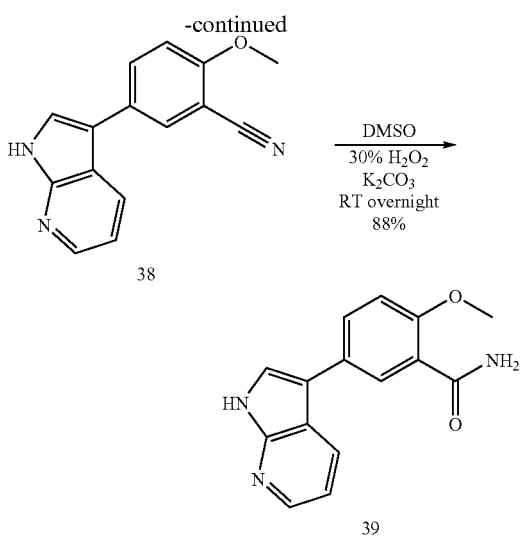

2-Methoxy-5-[1-(toluene-4-sulfonyl)-1H-pyrrolo[2,3-b]pyridin-3-yl]-benzaldehyde (36)

In a tube was placed boronate ester 35 (131 mg, 500 μmol), and 3 (175 mg, 500 μmol), with sodium carbonate (114 mg, 1.08 mmol) and tetrakis(triphenylphosphine)palladium(0) (22 mg, 19 μmol). Water (0.9 g) and Ethylene glycol dimethyl ether (2.1 g) were added and the mixture was deoxygenated. The tube was sealed and heated to 110 C overnight, with magnetic stirring. The crude product was extracted with ethyl acetate and water. The organics were washed with brine, dried over sodium sulfate, filtered and concentrated to give crude product. The crude was purified via flash chromatography and eluted with a gradient from 1:1 ethyl acetate/hexane to 100% ethyl acetate to 4/4/1 ethyl acetate/hexane/7N ammonia in methanol to give 36 (98 mg, 48%).

2-Methoxy-5-[1-(toluene-4-sulfonyl)-1H-pyrrolo[2,3-b]pyridin-3-yl]-benzonitrile (37)

The aldehyde 36 (98 mg, 241 μmol) was dissolved in tetrahydrofuran (5 ml). To this was added 30% aqueous ammonium hydroxide (3 ml) and iodine (79 mg, 313 μmol). The reaction was stirred at room temperature overnight. The reaction was diluted with water and extracted with ether and ethyl acetate. The organics were washed with aqueous sodium sulfite (50 mg) in water (10 ml). The organics were washed with brine, dried over sodium sulfate, filtered and concentrated to give 37 (95.8 mg, 98%).

2-Methoxy-5-(1H-pyrrolo[2,3-b]pyridin-3-yl)-benzonitrile (38)

The nitrile 37 (95.8 mg, 237 μmol) was dissolved in dioxane (5 ml) and treated with 2N sodium hydroxide in water (250 μl, 500 μmol). The reaction was sealed and heated to reflux for 2 hours. The reaction was concentrated to dryness and extracted with ethyl acetate and water. The organics were washed with brine, dried over sodium sulfate, filtered and concentrated to give crude product (72.3 mg). The crude was purified via flash chromatography and eluted with a gradient from 1:1 ethyl acetate/hexane to 100% ethyl acetate to 4/4/1 ethyl acetate/hexane/7N ammonia in methanol to give 38 (26.7 mg, 45%).

2-Methoxy-5-(1H-pyrrolo[2,3-b]pyridin-3-yl)-benzamide (39)

The de-tosylated nitrile 38 (26.7 mg, 107 μmol) was dissolved in dimethyl sulfoxide (2.49 g). To this was added potassium carbonate (32.7 mg, 237 μmol) and 30% hydrogen peroxide in water (85.5 mg) and the reaction was stirred at room temperature overnight. The reaction was diluted with water and the resulting precipitate was washed with water, acetonitrile and ether to give final product 39 (25.3 mg, 88%). $^1$H NMR DMSO-d6 11.86 (s, 1H), 8.28 (m, 1H), 8.19 (d, 1H), 8.11 (m, 1H), 7.81 (m, 2H), 7.70 (s, 1H), 7.55 (s, 1H), 7.21 (d, 1H), 7.16 (m, 1H), 3.91 (s, 3H). LC/MS (M+1)=268

4-Bromo-2-methoxybenzonitrile

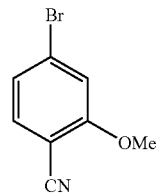

In a 1 L round-bottomed flask, 53.94 g (270 mmol) of 4-bromo-2-fluorobenzonitrile was dissolved in 500 mL of THF. Sodium methoxide (21.99 g, 407 mmol) was added and the mixture was heated to reflux until TLC ($SiO_2:CH_2Cl_2$) showed complete consumption of starting material. The mixture was poured into 1N HCl and the THF was evaporated in vacuo. The remaining mixture was extracted with diethyl ether. The extract was dried ($MgSO_4$) and filtered over a plug of silica gel. The plug was eluted with $CH_2Cl_2$ and the filtrate was evaporated in vacuo to afford 45.56 g (80%) of the product as a white solid. $^1$H NMR (500 MHz, $CDCl_3$) δ 7.42 (d, 1H), 7.17 (dd, 1H), 7.14 (d, 1H), 3.95 (s, 3H).

4-Cyano-3-methoxyphenyl boronic acid (28)

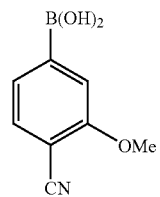

A 3-necked 1 L round-bottomed flask was equipped with an overhead stirrer, and a nitrogen line. The flask was charged with 45.56 g (215 mmol) of 4-bromo-2-methoxybenzonitrile, 64 mL (277 mmol) of tri-isopropylborate and 500 mL of THF. The solution was cooled to −78° C. in a dry-ice/acetone bath. n-Butyllithium (2.5M, 110 mL, 275 mmol) was added dropwise via addition funnel. The mixture was stirred for 30 minutes and 2N HCl was added. The mixture was stirred for an hour and poured into water. The mixture was extracted with $Et_2O$. The organic solution was backextracted with 1N NaOH. The aqueous layer was washed with $Et_2O$ and acidified with conc. HCl. The mixture was extracted with $Et_2O$. The organic extract was dried ($MgSO_4$) and evaporated in vacuo to afford 20.77 g (55%) of the product as a white solid. $^{1}$H NMR (500 MHz, d6-DMSO) δ 7.68 (d, 1H), 7.59 (s, 1H), 7.47 (d, 1H), 3.95 (s, 3H).

Schemes 7 and 8:

Scheme 7:

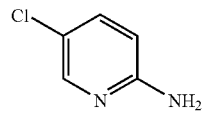 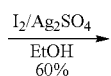

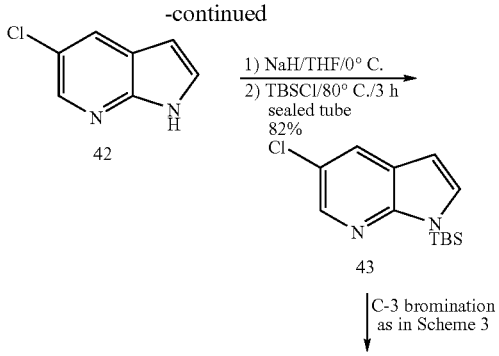

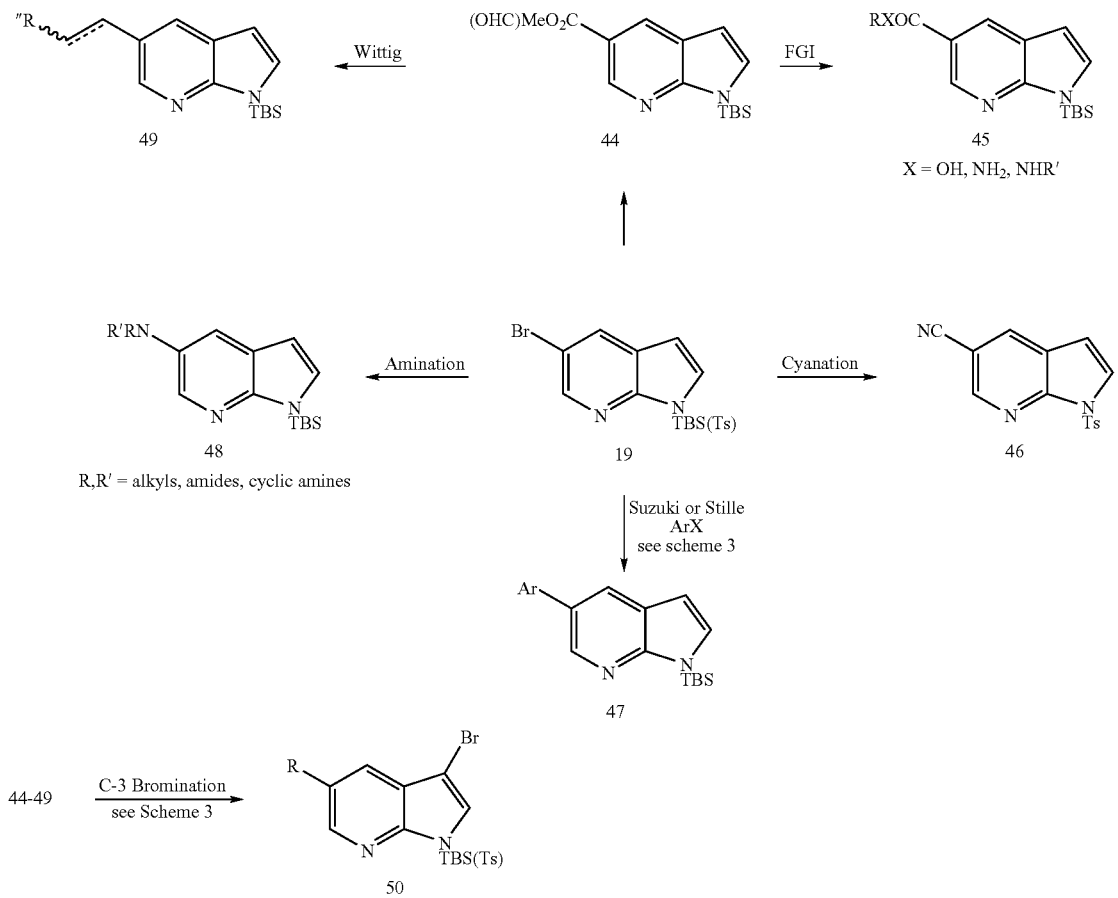

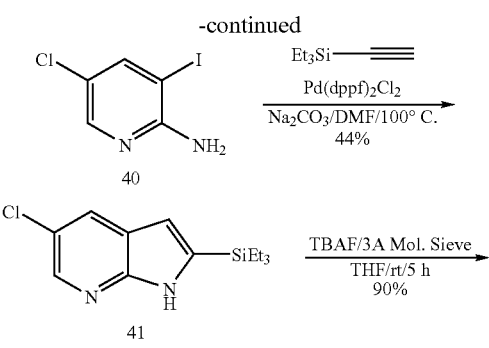

5-Chloro-3-iodo-pyridin-2-ylamine (40)

Iodine (16.28 g, 64 mmol) was added to a mixture of 1-amino-5-chloropyridine (8.25 g, 64 mmol) and silver sulfate (20 g, 64 mmol) in 400 mL of ethanol and the mixture was stirred at rt for 20 h. The mixture was filtered over celite and the solvent removed in vacuo. The residue was dissolved in DCM (600 mL) and washed with 5% aqueous NaOH (500 mL), water and brine. The organic layer was dried and concentrated in vacuo to solid residue that was subjected to flash chromatography (20% EtOAc-80% hexanes) to give 9.8 g (60%) of 40. $^{1}$H NMR (500 MHz, CDCl$_{3}$) 7.9 (s, 1H), 7.7 (s, 1H), 5.0 (bs, 2H).

5-Chloro-2-(triethyl-silanyl)-1H-pyrrolo[2,3-b]pyridine (41)

A mixture of 40 (9.5 g, 37.3 mmol) was dissolved in 320 mL of DMF and triethylsilylacetylene (20 mL, 112 mmol), Pd$_2$Cl$_2$ (dppf)$_2$ (1.52 g, 1.9 mmol), lithium chloride (1.58 g, 37.3 mmol) and 2M Na$_2$CO$_3$ (7.9 mL, 74.7 mL) were added and the mixture was stirred and refluxed at 90° C. for 15 h under nitrogen. Diluted with ethyl acetate-ether mixture (1:1) and the organic phase washed with water and brine then dried (Na$_2$SO$_4$) and concentrated in vacuo. The residue was subjected to flash chromatography (20% EtOAc/80% hexanes) to give 4.37 g (44%) of the desired product 41. $^1$H NMR (500 MHz, CDCl$_3$) 9.4 (bs, 1H), 8.2 (s, 1H), 7.9 (s, 1H), 6.6 (s, 1H), 0.9 (t, 9H), 0.75 (q, 6H).

5-Chloro-1H-pyrrolo[2,3-b]pyridine (42)

Compound 41 (4.37 g, 0.0164 mol) was dissolved in THF. Molecular sieve (10 g of 3 A) was added followed by TBAF (32.75 mL, 0.0328). The reaction mixture was stirred for 5 h at rt. Diluted with ethyl acetate and washed several times with water, brine and the organic layer was dried and concentrated in vacuo to an oil that was subjected to flash chromatography (30% EtOAc-70% hexanes) to give 02.3 g (90%) of the desired material 42. $^1$H NMR DMSO d$_6$ 11.8 (bs, 1H), 8.2 (s, 1H), 8.1 (s, 1H), 7.5 (s, 1H), 6.5 (s, 1H).

1-(tert-Butyl-dimethyl-silanyl)-5-chloro-1H-pyrrolo[2,3-b]pyridine (43)

In a sealed tube equipped with a septa under nitrogen was added 42 (600 mg, 0.00396 mol) and 20 mL of dry THF and the solution cooled to 0° C. NaH (110 mg, 0.00435 mol) was added portionwise and after 15 min. of stirring at 0° C., TBSCl (656 mg, 0.00435 mol) was added. The septa was replaced by a Teflon screw cap and the sealed tube heated at 80° C. for 3 h. Cooled and neutralized with ammonium chloride solution and extracted with hexanes. The organic phase was dried and concentrated in vacuo to an oil that was subjected to a short plug filtration (10% EtOAC-90% hexanes) to give 871 mg (82%) of compound 43. $^1$H NMR (500 MHz, CDCl$_3$) 8.2 (s, 1H), 7.8 (s, 1H), 7.25 (s, 1H), 6.4 (s, 1H), 0.9 (s, 9H), 0.6 (s, 6H).

Compound 43 can be brominated at C-3 as previously described in Scheme 3 for compound 21.

Compound 19 can be lithiated with, for example, t-BuLi and quenched with DMF to provide the 5-formyl azaindole 44. Compound 19 can also be treated with carbon monoxide and methanol in the presence of a palladium catalyst, for example, Pd(Ph$_3$P)$_4$ to provide the 5-carbomethoxy azaindole 44. Functional group interconversion to an acid, primary, secondary and tertiary amides such as 45 by standard transformations. Compound 44 can be homologated via, for example, a Wittig reaction to compounds like 49.

Compound 19 can be cyanated with, for example, KCN in heating DMF in the presence of a catalyst such as, copper or palladium to provide the 5-cyano azaindole 46.

Amination of compound 19 with, for example, and amine in the presence of a palladium catalyst can provide 5-aminated azaindoles such as 48.

Compound 19 can be arylated or heteroarylated using, for example, Suzuki or Stille coupling to provide compound like 47.

In another aspect, other synthetic schemes and compound syntheses are provided:

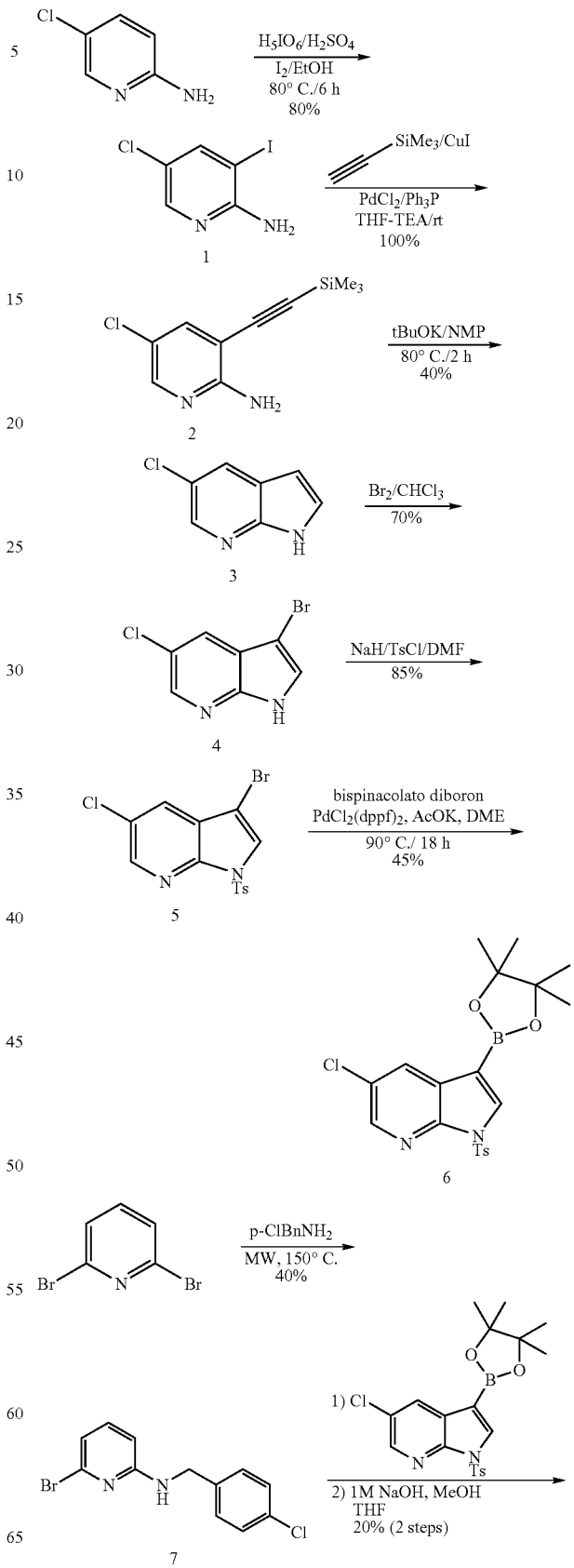

Scheme 9

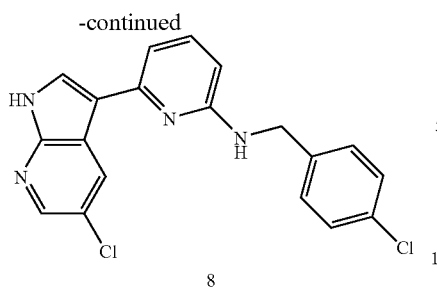

8

Example A

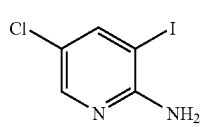

(1)

5-Chloro-3-iodo-pyridin-2-ylamine (1): A round bottom flask equipped with an air condenser was charged with 5-chloro pyridin-2-ylamine (26 g, 0.2 mol), acetic acid (78 ml) and water (18 ml). This was followed by dropwise addition of concentrated sulphuric acid (2.6 ml), portionwise addition of periodic acid (9.5 g, 0.04 mol), and iodine (20 g, 0.08 mol). The reaction mixture was vigorously stirred at 80° C. for 6 h and then allowed to cool the room temperature.

The reaction mixture was poured onto ice (~700 g). The pH of the suspension was adjusted to 8-9 with a 5M aqueous NaOH solution. A brown solid was filtered off and solubilised in EtOAc (1.21). The organic was washed with a saturated aqueous solution of $Na_2S_2O_3$, 1M NaOH solution and brine. The organic was dried over $MgSO_4$ and concentrated. The residue was recrystallised from cyclohexane to afford an orange solid (42 g, 80%). $^1$H NMR (CDCl$_3$): 4.8-5.1 (2H, brs), 7.9 (1H, s), 8.0 (1H, s)

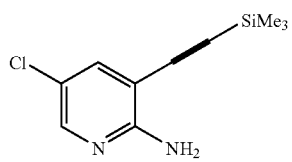

(2)

5-Chloro-3-(trimethyl-silanylethynyl)-pyridin-2-ylamine (2): A 250 ml round bottom flask was charged with 5-chloro-3-iodo-pyridin-2-ylamine (1) (42 g, 165 mmol), THF (100 ml), copper iodide (315 mg, 1.65 mmol) and PdCl$_2$(PPh$_3$)$_2$ (1.15 g, 1.65 mmol) under nitrogen. Triethylamine (70 ml, 0.5 mol), and trimethylsilyl acetylene (30 ml, 0.21 mol). The reaction mixture was stirred at room temperature for 2 h. The reaction mixture was then cooled to 0° C. and diethyl ether was added. The suspension was filtered through a celite and thoroughly washed with diethyl ether. The filtrate was concentrated and pre-absorbed onto silica gel and purified by column chromatography using as eluent, pentane/DCM 10% to 100%, to afford an off white solid (36 g, 100%). $^1$H NMR (CDCl$_3$): 0.3 (9H, s), 5.0-5.1 (2H, brs), 7.6 (1H, s), 7.9 (1H, s). MS (ES+): 225, 227.

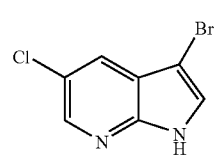

(3)

5-Chloro-1H-pyrrolo[2,3-b]pyridine (3): A solution of potassium tert-butoxide (36 g, 320 mmol) in N-methylpyrrolidone (70 ml) was heated to 80° C. under nitrogen. A solution of 5-chloro-3-(trimethyl-silanylethynyl)-pyridin-2-ylamine (2) (36 g, 160 mmol) in NMP (200 ml) was added dropwise via a dropping funnel. The reaction mixture was stirred at 80° C. for a further fifty minutes. The reaction mixture was allowed to cool to room temperature. Brine (500 ml) was added to the reaction mixture and extracted with diethyl ether (5×200 ml). The combined organics were washed with brine, dried over magnesium sulfate and concentrated in vacuo. The residue was purified by column chromatography, using as eluent pentane/EtOAc 0% to 40%, and further recrystallised from cyclohexane to afford the title compound (10 g, 41%). $^1$H NMR (CDCl$_3$) 6.5 (1H, s), 7.4 (1H, s), 8.0 (1H, s), 8.2 (1H, s), 10.4-10.6 (1H, brs). MS (ES+) 153.

(4)

3-Bromo-5-chloro-1H-pyrrolo[2,3-b]pyridine (4): A solution of bromine (3.5 ml) in chloroform (40 ml) was added dropwise to an ice-cold solution of the 5-chloro-1H-pyrrolo[2,3-b]pyridine (3) (10 g, 65 mM) in chloroform (260 ml). The reaction mixture was stirred for 60 minutes at 0° C. The reaction mixture was then hydrolysed with water and the pH of the solution was adjusted to 10. The resulting solid was removed by filtration, and the aqueous was extracted with dichloromethane. The organic was washed with water, dried over magnesium sulfate and concentrated in vacuo to afford the title compound (10.5 g, 69%). $^1$H NMR (DMSO-d$_6$) 7.8 (1H, s), 7.9 (1H, s), 8.3 (1H, s)

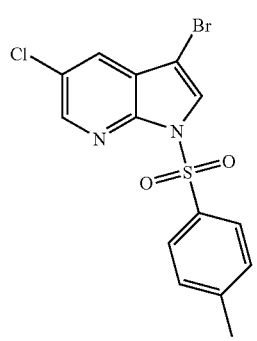

(5)

3-Bromo-5-chloro-1-(toluene-4-sulfonyl)-1H-pyrrolo[2,3-b]pyridine (5): Sodium hydride (2.2 g, 54 mmol) was added portionwise to an ice-cold solution of 3-bromo-5-chloro-1H-pyrrolo[2,3-b]pyridine (4) (10.5 g, 45 mmol) in dimethylformamide (70 ml) under nitrogen. Thirty minutes later, tosyl chloride (8.7 g, 46 mmol) was added to the reaction mixture and the reaction mixture was stirred at room temperature for 18 h. The reaction mixture was hydrolysed with water (~150 ml) and a brown solid was obtained by filtration and dried in vacuo to afford the title compound (14.8 g, 85%). 1H NMR (CDCl$_3$) 2.4 (3H, s), 7.3-7.4 (2H, d), 7.8-7.9 (2H. 2s), 8.1-8.2 (2H, d), 8.4 (1H, s); MS (ES+) 387

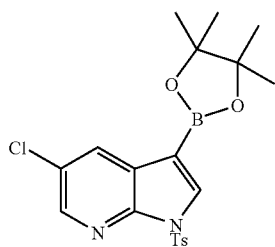

(6)

5-Chloro-3-(4,4,5,5-tetramethyl-[1,3,2]dioxaborolan-2-yl)-1-(toluene-4-sulfonyl-11H-[2,3-b]pyridine (6): A 500 ml round bottom flask was charged under nitrogen with 3-bromo-5-chloro-1-(toluene-4-sulfonyl)-1H-pyrrolo[2,3-b]pyridine (5) (6.9 g, 18 mmol), bispinacolato diboron (6.9 g, 27 mmol), PdCl$_2$(dppf)$_2$ (1.5 g, 1.8 mmol), potassium acetate (5.3 g, 54 mmol) and dimethoxyethane (100 ml). The reaction mixture was stirred at 90° C. for 18 h. The reaction mixture was diluted with ethyl acetate (200 ml) and washed with brine. The organic was dried over magnesium sulfate and concentrated in vacuo. The residue was purified by column chromatography, using as eluent pentane/EtOAc 0% to 20% and then triturated with pentane to afford the title compound (4 g, 50%). $^1$H NMR (CDCl$_3$) 1.4 (9H, s), 2.4 (3H, s), 7.2 (2H, d), 8.00-8.05 (2H, d), 8.10 (2H, s), 8.3 (1H, s). MS (ES+) 433

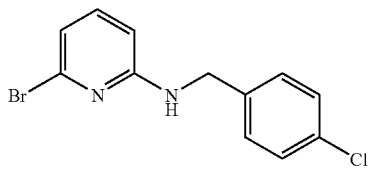

(7)

(6-Bromo-pyridin-2-yl)-(4-chloro-benzyl)-amine (7): A microwave vial was charged with 4-chloro benzylamine (700 mg; 5 mmol; 5 equivalents) and 2,6-dibromo pyridine (238 mg, 1 mmol). The reaction mixture was stirred in the microwave at 150° C. for three times ten minutes (200W maximum). The reaction mixture was diluted with diethyl ether (50 ml), washed with 10% aqueous citric acid, saturated aqueous sodium bicarbonate and brine. The organic was dried over magnesium sulfate and, after filtration, concentrated in vacuo to afford an oil as the title compound (300 mg, 100% yield). LC/MS: 299 [M+H]

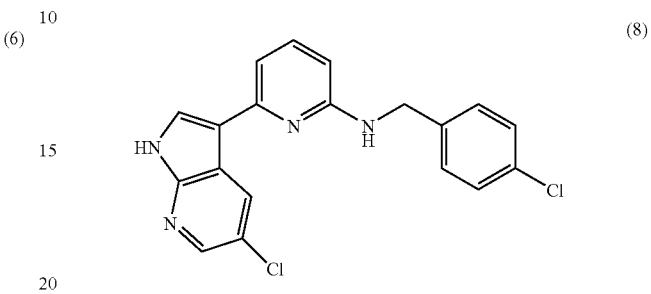

(8)

(4-Chloro-benzyl)-[6-(5-chloro-1H-pyrrolo[2,3-b]pyridin-3-yl)-pyridin-2-yl]-amine (8): A microwave vial was charged with (6-bromo-pyridin-2-yl)-(4-chloro-benzyl)-amine (300 mg, 1 mmol), 5-chloro-3-(4,4,5,5-tetramethyl-[1,3,2]dioxaborolan-2-yl)-1-(toluene-4-sulfonyl-1H-[2,3-b]pyridine (7) (215 mg, 0.5 mmol), tetrakis(triphenylphosphine) palladium (60 mg, 0.05 mmol), 2M sodium hydroxide (0.75 ml) and dimethoxyethane (5 ml). The suspension was degassed with nitrogen. The reaction mixture was stirred in the microwave at 130° C. for ten minutes (200W maximum). It was then diluted with ethyl acetate (60 ml), washed with brine twice, dried over magnesium sulfate and, after filtration, concentrated in vacuo. The compound was purified by flash chromatography (eluent: petroleum ether/ethyl acetate 60/40) to afford 50 mg of the tosyl protected title compound. This residue was taken up in a mixture of methanol and tetrahydrofuran (⅓ ml). 1M sodium hydroxide solution (1 ml) was added to the reaction mixture, which was then stirred at room temperature for three hours. The reaction mixture was then concentrated in vacuo and the residue was triturated with methanol. The suspension was filtered to afford the title compound (35 mg, 10%). $^1$H NMR (DMSO-d$_6$): 4.60-4.70 (2H, m), 6.35-6.40 (1H, d), 7.05-7.10 (1H, d), 7.20-7.25 (1H, t), 7.35-7.45 (4H, m), 8.15-8.20 (2H, m), 8.55-8.60 (1H, s), 12.5 (1H, s). LC/MS: 369 [M+H], 367 [M−H]

Table 3 below depicts data for certain exemplary compounds. Compound numbers correspond to those compounds depicted in Table 1. A "-" indicates that the measurement was not made.

TABLE 3

| Cmpd # | LC_MASS_PLUS | NMR_RESULT |
|---|---|---|
| 1 | — | 8.9 1H, d; 8.35 1H, s; 8.25 1H, d; 8.1 1H, d; 7.2 1H, dd, 7.1 1H, d; 6.5 1H s |
| 2 | 309.10 | CDCl3 9.21 (m, 1H) 9.18 (s, 1H) 8.51 (s, 1H), 8.16 (dd, J = 5.4, 1.0, 1H) 7.34 (dd, J = 8.0, 5.4, 1H), 7.25 (m 1H) 7.19 (m, 1H) 7.03 (m, 1H) 6.85 (s, 1H) |
| 3 | 324.00 | MeOD (500 MHz) 8.76 (s, 1H) 8.45 (s, 1H) 8.43 (s, 1H), 8.34 (s, 1H) 7.66 (m, 1H) 7.40 (m, 1H) 7.38 (m, 1H), 7.27 (m, 2H) |
| 4 | 288.00 | MeOD, 7.2 s (1H), 7.25 t (1H), 7.35 m (1H), 7.5 t (2H), 7.65 d (2H), 8.25 s (1H), 8.4 m (2H), 8.7 s (1H) |
| 5 | 310.00 | MeOD, 0.6 m (2H), 1.0 m (2H), 1.6 s (3H), 1.8 m (1H), 2.1 m (1H), 2.3 d (1H), 2.6 d (1H), 4.3 s (1H), 6.0 m (2H), 6.95 s (1H), 7.05 m (1H), 7.5 m (2H) |
| 6 | 212.00 | MeOD, 7.05 s (1H), 7.35 m (1H), 8.2 s (1H), 8.4 m (2H), 8.55 s (1H) |

TABLE 3-continued

| Cmpd # | LC_MASS_PLUS | NMR_RESULT |
|---|---|---|
| 7 | 302.00 | MeOD, 4.8 s (2H), 7.05 s (1H), 7.2-7.6 m (6H), 8.2 s (1H), 8.4 m (2H), 8.55 s (1H) |
| 8 | 240.10 | 1H 8.94, 1H 8.19, 1H 8.14, 2H 7.25, 1H 7.02, 2H 3.52,, 3H 1.31 |
| 9 | 337.00 | MeOD, 2.0 bs (2H), 2.1 s (3H), 3.6 m (2H), 3.8-4.3 bm (6H), 7.1 d (1H), 7.3 m (1H), 8.2 d (1H), 8.35 m (2H), 8.65 d (1H) |
| 10 | 332.00 | MeOD, 3.8 s (3H), 4.7 bs (2H), 7.0 m (3H), 7.35 m (4H), 8.2 s (1H), 8.4 m (2H), 8.6 bs (1H) |
| 11 | 308.00 | MeOD, 1.05 m (2H), 1.3 m (3H), 1.7 m (2H), 1.75-1.9 m (4H), 3.5 d (2H), 7.0 s (1H), 7.3 (1H), 8.1 s (1H), 8.35 d (1H), 8.4 d (1H), 8.6 s (1H) |
| 12 | 310.00 | MeOD1.4 m (2H), 1.7 m (2H), 2.0 m (1H), 2.65 s (1H), 3.45 m (2H), 3.6 m (1H), 4.0 d (2H), 7.0 s (1H), 7.35 m (1H), 8.2 s (1H), 8.35 d (1H), 8.45 m (1H), 8.6 s (1H) |
| 13 | 240.00 | MeOD; 1.3 t (3H), 3.65 m (2H), 7.0 s (1H), 7.3 m (1H), 8.2 s (1H), 8.4 d (2H), 8.6 m (1H) |
| 14 | 256.00 | MeOD; 3.7-3.9 dm (4H), 7.0 s (1H), 7.3 m (1H), 8.1 s (1H), 8.4 d (2H), 8.6 bs (1H) |
| 15 | 360.10 | $^1$H NMR 500 MHz (DMSO-d6) 12.35 ppm, 1H, s;, 11.02 ppm, 1H, s; 8.88 ppm, 1H, s; 8.63 ppm, 1H, d;, 8.42 ppm, 1H, s; 8.33 ppm, 2H, m; 7.25 ppm, 2H, m;, 6.97 ppm, 2H, m; 6.87 ppm, 1H, d; 3.78 ppm, 2H, s;, 3.77 ppm, 3H, s. |
| 16 | 302.00 | DMSO d$_6$ 8.7 (bs, 1H); 8.4 (bs, 1H); 8.25 (d, 1H); 8.1 (d, 1H); 7.4 (m, 2H); 7.25 (m, 3H); 7.2 (bs, 1H); 7.15 (bs, 1H); 4.7 (bs, 2H) |
| 17 | 313.00 | DMSO, 7.2 q (2H), 8.3 mm (3H), 8.6 d (2H), 8.85 dd (2H), 9.1 s (1H), 12.35 bs (2H) |
| 18 | 336.00 | MeOD, 4.8 s (2H), 7.0 s (1H), 7.3 bs (5H), 8.1 s (1H), 8.3 m (2H), 8.6 s (1H) |
| 19 | 295.00 | — |
| 20 | 337.00 | — |
| 21 | 347.90 | — |
| 22 | 347.90 | — |
| 23 | 365.90 | — |
| 24 | 422.90 | — |
| 25 | 343.95 | — |
| 26 | 328.00 | MeOD, 3.1 bm (2H), 4.0-4.4 bd (2H), 5.0-5.3 bs (2H), 7.25 s (1H), 7.3-7.35 m (4H), 7.4 m (1H), 8.3 s (1H), 8.4 d (1H), 8.5 d (1H), 8.7 s (1H) |
| 27 | 366.10 | $^1$H NMR 500 MHz (DMSO-d6) 12.33 ppm, 1H, s; 11.03 ppm, 1H, s; 8.86 ppm, 1H, s; 8.62 ppm, 1H, m; 8.43 ppm, 1H, s; 8.29 ppm, 2H, m; 7.45 ppm, 2H, m; 7.25 ppm, 1H, m; 7.20 ppm, 2H, m; 3.87 ppm, 2H, s;. |
| 28 | 348.00 | $^1$H NMR 500 MHz (DMSO-d6) 12.42 ppm, 1H, s; 11.05 ppm, 1H, s; 9.72 ppm, 1H, s; 8.89 ppm, 1H, s; 8.63 ppm, 1H, m; 8.43 ppm, 1H, s; 8.31 ppm, 2H, m; 7.25 ppm, 6H, m; 1H, m; 3.87 ppm, 2H, s; 3.00 ppm, 3H, s. |
| 29 | 423.10 | $^1$H NMR 500 MHz (DMSO-d6) 12.33 ppm, 1H, s; 11.00 ppm, 1H, s; 8.84 ppm, 1H, s; 8.59 ppm, 1H, m; 8.45 ppm, 1H, s; 8.30 ppm, 2H, m; 7.30 ppm, 6H, m; 3.83 ppm, 2H, s. |
| 30 | 330.00 | $^1$H NMR 500 MHz (DMSO-d6) 12.35 ppm, 1H, s; 11.10 ppm, 1H, s; 8.88 ppm, 1H, s; 8.62 ppm, 1H, m; 8.42 ppm, 1H, s; 8.31 ppm, 2H, m; 7.30 ppm, 5H, m; 3.90 ppm, 2H, s; |
| 31 | 348.00 | $^1$H NMR 500 MHz (DMSO-d6) 12.35 ppm, 1H, s; 11.10 ppm, 1H, s; 8.88 ppm, 1H, s; 8.62 ppm, 1H, m; 8.42 ppm, 1H, s; 8.31 ppm, 2H, m; 7.30 ppm, 5H, m; 3.90 ppm, 2H, s; |
| 32 | 309.00 | 12.25 (s, 1H), 8.67 (d, 1H), 8.40 (s, 1H),, 8.30 (d, 1H), 8.27 (d, 1H), 7.23 dd, 1H),, 7.09 (d, 1H), 4.63 (d, 2H), 3.30 (s, 2H), 2.80 (m, 2H), 2.45 (m, 1H), 1.07 (d, 6H), DMSO-d6, |
| 33 | 351.00 | 12.28 (s, 1H), 8.72 (d, 1H), 8.42 (s, 1H),, 8.31 (d, 1H), 8.28 (d, 1H), 7.25 (dd, 1H),, 7.14 (d, 1H), 4.71 (d, 2H), 4.10-4.70 (m, 2H), 3.30 (s, 1H), 3.12 (s, 2H), 2.09 (s, 3H),, 1.21 (m, 6H), DMSO-d6, |
| 34 | 308.00 | 8.90 (s, 1H), 8.60 (s, 1H), 8.39 (m, 1H),, 8.01 (m, 1H), 7.33 (m, 2H), 4.80 (s, 10H, solvent),, 3.55 (m, 1H), 3.30 (m, 14H, solvent), 1.92 (m, 2H), 1.81 (m, 3H), 1.72 (m, 1H),, 1.25-1.40 (m, 3H), 1.08-1.25 (m, 2H), MeOH-d4, |
| 35 | 385.00 | MeOD, 1.8-2.8 bm (2H), 2.35 bm (2H), 3.2 bm (1H), 3.6 (2H), 4.5-4.5 bs (3H), 7.0 bs (1H), 7.3 m (1H), 7. s (5H), 8.2 s (1H), 8.3 m (2H), 8.6 s (1H) |
| 36 | 367.00 | MeOD, 1.25 t (3H), 1.55 q (2H), 2.1 d (2H), 3.1 m (2H), 4.15 m (4H), 4.6 m (1H), 7.0 s (1H), 7.3 m (1H), 8.2 s (1H), 8.3 d (1H), 8.4 d (1H), 8.6 s (1H) |
| 37 | 337.00 | 12.32 (s, 1H), 9.3-10.5 (s, 4H), 9.01 (d, 1H), 8.51 (s, 1H), 8.48 (d, 1H), 8.19 (d, 1H), 7.53 (m, 1H), 7.25 (d, 1H), 4.82 (m, ½H),, 4.25-4.53 (m, 2½H), 3.81-3.93 (m, ½H), 3.58-3.71 (m, 1½H), 3.14-3.58 (m, 1½H),, 2.12 (s, 3H), 1.18-1.40 (m, 3H), CD3CN, |

TABLE 3-continued

| Cmpd # | LC_MASS_PLUS | NMR_RESULT |
|---|---|---|
| 38 | 337.00 | 12.4 (s, 1H), 8.96 (d, 1H),, 8.48 (s, 1H), 8.40 (d, 1H), 8.12 (d, 1H),, 7.49 (m, 1H), 7.20 (d, 1H), 4.8 (m, ½H),, 4.2-4.5 (m, 2 ½H), 3.79-3.91 (m, ½H), 3.58-3.69 (m, 1½H),, 3.12-3.58 (m, 1½H),, 2.1 (s, 3H), 1.12-1.35 (m, 3H), CD3CN,, |
| 39 | 351.00 | MeOD, 1.4 s (1H), 1.7 t (2H), 2.3 d (2H), 7.0 s (1H), 7.3 m (1H), 8.1 s (1H), 8.3 d (1H), 8.35 d (1H), 8.6 s (1H) |
| 40 | 378.90 | 12.9 (s, 1H); 9.1 (s, 1H); 8.9 (s, 1H); 8.8 (s, 1H); 8.7 (bs, 2H); 8.5 (d, 1H); 8.3 (d, 1H); 7.6 (bs, 1H); 7.4 (m, 6H); 4.7 (s, 2H) |
| 41 | 335.90 | CDCl3 8.7 (bs, 2H); 8.4 (bs, 2H); 8.3 (s, 1H); 7.4 (m, 5H); 4.8 (s, 2H) |
| 42 | 362.00 | 10.94 (m, 1H), 8.96 (d, 1H), 8.71 (s, 1H), 8.55 (s, 1H),, 8.19 (dd, 1H), 7.24 (d, 1H), 4.5-6.0 (6H), 3.7-4.3 (m, 6H),, 3.60 (m, 2H), 2.1 (s, 3H) |
| 43 | 302.00 | MeOD, 4.95 bs (2H), 6.6 d (1H), 7.2 m (1H), 7.3-7.5 mm (5H), 8.0 d (1H), 8.3 d (1H), 8.4 s (1H), 8.55 d (1H) |
| 44 | 230.10 | 1H 8.45, 3H 8.35, 2H 7.82, 1H 7.25 |
| 45 | 250.00 | 10.00 (s, 1H), 8.32 (m, 2H), 7.83 (s, 1H), 7.65 (d, 1H),, 7.40 (m, 2H), 7.20 (dd, 1H), 4.02 (s, 3H),, CD3CN |
| 46 | 268.00 | 11.99 (s, 1H), 8.32 (d, 1H), 8.24 (m, 1H),, 8.01 (m, 1H), 7.88 (d, 1H), 7.59 (s, 1H),, 7.40 (s, 1H), 7.37 (m, 2H), 7.15 (dd, 1H),, 4.00 (s, 3H),, DMSO-d6 |
| 47 | 268.00 | — |
| 48 | 238.00 | 11.98 (s, 1H), 8.32 (d, 1H), 8.26 (m, 1H), 8.15 (s, 1H),, 8.00 (s, 1H), 7.91 (d, 1H), 7.82 (d, 1H), 7.71 (d, 1H),, 7.47 (t, 1H), 7.34 (s, 1H), 7.16 (dd, 1H), DMSO-d6 |
| 49 | 238.00 | 11.97 (s, 1H), 8.29 (d, 1H), 8.21 (d, 1H), 7.92 (d, 1H),, 7.85 (d, 2H), 7.71 (d, 2H), 7.17 (s, 1H), 7.10 (dd, 1H), DMSO-d6 |
| 50 | 292.00 | 11.97 (s, 1H), 8.48 (s, 1H), 8.29 (m, 2H), 8.00 (d, 1H),, 7.88 (d, 1H), 7.71 (dd, 1H), 7.61 (s, 1H), 7.27 (d, 1H),, 7.21 (dd, 1H), 4.01 (s, 3H), DMSO-d6 |
| 51 | 301.00 | — |
| 52 | 301.00 | — |
| 53 | 255.00 | — |
| 54 | 285.00 | — |
| 55 | 241.00 | — |

Table 4 below depicts data for certain exemplary compounds. Compound numbers correspond to those compounds depicted in Table 2. A blank indicates that the measurement was not made.

TABLE 4

| Cmpd No. | LC_MASS_PLUS M + 1 (obs) | NMR_RESULT (1H NMR) | RT (mins) |
|---|---|---|---|
| 1 | 380.00 | 12.68 (m, 1H), 9.20 (s, 1H), 8.82 (s, 1H), 8.62 (m, 1H), 8.28 (m, 1H), 8.05 (s, 1H), 7.35 (s, 1H), 7.25 (m, 1H), 3.6-4.2 (m, 6H), 3.45 (m, 2H), 1.7-2.1 (m, 5H) DMSO-d6 | 1.45 |
| 2 | 379.00 | | 1.70 |
| 3 | 414.00 | | 2.30 |
| 4 | 335.90 | | 2.60 |
| 5 | 371.00 | | 2.10 |
| 6 | | MeOD 5.0 s (2H), 7.1 s (1H), 7.3 m (1H), 7.6 m (1H), 8.1 d (1H), 8.2 s (1H), 8.3-8.4m (2H), 8.55 d (1H), 8.6 s (1H), 8.7 s (1H) | |
| 7 | | MeOD 5.1 s (2H), 7.25 m (1H), 7.35 m (1H), 7.9 d (2H), 8.25 s (1H), 8.4 d (2H), 8.65 s (1H), 8.7 d (2H) | |
| 8 | 385.00, 385.00 | 11.35 (s, 1H), 9.25 (s, 1H), 9.10 (s, 1H), 9.00 (s, 1H), 8.69 (d, 1H), 7.82 (d, 1H), 5.00 (m, 2H), 4.10 (m, 2H), 2.73 (s, 3H), 1.91 (m, 6H)DMSO-d6, 12.5 (s, 1H), 8.70 (s, 1H), 8.50 (s, 1H), 8.31 (s, 1H), 8.29 (d, 1H), 7.10 (d, 1H), 4.66 (d, 2H), 4.2-4.6 (m, 2H), 3.15 (m, 2H), 2.09 (s, 3H), 1.20 (m 6H) DMSO-d6 | 2.02, 4.63 |
| 9 | 328.00 | 12.73 (s, 1H), 8.71 (s, 1H), 8.67 (s, 1H), 8.32 (s, 1H), 8.25 (d, 1H), 7.21 (m, 1H), 3.65-3.95 (m, 4H), 1.82 (m, 4H), 1.53 (m, 4H)DMSO-d6 | 2.35 |
| 10 | 346.00 | | 2.23 |
| 11 | 328.00 | 12.75 (s, 1H), 8.71 (s, 1H), 8.68 (s, 1H), 8.35 (s, 1H), 8.25 (d, 1H), 7.22 (d, 1H), 4.62 (m, 2H), 3.10 (m, 2H), 1.75 (m, 3H), 1.20 (m, 2H), 0.91 (m, 3H)DMSO-d6 | 2.40 |

TABLE 4-continued

| Cmpd No. | LC_MASS_PLUS M + 1 (obs) | NMR_RESULT (1H NMR) | RT (mins) |
|---|---|---|---|
| 12 | 332.00 | DMDO d6 12.6 (s, 1H); 9.5 (bs, 1H); 8.8 (s, 1H); 8.4 (s, 1H); 8.1 (s, 1H); 7.8 (bs, 1H): 7.4 (m, 5H); 7.1 (bs, 1H); 4.8 (d, 2H), 3.8 (s, 3H) | 2.10 |
| 13 | 346.00 | DMSO d6 12.8 (s, 1H); 9.4 (bs, 1H); 8.8 (s, 1H); 8.3 (s, 1H); 8.2 (s, 1H); 7.9 (bs, 1H): 7.4 (m, 5H); 7.2 (bs, 1H); 5.2 (bs, 1H), 3.8 (s, 3H); 1.5 (d, 3H) | 2.20 |
| 14 | 346.00 | DMSO d6 12.8 (s, 1H); 9.4 (bs, 1H); 8.8 (s, 1H); 8.3 (s, 1H); 8.2 (s, 1H); 7.9 (bs, 1H): 7.4 (m, 5H); 7.2 (bs, 1H); 5.2 (bs, 1H), 3.8 (s, 3H); 1.5 (d, 3H) | 2.20 |
| 15 | 413.00 | MeOD<br>1.2 s (3H), 1.9 m (1H), 2.2 m (1H), 2.55 m (1H), 2.6 s (3H), 3.2-3.4 m (2H), 3.55 m (1H), 3.8 m (1H), 4.5 s (2H), 5.5 bs (0.7H), 7.1 s (1H), 7.35 m (1H), 7.5-7.6 mm (5H), 8.3 s (1H), 8.4-8.5 mm (2H), 8.7 s (1H) | 1.31 |
| 16 | 320.00 | MeOD<br>4.9 s (2H), 7.0-7.6 mm (7H), 8.2 s (1H), 8.3 d (1H), 8.7 s (1H) | 1.98 |
| 17 | | MeOD<br>1.2 d (3H), 1.9 m (1H), 2.2 m (1H), 2.4 s (1H), 2.6 m (3H), 3.0 s (1H) 3.5 m (1H), 3.8 m (1H), 7.1 s (1H), 7.2 d (1H), 7.35 m (1H), 7.7 d (1H), 8.3 s (1H), 8.4 d (1H), 8.5 d (1H), 8.7 s (1H) | |
| 18 | 380.00, 380.00 | 11.95 (s, 1H), 10.47 (s, 3H), 8.51 (s, 1H), 8.17 (s, 1H), 8.09 (s, 1H), 7.77 (t, 1H), 7.18 (d, 1H), 6.87 (d, 1H), 4.4-4.6 (s, 2H) 3.99 (s, 3H), 3.32 (m, 2H), 2.13 (s, 3H), 1.35 (m, 6H) DMSO-d6, 9.82 (s, 1H), 8.32 (d, 1H), 8.08 (d, 1H), 7.93 (s, 1H), 7.58 (t, 1H), 7.20 (d, 1H), 6.66 (d, 1H), 4.2-4.7 (m, 4H), 3.91 (s, 3H), 3.12 (m, 2H), 2.10 (s, 3H), 1.35 (m, 6H) CD3CN | 1.98, 2.02 |
| 19 | 384.00, 384.00, 384.00, 384.00, 384.00, 384.00, 384.00, 384.00, 384.00 | 10.75 (s, 1H), 8.46 (s, 1H), 8.39 (s, 1H), 8.10 (s, 1H), 7.91 (t, 1H), 7.19 (d, 1H), 7.02 (d, 1H), 6.25-6.75 (s, 9H), 4.4-4.6 (s, 2H) 4.10 (d, 2H), 3.49 (m, 2H), 2.18 (s, 3H), 1.38 (d, 6H) DMSO-d6, good, good, good, 11-12.2 (s, 2H), 10.6-11.0 (s, 1H), 8.54 (s, 1H), 8.35 (s, 1H), 8.05 (s, 1H), 7.69 (t, 1H), 7.11 (d, 1H), 6.89 (d, 1H), 4.2-4.7 (s, 2H), 4.18 (d, 2H), 3.35 (m, 2H), 2.17 (s, 3H), 1.38 (m, 6H) CD3CN, 12.20 (s, 1H), 8.71 (s, 1H), 8.25 (d, 2H), 7.55 (t, 1H), 7.17 (d, 1H), 6.69 (d, 1H), 4.0-4.5 (s, 2H), 4.29 (d, 2H), 3.05 (m, 2H), 2.09 (s, 3H), 1.28 (m, 6H), 12.24 (s, 1H), 8.73 (s, 1H), 8.27 (d, 2H), 7.58 (t, 1H), 7.18 (d, 1H), 6.71 (d, 1H), 4.2-4.5 (m, 14H), 3.08 (m, 2H), 2.32 (s, 3H), 2.09 (s, 3H), 1.28 (s, 6H) DMSO-d6, 12.20 (s, 1H), 8.72 (s, 1H), 8.25 (d, 2H), 7.57 (t, 1H), 7.19 (d, 1H), 6.71 (d, 1H), 4.3-4.7 (s, 1H), 4.3 (d, 2H), 3.27 (s, 9H), 3.07 (m, 2H), 2.70 (q, 1H), 2.10 (s, 3H), 1.29 (s, 6H) DMSO-d6 DMSO-d6, 12.31 (s, 1H), 8.70 (s, 1H), 8.29 (m, 2H), 7.65 (m, 1H), 7.20 (d, 1H0, 6.80 (d, 1H), 6.5-6.8 (s, 4H), 4.28 (d, 2H), 4.0-4.6 (s, 1H), 3.15 (m, 2H), 2.41 (s, 6H), good | 2.39, 2.70, 3.26, 2.42, 3.22, 2.39, 3.35, 3.38, 3.32, 3.32, 3.32 |
| 20 | 335.00 | 10.55 (s, 1H), 8.38 (m, 1H), 8.30 (m, 2H), 7.89 (t, 1H), 7.41 (m, 4H), 7.34 (m, 1H), 7.12 (d, 1H), 6.73 (d, 1H), 4.7-5.7 (s, 4H) 4.60 (s, 2H) CD3CN | 2.39 |
| 21 | 336.00 | MeOD<br>2.65 s (0.3H, DMSO), 4.9 s (2H), 7.1 s (1H), 7.3-7.5 m (6H), 8.2 s (1H), 8.4-8.5 m (2H), 8.7 s (1H) | 2.20 |
| 22 | 370.00 | MeOD<br>4.9 s (2H), 7.1 s (1H), 7.3 bs (1H), 7.6-7.8 m (5H), 8.2 s (1H), 8.4 m (2H), 8.675 s (1H) | 2.60 |
| 23 | 378.00 | MeOD<br>2.65 s (0.9H, DMSO) 4.9 s (2H), 7.1 s (1H), 7.3-7.5 m (6H), 7.6-7.7 m (5H), 8.2 s (1H), 8.4 m (2H), 8.65 s (1H) | 2.60 |
| 24 | 367.00 | DMSO d6 12.5 (bs, 1H); 8.5 (bs, 1H); 8.2 (m, 2H); 8.0 (d, 1H); 7.3 (d, 1H); 4.0 (bs, 2H); 3.9 (s, 3H); 3.8 (bs, 2H); 3.5 (t, 2H); 2.5 (s, 3H); 1.9 (bs, 1H) | 1.70 |
| 25 | 381.10, 381.40 | DMSO d6 12.5 (bs, 1H); 8.4 (s, 1H); 8.3 (d, 1H); 8.25 (s, 1H); 8.1 (s, 1H); 7.3 (d, 1H); 4.7 (app d, 2H); 3.9 (s, 3H); 3.2 (bd, 2H); 2.1 (s, 3H); 1.2 (bs, 6H), DMSO d6 12.3 (bs, 1H); 8.5 (s, 1H); 8.25 (m, 2H); 8.1 (d, 1H); 7.2 (d, 1H); 4.65 (d, 4H); 3.9 (s, 3H); 3.2 (bd, 2H); 2.1 (s, 3H); 1.2 (bs, 6H) | 2.00, 2.00 |

TABLE 4-continued

| Cmpd No. | LC_MASS_PLUS M + 1 (obs) | NMR_RESULT (1H NMR) | RT (mins) |
|---|---|---|---|
| 26 | 316.00 | H1 MeOD: 1.3 m (1H), 3.4 s (3H), 5.1 s (2H), 7.0 s (1H), 7.1-7.4 m (7H), 8.1 s (1H), 8.3 d (1H), 8.6 s (1H) | 2.10 |
| 27 | 320.00 | H1 DMSO: 4.7 s (2H), 7.2 t (4H), 7.3 m (1H), 7.55 m (2H), 8.3 m (3H), 8.7 s (1H), 9.1-9.3 bs (0.75H) | 2.00 |
| 28 | 317.00 | H1 MeOD: 1.8 bs (2H), 4.7 s (2H), 6.7-6.85 mm (4H) 7.0-7.2 m (1H), 7.3 m (1H), 8.15 s (1H), 8.3 m (2H), 8.6 s (1H) | 1.60 |
| 29 | 338.00 | MeOD 4.9 s (2H), 6.9 m (1H), 7.0 m (2H), 7.2 s (1H), 7.3 m (1H), 8.2 s (1H), 8.4 m (2H), 8.65 s (1H) | 2.00 |
| 30 | 403.20 | CD3CN, 10.7 (bs, 1H); 8.15 (s, 1H); 8-8.1 (m, 3H); 7 (d, 1H); 3.8-4.05 (bs, 4H); 3.8 (s, 3H); 3.6 (bs, 2H); 3.3 (t, 2H); 2.8 (s, 3H); 2.4 (s, 2H) | 1.90 |
| 31 | 417.20 | CD3CN, 10.7 (s, 1H); 8.15 (s, 1H); 8 (m, 3H); 7 (d, 1H); 3.8-4 (bs, 4H); 3.85 (s, 3H); 3.6 (bs, 2H); 3.3 (m, 4H); 2.9 (m, 2H); 1.1 (m, 3H) | 2.00 |
| 32 | 427.00 | 12.33 (s, 1H), 8.78 (d, 1H), 8.37 (d, 1H), 8.28 (d, 1H), 7.87 (s, 1H), 7.69 (d, 1H), 7.49 (s, 1H), 7.44 (d, 1H), 4.37 (s, 2H), 3.5-4.2 (m, 14H), 3.10 (m, 2H), 2.08 (s, 3H), 1.32 (m, 6H) DMSO-d6 | 2.24 |
| 33 | 397.30 | DMSO-d6 12.25 (1H, bs); 8.5 (1H, s); 8.3 (1H, d); 8.2 (1H, d); 8.05 (1H, d); 7.15 (1H, bs); 4.0 (4H, m); 3.9 (3H, s); 3.8-4.0 (4H, bm); 3.6-3.8 (2H, bs); 3.4 (2H, bs); 1.1 (3H, bm) | 2.10 |
| 34 | 411.30 | DMSO-d6 12.25 (1H, bs); 8.5 (1H, s); 8.3 (1H, d); 8.2 (1H, d); 8.05 (1H, d); 7.15 (1H, bs); 3.85 (3H, s); 3.7-4.0 (8H, bm); 3.6-3.8 (2H, bs); 3.4 (2H, bs); 1.5 (2H, bs); 0.8 (3H, bm) | 2.30 |
| 35 | 408.30, 408.29 | DMSOd6 12.4 (s, 1H); 9.5 (s, 1H); 8.8 (s, 1H); 8.3 (s, 1H); 7.5 (dd, 1H); 7.2 (d, 1H); 6.7 (d, 1H); 4.6 (bs, 2H); 4.3 (d, 2H); 3.9 (s, 3H); 3.1 (bd, 2H); 2.1 (s, 3H); 1.2 (bs, 6H) | 2.90, 2.94 |
| 36 | 428.00 | 12.41 (s, 1H), 8.78 (d, 1H), 8.41 (s, 1H), 8.29 (s, 1H), 7.95 (d, 1H), 7.45 (d, 1H), 6.3-7.5 (s, 1H), 4.39 (s, 2H), 3.69 (m, 2H), 3.23 (m, 2H), 2.05 (s, 3H), 1.29 (m, 6H) DMSO-d6 | 2.38 |
| 37 | 465.40, 465.30 | DMSOd6 11.9 (s, 1H); 9.4 (s, 1H); 9.2 (s, 1H); 8.2 (s, 1H); 7.5 (dd, 1H); 7.2 (d, 1H); 6.6 (d, 1H); 4.4 (bs, 4H); 3.1 (bs, 2H); 2.1 (s, 3H); 1.5 (s, 9H); 1.2 (bs, 6H) | 3.10, 3.10 |
| 38 | 365.20 | 8.9 (s, 1H); 8.4 (s, 1H); 8.2 (s, 1H); 7.7 (dd, 1H); 7.2 (d, 1H); 6.9 (d, 1H); 4.4 (bs, 4H); 3.3 (bs, 2H); 2.2 (s, 3H); 1.4 (bs, 6H) | 2.53 |
| 39 | 315.10 | DMSO-d6: 12.3 (1H, bs); 8.3 (2H, m); 8.2 (1H, bs); 7.8 (1H, bs); 7.5 (6H, m); 6.8 (1H, bs); 4.7 (2H, s); 4-4.5 (1H, bs); 2.3 (3H, s) | 2.30 |
| 40 | 350.09 | DMSO-d6: 11.9 (bs, 1H); 8.5 (d, 1H); 8.2 (s, 1H); 8.1 (s, 1H); 7.5 (t, 1H); 7.1 (t, 1H); 6.5 (d, 1H); 3.9-4.5 (bs, 1H); 4.0 (t, 1H); 3.7 (m, 4H); 3.4 (dt, 2H); 2.4 (s, 3H); 2.1 (s, 3H); 1.9 (m, 2H) | 1.90 |
| 41 | 364.20 | DMSO-d6: 11.9 (s, 1H); 8.5 (s, 1H); 8.2 (s, 1H); 8.1 (s, 1H); 7.6 (dd, 1H); 7.2 (d, 1H); 6.7 (d, 1H); 4.5-5.4 (bs, 1H); 4.3 (d, 4H); 3.1 (bd, 2H); 2.4 (s, 3H); 2.1 (s, 3H); 1.3 (bs, 6H) | 2.40 |
| 42 | 379.00 | 12.6-13.0 (s, 1H), 12.38 (s, 1H), 8.65 (s, 1H), 8.61 (m, 1H), 8.40 (m, 1H), 8.21 (m, 1H), 8.06 (d, 1H), 7.49 (d, 2H), 7.31 (t, 2H), 7.21 (t, 1H), 7.18 (d, 1H), 6.1-6.9 (s, 1H), 4.88 (m, 2H), 3.4-4.7 (s, 2H) DMSO-d6 | 3.18 |
| 43 | 393.00 | 12.39 (s, 1H), 8.60 (s, 1H), 8.50 (t, 1H), 8.41 (s, 1H), 8.22 (s, 1H), 8.09 (d, 1H), 7.39 (m, 2H), 7.29 (m, 2H), 7.20 (m, 1H), 6.3-6.8 (m, 3H), 4.90 (d, 2H), 3.85 (s, 3H) DMSO-d6 | 3.92 |
| 44 | 379.00 | 12.12 (s, 1H), 8.20 (s, 1H), 8.10 (s, 1H), 7.82 (m, 2H), 7.32 (m, 3H), 7.21 (m, 2H), 6.50 (d, 1H), 4.60 (s, 2H), 3.8-4.5 (s, 8H) DMSO-d6 | 2.20 |
| 45 | 393.00 | 9.94 (s, 1H), 8.20 (d, 2H), 7.88 (d, 1H), 7.73 (s, 1H), 7.31-7.42 (m, 4H), 7.26 (t, 1H), 6.44 (d, 1H), 6.27 (m, 1H), 4.68 (d, 2H), 3.70 (s, 3H) CD3CN | 2.52 |
| 46 | 378.00 | mixture | 2.94 |
| 47 | 394.27 | DMSOD6 12.3 (s, 1H); 9.4 (s, 1H); 8.8 (s, 1H); 8.2 (s, 1H); 7.5 (dd, 1H); 7.2 (d, 1H); 6.7 (d, 1H); 4.4 (d, 4H); 3.1 (bd, 2H); 2.1 (s, 3H); 1.2 (bs, 6H) | 2.47 |
| 48 | 319.20 | DMSOd6 12.3 (bs, 1H); 8.4 (bd, 1H); 8.3 (d, 2H); 7.6 (bs, 1H); 7.5 (m, 4H); 7.2 (dd, 1H); 7.1 (bd, 1H); 6.5 (bs, 1H); 4.5 (s, 2H) | 2.30 |

TABLE 4-continued

| Cmpd No. | LC_MASS_PLUS M + 1 (obs) | NMR_RESULT (1H NMR) | RT (mins) |
|---|---|---|---|
| 49 | 354.30 | DMSOd6 12.2 (bs, 1H); 8.4 (app.t, 1H); 8.2 (m, 2H); 7.5 (dd, 1H); 7.1 (dd, 1H); 6.5 (bs, 1H); 3.9 (t, 1H); 3.8-3.6 (m, 4H); 3.4 (dt, 2H); 2.1 and 1.8 (s, 3H); 2.0 (t, 1H) | 2.20 |
| 50 | 368.40 | DMSO D6 12.1 (s, 1H); 8.5 (dd, 1H); 8.2 (s, 2H); 7.6 (dd, 1H); 7.2 (d, 1H); 6.8 (d, 1H); 4.3 (bd, 4H); 3.1 (db, 2H); 2.1 (s, 3H); 1.2 (bs, 6H) | 2.90 |
| 51 | 462.00 | 11.60 (s, 1H), 8.70 (s, 1H), 8.48 (s, 1H), 8.11 (s, 1H), 7.82 (t, 1H), 7.15 (d, 1H), 7.1-8.1 (s, 4H), 6.95 (d, 1H), 4.55 (s, 2H), 4.14 (m, 2H), 3.68 (m, 6H), 3.39 (m, 2H), 2.15 (s, 3H), 1.38 (m, 6H) CD3CN | 1.84 |
| 52 | 490.00 | 11.29 (s, 1H), 8.90 (s, 1H), 8.50 (s, 1H), 8.61 (m, 2H), 8.11 (s, 1H), 7.68 (t, 1H), 7.12 (d, 1H), 6.78 (d, 1H), 4.0-4.5 (m, 12H), 3.40 (m, 2H), 3.27 (m, 4H), 2.15 (s, 3H), 1.25-1.45 (m, 12H) | 1.89 |
| 53 | 436.40 | DMSO d6 12.4 (s, 1H); 9.4 (s, 1H); 8.8 (s, 1H); 8.3 (s, 1H); 7.5 (t, 1H); 7.2 (d, 1H); 6.7 (d, 1H); 5.2 (sept, 1H); 4.3 (bs, 4H); 3.1 (bs, 2H); 2.1 (s, 3H); 1.3 (d, 6H0; 1.2 (bs, 6H) | 3.40 |
| 54 | 461.00 | | |
| 55 | 475.00 | | |
| 56 | 462.00 | | |
| 57 | 476.00 | | |
| 58 | 475.00 | | |
| 59 | 407.00 | | |
| 60 | 421.00 | | |
| 61 | 499.30 | DMSO-d6: 11.9 ppm (s, 1H), 10.2 (s, 1H), 9.2 (s, 1H), 8.2 (s, 1H), 8.15 (s, 1H), 7.5 (t, 1H), 7.15-7.25 (dd, 4H), 7.15 (s, 1H), 6.7 (d, 1H), 4.2-4.8 (bs, 4H), 3.0 (bd, 2H), 2.5 (s, 6H), 2.3 (s, 3H), 2.0 (s, 3H) | 3.40 |
| 62 | 451.30 | DMSO-d6: 11.9 ppm (s, 1H), 9.6 (s, 1H), 9.1 (s, 1H), 8.15 (s, 1H), 8.1 (s, 1H), 7.5 (t, 1H), 7.1 (d, 1H), 6.7 (d, 1H), 4.35 (m, 4H), 4.1 (t, 2H), 3.05 (bd, 2H), 2.1 (s, 3H), 1.7 (m, 2H), 1.3 (bs, 6H), 0.95 (t, 3H) | 2.90 |
| 63 | 465.40 | DMSO-d6: 11.9 ppm (s, 1H), 9.6 (s, 1H), 9.1 (s, 1H), 8.15 (s, 1H), 8.1 (s, 1H), 7.5 (t, 1H), 7.1 (d, 1H), 6.7 (d, 1H), 4.35 (m, 4H), 3.9 (d, 2H), 3.05 (bd, 2H), 2.1 (s, 3H), 1.9 (m, 1H), 1.3 (bs, 6H), 0.95 (d, 6H) | 3.20 |
| 64 | 479.40 | DMSO-d6: 11.9 ppm (s, 1H), 9.6 (s, 1H), 9.1 (s, 1H), 8.15 (s, 1H), 8.1 (s, 1H), 7.5 (t, 1H), 7.1 (d, 1H), 6.7 (d, 1H), 4.35 (m, 4H), 3.85 (s, 2H), 3.05 (bd, 2H), 2.1 (s, 3H), 1.3 (bs, 6H), 0.95 (s, 9H) | 3.40 |
| 65 | 451.40 | DMSO-d6: 11.9 ppm (s, 1H), 9.6 (s, 1H), 9.1 (s, 1H), 8.15 (s, 1H), 8.1 (s, 1H), 7.5 (t, 1H), 7.1 (d, 1H), 6.7 (d, 1H), 4.9 (q, 1H), 4.35 (m, 4H), 3.05 (bd, 2H), 2.1 (s, 3H), 1.3 (m, 12H) | 2.90 |
| 66 | 423.30 | DMSO-d6: 11.9 ppm (s, 1H), 9.6 (s, 1H), 9.1 (s, 1H), 8.15 (s, 1H), 8.1 (s, 1H), 7.5 (t, 1H), 7.1 (d, 1H), 6.7 (d, 1H), 4.35 (m, 4H), 3.7, (s, 3H), 3.05 (bd, 2H), 2.1 (s, 3H), 1.3 (bs, 6H) | 2.40 |
| 67 | 428.00 | 12.31 (s, 1H), 8.71 (d, 1H), 8.41 (d, 1H), 8.29 (d, 1H), 7.56 (s, 1H), 7.07 (s, 1H), 4.0-4.8 (m, 4H), 3.3-3.9 (m, 20H), 3.13 (m, 2H), 2.10 (s, 3H), 1.16 (m, 6H) | 3.20 |
| 68 | 427.00 | 12.54 (s, 1H), 8.50 (d, 1H), 8.35 (d, 1H), 8.31 (d, 1H), 8.09 (s, 1H), 8.07 (s, 1H), 4.0-5.4 (m, 9H), 3.3 (m, 2H), 2.09 (s, 3H), 1.26 (m, 6H) | 3.70 |
| 69 | 485.30 | DMSO d6 11.9 (s, 1H), 10.3 (s, 1H), 9.2 (s, 1H), 8.25 (s, 1H), 8.15 (s, 1H), 7.5 (t, 1H), 7.45 (t, 2H), 7.25 (d, 3H), 7.15 (d, 1H), 6.7 (d, 1H), 4.0-4.8 (bs, 4H), 3.0 (bd, 2H), 2.0 (s, 3H), 1.2 (bs, 6H) | 3.20 |
| 70 | 437.30 | DMSO d6 11.8 (s, 1H), 9.6 (s, 1H), 9.1 (s, 1H), 8.2 (s, 1H), 8.1 (s, 1H), 7.5 (t, 1H), 7.1 (d, 1H), 6.7 (d, 1H), 4.4 (m, 4H), 4.15 (q, 2H), 3.0 (bd, 2H), 2.0 (s, 3H), 1.25 (m, 9H) | 3.20 |
| 71 | 515.30 | DMSO d6 11.9 (s, 1H), 10.2 (s, 1H), 9.2 (s, 1H), 8.2 (s, 1H), 8.15 (s, 1H), 7.5 (t, 1H), 7.1 (m, 3H), 7.0 (d, 2H), 6.7 (d, 1H), 4.0-4.8 (bs, 4H), 3.8 (s, 3H), 3.0 (bd, 2H), 2.0 (s, 3H), 1.2 (m, 6H) | 3.20 |
| 72 | 445.00 | 12.17 (s, 1H), 8.41 (d, 1H), 8.27 (d, 1H), 7.88 (d, 1H), 7.77 (s, 1H), 7.61 (s, 1H), 7.59 (s, 1H), 7.50 (s, 1H), 6.48 (s, 1H), 4.05 (m, 2H), 3.10 (m, 2H), 2.08 (s, 3H), 1.31 (m, 6H) DMSO-d6 | 2.84 |
| 73 | 422.40 | DMSOd6 12.3 (bs, 1H); 9.3 (s, 1H); 8.8 (s, 1H); 8.2 (s, 1H); 7.5 (dd, 1H); 7.2 (d, 1H); 6.8 (d, 1H); 4.4 (q, 2H); 4.3 (bs, 4H); 3.1 (bs, 2H); 2.1 (s, 3H); 1.3 (t, 3H); 1.2 (bs, 6H) | 3.20 |

TABLE 4-continued

| Cmpd No. | LC_MASS_PLUS M + 1 (obs) | NMR_RESULT (1H NMR) | RT (mins) |
|---|---|---|---|
| 74 | 450.40 | DMSOd6 12.3 (bs, 1H); 9.4 (s, 1H); 8.9 (s, 1H); 8.2 (s, 1H); 7.7 (dd, 1H); 7.2 (d, 1H); 6.8 (d, 1H); 4.4 (bd, 4H); 4.1 (d, 2H); 3.1 (bs, 2H); 2.1 (s, 3H); 2.05 (m, 1H); 1.3 (bs, 6H); 1.0 (d, 6H) | 3.70 |
| 75 | 429.00 | good | 3.70 |
| 76 | 399.00 | good | 3.17 |
| 77 | 366.30 | MeOD4 8.4 (s, 1H); 8.1 (s, 1H); 7.9 (s, 1H); 7.6 (dd, 1H); 7.2 (d, 1H); 6.8 (d, 1H); 4.3 (bs, 4H); 3.2 (bs, 2H); 2.2 (s, 3H); 1.3 (bs, 6H) | 2.10 |
| 78 | 429.00 | | |
| 79 | 423.00 | | |
| 80 | 423.00 | | |
| 81 | 399.00 | 12.43 (s, 1H), 8.48 (s, 1H), 8.33 (d, 1H), 8.06 (d, 1H), 7.59 (d, 1H), 6.87 (d, 1H), 4.7-6.3 (m, 4H), 4.2-4.6 (m, 1H), 4.20 (m, 2H), 3.05 (m, 2H), 2.06 (s, 3H), 1.25 (m, 6H) DMSO-d6 | 2.21 |
| 82 | 368.50 | DMSO d6 12.3 (s, 1H); 8.9 (s, 1H); 8.2 (s, 1H); 7.6 (s, 1H); 7.2 (s, 1H); 6.7 (s, 1H); 4.4 (d, 1H); 3.7-4.1 (m, 5H); 2.9 (s, 3H); 1.9-2.4 (m, 5H); 1.6 (s, 1H) | 2.10 |
| 83 | 386.40 | DMSO d6 12.2 ppm (s, 1H), 8.7 (s, 1H), 8.26 (s, 1H), 8.23 (s, 1H), 7.5 (t, 1H), 7.1 (d, 1H), 6.5 (d, 1H), 3.8 (m, 2H), 3.75 (t, 2H), 3.6 (m, 2H), 3.55 (s, 1H), 3.45 (s, 1H), 3.35 (m, 2H), 1.9 (m, 3H) | 3.10 |
| 84 | 400.40 | DMSO d6 12.2 ppm (s, 1H), 8.7 (s, 1H), 8.26 (s, 1H), 8.23 (s, 1H), 7.5 (t, 1H), 7.1 (d, 1H), 6.5 (d, 1H), 4.0 (m, 1H), 3.9 (m, 1H), 3.8 (m, 2H), 3.75 (m, 2H), 3.65 (m, 2H), 3.35 (m, 2H), 1.9 (m, 2H), 1.0 (dt, 3H) | 3.30 |
| 85 | 369.90 | DMSO-D6: 12.2 (1H, s); 8.7 (1H, s); 8.25 (2H, m); 7.6 (1H, dd); 7.25 (1H, d); 6.7 (1H, d); 3.8-3.5 (8H, m); 2.4 (2H, q); 1.05 (3H, t). | 2.62 |
| 86 | 384.00 | DMSO-D6: 12.2 (1H, s); 8.7 (1H, s); 8.25 (2H, m); 7.6 (1H, dd); 7.25 (1H, d); 6.7 (1H, d); 3.8-3.5 (8H, m); 2.4 (2H, q); 1.55 (2H, sextet); 0.95 (3H, t). | 2.86 |
| 87 | 302.90 | DMSO d6: 12.2 (s, 1H), 10.3 (s, 1H), 9.3 (d, 1H), 8.3 (d, 1H), 8.2 (d, 1H), 7.7 (t, 1H), 7.6 (m, 2H), 3.7 (s, 3H) | 3.20 |
| 88 | 330.90 | DMSO d6: 12.2 (s, 1H), 10.3 (s, 1H), 9.3 (s, 1H), 8.35 (s, 1H), 8.25 (s, 1H), 7.7 (t, 1H), 7.6 (d, 1H), 7.55 (d, 1H), 4.1 (t, 2H), 1.7 (m, 2H), 2.0 (t, 3H) | 3.90 |
| 89 | 398.00 | DMSO-D6: 12.2 (1H, s); 8.7 (1H, s); 8.25 (2H, m); 7.6 (1H, dd); 7.2 (1H, d); 6.7 (1H, d); 3.6-3.3 (8H, m); 2.3 (2H, d); 2.0 (1H, m); 0.9 (6H, d). | 3.08 |
| 90 | 344.80 | DMSO d6: 12.2 ppm (s, 1H), 10.3 (s, 1H), 9.3 (s, 1H), 8.3 (s, 1H), 8.25 (s, 1H), 7.7 (t, 1H), 7.6 (d, 1H), 7.55 (d, 1H), 3.95 (d, 2H), 2.0 (m, 1H), 1.0 (d, 6H) | 4.20 |
| 91 | 378.80 | DMSO d6: 12.2 ppm (s, 1H), 10.4 (s, 1H), 9.3 (s, 1H), 8.3 (s, 1H), 8.2 (s, 1H), 7.7 (t, 1H), 7.62 (d, 1H), 7.57 (d, 1H), 7.5 (m, 2H), 7.4 (m, 2H), 5.2 (s, 2H) | 4.20 |
| 92 | 409.00 | 12.56 (s, 1H), 8.73 (d, 1H), 8.52 (d, 1H), 8.32 (d, 1H), 8.05 (d, 1H), 7.52 (d, 1H), 4.0-4.7 (m, 4H), 3.24 (m, 2H), 2.09 (s, 3H), 1.36 (m, 6H) DMSO-d6 | 2.95 |
| 93 | 409.00 | 12.54 (s, 1H), 8.57 (d, 1H), 8.36 (d, 1H), 8.33 (d, 1H), 7.93 (d, 1H), 6.92 (d, 1H), 4.0-4.6 (m, 4H), 3.2 (m, 2H), 2.05 (s, 3H), 1.24 (m, 6H) DMSO-d6 | 2.82 |
| 94 | 437.00 | DMSO d6 8.2 (s, 1H); 8.1 (s, 1H); 8.0 (s, 1H); 7.6 (dd, 1H); 7.1 (d, 1H); 6.8 (d, 1H); 4.5 (t, 2H); 4.4 (bs, 2H); 4.3 (d, 2H); 3.7 (bs, 2H); 3.1 (bs, 2H); 3.0 (s, 6H); 2.0 (s, 3H); 1.2 (bs, 6H) | 1.59 |
| 95 | 479.00 | DMSO d6 8.2 (s, 1H); 8.1 (s, 1H); 7.9 (s, 1H); 7.5 (dd, 1H); 7.0 (d, 1H); 6.6 (d, 1H); 4.7 (t, 2H); 4.4 (d, 2H); 4.0-3.8 (bs, 6H); 3.8 (t, 2H); 3.7-3.5 (bs, 4H); 3.1 (bs, 2H); 3.0 (s, 6H); 2.0 (s, 3H); 1.2 (bs, 6H) | 1.63 |
| 96 | 436.00 | DMSO d6 8.2 (s, 1H); 8.1 (s, 1H); 7.9 (s, 1H); 7.5 (dd, 1H); 7.0 (d, 1H); 6.6 (d, 1H); 4.7 (t, 2H); 4.4 (d, 2H); 4.0-3.8 (bs, 6H); 3.8 (t, 2H); 3.7-3.5 (bs, 4H); 3.1 (bs, 2H); 3.0 (s, 6H); 2.0 (s, 3H); 1.2 (bs, 6H) | 2.25 |
| 97 | 427.00 | 12.29 (s, 1H), 8.73 (d, 1H), 8.30 (m, 2H), 8.09 (s, 1H), 7.59 (s, 1H), 7.52 (s, 1H), 7.06 (s, 1H), 4.1-4.8 (m, 4H), 3.1 (m, 2H), 2.09 (s, 3H), 1.25 (m, 6H) DMSO-d6 | 2.35 |
| 98 | 409.00 | 12.39 (s, 1H), 8.70 (d, 1H), 8.43 (d, 1H), 8.31 (s, 1H), 7.52 (s, 1H), 7.17 (s, 1H), 4.39 (m, 4H), 3.15 (m, 2H), 2.09 (s, 3H), 1.25 (m, 6H) DMSO-d6 | 3.04 |

TABLE 4-continued

| Cmpd No. | LC_MASS_PLUS M + 1 (obs) | NMR_RESULT (1H NMR) | RT (mins) |
|---|---|---|---|
| 99 | 300.90 | CDCl3: 10.3 (s, 1H); 9.7 (s, 1H); 8.3 (s, 1H); 8.1 (s, 1H); 7.9 (s, 1H); 7.7 (dd, 1H); 6.8 (d, 1H); 6.5 (d, 1H); 3.05 (d, 2H); 2.0 (m, 1H); 1.0 (d 6H). | 2.01 |
| 100 | 364.90 | DMSO-D6: 12.3 (br s, 1H); 8.6 (s, 1H); 8.3 (s, 1H); 8.2 (s, 1H); 7.5 (m, 3H); 7.3 (m, 2H); 7.2 (m 1H); 7.1 (m, 1H); 6.5 (br s, 1H); 5.05 (br s 1H); 3.75 (m, 1H); 3.7 (m, 1H). | 1.99 |
| 101 | 364.90 | CDCl3: 10.6 (br s, 1H); 10.25 (br s, 1H); 8.3 (s, 1H); 8.1 (s, 1H); 7.9 (s, 1H); 7.6 (dd, 1H); 7.3 (m, 6H); 6.8 (d, 1H); 6.25 (d, 1H); 4.6 (m, 1H); 3.95 (m, 1H); 3.9 (m, 1H). | 1.98 |
| 102 | 302.90 | DMSO-D6 (~2:1 rotational mixture): 12.6 (br s, 1H); 12.2 (br s, 1H); 8.7 (s, .33H); 8.6 (s, .67H); 8.3 (s, .67H); 8.25 (s, 1H); 8.2 (s, .33H); 7.8 (s, .67H); 7.5 (s, .33H); 7.15 (d, .67H); 7.05 (d, .33H); 6.8 (s, .67H); 6.45 (s, .33H); 4.5 (m, 1H); 4.1 (m, 1H); 3.6 (m, 2H); 1.3 (d, .6H); 1.2 (d, 2.4H). | 1.62 |
| 103 | 302.90 | DMSO-D6 (~2:1 rotational mixture): 12.65 (br s, 1H); 12.25 (br s, 1H); 8.7 (s, .4H); 8.6 (s, .6H); 8.35 (s, .67H); 8.3 (s, 1H); 8.25 (s, .33H); 7.8 (s, .67H); 7.5 (s, .33H); 7.2 (d, .67H); 7.1 (d, .33H); 6.8 (s, .67H); 6.5 (s, .33H); 4.5 (m, 1H); 4.05 (m, 1H); 3.5 (m, 2H); 1.3 (d, .6H); 1.2 (d, 2.4H). | 1.63 |
| 104 | 272.80 | DMSO d6 12.3 (s, 1H); 8.4 (s, 1H); 8.3 (s, 1H); 8.1 (s, 1H); 8.0 (d, 1H); 7.8 (d, 1H). | 2.61 |
| 105 | 271.90 | DMSO d6 12.2 (s, 1H); 8.4 (s, 1H); 8.3 (s, 1H); 8.1 (s, 1H); 7.9 (d, 1H); 7.8 (d, 1H). | 2.26 |
| 106 | 273.80 | DMSO d6 12.4 (s, 1H); 9.2 (s, 1H); 8.9 (s, 1H); 8.5 (s, 1H); 8.3 (s, 1H); 8.2 (d, 1H); 8.0 (d, 1H). | 2.34 |
| 107 | 272.90 | DMSO d6 12.3 (s, 1H); 9.1 (s, 1H); 8.9 (s, 1H); 8.5 (s, 1H); 8.3 (s, 1H); 8.1 (d, 1H); 8.0 (bs, 1H); 7.9 (d, 1H); 7.5 (bs, 1H). | 2.01 |
| 108 | 506.00 | DMSO-d6: 12.2 (s, 1H); 9.6 (br s, 1H); 9.25 (s, 1H); 8.8 (s, 1H); 8.25 (s, 1H); 7.6 (dd, 1H); 7.2 (d, 1H); 6.7 (d, 1H); 4.4 (br s, 4H); 4.0 (m, 2H); 3.8-3.6 (m, 6H); 3.35 (m, 2H); 3.2 (br s, 2H); 3.1 (br s, 2 H); 2.1 (s, 3H); 1.3 (s, 6H). | 1.59 |
| 109 | 533.00 | DMSO-d6: 12.2 (s, 1H); 9.2 (s, 1H); 8.75 (s, 1H); 8.6 (br s, 1H); 8.2 (s, 1H); 7.6 (dd, 1H); 7.2 (d, 1H); 6.75 (d, 1H); 4.4 (br s, 4H); 3.6-2.7 (m, 17H); 2.1 (s, 3H); 1.9 (m, 2H); 1.3 (s, 6H). | 1.46 |
| 110 | 452.00 | 12.09 (s, 1H), 8.28 (d, 1H), 8.20 (d, 1H), 7.77 (d, 1H), 7.11 (d, 1H), 6.97 (d, 1H), 4.0-4.7 (m, 4H), 3.30 (s, 8H), 3.18 (m, 2H), 2.10 (s, 3H), 1.28 (m, 6H) DMSO-d6 | 2.31 |
| 111 | 452.00 | 12.32 (s, 1H), 8.76 (d, 1H), 8.37 (d, 1H), 8.31 (d, 1H), 7.71 (s, 1H), 7.27 (s, 1H), 4.0-4.7 (m, 4H), 3.30 (s, 6H), 3.20 (m, 2H), 2.09 (s, 3H), 1.29 (m, 6H) DMSO-d6 | 2.59 |
| 112 | 366.00 | DMSOd6 12.2 (bs, 1H); 8.2 (s, 1H); 8.1 (s, 1H); 8.0 (s, 1H); 7.6 (dd, 1H); 7.1 (dd, 1H); 6.5 (dd, 1H); 4.0 (m, 1H); 3.9 (s, 3H); 3.8 (m, 2H); 3.75 (m, 1H); 3.7 (m, 2H); 3.5 (m, 2H); 2.0 (s, 3H); 1.9 (m, 2H) | 1.90 |
| 113 | 407.00 | DMSO d6: 11.8 ppm (s, 1H), 10 (s, 1H), 9.2 (s, 1H), 8.2 (s, 1H), 8.1 (s, 1H), 7.5 (t, 1H), 7.1 (d, 1H), 6.7 (d, 1H), 4.4 (m, 4H), 3.05 (m, 2H), 2.1 (s, 3H), 2.08 (s, 3H), 1.3 (bs, 6H) | 2.10 |
| 114 | 421.00 | DMSO d6: 11.8 ppm (s, 1H), 9.9 (s, 1H), 9.3 (s, 1H), 8.2 (s, 1H), 8.1 (s, 1H), 7.5 (t, 1H), 7.1 (d, 1H), 6.7 (d, 1H), 4.4 (m, 4H), 3.0 (m, 2H), 2.4 (m, 2H), 2.1 (s, 3H), 1.3 (bs, 6H), 1.1 (t, 3H) | 2.20 |
| 115 | 491.00 | DMSO d6: 11.9 ppm (s, 1H), 10 (s, 1H), 9.3 (s, 1H), 8.6 (bs, 1H), 8.2 (s, 1H), 8.15 (s, 1H), 7.5 (t, 1H), 7.1 (d, 1H), 6.7 (d, 1H), 4.4 (m, 4H), 3.4 (bs, 2H), 3.2 (bs, 4H), 3.0 (m, 2H), 2.9 (bs, 4H), 2.1 (s, 3H), 1.3 (bs, 6H) | 1.50 |
| 116 | 492.00 | DMSO d6: 12 ppm (s, 1H), 10.7 (bs, 1H), 9.3 (s, 1H), 8.22 (s, 1H), 8.19 (s, 1H), 7.5 (t, 1H), 7.2 (d, 1H), 6.7 (d, 1H), 4.4 (m, 4H), 4.2 (bs, 2H), 3.8 (t, 4H), 3.1 (m, 4H), 3.0 (m, 2H), 2.1 (s, 3H), 1.3 (bs, 6H) | 1.60 |
| 117 | 435.00 | DMSO d6: 11.8 ppm (s, 1H), 9.9 (s, 1H), 9.3 (s, 1H), 8.2 (s, 1H), 8.1 (s, 1H), 7.5 (t, 1H), 7.1 (d, 1H), 6.7 (d, 1H), 4.4 (m, 4H), 3.0 (m, 2H), 2.6 (m, 1H), 2.1 (s, 3H), 1.3 (bs, 6H), 1.1 (d, 6H) | 2.40 |
| 118 | 419.00 | DMSO d6: 11.9 ppm (s, 1H), 10.2 (s, 1H), 9.4 (s, 1H), 8.2 (s, 1H), 8.1 (s, 1H), 7.5 (t, 1H), 7.1 (d, 1H), 6.7 (d, 1H), 6.5 (m, 1H), 6.3 (d, 1H), 5.8 (d, 1H), 4.4 (m, 4H), 3.0 (m, 2H), 2.1 (s, 3H), 1.3 (bs, 6H) | 2.30 |
| 119 | 493.00 | DMSO d6: 11.8 ppm (s, 1H), 10.0 (s, 1H), 9.3 (s, 1H), 8.2 (s, 1H), 8.1 (s, 1H), 7.5 (t, 1H), 7.1 (d, 1H), 6.7 (d, 1H), 4.4 (m, 4H), 4.0 (m, 4H), 3.0 (m, 2H), 2.6 (m, 2H), 2.1 (s, 3H), 1.3 (bs, 6H), 1.2 (t, 3H) | 2.50 |
| 120 | 452.00 | 8.79 (d, 1H), 8.46 (s, 1H), 8.26 (d, 1H), 8.07 (s, 1H), 7.69 (d, 1H), 7.40 (d, 1H), 5.71 (s, 2H), 4.91 (s, 2H), 4.20 (s, | 2.43 |

TABLE 4-continued

| Cmpd No. | LC_MASS_PLUS M + 1 (obs) | NMR_RESULT (1H NMR) | RT (mins) |
|---|---|---|---|
| | | 2H), 3.70 (s, 4H), 3.40 (m, 2H), 3.25 (s, 1H), 3.12 (s, 1H), 3.03 (s, 1H), 2.95 (m, 2H), 1.99 (s, 3H), 1.09 (m, 6H) CD3CN with 4 drops of DMSO-d6 | |
| 121 | 506.30 | DMSO d6: 11.9 ppm (s, 1H), 10.3 (S, 1H), 9.3 (S, 1H), 8.2 (s, 1H), 8.1 (s, 1H), 7.5 (t, 1H), 7.1 (d, 1H), 6.7 (d, 1H), 4.4 (m, 4H), 4.0 (d, 2H), 3.7 (t, 2H), 3.5 (m, 4H), 3.1 (m, 4H), 3.0 (t, 2H), 2.1 (s, 3H), 1.3 (bs, 6H) | 1.70 |
| 122 | 272.90 | DMSO-d6: 12.2 (br s, 1H); 8.8 (s, 1H); 8.25 (m, 2H); 7.55 (dd, 1H); 7.1 (d, 1H); 6.5 (d, 1H); 3.1 (s, 6H). | 2.05 |
| 123 | 315.00 | DMSO-d6: 12.2 (br s, 1H); 8.8 (s, 1H); 8.25 (m, 2H); 7.5 (dd, 1H); 7.1 (d, 1H); 6.45 (m, 1H); 3.5 (d, 2H); 3.1 (s, 3H); 2.15 (m, 1H); 0.95 (d, 6H). | 3.55 |
| 124 | 492.00 | DMSO-d6: 12.2 (br s, 1H); 9.7 (br s, 1H); 9.2 (m, 1H); 8.8 (s, 1H); 8.2 (s, 1H); 7.5 (m, 1H); 7.1 (m, 1H); 6.5 (m, 1H); 4.1-3.5 (m, 14H); 3.4 (m, 4H); 3.2 (br s, 2H); 2.0-1.8 (m, 5H). | 2.24 |
| 125 | 519.10 | DMSO-d6: 12.2 (br s, 1H); 9.2 (d, 1H); 8.8 (s, 1H); 8.65 (br s, 1H); 8.2 (s, 1H); 7.5 (m, 1H); 7.1 (m, 1H); 6.5 (dd, 1H); 4.1-3.1 (m, 18H); 3.0 (br s, 4H); 2.8 (s, 3H); 2.0-1.8 (m, 5H). | 1.75 |
| 126 | 379.90 | DMSO-d6: 11.8 (br s, 1H); 9.2 (s, 1H); 8.8 (s, 1H); 8.0 (s, 1H); 7.5 (dd, 1H); 7.1 (d, 1H); 6.5 (dd, 1H); 4.0 (m, 1H); 3.8-3.65 (m, 5H); 3.4 (m, 2H); 2.0-1.8 (m, 5H). | 1.83 |
| 127 | 477.90 | DMSO d6: 11.8 ppm (s, 1H), 9.0 (s, 1H), 8.6 (s, 1H), 8.2 (s, 1H), 8.1 (s, 1H), 7.5 (t, 1H), 7.1 (d, 1H), 6.7 (d, 1H), 4.3 (m, 4H), 3.6 (t, 4H), 3.5 (t, 4H), 3.0 (m, 2H), 2.1 (s, 3H), 1.2 (bs, 6H) | 2.10 |
| 128 | 505.00 | DMSO d6: 11.9 ppm (s, 1H), 10.3 (s, 1H), 9.3 (s, 1H), 8.2 (s, 1H), 8.1 (s, 1H), 7.5 (t, 1H), 7.1 (d, 1H), 6.7 (d, 1H), 4.4 (m, 4H), 3.3 (m, 12H), 3.0 (m, 2H), 2.8 (m, 2H), 2.1 (3H), 1.3 (bs, 6H) | 1.50 |
| 129 | 355.10 | MeOD-D4: 8.4 (s, 1H); 8.35 (s, 1H); 8.1 (s, 1H); 8.0 (dd, 1H); 7.2 (d, 1H); 7.0 (d, 1H); 3.75 (m, 1H); 1.9-1.8 (m, 3H); 1.7 (m, 1H); 1.55 (m, 1H); 1.3-1.1 (m, 9H). | 2.40 |
| 130 | 315.10 | MeOD-D4: 8.4 (s, 1H); 8.35 (s, 1H); 8.15 (s, 1H); 8.0 (dd, 1H); 7.2 (d, 1H); 7.0 (d, 1H); 3.8 (m, 1H); 1.9 (m, 1H); 1.3 (d, 3H); 1.0 (m, 6H). | 2.00 |
| 131 | 367.00 | MeOD-D4: 8.3 (m, 2H); 8.1 (s, 1H); 7.9 (dd, 1H); 7.5 (m, 2H); 7.2 (d, 1H); 7.1 (m, 2H); 6.75 (d, 1H); 5.0 (m, 1H); 1.65 (d, 3H). | 2.40 |
| 132 | 342.80 | DMSO-D6: 12.5 (br s, 1H); 8.7 (br s, 1H); 8.35-8.15 (m, 2H); 7.7 (br s, 1H); 7.1 (m, 1H); 6.8 (br s, 1H); 3.8 (br s, 1H); 3.7-3.5 (m, 2H); 2.0 (m, 1H); 1.25-0.8 (m, 8H). | 2.00 |
| 133 | 360.90 | DMSO-D6: 12.3 (br s, 1H); 8.8 (br s, 1H); 8.25 (m, 2H); 7.6 (br s, 1H); 7.4-7.1 (m, 5H); 6.5 (br s, 1H); 5.6 (br s, 1H); 3.0 (m, 1H); 2.9 (m, 1H); 2.6 (m, 1H); 1.95 (m, 1H). | 3.00 |
| 134 | 330.80 | DMSO-D6: 12.5 (br s, 1H); 8.7 (br s, 1H); 8.3-8.25 (m, 2H); 7.6 (br s, 1H); 7.2 (br s, 1H); 6.7 (br s, 1H); 3.8 (br s, 1H); 3.65-3.5 (m, 3H); 2.0 (m, 1H); 1.0 (m, 7H). | 2.00 |
| 135 | 330.80 | DMSO-D6: 12.5 (br s, 1H); 8.6 (br s, 1H); 8.3-8.2 (m, 2H); 7.7 (br s, 1H); 7.1 (br s, 1H); 6.8 (br s, 1H); 3.8 (br s, 1H); 3.7-3.5 (m, 3H); 2.0 (m, 1H); 1.0 (m, 7H). | 2.00 |
| 136 | 376.90 | DMSO-D6: 12.5 (br s, 1H); 8.7 (br s, 1H); 8.3 (m, 2H); 7.4-7.1 (m, 5H); 5.5 (br s, 1H); 4.7 (m, 1H); 3.2 (m, 1H); 2.9 (m, 1H). | 2.40 |
| 137 | 376.90 | DMSO-D6: 12.1 (br s, 1H); 8.8 (br s, 1H); 8.2 (m, 2H); 7.45-7.05 (m, 5H); 6.5-6.4 (m, 2H); 5.5 (br s, 1H); 4.7 (m, 1H); 3.15 (m, 1H); 2.9 (m, 1H). | 2.40 |
| 138 | 430.00 | DMSO-d6 11.9 ppm (s, 1H), 10.2 (s, 1H), 9.3 (s, 1H), 8.3 (s, 1H), 8.1 (s, 1H), 7.5 (m, 1H), 7.1 (m, 2H), 6.5 (m, 2H), 6.3 (d, 1H), 5.8 (d, 1H), 3.5-4.0 (m, 10H), 1.9 (m, 2H) | 2.30 |
| 139 | 405.10 | DMSO-d6 11.9 ppm (s, 1H), 10.2 (s, 1H), 9.3 (s, 1H), 8.3 (s, 1H), 8.1 (s, 1H), 7.5 (m, 1H), 7.1 (m, 1H), 6.5 (m, 2H), 6.3 (s, 1H), 5.8 (s, 1H), 4.0 (t, 1H), 3.8 (dt, 2H), 3.7 (m, 3H), 3.4 (m, 2H), 2.0 (s, 1H), 1.9 (t, 1H), 1.8 (s, 3H) | 2.00 |
| 140 | 393.10 | DMSO-d6 11.9 ppm (s, 1H), 10.0 (s, 1H), 9.1 (s, 1H), 8.2 (s, 1H), 8.1 (s, 1H), 7.5 (m, 1H), 7.1 (m, 1H), 6.5 (m, 2H), 4.0 (t, 1H), 3.8 (dt, 2H), 3.7 (m, 3H), 3.4 (m, 2H), 2.1 (s, 3H), 2.0 (s, 1H), 1.9 (t, 1H), 1.8 (s, 3H) | 1.70 |
| 141 | 407.00 | DMSO-d6 11.8 ppm (s, 1H), 9.9 (s, 1H), 9.1 (s, 1H), 8.2 (s, 1H), 8.1 (s, 1H), 7.5 (m, 1H), 7.1 (m, 1H), 6.5 (m, 2H), 4.0 (t, 1H), 3.8 (dt, 2H), 3.7 (m, 3H), 3.4 (m, 2H), 2.4 (q, 2H), 2.0 (s, 1H), 1.9 (t, 1H), 1.8 (s, 3H), 1.1 (t, 3H) | 1.90 |
| 142 | 334.80 | DMSOD6 12.2 (bs, 1H); 8.3 (s, 1H); 8.15 (s, 1H); 8.0 (s, 1H); 7.6 (d, 2H); 7.5 (dd, 2H); 7.4 (dd, 2H); 7.3 (d, 2H); 6.95 (d, 1H); 5.1 (s, 2H) | 4.60 |

TABLE 4-continued

| Cmpd No. | LC_MASS_PLUS M + 1 (obs) | NMR_RESULT (1H NMR) | RT (mins) |
|---|---|---|---|
| 143 | 287.80 | DMSO D6 12.1 (bs, 1H); 8.3 (s, 2H); 7.9 (s, 1H); 7.55 (d, 1H); 7.4 (dd, 2H); 7.2 (d, 1H); 2.95 (hept, 1H); 1.25 (d, 6H) | 4.60 |
| 144 | 271.90 | DMSO D6 12.1 (bs, 1H); 8.3 (s, 2H); 7.9 (s, 1H); 7.3 (d, 1H); 7.2 (bs, 2H); 6.8 (app d, 1H); 2.9 (s, 6H) | 2.60 |
| 145 | 333.80 | | 4.10 |
| 146 | 382.90 | DMSO d6 12.1 (bs, 1H); 8.3 (s, 1H); 8.25 (s, 1H); 8.0 (s, 1H); 7.3 (dd, 1H); 7.2 (m, 2H); 6.9 (s, 1H); 4.2 (bs, 2H); 3.6 (d, 2H); 2.8 (bs, 2H); 2.0 (s, 3H); 1.3 (bs, 6H) | 3.70 |
| 147 | 378.10 | | 3.00 |
| 148 | 288.10 | | 2.00 |
| 149 | 395.10 | DMSO-D6: 12.4 (s, 1H); 8.7 (d, 1H); 8.4 (s, 1H); 8.25 (s, 1H), 7.5 (s, 1H); 6.9 (d, 1H); 4.0-3.65 (m, 6H); 3.4 (m, 2H); 2.0-1.8 (m, 5H). | 3.30 |
| 150 | 326.00 | DMSO-D6: 12.3 (s, 1H); 8.9 (s, 1H); 8.4 (s, 1H); 8.25 (s, 1H), 7.35 (s, 1H); 7.25 (m, 1H); 6.6 (s, 1H); 3.2 (m, 2H); 2.0 (m, 1H); 1.0 (d, 6H). | 3.70 |
| 151 | 353.00 | DMSO-D6: 12.4 (s, 1H); 8.75 (br s, 1H) 8.7 (s, 1H); 8.45 (s, 1H); 8.3 (s, 1H), 7.6 (s, 1H); 7.0 (s, 1H); 4.0 (m, 2H); 3.8 (m, 2H); 3.35 (m, 2H); 3.2 (m, 2H); 2.1 (m, 2H). | 1.80 |
| 152 | 519.20 | DMSO d6: 11.9 ppm (s, 1H), 10.1 (s, 1H), 9.3 (s, 1H), 9.0 (bs, 1H), 8.2 (s, 1H), 8.1 (s, 1H), 7.5 (t, 1H), 7.15 (d, 1H), 6.7 (d, 1H), 4.3 (m, 4H), 3.0-3.8 (m, 14H), 3.1 (m, 2H), 2.1 (s, 3H), 2.0 (q, 2H), 1.3 (bs, 6H) | 1.40 |
| 153 | 520.20 | DMSO d6: 11.9 ppm (s, 1H), 10.1 (s, 1H), 9.3 (s, 1H), 8.2 (s, 1H), 8.1 (s, 1H), 7.5 (t, 1H), 7.1 (d, 1H), 6.7 (d, 1H), 4.3 (m, 4H), 4.0 (d, 2H), 3.7 (t, 4H), 3.5 (d, 2H), 3.2 (m, 2H), 3.1 (m, 4H), 2.1 (s, 3H), 2.0 (q, 2H), 1.3 (bs, 6H) | 1.60 |
| 154 | 433.10 | DMSO d6: 11.9 ppm (s, 1H), 9.9 (s, 1H), 9.3 (s, 1H), 8.3 (s, 1H), 8.1 (s, 1H), 7.5 (t, 1H), 7.1 (d, 1H), 6.7 (d, 1H), 5.9 (s, 1H), 5.5 (s, 1H), 4.4 (m, 4H), 3.0 (m, 2H), 2.1 (s, 3H), 2.0 (s, 3H), 1.3 (bs, 6H) | 2.20 |
| 155 | 473.10 | DMSO d6: 11.8 ppm (s, 1H), 9.6 (s, 1H), 9.3 (s, 1H), 8.3 (s, 1H), 8.1 (s, 1H), 7.5 (t, 1H), 7.1 (d, 1H), 6.75 (t, 1H), 6.7 (d, 1H), 4.4 (m, 4H), 3.0 (m, 2H), 2.3 (m, 2H), 2.2 (m, 2H), 2.1 (s, 3H), 1.7 (m, 2H), 1.6 (m, 2H), 1.3 (bs, 6H) | 2.60 |
| 156 | 469.10 | DMSO d6: 11.9 ppm (s, 1H), 10.3 (s, 1H), 9.4 (s, 1H), 8.4 (s, 1H), 8.1 (s, 1H), 8.0 (d, 2H), 7.6 (m, 4H), 7.2 (d, 1H), 6.7 (d, 1H), 4.4 (m, 4H), 3.1 (m, 2H), 2.1 (s, 3H), 1.3 (bs, 6H) | 2.50 |
| 157 | 459.10 | DMSO d6: 11.9 ppm (s, 1H), 9.7 (s, 1H), 9.3 (s, 1H), 8.3 (s, 1H), 8.1 (s, 1H), 7.5 (t, 1H), 7.1 (d, 1H), 6.75 (s, 1H), 6.7 (d, 1H), 4.4 (m, 4H), 3.1 (m, 2H), 2.6 (dt, 4H), 2.1 (s, 3H), 1.9 (q, 2H), 1.3 (bs, 6H) | 2.40 |
| 158 | 475.20 | DMSO d6: 11.8 ppm (s, 1H), 9.8 (s, 1H), 9.3 (s, 1H), 8.15 (s, 1H), 8.1 (s, 1H), 7.5 (t, 1H), 7.1 (d, 1H), 6.7 (d, 1H), 4.4 (m, 4H), 3.1 (m, 2H), 2.4 (m, 1H), 2.1 (s, 3H), 1.8 (dd, 4H), 1.4 (q, 2H), 1.3 (bs, 10H) | 2.60 |
| 159 | 379.00 | 12.03 (s, 1H), 8.7-9.8 (s, 5H), 8.40 (s, 1H), 8.08 (s, 1H), 7.96 (s, 1H), 7.77 (t, 1H), 7.15 (d, 1H), 6.90 (d, 1H), 4.15-4.7 (m, 4H), 3.31 (m, 2H), 2.95 (s, 3H), 2.16 (s, 3H), 1.37 (m, 6H) CD3CN | 1.70 |
| 160 | 440.90 | DMSO d6 12.3 (bs, 1H); 10.0 (bs, 1H); 8.6 (s, 1H); 8.2 (s, 1H); 8.1 (s, 1H); 7.3 (s, 1H); 7.1 (s, 1H); 4.4 (bs, 2H); 4.2 (d, 2H); 3.1 (bd, 2H); 2.05 (s, 3H); 2.01 (s, 3H); 1.3 (bs, 6H) | 2.40 |
| 161 | 447.00 | DMSO d6: 11.8 ppm (s, 1H), 9.7 (s, 1H), 9.3 (s, 1H), 8.3 (s, 1H), 8.1 (s, 1H), 7.5 (t, 1H), 7.1 (d, 1H), 6.7 (d, 1H), 6.5 (q, 1H), 4.4 (m, 4H), 3.1 (m, 2H), 2.1 (s, 3H), 1.9 (s, 3H), 1.8 (d, 3H), 1.2 (bs, 6H) | 2.40 |
| 162 | 475.90 | DMSO d6: 11.9 ppm (s, 1H), 10.5 (s, 1H), 9.4 (s, 1H), 9.3 (s, 1H), 8.5 (s, 1H), 8.45 (s, 1H), 8.1 (s, 1H), 7.6 (t, 1H), 7.1 (d, 1H), 6.7 (d, 1H), 4.3 (m, 4H), 3.1 (m, 2H), 2.1 (s, 3H), 1.3 (bs, 6H) | 2.30 |
| 163 | 470.00 | DMSO d6: 11.9 ppm (s, 1H), 10.6 (s, 1H), 9.4 (s, 1H), 9.3 (s, 1H), 9.2 (s, 1H), 8.8 (d, 1H), 8.4 (s, 1H), 8.4 (d, 1H), 8.2 (s, 1H), 7.7 (q, 1H), 7.6 (t, 1H), 7.2 (d, 1H), 6.7 (d, 1H), 4.4 (m, 4H), 3.1 (m, 2H), 2.1 (s, 3H), 1.3 (bs, 6H) | 2.10 |
| 164 | 471.00 | DMSO d6: 11.9 ppm (s, 1H), 10.9 (s, 1H), 9.5 (s, 1H), 9.3 (s, 1H), 9.0 (s, 1H), 8.8 (s, 1H), 8.5 (s, 1H), 8.2 (s, 1H), 7.6 (t, 1H), 7.1 (d, 1H), 6.7 (d, 1H), 4.4 (m, 4H), 3.0 (m, 2H), 2.1 (s, 3H), 1.3 (bs, 6H) | 2.30 |
| 165 | 433.00 | DMSO d6: 11.8 ppm (s, 1H), 10.2 (s, 1H), 9.3 (s, 1H), 8.2 (s, 1H), 8.1 (s, 1H), 7.5 (t, 1H), 7.1 (d, 1H), 6.7 (d, 1H), 4.3 (bd, 4H), 3.0 (bd, 2H), 2.1 (s, 1H), 1.8 (m, 1H), 1.3 (bs, 6H), 0.8 (m, 4H) | 2.30 |

TABLE 4-continued

| Cmpd No. | LC_MASS_PLUS M + 1 (obs) | NMR_RESULT (1H NMR) | RT (mins) |
|---|---|---|---|
| 166 | 461.10 | DMSO d6: 11.8 ppm (s, 1H), 9.9 (s, 1H), 9.3 (s, 1H), 8.2 (s, 1H), 8.1 (s, 1H), 7.5 (t, 1H), 7.1 (d, 1H), 6.7 (d, 1H), 4.4 (bd, 4H), 3.0 (bd, 2H), 2.8 (q, 1H), 2.1 (s, 1H), 1.9 (m, 1H), 1.8 (m, 1H), 1.7 (m, 1H), 1.6 (m, 1H), 1.3 (bs, 6H) | 2.60 |
| 167 | 460.00 | DMSO d6: 12.0 ppm (s, 1H), 10.9 (s, 1H), 9.3 (s, 1H), 8.8 (s, 1H), 8.4 (s, 1H), 8.2 (s, 1H), 7.6 (t, 1H), 7.2 (s, 1H), 7.15 (d, 1H), 6.7 (d, 1H), 4.4 (bd, 4H), 3.1 (bd, 2H), 2.1 (s, 3H), 1.3 (bs, 6H) | 2.30 |
| 168 | 483.00 | DMSO d6: 11.9 ppm (s, 1H), 10.3 (s, 1H), 9.4 (s, 1H), 8.4 (s, 1H), 8.2 (s, 1H), 7.85 (s, 1H), 7.8 (d, 1H), 7.6 (t, 1H), 7.4 (s, 2H), 7.4 (q, 1H), 7.2 (d, 1H), 6.7 (d, 1H), 4.4 (bd, 4H), 3.1 (bd, 2H), 2.4 (s, 3H), 2.1 (s, 3H), 1.3 (bs, 6H) | 2.70 |
| 169 | 487.00 | DMSO d6: 11.9 ppm (s, 1H), 10.4 (s, 1H), 9.4 (s, 1H), 8.4 (s, 1H), 8.2 (s, 1H), 7.9 (d, 1H), 7.8 (d, 1H), 7.6 (q, 1H), 7.55 (t, 1H), 7.45 (t, 1H), 7.2 (d, 1H), 6.7 (d, 1H), 4.4 (bd, 4H), 3.1 (bd, 2H), 2.1 (s, 3H), 1.3 (bs, 6H) | 2.70 |
| 170 | 437.00 | DMSO d6: 11.9 ppm (s, 1H), 9.8 (s, 1H), 9.3 (s, 1H), 8.3 (s, 1H), 8.1 (s, 1H), 7.5 (t, 1H), 7.1 (d, 1H), 6.7 (d, 1H), 4.4 (bd, 4H), 4.1 (s, 2H), 3.4 (s, 1H), 3.0 (bd, 2H), 2.1 (s, 3H), 1.3 (bs, 6H) | 2.10 |
| 171 | 476.00 | DMSO d6: 12.0 ppm (s, 1H), 10.5 (s, 1H), 9.0 (s, 1H), 8.3 (s, 1H), 8.2 (s, 1H), 7.6 (t, 1H), 7.1 (d, 1H), 6.7 (d, 1H), 4.4 (bd, 4H), 3.3 (m, 2H), 3.0 (bd, 2H), 2.3 (m, 2H), 2.1 (s, 3H), 1.5-1.9 (m, 4H), 1.3 (bs, 6H) | 1.70 |
| 172 | 487.00 | DMSO d6: 11.9 ppm (s, 1H), 10.4 (s, 1H), 9.4 (s, 1H), 8.3 (s, 1H), 8.2 (s, 1H), 7.7 (t, 1H), 7.6 (q, 1H), 7.5 (t, 1H), 7.4 (q, 2H), 7.2 (d, 1H), 6.7 (d, 1H), 4.4 (bd, 4H), 3.1 (bd, 2H), 2.1 (s, 3H), 1.3 (bs, 6H) | 2.60 |
| 173 | 502.90 | DMSO d6: 11.9 ppm (s, 1H), 10.5 (s, 1H), 9.4 (s, 1H), 8.3 (s, 1H), 8.2 (s, 1H), 7.4-7.7 (m, 5H), 7.2 (d, 1H), 6.7 (d, 1H), 4.4 (bd, 4H), 3.1 (bd, 2H), 2.0 (s, 3H), 1.3 (bs, 6H) | 2.60 |
| 174 | 502.90 | DMSO d6: 11.9 ppm (s, 1H), 10.5 (s, 1H), 9.4 (s, 1H), 8.4 (s, 1H), 8.2 (s, 1H), 8.0 (d, 1H), 7.7 (s, 1H), 7.6 (t, 1H), 7.5 (t, 1H), 7.2 (d, 1H), 6.7 (d, 1H), 4.4 (bd, 4H), 3.1 (bd, 2H), 2.1 (s, 3H), 1.3 (bs, 6H) | 2.90 |
| 175 | 307.00 | DMSO d6 12.4 (bs, 1H); 8.4 (s, 1H); 8.3 (s, 1H); 8.2 (s, 1H); 7.95 (d, 2H); 7.9 (s, 1H) | 2.80 |
| 176 | 253.70 | DMSO d6 12.4 (bs, 1H); 8.5 (s, 1H); 8.3 (s, 1H); 8.2 (s, 1H); 8.0 (d, 2H); 7.9 (d, 1H) | 3.10 |
| 177 | 350.95 | DMSO d6 12.4 (bs, 1H); 8.35 (s, 1H); 8.3 (s, 1H); 8.2 (m, 2H); 8.1 (s, 1H); 7.9 (s, 1H) | 3.16 |
| 178 | 287.01 | DMSO d6 12.2 (bs, 1H); 8.4 (s, 1H); 8.3 (s, 1H); 8.0 (s, 1H); 7.65 (s, 1H); 7.6 (dd, 1H); 7.4 (dd, 1H); 7.2 (dd, 1H); 3.8 (S, 2H) | 2.69 |
| 179 | 494.00 | DMSO d6: 11.9 ppm (s, 1H), 10.5 (s, 1H), 9.4 (s, 1H), 8.45 (s, 1H), 8.4 (s, 1H), 8.3 (d, 1H), 8.2 (s, 1H), (8.1 (d, 1H), 7.8 (t, 1H), 7.6 (t, 1H), 7.2 (d, 1H), 6.7 (d, 1H), 4.4 (bd, 4H), 3.1 (bd, 2H), 2.1 (s, 3H), 1.3 (bs, 6H) | 2.60 |
| 180 | 449.10 | DMSO d6: 11.8 ppm (s, 1H), 9.9 (s, 1H), 9.3 (s, 1H), 8.2 (s, 1H), 8.1 (s, 1H), 7.6 (t, 1H), 7.1 (d, 1H), 6.7 (d, 1H), 4.4 (bd, 4H), 3.1 (bd, 2H), 2.4 (m, 1H), 2.1 (s, 3H), 1.6 (m, 1H), 1.4 (m, 1H), 1.3 (bs, 6H), 1.1 (d, 3H), 0.9 (t, 3H) | 2.50 |
| 181 | 433.00 | DMSO d6: 11.9 ppm (s, 1H), 10.0 (s, 1H), 9.3 (s, 1H), 8.2 (s, 1H), 8.1 (s, 1H), 7.5 (t, 1H), 7.1 (d, 1H), 6.8 (m, 1H), 6.7 (d, 1H), 6.2 (d, 1H), 4.4 (bd, 4H), 3.1 (bd, 2H), 2.1 (s, 3H), 1.9 (d, 3H), 1.3 (bs, 6H) | 2.30 |
| 182 | 474.90 | DMSO d6: 11.9 ppm (s, 1H), 10.3 (s, 1H), 9.3 (s, 1H), 8.4 (s, 1H), 8.2 (s, 1H), 8.0 (d, 1H), 7.9 (d, 1H), 7.6 (t, 1H), 7.25 (t, 1H), 7.2 (d, 1H), 6.7 (d, 1H), 4.4 (bd, 4H), 3.1 (bd, 2H), 2.1 (s, 3H), 1.3 (bs, 6H) | 2.50 |
| 183 | 228.80 | DMSO d6 12.2 (bs, 1H); 8.3 (s, 1H); 8.25 (s, 1H); 8.0 (s, 1H); 7.7 (d, 2H); 7.4 (dd); 7.2 (dd, 1H) | 3.40 |
| 184 | 230.10 | DMSO d6 12.2 (bs, 1H); 8.3 (s, 1H); 8.25 (s, 1H); 8.0 (s, 1H); 7.7 (d, 2H); 7.4 (dd); 7.2 (dd, 1H) | 1.60 |
| 185 | 243.10 | DMSO d6 12.2 (bs, 1H); 8.3 (s, 1H); 8.25 (s, 1H); 7.9 (s, 1H); 7.5 (dd, 2H); 7.3 (dd, 1H); 7.1 (d, 1H); 2.3 (s, 3H) | 3.40 |
| 186 | 334.10 | DMSO d6 12.2 (bs, 1H); 8.25 (s, 1H); 8.2 (s, 1H); 8.0 (s, 1H); 7.5 (d, 1H); 7.4 (dd, 2H); 7.3 (d, 1H); 7.05 (dd, 2H); 6.7 (d, 2H); 6.55 (dd, 1H); 4.3 (s, 2H) | 2.60 |
| 187 | 401.80 | DMSO d6 12.2 (bs, 1H); 8.3 (s, 1H); 8.05 (s, 1H); 8.0 (s, 1H); 7.5 (m, 5H); 7.3 (dd, 1H); 7.2 (s, 1H); 7.1 (s, 1H); 6.8 (s, 1H); 4.4 (s, 2H) | 3.90 |
| 188 | 291.02 | | 2.30 |
| 189 | 487.00 | DMSO d6: 11.9 ppm (s, 1H), 10.3 (s, 1H), 9.3 (s, 1H), 8.4 (s, 1H), 8.15 (s, 1H), 8.1 (m, 2H), 7.5 (t, 1H), 7.4 (t, 2H), 7.15 (d, 1H), 6.7 (d, 1H), 4.4 (bd, 4H), 3.1 (bd, 2H), 2.1 (s, 3H), 1.3 (bs, 6H) | 2.60 |

TABLE 4-continued

| Cmpd No. | LC_MASS_PLUS M + 1 (obs) | NMR_RESULT (1H NMR) | RT (mins) |
|---|---|---|---|
| 190 | 460.00 | DMSO d6: 11.9 ppm (s, 1H), 10.6 (bs, 1H), 9.3 (s, 1H), 8.5 (s, 1H), 8.2 (s, 1H), 7.5 (t, 1H), 7.1 (d. 1H), 6.7 (d, 1H), 4.4 (bd, 4H), 3.1 (bd, 2H), 2.1 (s, 3H), 1.2 (bs, 6H) | 2.00 |
| 191 | 445.00 | DMSO d6: 11.9 ppm (s, 1H), 10.2 (bs, 1H), 9.4 (s, 1H), 8.3 (s, 1H), 8.1 (s, 1H), 7.5 (t, 1H), 7.2 (m, 1H), 7.1 (d. 1H), 6.7 (d, 1H), 6.6 (m, 1H), 6.3 (d, 1H), 5.7 (d, 1H), 5.5 (d, 1H), 4.4 (bd, 4H), 3.1 (bd, 2H), 2.1 (s, 3H), 1.2 (bs, 6H) | 2.40 |
| 192 | 452.90 | DMSO d6: 11.9 ppm (s, 1H), 10.3 (s, 1H), 9.3 (s, 1H), 8.2 (s, 1H), 8.1 (s, 1H), 7.5 (t, 1H), 7.4 (d, 1H), 7.1 (d, 1H), 6.7 (d, 1H), 6.7 (s, 1H), 4.4 (bd, 4H), 3.1 (bd, 2H), 2.1 (s, 3H), 1.2 (bs, 6H) | 2.50 |
| 193 | 456.10 | DMSO-d6: 11.9 (bs, 1H); 8.3 (s, 1H); 8.1 (m, 2H); 7.55 (dd, 1H); 7.45 (d, 2H); 7.4 (dd, 2H); 7.3 (m, 1H); 7.15 (d, 1H); 6.7 (d, 1H); 5.2 (s, 2H); 4.2 (d, 4H); 3.1 (m, 2H); 2.05 (s, 3H); 1.25 (s, 6H). | 3.00 |
| 194 | 451.20 | DMSO-d6: 11.9 (bs, 1H); 8.25 (s, 1H); 8.1 (s, 1H); 8.05 (s, 1H); 7.55 (dd, 1H); 7.15 (d, 1H); 6.7 (d, 1H); 4.3 (d, 4H); 4.15 (m, 2H); 3.25 (m, 2H); 3.05 (m, 2H); 2.8 (s, 6H); 2.15 (m, 2H); 2.05 (s, 3H); 1.25 (s, 6H). | 1.60 |
| 195 | 279.80 | (d4-methanol, free base) 8.87 (s, 1H), 8.70 (s, 1H), 8.50 (s, 1H), 8.38 (s, 1H), 8.20 (d, 1H), 8.18 (d, 1H), 8.10 (m, 1H), 7.96 (m, 1H) | 2.86 |
| 196 | 311.80 | (d4-methanol, salt) 8.88 (s, 1H), 8.25 (m, 2H), 7.86 (s, 1H), 7.34 (m, 1H), 2.72 (s, 3H) | 3.95 |
| 197 | 293.80 | (d4-methanol, salt) 8.71-7.45 (m, 8H), 2.90 (s, 3H) | 2.33 |
| 198 | 293.90 | (d4-methanol, salt) 8.53-7.82 (m, 7H), 7.41 (s, 1H), 4.34 (s, 3H) | 2.33 |
| 199 | 278.90 | (d4-methanol, salt) 8.39 (dd, 1H), 8.25 (s, 1H), 8.11 (s, 1H), 7.94-7.79 (m, 5H), 7.51-7.44 (m, 2H) | 3.87 |
| 200 | 279.90 | (d4-methanol, salt) 9.16-7.99 (m, 9H) | 3.87 |
| 201 | 259.90 | (d4-methanol, salt) 8.86 (d, 1H), 8.23 (s, 1H), 8.09 (s, 1H), 7.99 (m, 1H), 7.70 (d, 1H), 7.39 (dd, 1H), 6.65 (d, 1H), 4.17 (s, 3H) | 3.46 |
| 202 | 279.80 | (d4-methanol, salt) 9.01 (d, 1H), 8.98 (d, 1H), 8.32 (s, 1H), 8.31 (s, 1H), 8.28 (d, 1H), 8.17 (d, 1H), 8.01-7.97 (m, 2H), 7.94 (s, 1H) | 2.50 |
| 203 | 287.90 | (CDCl3) 10.00 (br s, 1H), 8.49 (s, 1H), 8.27 (s, 1H), 8.00 s, 1H), 7.71 (m, 1H), 7.48 (m, 1H), 7.20 (m, 1H), 7.19 (d, 1H), 1.97 (s, OH, 1H), 1.57 (s, 6H) | 2.56 |
| 204 | 412.90 | DMSO d6 12.2 (bs, 1H); 8.7 (t, 1H); 8.4 (s, 1H); 8.2 (s, 1H); 8.1 (s, 1H); 8.0 (s, 1H); 4.8 (q, 1H); 3.9 (s, 3H); 3.85 (m, 2H); 1.15 (d, 3H) | 1.90 |
| 205 | 394.20 | | 2.10 |
| 206 | 408.10 | | 2.20 |
| 207 | 420.20 | | 2.30 |
| 208 | 493.20 | | 1.70 |
| 209 | 452.20 | | 2.20 |
| 210 | 343.00 | 1H NMR (CDCl3) 0.30 (9H, s), 7.33-7.54 (8H, m), 7.59-7.68 (2H, m), 8.05-8.08 (1H, m), 8.61-8.65 (1H, m), 9.70 (1H, brs). | |
| 211 | 349.10 | (400 MHz, DMSO-d6) 7.30-7.43 (8H, br m), 7.48 (2H, d), 7.98 (1H, d), 8.34 (1H, d), 12.36 (1H, br m). | |
| 212 | 364.40 | (400 MHz, DMSO-d6) 7.00 (2H, d), 7.23 (2H, d), 7.34 (3H, m), 7.49 (2H, dd), 7.97 (1H, s), 8.33 (1H, d) and 12.38 (1H, s). | |
| 213 | 271.00 | 1H NMR (CDCl3) 7.30-7.57 (6H, m), 7.60-7.77 (5H, m), 8.44-8.48 (1H, m), 8.65-8.70 (1H, m), 11.21 (1H, brs). | |
| 214 | 301.00 | 1H NMR (DMSO) 3.84 (3H, s), 6.80-6.88 91H, m), 7.25-7.30 (1H, m), 7.32-7.41 (3H, m), 7.45-7.54 (2H, m), 7.72-7.81 (2H, m), 7.90-7.98 (1H, m), 8.39-8.43 91H, m), 8.54-8.60 (1H, m), 12.04 (1H, brs). | |
| 215 | 315.00 | 1H NMR (DMSO) 1.36 (3H, t, J = 6.9 Hz), 4.10 (2H, q, J = 6.9 Hz), 6.80-6.86 (1H, m), 7.22-7.29 (1H, m), 7.30-7.41 (3H, m), 7.45-7.55 (2H, m), 7.73-7.80 (2H, m), 7.91-7.98 (1H, m), 8.38-8.41 (1H, m), 8.53-8.59 (1H, m), 12.02 91H, brs). | |
| 216 | 331.00 | 1H NMR (DMSO) 3.70-3.80 (6H, m), 6.81-6.90 (1H, m), 7.02-7.15 (2H, m), 7.32-7.40 (1H, m), 7.42-7.51 (2H, m), 7.66-7.79 (3H, m), 8.11-8.16 (1H, m), 8.50-8.56 (1H, m), 11.95 (1H, brs). | |
| 217 | 436.70 | (400 MHz, DMSO-d6) 12.31 (1H, s), 8.32 (1H, d), 7.94 (1H, d), 7.52 (2H, d), 7.33 (3H, m), 7.10 (2H, d), 6.98 (2H, d), 3.75 (4H, dd) and 3.15 (4H, dd). | |
| 218 | 349.00 | 1H NMR (DMSO) 3.30 (3H, s), 7.34-7.45 (1H, m), 7.49-7.83 (6H, m), 8.16 (1H, s), 8.18-8.28 (2H, m), 8.45-8.49 91H, m), 8.58-8.62 (1H, m), 12.21 (1H, brs). | |

TABLE 4-continued

| Cmpd No. | LC_MASS_PLUS M + 1 (obs) | NMR_RESULT (1H NMR) | RT (mins) |
|---|---|---|---|
| 219 | 342.00 | 1H NMR (DMSO) 3.00 (6H, s), 7.35-7.42 (1H, m), 7.45-7.68 (4H, m), 7.75-7.90 (4H, m), 8.03 (1H, s), 8.45-8.50 (1H, m), 8.56-8.60 (1H, m), 12.11 (1H, brs). | |
| 220 | 370.00 | 1H NMR (DMSO) 0.91 (3H, t, J = 7.4 Hz), 1.30-1.42 (2H, m), 1.49-1.59 (2H, m), 3.25-3.34 (2H, m), 7.35-7.42 (1H, m), 7.46-7.58 (3H, m), 7.68-7.81 (3H, m), 7.92-8.03 (2H, m), 8.19-8.22 (1H, m), 8.44-8.49 (1H, m), 8.50-8.61 (2H, m), 12.10 (1H, brs). | |
| 221 | 367.00 | 1H NMR (DMSO) 3.36 (3H, s), 7.28-7.39 (2H, m), 7.50-7.88 (5H, m), 8.10-8.26 (3H, m), 8.43-8.46 (1H, m), 8.57-8.59 (1H, m), 12.25 (1H, brs). | |
| 222 | 349.00 | 1H NMR (DMSO) 3.79 (3H, s), 3.86 (3H, s), 7.00-7.05 (1H, m), 7.26-7.37 (4H, m), 7.78-7.89 (2H, m), 8.35-8.40 (1H, m), 8.50-8.56 (1H, m), 11.93 (1H, brs). | |
| 223 | 307.00 | 1H NMR (DMSO) 7.22-7.37 (4H, m), 7.78-7.88 (4H, m), 7.92 (1H, brs), 8.36-8.41 91H, m), 8.51-8.58 (1H, m), 12.02 (1H, brs). | |
| 224 | 319.00 | 1H NMR (DMSO) 3.80 (3H, s), 6.99-7.06 (2H, m), 7.26-7.36 (2H, m), 7.68-7.84 (5H, m), 8.33-8.39 (1H, m), 8.50-8.57 (1H, m), 11.91 (1H, brs). | |
| 225 | 452.00 | 1H NMR (DMSO) 3.30-3.80 (8H, m), 7.25-7.32 (1H, m), 7.50-7.63 (2H, m), 7.80 (1H, s), 7.88-7.99 (2H, m), 8.05 (1H, s), 8.49-8.54 (1H, m), 8.60-8.68 (1H, m), 12.20 (1H, brs). | |
| 226 | 410.00 | 1H NMR (DMSO) 1.16 (3H, t), 3.20-3.42 (2H, m), 7.50-7.76 (3H, m), 7.88-7.95 (2H, m), 7.98-8.06 (2H, m), 8.20 (1H, s), 8.51-8.66 (3H, m), 12.18 (1H, brs). | |
| 227 | 332.00 | 1H NMR (DMSO) 7.28-7.39 (3H, m), 7.79-8.03 (7H, m), 8.09 (1H, brs), 8.48-8.51 (1H, m), 8.53-8.59 (1H, m), 12.14 (1H, brs). | |
| 228 | 332.00 | 1H NMR (DMSO) 7.30-7.48 (3H, m), 7.42 (1H, brs), 7.50-7.58 (1H, m), 7.70-7.86 (3H, m), 7.92-8.11 (3H, m), 8.20 (1H, brs), 8.41-8.49 (1H, m), 8.54-8.59 (1H, m), 12.09 (1H, brs). | |
| 229 | 299.00 | 1H NMR (DMSO) 7.38-7.43 91H, m), 7.48-7.55 (2H, m), 7.78-7.83 (2H, m), 7.97 92H, d, J = 8.2 Hz), 8.09 (2H, d, J = 8.2 Hz), 8.21 (1H, s), 8.54-8.62 92H, m), 10.00 91H, s), 12.30 (1H, brs). | |
| 230 | 342.00 | 1H NMR (DMSO) 1.90 93H, s), 4.20-4.30 92H, m), 7.27-7.40 (3H, m), 7.45-7.51 92H, m), 7.70-7.80 (4H, m), 7.85-7.91 (1H, m), 8.30-8.41 (2H, m), 8.51-8.60 (1H, m), 12.00 (1H, brs). | |
| 231 | 313.00 | 1H NMR (DMSO) 2.60 (3H, s), 7.36-7.42 (1H, m), 7.47-7.55 (2H, m), 7.76-7.83 (2H, m), 7.95-8.08 (4H, m), 8.15 (1H, s), 8.50-8.56 (1H, m), 8.58-8.63 91H, m), 12.24 (1H, brs). | |
| 232 | 286.00 | 1H NMR (DMSO) 5.08 (2H, brs), 6.63-6.70 (2H, m), 7.30-7.52 95H, m), 7.60-7.66 (1H, m), 7.70-7.80 (2H, m), 8.30-8.35 (1H, m), 8.50-8.55 (1H, m), 11.75 (1H, brs). | |
| 233 | | 1H NMR (DMSO) 2.40-2.48 (3H, m), 7.36-7.55 (4H, m), 7.78-7.85 (4H, m), 8.02-8.09 (2H, m), 8.15 (1H, s), 8.52-8.56 (1H, m), 8.59-8.62 (1H, m), 12.25 (1H, brs). | |
| 234 | 364.00 | 1H NMR (DMSO) 3.00 (3H, s), 7.25-7.54 (5H, m), 7.70-7.90 (5H, m), 8.40-8.48 (1H, m), 8.52-8.60 (1H, m), 9.73 (1H, brs), 12.00 (1H, brs). | 8.93 |
| 235 | 304.00 | 1H NMR (DMSO) 7.15 (1H, s), 7.35 (1H, brs), 7.78 (1H, s), 7.85-8.08 (7H, m), 8.31 (1H, s), 8.49 91H, brs), 8.61 (1H, brs), 12.08 (1H, brs). | 7.68 |
| 236 | 320.00 | 1H NMR (DMSO) 7.30 (1H, s), 7.60-7.76 (2H, m), 7.82-8.10 (7H, m), 8.55 (1H, brs), 8.70 (1H, s), 12.10 (1H, brs). | 8.14 |
| 237 | 370.00 | (400 MHz, MeOH-d4): 4.70-4.85 (2H, brs), 6.35-6.45 (1H, s), 7.30-7.50 (5H, m), 8.05-8.15 (1H, d), 8.20-8.25 (1H, s), 8.60-8.70 (1H, brs) | 4.87 |
| 238 | 388.00 | 1H NMR (DMSO-d6): 3.33 (1H, s), 4.75-4.80 (2H, m), 7.35-7.45 (4H, m), 8.15 (1H, s), 8.20-8.25 (2H, m), 8.28-8.35 1H, m), 8.50 (1H, s) | 4.87 |
| 239 | 344.00 | 1H NMR (DMSO) 3.85 (3H, s), 6.91-7.00 (1H, m), 7.26-7.49 (4H, m), 7.85-8.10 (6H, m), 8.50 (1H, brs), 8.60 (1H, brs), 12.15 (1H, brs). | 8.38 |
| 240 | 308.24 | 1H NMR (DMSO-d6): 7.22 (1H, m), 7.47 (2H, m), 7.85 (1H, s), 8.21 (1H, s), 8.64 (1H, s), 11.19 (1H, br s) | 4.93 |
| 241 | 299.38 | 1H NMR (CDCl3): 2.04 (4H, s), 3.53 (4H, s), 6.22 (1H, d), 6.86 (1H, d), 7.44 (1H, t), 7.81 (1H, s), 8.17 (1H, s), 8.87 (1H, s) | 5.15 |
| 242 | 369.00 | 1H NMR (DMSO-d6): 4.60-4.70 (2H, m), 6.35-6.40 (1H, d), 7.05-7.10 (1H, d), 7.20-7.25 (1H, t), 7.35-7.45 (4H, m), 8.15-8.20 (2H, m), 8.55-8.60 (1H, s), 12.5 (1H, s) | 4.99 |

TABLE 4-continued

| Cmpd No. | LC_MASS_PLUS M + 1 (obs) | NMR_RESULT (1H NMR) | RT (mins) |
|---|---|---|---|
| 243 | 321.00 | 1H NMR (DMSO-d6): 6.70-6.75 (1H, d), 6.90-6.95 (1H, t), 7.30-7.35 (3H, qd), 7.50-7.65 (3H, m), 8.25-8.30 (2H, m), 8.80 (1H, s), 9.05 (1H, s), 12.5 (1H, s) | 4.84 |
| 244 | 401.49 | 1H NMR (DMSO-d6): 4.63 (2H, d), 5.20 (1H, br s), 6.45 (1H, d), 7.08 (1H, d), 7.27 (1H, t), 7.37 (2H, s), 7.43 (1H, t), 7.64 (1H, s), 8.16 (2H, d), 8.39 (1H, s), 12.48 (1H, br s) | 5.20 |
| 245 | 513.00 | (d6-DMSO, 400 MHz 3.16 (3H, s), 5.30 (2H, s), 7.52 (1H, d), 7.60 (2H, d), 7.70 (1H, d), 7.81 (1H, t), 7.91 (2H, d), 8.17 (1H, d), 8.28 (1H, d), 8.36 (1H, s), 12.31 (1H, s) | 4.89 |
| 246 | 245.00 | (d6-DMSO, 400 MHz) 5.98 (2H, brs), 6.25 (1H, d), 7.01 (1H, d), 7.37 (1H, t), 8.18 (1H, s), 8.24 (1H, d), 8.96 (1H, d), 12.12 (1H, s) | 3.80 |
| 247 | 413.00 | (d6-DMSO, 400 MHz) 3.15 (3H, s), 4.71 (2H, s), 6.38 (1H, d), 7.06 (1H, d), 7.42 (1H, t), 7.65 (2H, d), 7.88 (2H, d), 8.18 (2H, s), 8.53 (1H, s), 12.12 (1H, s) | 4.00 |
| 248 | 372.00 | 1H NMR (DMSO-d6): 7.05-7.10 (1H, t), 7.35-7.40 (1H, m), 7.60-7.65 (1H, t), 7.70-7.80 (3H, m), 7.82-7.88 (1H, d), 7.95 (1H, s), 8.25 (1H, s), 8.40 (1H, s), 12.5 (1H, s) | 5.22 |
| 249 | 349.00 | (d6-DMSO, 400 MHz) 7.56-7.60 (2H, m), 7.63 (1H, d), 7.69 (1H, d), 7.82 (1H, t), 7.97 (1H, s), 8.00 (2H, d), 8.27 (1H, s), 8.42 (1H, s), 9.28 (1H, s), 10.81 (1H, s), 12.29 (1H, s) | 4.59 |
| 250 | 345.00 | (d6-DMSO, 400 MHz) 1.53 (9H, s), 7.56 (2H, dd), 7.69 (1H, t), 8.25 (1H, d), 8.36 (1H, s), 9.30 (1H, s), 10.06 (1H, s), 12.22 (1H, s) | 4.90 |
| 251 | 405.00 | NMR (DMSO 4.6 (2H, d, CH2), 6.4 (H, d, ar), 7.05 (H, d, ar), 7.3 (H, m, ar), 7.4 (H, d, ar), 7.45 (H, t, ar), 7.6 (H, d, ar), 7.65 (H, s, ar), 8.15 (2H, s, ar), 8.5 (H, s, NH) and 12.15 (H, s, NH). | 5.15 |
| 252 | 349.00 | 1H NMR (DMSO-d6): 1.50-1.55 (3H, d), 5.05-5.15 (2H, m), 6.30-3.35 (1H, d), 6.95-7.05 (1H, d), 7.10-7.15 (1H, d), 7.15-7.20 (1H, t), 7.25-7.40 (3H, m), 7.45-7.50 (2H, d), 8.15 (1H, s), 8.20 (1H, s), 8.75 (1H, s), 12.5 (1H, s) | 4.93 |
| 253 | 315.70 | CDCl3 3.23 (6H, m), 6.45 (1H, d), 7.03 (1H, d), 7.43 (1H, m), 7.5-7.57 (3H, m), 7.70-7.73 (2H, m), 7.88 (1H, s), 8.65 (1H, s), 9.10 (1H, s), 9.25 (1H, s). | 10.37 |
| 254 | 349.00 | NMR (DMSO 2.2 (3H, s, CH3), 4.5 (2H, s, CH2), 6.3 (H, s, ar), 6.8-7.4 (7H, m, ar), 8.1-8.3 (2H, m, ar) and 8.7 (H, s, NH). | 5.03 |
| 255 | 407.00 | 1H NMR (DMSO 3.01 (3H, s), 7.28-7.39 (3H, m), 7.70-8.10 (8H, m), 8.45 (1H, brs), 8.55 (1H, brs), 9.80 (1H, brs), 12.14 (1H, brs). | |
| 256 | 407.00 | 1H NMR (DMSO 2.45 (3H, brs), 7.31 (1H, brs), 7.51 (1H, brs), 7.80-8.15 (10H, m), 8.60 (1H, brs), 8.67 (1H, brs), 12.21 (1H, brs). | |
| 257 | 414.53 | 1H NMR (DMSO-d6): 1.44 (9H, s), 3.41 (4H, s), 3.57 (4H, d), 6.69 (1H, d), 7.22 (1H, d), 7.57 (1H, t), 8.27 (2H, s), 8.67 (1H, s), 12.25 (1H, s | 2.50 |
| 258 | 365.40 | 1H NMR (DMSO-d6): 3.70 (3H, s), 6.35 (1H, d), 6.88 (2H, d), 7.03 (1H, d), 7.11 (1H, t), 7.34 (2H, d), 7.37 (1H, t), 8.18 (1H, s), 8.21 (1H, d), 8.76 (1H, s), 12.13 (1H, s) | 4.78 |
| 259 | 329.70 | CDCl3 1.05 (3H, t), 1.7-1.8 (2H, m), 3.4-3.5 (2H, m), 4.6 (1H, s), 6.32 (1H, d), 7.03 (1H, d), 7.45 (1H, m), 7.5-7.6 (3H, m), 7.75 (2H, d), 7.78 (1H, s), 8.65 (1H, s), 8.97 (1H, s), 9.12 (1H, s) | 4.99 |
| 260 | 349.00 | (400 MHz, MeOH-d4): 1.55-1.60 (3H, d), 5.05-5.15 (1H, m), 6.30-6.35 (1H, d), 6.95-7.05 (1H, d), 7.10-7.15 (1H, m), 7.15-7.20 (1H, t), 7.25-7.40 (3H, m), 7.45-7.50 (2H, d), 7.95 (1H, s) 8.15 (1H, s), 8.75 (1H, s) | 4.93 |
| 261 | 445.00 | NMR (DMSO 4.7 (2H, d, CH2), 6.35 (H, d, ar), 7.15 (H, d, ar), 7.2 (H, t, ar), 7.3-7.55 (7H, m, ar), 7.6 (s, H, ar), 8.2 (H, s, ar), 8.5 (H, s, NH) and 8.9 (H, s, NH). | 5.30 |
| 262 | 391.00 | NMR (DMSO 2.2 (3H, s, Me), 4.6 (2H, d, CH2), 6.3 (H, d, ar), 7.05-7.1 (4H, m, ar), 7.25 (2H,, d, ar), 7.3-7.45 (4H, m, ar), 7.6 (2H, d, ar), 8.15 (H, s, ar), 8.5 (H, s, NH) and 9.05 (H, s, NH). | 5.14 |
| 263 | 355.00 | 1H NMR (DMSO-d6): 6.70-6.80 (1H, d), 7.10-7.20 (1H, t), 7.30-7.40 (2H, m), 7.50-7.60 (2H, m), 7.80-7.90 (1H, d), 8.15 (1H, s), 8.25 (1H, s), 8.50 (2H, s), 12.2 (1H, s) | 4.92 |
| 264 | 349.00 | 1H NMR (DMSO-d6): 2.95-3.00 (2H, t), 3.55-3.60 (2H, m), 6.30-6.35 (1H, d), 6.65-6.70 (1H, t), 7.05-7.10 (1H, d), | 4.67 |

TABLE 4-continued

| Cmpd No. | LC_MASS_PLUS M + 1 (obs) | NMR_RESULT (1H NMR) | RT (mins) |
|---|---|---|---|
| | | 7.15-7.20 (1H, t), 7.30 (4H, m), 7.32-7.40 (1H, t), 8.17 (1H, s), 8.20 (1H, s), 8.85 (1H, s), 12.2 (1H, s) | |
| 265 | 363.00 | NMR (DMSO) 6.7 (H, d, ar), 6.9 (H, t, ar), 7.35-7.4 (2H, m, ar), 7.4-7.5 (4H, m, ar), 7.5-7.75 (5H, m, ar), 8.25 (H, s, ar), 8.6 (H, s, ar), 8.9 (H, s, ar), 9.3 (H, s, NH) and 12.1 (H, s, NH). | 4.64 |
| 266 | 397.00 | NMR (DMSO) 6.8 (H, d, ar), 7.0 (H, m, ar), 7.2 (H, m, ar), 7.2-7.6 (7H, m, ar), 7.65 (H, m, ar), 8.0 (H, m, ar), 8.2 (H, s, ar), 8.4 (H, m, NH), 8.5 (H, s, ar), 8.7 (H, s, ar) and 12.1 (H, brs, NH). | 5.20 |
| 267 | 314.43, 314.00 | 1H NMR (DMSO-d6): 3.11 (4H, s), 3.88 (4H, d), 6.78 (1H, d), 7.30 (1H, d), 7.65 (1H, t), 8.30 (2H, d), 8.63 (1H, s), 8.77 (2H, br s), 12.30 (1H, s), DMSO D6 2.82-2.93 (4H, m), 3.48-3.55 (4H, m), 6.65 (1H, d), 7.15 (1H, d), 7.55 (1H, t), 8.25-8.30 (2H, m), 8.69 (1H, s) | 3.42, 2.75 |
| 268 | 287.60 | CDCl3 4.48 (2H, s), 6.45 (1H, d), 7.12 (1H, d), 7.42 (1H, t), 7.5-7.6 (3H, m), 7.75 (2H, t), 7.88 (1H, s), 8.7 (1H, s), 8.88 (1H, s), 9.52 (1H, s) | 2.79 |
| 269 | 377.60 | CDCl3 4.7 (2H, d), 5.0 (1H, s), 6.35 (1H, d), 7.08 (1H, d), 7.3-7.4 (9H, t), 7.5-7.6 (3H, m), 7.68 (2H, d), 7.88 (1H, s), 8.65 (1H, s), 8.95 (1H, s), 9.43 (1H, s) | 5.00 |
| 270 | 289.00 | 1H NMR (DMSO-d6): 3.45-3.50 (2H, m), 3.60-3.65 (2H, m), 4.70-4.77 (1H, t), 6.25-6.30 (1H, d), 6.50-6.55 (1H, t), 7.00-7.05 (1H, d), 7.30-7.40 (1H, t), 8.20 (1H, s), 8.25 (1H, s), 8.85 (1H, s), 12.2 (1H, s) | 3.79 |
| 271 | 330.00 | 1H NMR (DMSO-d6): 2.00-2.10 (2H, m), 2.80-2.85 (6H, s), 3.20-3.30 (2H, m), 3.40-3.50 (2H, m), 6.25-6.30 (1H, m), 6.60-6.80 (1H, m), 7.00-7.05 (1H, d), 7.30-7.40 (1H, t), 8.20-8.30 (2H, m), 8.85 (1H, s), 12.2 (1H, s) | 3.34 |
| 272 | 225.00 | (d6-DMSO) 2.90 (3H, d), 6.24 (1H, d), 6.42-6.44 (1H, m), 7.00 (1H, d), 7.14 (1H, dd), 7.37 (1H, t), 8.08 (1H, s), 8.23 (1H, d), 8.85 (1H, s), 11.87 (1H, s) | 3.32 |
| 273 | 355.00 | 1H NMR (DMSO-d6): 6.60-6.65 (1H, m), 6.70-6.80 (1H, d), 7.00-7.10 (1H, m), 7.15-7.30 (1H, m), 7.20-7.30 (1H, m), 7.55-7.65 (2H, m), 7.90 (1H, s), 8.15 (1H, s), 8.30 (1H, s), 8.60 (1H, s), 8.90-8.95 (1H, m), 12.2 (1H, s) | |
| 274 | 349.48 | 1H NMR (DMSO-d6): 3.14 (3H, s), 4.92 (4H, s), 6.42 (1H, d), 7.09 (1H, d), 7.23 (1H, t), 7.31 (4H, m), 7.48 (1H, t), 8.11 (1H, s), 8.21 (1H, s), 8.55 (1H, s), 12.20 (1H, br s) | 5.25 |
| 275 | 328.46 | 1H NMR (DMSO-d6): 2.24 (3H, s), 3.31 (4H, s), 3.56 (4H, s), 6.67 (1H, d), 7.19 (1H, d), 7.54 (1H, t), 8.27 (2H, s), 8.69 (1H, s), 12.23 (1H, s) | 4.37 |
| 276 | 354.64 | 1H NMR (DMSO-d6): 2.07 (3H, s), 3.57 (8H, m), 6.70 (1H, d), 7.23 (1H, d), 7.58 (1H, t), 8.28 (2H, s), 8.68 (1H, s), 12.25 (1H, s) | 4.25 |
| 277 | 331.70 | DMSO 3.55 (1H, m), 3.65 (1H, m), 4.82 (1H, m), 6.35 (1H, d), 6.52 (1H, m), 7.05 (1H, d), 7.4 (1H, t), 7.55 (1H, t), 7.75 (1H, d), 8.15 (1H, s), 8.58 (1H, s), 9.08 (1H, s) | 4.24 |
| 278 | 301.70 | DMSO 2.92 (3H, s), 6.30 (1H, d), 6.51 (1H, m), 7.08 (1H, d), 7.35-7.42 (2H, m), 7.5-7.6 (2H, m), 7.72 (2H, d), 8.13 (1H, s), 8.65 (1H, s), 9.18 (1H, s) | 4.62 |
| 279 | 315.00 | NMR (DMSO) 1.1 (6H, d, iPr), 2.85 (H, m, CH), 3.3 (H, brs, NH), 7.55 (H, d, ar), 7.65 (H, t, ar), 7.85 (H, t, ar), 8.2 (H, s, ar), 8.3 (H, s, ar), 9.1 (H, s, ar) and 10.3 (H, s, NH). | 4.47 |
| 280 | 363.00 | NMR (DMSO) 3.85 (2H, s, CH2), 7.15 (5H, m, ar), 7.6 (H, d, ar), 7.7 (H, t, ar), 7.9 (h, d, ar), 8.3 (H, s, ar), 84 (H, s, ar), 9.1 (H, s, ar), 10.6 (H, s, NH) and 12.3 (H, brs, NH). | 4.72 |
| 281 | 383.00 | (DMSO) 7.45-7.7 (3H, m, ar), 7.7-7.8 (2H, m, ar), 7.8 (H, t, ar), 8.0 (H, m, ar), 8.25 (H, s, ar), 8.4 (H, s, ar), 9.2 (H, s, ar), 11.1 (H, s, NH), and 12.3 (H, s, NH). | 4.68 |
| 282 | 383.00 | DMSO) 6.6 (H, m, ar), 7.7 (2H, d ar), 7.85 (H, t, ar), 8.0 (H, m, ar), 8.1 (H, s, ar), 8.25 (H, s, ar), 8.45 (H, s, ar), 9.3 (H, s, ar), 10.8 (0.5H, s, NH) and 12.3 (0.5H, s, NH). | 4.95 |
| 283 | 287.00 | (DMSO) 2.2 (3H, s, Me), 7.55 (H, m, ar), 7.7 (H, m, ar), 7.85 (H, m, ar), 8.2 (H, m, ar), 8.4 (H, m, ar), 10.4 (H, s, NH) and 12.3 (H, s, NH) | 4.05 |
| 284 | 335.00 | 1H NMR (DMSO-d6): 3.50-3.55 (3H, m), 6.40-6.45 (1H, m), 7.25-7.30 (2H, m), 7.32-7.37 (2H, m), 7.45-7.55 (3H, m), 8.15 (1H, s), 8.30 (1H, s), 8.45 (1H, s), 12.2 (1H, s) | 5.27 |
| 285 | 386.46 | 1H NMR (CDCl3): 1.69 (3H, d, J = 6.9 Hz), 5.29 (1H, m), 5.42 (1H, 6.8 Hz), 7.07 (2H, m), 7.44 (2H, m), 8.04 (1H, | 4.97 |

TABLE 4-continued

| Cmpd No. | LC_MASS_PLUS M + 1 (obs) | NMR_RESULT (1H NMR) | RT (mins) |
|---|---|---|---|
|  |  | m), 8.09 (1H, m), 8.27 (1H, m), 8.65 (1H, m), 8.87 (1H, br s) |  |
| 286 | 368.46 | 1H NMR (CDCl3): 1.69 (3H, d, J = 6.8), 5.33 (1H, m), 5.45 (1H, m), 7.38 (2H, m), 7.47 (2H, m), 8.04 (1H, d), 8.08 (1H, d), 8.27 (1H, d), 8.70 (2H, m) | 4.90 |
| 287 | 369.80 | DMSO 1.1-1.3 (6H, m), 1.6-1.7 (2H, m), 2.0-2.08 (2H, m), 4.0 (1H, m), 6.26 (1H, d), 6.35 (1H, d), 7.0 (1H, d), 7.3-7.4 (2H, m), 7.52 (2H, t), 7.7 (2H, d), 8.15 (1H, s), 8.55 (1H, s), 9.1 (1H, s) | 5.27 |
| 288 | 355.00 | (DMSO) 1.1-1.5 (5H, m, cyhex), 1.6-1.9 (5H, m, cyhex), 2.65 (1H, m, cyhex), 7.6 (H, d, ar), 7.75 (H, t, ar), 7.95 (H, d, ar), 8.3 (H, s, ar), 8.4 (H, s, ar), 9.15 (H, s, ar), 10.35 (H, s, NH) and 12.2 (H, s, NH). | 4.95 |
| 289 | 313.45 | 1H NMR (DMSO-d6): 1.55 (6H, m), 2.01 (2H, s), 4.20 (1H, m), 6.27 (1H, d), 6.54 (1H, d), 7.01 (1H, d), 7.34 (1H, t), 8.23 (1H, s), 8.30 (1H, s), 8.96 (1H, s), 12.13 (1H, s) | 5.09 |
| 290 | 327.45 | 1H NMR (DMSO-d6): 1.27 (3H, m), 1.45 (2H, m), 1.69 (1H, d), 1.81 (2H, d), 2.09 (2H, d), 3.81 (1H, m), 6.24 (1H, d), 6.39 (1H, d), 6.97 (1H, d), 7.31 (1H, t), 8.20 (2H, s), 8.88 (1H, s), 12.20 (1H, br s) | 5.25 |
| 291 | 341.49 | 1H NMR (DMSO-d6): 1.51 (6H, m), 1.67 (4H, m), 2.01 (2H, 2), 4.02 (1H, s), 6.26 (1H, d), 6.44 (1H, d), 6.98 (1H, d), 7.33 (1H, t), 8.19 (1H, s), 8.24 (1H, s), 8.93 (1H, s), 12.13 (1H, br s) | 5.37 |
| 292 | 273.38 | 1H NMR (DMSO-d6): 2.94 (3H, s), 3.53 (3H, s), 6.56 (1H, s), 7.05 (1H, s), 7.58 (1H, s), 8.31 (1H, s), 8.36 (1H, s), 8.78 (1H, s) | 4.59 |
| 293 | 341.55 | 1H NMR (CDCl3): 2.04 (4H, m), 3.61 (4H, m), 6.24 (1H, d, J = 8.3), 6.98 (1H, d, J = 7.4), 7.39 (1H, m), 7.48-7.52 (3H, m), 7.70 (2H, m), 7.88 (1H, m), 8.61 (1H, s), 9.16 (1H, s), 9.33 (1H, br s) | 5.32 |
| 294 | 350.00 | DMSO) 7.7-7.8 (2H, m, ar), 7.9 (H, t, ar), 8.05 (H, d, ar), 8.15 (H, t, ar), 8.25 (H, d, ar), 8.3 (H, s, ar), 8.45 (H, s, ar), 8.8 (H, d, ar), 9.0 (H, s, ar), 10.6 (H, s, NH) and 12.4 (H, s, NH). | 4.85 |
| 295 | 383.00 | (400 MHz, MeOH-d4): 7.85-7.95 (2H, d), 8.05-8.10 (2H, d), 8.25-8.30 (2H, s), 8.35-8.37 (1H, s), 8.70 (1H, s) | 3.98 |
| 296 | 350.00 | (DMSO) 7.6-7.7 (H, m, ar), 7.75 (H, m, ar), 7.85 (H, m, ar), 8.0 (H, m, ar), 8.3 (H, m, ar), 8.4 (H, m, ar), 8.8 (H, s, ar), 9.15 (h, s, ar), 9.3 (H, s, ar), 11.0 (H, s, ar) and 12.35 (H, s, NH) | 4.22 |
| 297 | 395.55 | 1H NMR (DMSO-d6): 3.69 (6H, d), 4.41 (2H, br s), 6.34 (1H, s), 6.88 (2H, m), 6.94 (2H, s), 7.02 (1H, m), 7.36 (1H, t), 8.19 (2H, m), 8.76 (1H, s), 12.13 (1H, s) | 4.64 |
| 298 | 257.59 | 1H NMR (DMSO-d6): 2.89 (3H, s), 6.26 (1H, d), 6.54 (1H, d), 7.03 (1H, d), 7.38 (1H, t), 8.21 (1H, s), 8.24 (1H, s), 8.94 (1H, s), 12.14 (1H, s) | 4.40 |
| 299 | 354.00 | (400 MHz, MeOH-d4): 2.35-2.40 (3H, s), 7.30-7.45 (4H, m), 8.05-8.15 (3H, m), 8.20-8.25 (1H, s) | 4.87 |
| 300 | 368.00 | (400 MHz, DMSO-d6): 2.20 (6H, s), 7.25 (3H, m), 7.70-7.80 (1H, s), 8.05 (1H, m), 8.15 (1H, m), 8.30 (1H, m), 9.10 (1H, s), 12.2 (1H, s) | 4.93 |
| 301 | 406.00 | (400 MHz, DMSO-d6): 7.80-7.85 (1H, m), 7.90-7.95 (2H, d), 8.05-8.10 (2H, d), 8.15-8.35 (3H, m), 8.50 (1H, s), 8.60 (1H, s), 9.50-9.55 (1H, s), 9.85-9.90 (1H, s), 12.2 (1H, s) | 4.53 |
| 302 |  | (400 MHz, MeOH-d4): 2.10-2.0 (1H, m), 2.70-2.80 (1H, m), 2.95-3.05 (1H, m), 3.10-3.20 (1H, m), 5.90-6.00 (1H, t), 7.20-7.40 (4H, m), 8.05-8.10 (1H, s), 8.15-8.20 (2H, d), 8.85 (1H, s) |  |
| 303 | 342.60 | (DMSO) 2.9-3.1 (4H, m), 7.0-7.5 (6H, m), 7.7-7.8 (2H, m), 7.8-8.2 (6H, m), 11.9 (0.7H, s) | 4.30 |
| 304 | 346.50 | (DMSO) 7.1-7.2 (3H, m), 7.2-7.4 (3H, m), 7.8-7.9 (2H, m), 7.9-8.1 (3H, m), 8.1-8.2 (1H, m), 8.4 (1H, s), 8.5 (1H, s), 12.3-12.4 (0.7H, s) | 4.34 |
| 305 | 398.00 | (400 MHz, CDCl3): 1.65-1.70 (3H, d), 5.25-5.30 (1H, m), 5.40-5.45 (1H, m), 6.80-6.85 (1H, d), 7.0 (1H, s), 7.05-7.10 (1H, d), 7.30-7.35 (1H, t), 8.05-8.10 (2H, m), 8.30 (1H, s), 8.70 (1H, s), 9.20-9.50 (1H, brs) | 4.87 |
| 306 | 384.00 | (400 MHz, MeOH-d4): 1.65-1.70 (3H, d), 5.40-5.50 (1H, m), 6.65-6.80 (1H, d), 6.95 (1H, s), 7.00-7.05 (1H, d), 7.15-7.20 (1H, t), 8.00-8.10 (2H, m), 8.20 (1H, s), 8.70 (1H, s) | 4.45 |
| 307 | 410.80 | CDCl3 1.7 (3H, m), 3.97 (3H, s), 5.42 (1H, br s), 5.57 (1H, m), 7.03 (2H, t), 7.5-7.6 (2H, m), 8.12 (1H, s), 8.2 (1H, s), 9.1 (1H, s), 9.52 (1H, s), 10.15 (1H, br s) | 4.64 |

TABLE 4-continued

| Cmpd No. | LC_MASS_PLUS M + 1 (obs) | NMR_RESULT (1H NMR) | RT (mins) |
|---|---|---|---|
| 308 | 405.00 | (d6-DMSO, 400 MHz) 4.73 (2H, s), 7.38 (2H, d), 7.54 (2H, d), 8.30 (1H, d), 8.50 (1H, s), 8.62 (2H, d) | 5.50 |
| 309 | 409.80 | DMSO 1.62 (3H, d), 2.88 (3H, m), 5.58 (1H, d), 7.1 (2H, m), 7.62 (2H, m), 8.1-8.25 (3H, m), 8.55 (1H, m), 8.72 (1H, s), 9.15 (1H, s), 12.3 (1H, s) | 3.95 |
| 310 | 413.51 | 1H NMR (DMSO-d6): 1.58 (3H, d), 5.50 (1H, t), 7.67 (2H, d), 7.79 (2H, d), 8.16 (3H, m), 8.21 (2H, d), 8.37 (1H, s) | 4.82 |
| 311 | 402.48 | 1H NMR (DMSO-d6): 1.71 (3H, d), 5.43 (1H, m), 7.28 (1H, s), 7.54 (2H, d), 7.61 (2H, d), 7.66 (1H, s), 7.94 (1H, s), 8.26 (1H, s), 8.47 (1H, s), 12.49 (1H, s) | 4.89 |
| 312 | 388.42 | 1H NMR (DMSO-d6): 4.74 (2H, d), 7.28 (1H, t), 7.38 (2H, m), 7.48 (1H, s), 8.19 (1H, s), 8.23 (2H, m), 8.33 (1H, t), 8.52 (1H, s), 12.33 (1H, s) | 4.95 |
| 313 | 383.50 | 1H NMR (DMSO-d6): 1.66 (3H, d), 5.45 (1H, q), 6.85 (2H, d), 7.31 (1H, s), 8.20 (1H, d), 8.23 (1H, s), 8.54 (2H, d) | 4.64 |
| 314 | 389.00 | (d6-DMSO, 400 MHz) 5.69 (2H, s), 7.49 (2H, d), 7.59 (2H, d), 8.32 (1H, s), 8.42 (1H, s), 8.65-8.67 (2H, m), 12.56 (1H, s) | 5.32 |
| 315 | 306.46 | 1H NMR (DMSO-d6): 4.48 (1H, m), 8.23 (1H, s), 8.35 (2H, m), 8.68 (1H, s), 12.59 (1H, s) | 4.80 |
| 316 | 355.46 | 1H NMR (DMSO-d6): 4.87 (2H, d), 7.36 (1H, m), 7.51 (1H, d), 7.87 (1H, m), 8.12 (1H, s), 8.24 (1H, s), 8.29 (1H, d), 8.43 (1H, s), 8.62 (2H, d), 12.39 (1H, s) | 4.10 |
| 317 | 355.46 | 1H NMR (DMSO-d6): 4.86 (2H, d), 7.73 (1H, m), 8.26 (2H, s), 8.30 (1H, d), 8.44 (1H, s), 8.54 (1H, s), 8.65 (1H, d), 8.86 (1H, s) 12.43 (1H, s) | 4.10 |
| 318 | 355.46 | 1H NMR (DMSO-d6): 4.93 (2H, d), 7.90 (2H, d), 8.16 (1H, s), 8.23 (2H, d), 8.31 (1H, s), 8.55 (1H, s), 8.78 (2H, d), 12.37 (1H, s) | 4.00 |
| 319 | 231.38 | 1H NMR (DMSO-d6): 7.27 (1H, t), 8.32 (1H, s), 8.41 (1H, s), 8.80 (3H, m) | 4.20 |
| 320 | 455.00 | 1H NMR (DMSO-d6): 1.55-1.60 (3H, d), 2.15-2.20 (6H, s), 2.55-2.60 (2H, m), 3.95-4.00 (2H, m), 5.35-5.40 (1H, m), 6.60-6.40 (1H, m), 7.00-7.10 (2H, m), 7.15-7.20 (1H, t), 8.05-8.10 (1H, m), 8.15-8.20 (2H, m), 8.25 (1H, s), 8.60 (1H, s), 12.2 (1H, s) | 4.49 |
| 321 | 453.00 | 1H NMR (DMSO-d6): 1.60-1.70 (3H, d), 2.20-2.30 (2H, m), 3.4-3.5 (4H, m), 5.15-5.20 (1H, m), 5.55-5.62 (1H, m), 6.85-6.90 (1H, d), 7.05-7.10 (1H, s), 7.18-7.23 (1H, d), 7.35-7.40 (1H, t), 8.30-8.35 (3H, m), 8.50 (1H, s) | 4.25 |
| 322 | 382.00 | NMR (DMSO) 1.65 (3H, d, CH3), 2.15 (3H, s, CH3), 5.55 (H, m, alpha), 7.1 (H, d, ar), 7.1-7.2 (H, m, ar), 7.6 (2H, m, ar), 8.05 (1H, s, ar), 8.2 (1H, s, ar), 8.3 (1H, s, ar), 8.63 (1H, s, ar) and 12.3 (1H, s, ar) | 4.99 |
| 323 | 412.00 | NMR (DMSO) 1.5 (3H, d, CH3), 5.4 (H, m alpha), 7.0 (H, s, ar), 7.1-7.25 (2H,, m, ar), 7.5-7.6 (2H, m, ar), 8.3 (H, s, ar), 8.4 (2H, brs, ar), 8.65 (H, s, ar) and 12.4 (H, s, ar). | 4.10 |
| 324 | 382.00 | NMR (DMSO) 1.5 (3H, s, CH3), 2.25 (3H, s, CH3), 5.3 (H, m, alpha), 6.2 (H, m, ar), 7.3 (2H, m, ar), 7.5 (2H, m, ar), 7.75 (H, m, ar), 8.2 (H, m, ar), 8.3 (H, m, ar), 8.65 (H, m, ar) and 12.3 (H, m, ar) | 4.92 |
| 325 | 361.44 | 1H NMR (DMSO-d6): 1.53 (3H, m), 1.81 (2H, m), 1.98 (1H, m), 2.90 (1H, m), 3.31 (1H, m), 3.43 (1H, m), 3.58 (2H, m), 7.85 (1H, s), 8.30 (2H, d), 8.36 (1H, s), 8.68 (1H, d), 8.84 (1H, s), 12.52 (1H, s) | 3.70 |
| 326 | 361.44 | 1H NMR (DMSO-d6): 1.34 (1H, m), 1.60 (1H, m), 1.92 (2H, m), 2.20 (1H, m), 2.78 (2H, m), 3.24 (3H, m), 3.54 (1H, m), 7.99 (1H, s), 8.23 (1H, m), 8.30 (2H, d), 8.60 (1H, d), 8.70 (1H, s), 12.45 (1H, s) | 3.59 |
| 327 | 361.44, 361.00 | 1H NMR (DMSO-d6): 1.41 (2H, m), 1.92 (2H, m), 2.08 (1H, m), 2.83 (2H, m), 3.29 (2H, m), 3.44 (2H, m), 7.97 (1H, s), 8.20 (1H, s), 8.25 (1H, s), 8.30 (1H, s), 8.48 (1H, d), 8.71 (1H, s), 12.43 (1H, s), 1H NMR (DMSO-d6): 1.41 (2H, m), 1.92 (2H, m), 2.08 (1H, m), 2.83 (2H, m), 3.29 (2H, m), 3.44 (2H, m), 8.20 (1H, s), 8.25 (1H, s), 8.30 (1H, s), 8.48 (1H, d), 8.71 (1H, s), 12.43 (1H, s) | 3.57, 3.55 |
| 328 | 347.40 | 1H NMR (DMSO-d6): 1.94 (1H, m), 1.96 (2H, m), 2.14 (1H, m), 3.20 (2H, m), 3.71 (2H, m), 3.83 (1H, m), 7.89 (1H, s), 8.30 (4H, m), 8.69 (1H, s), 8.91 (1H, s), 12.58 (1H, s) | 3.67 |
| 329 | 347.40 | 1H NMR (DMSO-d6): 1.77 (1H, m), 2.12 (1H, m), 2.77 (1H, m), 3.00 (1H, m), 3.17 (1H, m), 3.34 (2H, m), 3.60 (2H, m), 7.98 (1H, s), 8.23 (1H, d), 8.31 (2H, m), 8.71 (3H, m), 12.53 (1H, s) | 3.54 |

TABLE 4-continued

| Cmpd No. | LC_MASS_PLUS M + 1 (obs) | NMR_RESULT (1H NMR) | RT (mins) |
|---|---|---|---|
| 330 | 394.45 | 1H NMR (DMSO-d6): 2.04 (4H, m), 2.84 (2H, m), 3.33 (1H, s), 5.61 (1H, m), 7.18 (3H, m), 7.27 (1H, d), 8.00 (1H, d), 8.21 (1H, t), 8.23 (1H, s), 8.26 (1H, s), 8.68 (1H, s), 12.34 (1H, s) | 5.28 |
| 331 | 483.00 | (d6-DMSO, 400 MHz) 1.44 (9H, s), 1.54 (3H, d), 5.34-5.37 (1H, m), 7.11 (1H, brs), 7.19 (2H, d), 7.63 (1H, s), 8.10-8.12 (2H, m), 8.18 (1H, d), 8.23 (1H, d), 8.54 (1H, d), 9.27 (1H, brs), 12.29 (1H, brs) | 4.95 |
| 332 | 264.00 | NMR (DMSO) 7.3 (2H, brs, NH2), 8.1 (1H, s, ar), 8.2 (1H, s, ar), 8.3 (1H, s, ar), 8.95 (1H, s, ar) and 12.35 (1H, s, NH). | 3.87 |
| 333 | 383.00 | (d6-DMSO, 400 MHz) 1.55 (3H, d), 5.36-5.40 (1H, m), 6.76 (1H, brs), 6.98 (1H, brs), 7.21 (2H, brs), 8.16 (1H, d), 8.23 (1H, d), 8.26 (2H, d), 8.58 (1H, s), 12.36 (1H, s) | 4.42 |
| 334 | 382.80 | DMSO 1.58 (3H, d), 4.65 (2H, d), 5.28 (1H, t), 5.5-5.6 (1H, m), 7.15 (2H, m), 7.6 (2H, m), 8.05 (1H, m), 8.2 (1H, s), 8.26 (1H, m), 8.68 (1H, s), 11.95 (1H, s) | 3.90 |
| 335 | 456.00 | 1H NMR (MeOD-d4): 1.60-1.70 (3H, d), 3.60 (3H, s), 4.65 (2H, s), 5.40-5.45 (1H, m), 6.70-6.75 (1H, d), 7.03 (1H, s), 7.12-7.18 (1H, d), 7.25-7.30 (1H, t), 8.00-8.07 (2H, m), 8.15 (1H, s), 8.60 (1H, s) | 4.70 |
| 336 | 442.00 | 1H NMR (DMSO-d6): 1.35-1.40 (3H, d), 4.00-4.05 (2H, s), 5.25-5.35 (1H, m), 6.50-6.55 (1H, d), 6.95-7.00 (2H, m), 7.05-7.15 (1H, m), 8.05-8.13 (3H, m), 8.18 (1H, s), 8.55 (1H, s), 12.5 (1H, s) | 3.82 |
| 337 | 363.00 | 1H NMR (CD3OD): 1.60-1.70 (3H, d), 3.10-3.20 (3H, s), 3.35-3.45 (3H, s), 5.30-5.35 (1H, m), 8.15-8.20 (2H, m), 8.30-8.35 (1H, s), 8.75-8.80 (1H, s) | 4.07 |
| 338 | 375.00 | 1H NMR (DMSO-d6): 0.30-0.40 (1H, m), 0.42-0.47 (1H, m), 1.35-1.40 (3H, d), 2.55-2.60 (1H, m), 4.40-4.50 (1H, m), 7.58-7.63 (1H, d), 8.15-8.25 (3H, m), 8.28 (1H, s), 8.65 (1H, s), 12.0 (1H, s) | 3.84 |
| 339 | 398.47 | 1H NMR (CDCl3): 1.63 (3H, m), 3.44 (1H, s), 4.57 (2H, m), 5.31 (1H, br s), 6.02 (1H, br s), 7.06 (2H, m), 7.39 (2H, m), 8.19 (1H, m), 8.30 (1H, m), 8.76 (1H, br s), 8.93 (1H, br s) | 4.59 |
| 340 | 349.00, 349.00 | 1H NMR (DMSO-d6): 1.35-1.40 (3H, d), 2.55-2.60 (3H, m), 4.40-4.50 (1H, m), 7.58-7.63 (1H, d), 8.00-8.05 (1H, m), 8.15-8.25 (2H, m), 8.28 (1H, s), 8.65 (1H, s), 12.0 (1H, s), 1H NMR (DMSO-d6): 1.35-1.40 (3H, d), 2.55-2.60 (3H, m), 4.40-4.50 (1H, m), 7.58-7.63 (1H, d), 8.00-8.05 (1H, m), 8.15-8.25 (2H, m), 8.28 (1H, s), 8.65 (1H, s), 12.0 (1H, s) | 3.59, 2.84 |
| 341 | 428.00 | 1H NMR (DMSO-d6): 1.35-1.40 (3H, d), 3.6-3.7 (2H, m), 3.95-4.00 (2H, m), 4.80-4.90 (1H, m), 5.4-5.5 (1H, m), 6.7-6.8 (1H, m), 7.00-7.10 (2H, m), 7.20-7.25 (1H, m), 8.10-8.25 (3H, m), 8.65 (1H, s), 12.0 (1H, s) | 4.47 |
| 342 | | (400 MHz, DMSO) 1.57 (3H, d), 5.50-5.57 (1H, m), 7.11-7.15 (2H, m), 7.57-7.60 (2H, m), 8.20 (1H, d), 8.25 (1H, d), 8.36 (1H, s), 9.15 (1H, d), 9.45 (1H, d), 12.90 (1H, brs). | |
| 343 | | (400 MHz, DMSO) 1.55 (3H, d), 4.85 (2H, s), 5.45-5.53 (1H, m), 7.09-7.14 (2H, m), 7.55-7.58 (2H, m), 7.62 (1H, s), 7.72 (1H, d), 7.87 (1H, s), 7.95 (1H, d), 8.10 (1H, d), 11.55 (1H, s). | |
| 344 | 333.00 | 1H NMR (CD3OD): 2.40-2.50 (2H, m), 2.6-2.7 (2H, m), 3.50-3.60 (3H, m), 3.7-3.8 (1H, m), 5.2-5.3 (1H, m), 8.40 (1H, s), 8.50 (1H, m), 8.55 (1H, s), 8.75 (1H, s) | 3.54 |
| 345 | 347.00, 347.40 | 1H NMR (DMSO-d6): 1.80-1.90 (2H, m), 2.1-2.2 (2H, m), 3.05-3.15 (2H, m), 3.4-3.5 (2H, m), 4.30-4.40 (1H, m), 7.65-7.70 (1H, m), 8.30-8.35 (2H, m), 8.40-8.50 (1H, s), 8.60-8.70 (1H, m), 8.75-8.80 (1H, m), 12.0 (1H, s), 1H NMR (DMSO-d6): 1.84 (2H, m), 2.33 (2H, m), 3.14 (2H, m), 3.44 (2H, m), 4.36 (1H, m), 7.88 (1H, s), 8.25 (1H, m), 8.30 (2H, d), 8.37 (1H, m), 8.60 (1H, m), 8.69 (1H, s), 12.44 (1H, s) | 3.50, 3.50 |
| 346 | 423.56 | 1.73 (3H, d, J 6.8, Me), 3.06 (3H, br s, Me), 3.24 (3H, br s, Me), 5.53-5.47 (1H, m, CH), 5.75 (1H, br s, NH), 7.07-7.03 (2H, m, 2 × ArH), 7.46-7.43 (2H, m, 2 × ArH), 8.14 (1H, d, J 3.7, ArH), 8.46 (1H, d, J 1.8, ArH), 8.77 (2H, s, 2 × ArH). | 4.02 |
| 347 | 347.47 | 1H NMR (DMSO-d6): 1.66 (1H, m), 1.85 (1H, m), 1.98 (1H, m), 2.11 (1H, m), 2.90 (2H, m), 3.32 (1H, m), 3.47 (1H, m), 4.46 (1H, m), 7.57 (1H, d), 8.31 (3H, m), 8.66 (3H, m), 12.47 (1H, s) | 3.68 |

TABLE 4-continued

| Cmpd No. | LC_MASS_PLUS M + 1 (obs) | NMR_RESULT (1H NMR) | RT (mins) |
|---|---|---|---|
| 348 | 348.44 | 1H NMR (DMSO-d6): 1.67 (2H, m), 1.96 (2H, d), 3.49 (2H, t), 3.96 (2H, d), 4.30 (1H, m), 7.62 (1H, d), 8.18 (1H, s), 8.22 (1H, s), 8.29 (1H, s), 8.72 (1H, s), 12.36 (1H, s) | 4.42 |
| 349 | 360.46 | 1H NMR (DMSO-d6): 1.17 (5H, m), 1.70 (6H, m), 2.67 (2H, d), 8.27 (1H, s), 8.42 (2H, s), 8.72 (1H, s), 12.57 (1H, s) | 5.39 |
| 350 | 396.46 | (DMSO, D6); 1.55 (3H, d, J 6.8, Me), 5.53 (1H, t, J 6.8, CH), 7.13-7.09 (2H, m, 2 × ArH), 7.63-7.60 (2H, m, 2 × ArH), 8.15-8.14 (1H, m, NH), 8.22-8.19 (2H, m, 2 × ArH), 8.83 (1H, s, ArH), 9.30 (1H, s, ArH). | 3.27 |
| 351 | 392.00 | 1H NMR (DMSO-d6): 1.35-1.40 (9H, s), 1.50-1.55 (3H, d), 4.10-4.15 (1H, m) 4.40-4.50 (1H, m), 7.95-8.00 (1H, d), 8.20 (1H, s), 8.30 (1H, m), 8.35 (1H, m), 8.75 (1H, s) | 4.87 |
| 352 | 347.00 | (d6-DMSO, 400 MHz) 1.86-1.94 (1H, m), 2.28 (3H, s), 2.33 (1H, brs), 2.53-2.57 (1H, m), 2.60-2.67 (2H, m), 2.84-2.88 (1H, m), 4.62 (1H, brs), 7.67 (1H, d), 8.17 (1H, d), 8.21 (1H, s), 8.28 (1H, d), 12.35 (1H, s) | 4.00 |
| 353 | 255.00 | DMSO D6 7.60 (1H, d), 8.32 (1H, s), 8.43 (1H, s), 8.56 (1H, s), 8.82-8.86 (2H, m) 12.55 (1H, s). | 4.52 |
| 354 | 382.46 | 1H NMR (DMSO-d6): 0.95 (3H, t), 1.85 (1H, m), 1.97 (1H, m), 7.19 (1H, t), 7.34 (2H, t), 7.53 (2H, d), 8.08 (1H, d), 8.16 (2H, s), 8.26 (1H, s), 8.66 (1H, s), 12.31 (1H, s) | 4.92 |
| 355 | 374.50 | 1H NMR (DMSO-d6): 1.15 (8H, m), 1.28 (2H, m), 1.72 (2H, m), 1.84 (2H, m), 4.23 (1H, m), 7.43 (1H, d), 8.12 (1H, s), 8.18 (1H, s), 8.27 (1H, s), 8.73 (1H, s), 12.32 (1H, s) | 5.47 |
| 356 | 346.43 | 1H NMR (DMSO-d6): 0.85 (1H, m), 1.48 (4H, m), 1.68 (1H, d), 1.81 (2H, m), 2.04 (2H, m), 4.03 (1H, m), 7.49 (1H, d), 8.13 (1H, s), 8.19 (1H, s), 8.29 (1H, s), 8.73 (1H, s), 12.21 (1H, s) | 5.25 |
| 357 | 432.70 | CDCl3 0.8 (3H, d), 5.45 (1H, m), 5.6 (1H, br s), 7.1 (2H, m), 7.45 (2H, m), 8.15 (1H, s), 8.4 (1H, s), 8.5-8.6 (1H, br s), 8.78 (1H, s), 9.65 (1H, br s) | 5.00 |
| 358 | 439.00 | (DMSO) 1.27 (3H, t, J 7.1), 1.56 (3H, d, J 7.0), 4.17 (2H, q, J 7.1), 5.64 (1H, t, J 7.0), 7.10 (2H, t, J 8.9), 7.60-7.56 (2H, m), 8.04-8.00 (2H, m), 8.15 (1H, d, J 3.8), 8.22 (1H, d, J 2.1), 8.96 (1H, br s), 9.65 (1H, br s), 11.96 (1H, br s). | 4.39 |
| 359 | 425.51 | 1H NMR (DMSO): 1.52 (3H, m), 2.85 (3H, m), 5.33 (1H, m), 7.00 (1H, s), 7.15 (2H, m), 7.48 (2H, m), 8.24 (2H, m), 8.49 (1H, s), 8.66 (1H, s), 8.87 (1H, m), 12.4 (1H, br s) | 4.82 |
| 360 | 336.00 | 1H NMR (DMSO-d6): 1.45-1.50 (3H, d), 4.50-4.60 (1H, m), 8.05-8.25 (5H, m), 8.60 (1H, m), 12.3-12.4 (1H, s), 12.50-1.270 (1H, brs) | 3.20 |
| 361 | 363.00 | 1H NMR (CD3OD): 1.10-1.20 (3H, t), 1.90-2.20 (2H, m), 2.85 (3H, s), 4.65-4.70 (1H, m), 8.25-8.35 (3H, m), 8.65 (1H, s) | 3.92 |
| 362 | 377.00 | 1H NMR (CD3OD): 1.10-1.20 (6H, m), 2.3-2.4 (1H, m), 2.80 (3H, s), 4.70-4.75 (1H, d), 8.25-8.35 (3H, m), 8.80 (1H, s) | 4.27 |
| 363 | 377.00 | 1H NMR (CD3OD): 1.05-1.15 (6H, m), 1.50-1.60 (3H, m), 3.95-4.05 (1H, m), 4.50-4.65 (1H, m), 8.10-8.25 (3H, m), 8.80 (1H, s) | 4.07 |
| 364 | 391.00 | 1H NMR (CD3OD): 0.70-0.80 (6H, m), 1.55-1.60 (3H, d), 1.70-1.80 (1H, m), 2.85-2.95 (1H, m), 3.10-3.15 (1H, m), 4.50-4.65 (1H, m), 8.10-8.25 (3H, m), 8.80 (1H, s) | 4.22 |
| 365 | 381.00 | 1H NMR (CD3OD): 1.55-1.60 (3H, d), 3.45-3.55 (2H, m), 4.25-4.35 (1H, m), 4.40-4.45 (1H, m), 4.55-4.65 (1H, m), 8.10-8.25 (3H, m), 8.80 (1H, s) | 3.79 |
| 366 | 362.00 | (d6-DMSO, 400 MHz) 1.23-1.33 (2H, m), 1.72 (2H, d), 1.99-2.04 (1H, m), 3.27 (2H, t), 3.41 (2H, t), 3.85-3.89 (2H, m), 7.80 (1H, t), 8.14 (1H, d), 8.21 (1H, s), 8.28 (1H, d), 8.74 (1H, d), 12.35 (1H, brs) | 4.50 |
| 367 | 363.00 | 1H NMR (DMSO-d6): 0.95-1.05 (3H, t), 1.35-1.40 (3H, d), 3.00-3.10 (2H, m), 4.45-4.55 (1H, m), 7.55-7.60 (1H, d), 8.05-8.10 (1H, m), 8.18-8.22 (2H, m), 8.28 (1H, s), 8.70 (1H, s), | 3.92 |
| 368 | 456.00, 456.07 | 1H NMR (DMSO-d6): 1.40-1.50 (3H, d), 2.80 (3H, s), 2.85-3.05 (2H, m), 3.15-3.25 (2H, m), 4.50-4.60 (1H, m), 7.00-7.05 (1H, m), 7.60-7.65 (1H, d), 8.12-8.17 (1H, m), 8.19 (1H, m), 8.22 (1H, s), 8.28 (1H, s), 8.70 (1H, s),, 1H NMR (DMSO): 1.45 (3H, d), 2.89 (2H, m), 3.15 (2H, m), 3.31 (3H, s), 4.55 (1H, m), 7.04 (1H, s), 7.69 (1H, d), 8.19 (2H, m), 8.26 (1H, s), 8.67 (1H, s), 12.35 (1H, s) | 3.57, 2.84 |
| 369 | 417.00, 416.90 | 1H NMR (CD3OD): 1.55-1.60 (3H, d), 3.85-4.00 (2H, m), 4.70-4.80 (1H, m), 8.10-8.25 (3H, m), 8.80 (1H, s), DMSO | 4.09, 2.30 |

TABLE 4-continued

| Cmpd No. | LC_MASS_PLUS M + 1 (obs) | NMR_RESULT (1H NMR) | RT (mins) |
|---|---|---|---|
| | | d6 12.4 (bs, 1H); 8.8 (t, 1H); 8.7 (s, 1H); 8.3 (s, 2H); 8.2 (s, 1H); 7.9 (bs, 1H); 4.7 (q, 1H); 4.0 (m, 2H); 1.3 (d, 3H) | |
| 370 | 412.44 | 1H NMR (DMSO): 1.60 (3H, m), 5.51 (1H, br s), 7.08-7.21 (2H, m), 7.49-7.53 (2H, m), 8.29 (1H, m), 8.39 (1H, m), 8.53 (1H, m), 8.79 (2H, m), 12.6 (1H, s) | 4.22 |
| 371 | 436.48 | 1H NMR (CDCl3): 1.64 (3H, m), 5.31 (1H, m), 5.77 (1H, m), 7.05 (2H, m), 7.40 (2H, m), 7.95 (1H, m), 8.32 (1H, br s), 8.58 (1H, m), 8.94 (1H, m) | 5.17 |
| 372 | 375.00 | (d6-DMSO, 400 MHz) 1.14-1.24 (2H, m), 1.75-1.80 (5H, m), 2.11 (3H, s), 2.75 (2H, d), 3.40 (2H, t), 7.80 (1H, t), 8.13 (1H, d), 8.20 (1H, s), 8.28 (1H, d), 8.73 (1H, d), 12.35 (1H, s) | 3.95 |
| 373 | 348.00 | (d6-DMSO, 400 MHz) 1.66-1.74 (1H, m), 1.99-2.08 (1H, m), 2.67-2.74 (1H, m), 3.49-3.51 (2H, m), 3.58-3.67 (2H, m), 3.73 (1H, t), 3.79-3.84 (1H, m), 7.88 (1H, t), 8.16 (1H, d), 8.22 (1H, s), 8.29 (1H, d), 8.74 (1H, d), 12.36 (1H, brs) | 3.27 |
| 374 | 376.70 | CDCl3 1.75 (3H, d), 3.23 (1H, s), 5.30-5.35 (1H, m), 5.5-5.56 (1H, m), 7.08-7.18 (2H, m), 7.5-7.58 (2H, m), 8.22 (2H, m), 8.55 (1H, br s), 8.9 (1H, s), 10.65 (1H, br s) | 3.54 |
| 375 | | 1H NMR (CD3OD): 1.68-1.73 (3H, d), 4.50 (2H, s), 5.40-5.50 (1H, m), 6.7-6.8 (1H, m), 7.05-7.10 (1H, m), 7.15-7.20 (1H, d), 7.30-7.40 (1H, t), 8.30-8.40 (2H, m), 8.45 (1H, s), 8.50 (1H, s) | 3.25 |
| 376 | 455.00 | 1H NMR (CD3OD): 1.68-1.73 (1H, d), 2.75-2.80 (3H, s), 4.50 (2H, s), 5.40-5.50 (1H, m), 6.8-6.9 (1H, m), 7.05-7.10 (1H, m), 7.15-7.20 (1H, d), 7.30-7.40 (1H, t), 8.05-8.10 (2H, m), 8.20 (1H, s), 8.60 (1H, s) | 3.38 |
| 377 | 469.00 | 1H NMR (CD3OD): 1.68-1.73 (3H, d), 2.15-2.20 (2H, m), 2.90-2.95 (6H, s), 3.10-3.20 (2H, m), 4.05-4.10 (2H, m), 5.50-5.60 (1H, m), 6.8-6.9 (1H, m), 7.05-7.10 (1H, m), 7.15-7.20 (1H, d), 7.30-7.40 (1H, t), 8.20-8.24 (1H, d), 8.25-8.30 (2H, m), 8.60 (1H, s) | 3.29 |
| 378 | 406.75 | CDCl3 1.75 (3H, d), 3.55 (1H, s), 4.65 (2H, s), 5.30-5.35 (1H, m), 5.42-5.48 (1Hm), 7.1-7.18 (2H, m), 7.45-7.52 (2H, m), 8.1-8.18 (2H, m), 8.45 (1H, br s), 8.78 (1H, s), 9.4 (1H, br s) | 3.15 |
| 379 | 347.47 | 1H NMR (CDCl3/MeOD): 0.83 (2H, m), 1.94 (1H, m), 2.32 (1H, m), 3.00 (1H, m), 3.30 (1H, m), 3.36 (2H, m), 3.46 (1H, m), 3.60 (1H, m), 3.87 (1H, m), 8.15 (1H, s), 8.24 (1H, s), 8.29 (1H, s), 8.68 (1H, s) | 3.54 |
| 380 | 333.51 | 1H NMR (DMSO-d6): 2.15 (1H, m), 2.30 (2H, m), 3.35 (2H, m), 3.58 (1H, m), 4.77 (1H, m), 7.87 (1H, m), 8.29 (3H, m), 8.81 (1H, s), 8.94 (2H, br s), 12.45 (1H, s) | 5.00 |
| 381 | 333.40 | 1H NMR (DMSO-d6): 2.17 (1H, m), 2.34 (1H, m), 3.34 (3H, m), 3.58 (1H, m), 4.79 (1H, m), 7.87 (1H, d), 8.27 (3H, m), 8.68 (1H, s), 8.81 (2H, br s), 12.45 (1H, s) | 5.00 |
| 382 | 302.37 | 1H NMR (DMSO-d6): 3.16 (1H, s), 4.29 (2H, m), 8.29 (4H, m), 8.88 (1H, s), 12.40 (1H, s) | 3.22 |
| 383 | 403.48 | 1H NMR (DMSO-d6): 0.82 (2H, m), 1.11 (1H, m), 1.22 (1H, m), 1.85 (2H, t), 1.98 (3H, s), 2.07 (1H, br s), 3.00 (1H, t), 3.51 (1H, s), 3.83 (1H, m), 4.40 (1H, d), 8.40 (1H, s), 8.44 (1H, d), 8.65 (1H, s), 8.88 (1H, s), 9.20 (1H, br s), 12.91 (1H, s) | 3.18 |
| 384 | 420.80 | CDCl3 1.72 (3H, d), 3.55 (3H, s), 4.45 (2H, s), 5.32-5.36 (1H, m), 5.47-5.53 (1H, m), 7.05-7.1 (2H, m), 7.45-7.5 (2H, m), 8.15 (2H, m), 8.5 (1H, br s), 8.85 (1H, s), 10.05 (1H, br s) | 3.59 |
| 385 | 391.00 | 1H NMR (CD3OD): 1.15-1.20 (9H, s), 2.80 (3H, s), 4.70-4.75 (1H, s), 8.05-8.10 (1H, m), 8.12-8.15 (2H, m), 8.85 (1H, s) | 3.50 |
| 386 | 396.53 | 1H NMR (DMSO): 1.18 (3H, t), 1.55 (3H, d), 2.56 (2H, q), 5.51 (1H, m), 7.07-7.15 (3H, m), 7.52 (2H, m), 7.98 (1H, s), 8.14 (1H, s), 8.23 (1H, d), 8.60 (1H, d), 12.22 (1H, s) | 3.88 |
| 387 | 365.00 | (d6-DMSO, 400 MHz) 2.61 (3H, d), 3.82-3.83 (2H, m), 4.60 (1H, dd), 5.02 (1H, t), 7.32 (1H, d), 8.05 (1H, d), 8.20 (1H, s), 8.24 (1H, d), 8.27 (1H, s), 8.66 (1H, d), 12.36 (1H, brs) | 2.55 |
| 388 | 379.00 | (d6-DMSO, 400 MHz) 2.61 (3H, d), 3.30 (3H, s), 3.74 (2H, brs), 4.82 (1H, dd), 7.54 (1H, d), 8.13 (1H, d), 8.23 (2H, brs), 8.27 (1H, s), 8.66 (1H, s), 12.36 (1H, brs) | 2.82 |
| 389 | 441.00 | 1H NMR (CD3OD): 1.68-1.73 (3H, d), 2.80-2.85 (3H, s), 3.10-3.25 (2H, m), 3.35-3.55 (2H, m), 4.55-4.60 (1H, m), 8.10 (1H, m), 8.15 (1H, s), 8.20 (1H, s), 8.75 (1H, s) | 2.68 |

TABLE 4-continued

| Cmpd No. | LC_MASS_PLUS M + 1 (obs) | NMR_RESULT (1H NMR) | RT (mins) |
|---|---|---|---|
| 390 | 453.00 | 1H NMR (CD3OD): 1.68-1.73 (3H, d), 2.10-2.50 (2H, m), 2.90-3.20 (4H, m), 4.50-4.60 (2H, m), 8.10-8.15 (2H, m), 8.20 (1H, s), 8.80 (1H, s) | 1.74 |
| 391 | 379.00 | 1H NMR (CD3OD): 1.68-1.73 (3H, d), 3.35-3.40 (2H, m), 3.50-3.60 (2H, m), 4.60-4.70 (1H, m), 8.10 (1H, m), 8.15 (1H, s), 8.20 (1H, s), 8.80 (1H, s) | 2.63 |
| 392 | 393.00 | 1H NMR (CD3OD): 1.68-1.73 (3H, d), 3.15-3.20 (3H, s), 3.30-3.60 (4H, m), 4.60-4.70 (1H, m), 8.10 (1H, m), 8.15 (1H, s), 8.20 (1H, s), 8.80 (1H, s) | 2.80 |
| 393 | 391.00 | (d6-DMSO, 400 MHz) 0.89 (3H, d), 0.94 (3H, d), 1.58-1.81 (3H, m), 2.60 (3H, d), 4.61-4.67 (1H, m), 7.59 (1H, d), 8.03 (1H, d), 8.21 (1H, d), 8.22 (1H, s), 8.27 (1H, d) 8.68 (1H, d), 12.36 (1H, s) | 3.33 |
| 394 |  | (400 MHz, DMSO) 1.56 (3H, d), 5.41-5.48 (1H, m), 7.15 (2H, t), 7.56 (2H, dd), 8.17 (1H, d), 8.21 (1H, d), 8.28 (1H, s), 8.64 (1H, d), 8.84 (1H, d), 12.75 (1H, brs). |  |
| 395 | 367.00 | (400 MHz, DMSO) 1.50 (3H, d), 5.10-5.14 (1H, m), 6.32 (1H, d), 6.99 (1H, d), 7.08-7.14 (3H, m), 7.34 (1H, t), 7.46-7.49 (2H, m), 8.14 (1H, s), 8.20 (1H, d), 8.64 (1H, s), 12.11 (1H, brs)., MeOD-D4: 8.35 (m, 2H); 8.1 (s, 1H); 7.95 (dd, 1H); 7.5 (m, 2H); 7.2 (d, 1H); 7.15 (m, 2H); 6.8 (d, 1H); 5.0 (m, 1H); 1.65 (d, 3H). | 2.50 |
| 396 |  | (400 MHz, DMSO) 1.60 (3H, d), 3.88 (3H, s), 7.15 (2H, t), 7.46-7.49 (2H, m), 7.98 (1H, d), 8.25-8.30 (2H, m), 8.34 (1H, d), 8.56 (1H, s), 12.65 (1H, brs). |  |
| 397 |  | (400 MHz, DMSO) 1.51 (3H, s), 5.31-5.36 (1H, m), 7.12 (2H, t), 7.41-7.46 (3H, m), 7.80-8.08 (2H, m), 8.17 (1H, d), 11.98 (1H, brs). |  |
| 398 |  | (400 MHz, DMSO)1.51 (3H, d), 5.33-5.38 (1H, m), 7.14 (2H, t), 7.42-7.45 (2H, m), 7.70-7.76 (3H, m), 7.88 (1H, d), 8.21 (1H, s), 12.20 (1H, brs). |  |
| 399 | 339.00 | DMSO D6 2.78-2.92 (4H, m), 3.50-3.62 (4H, m), 7.05 (1H, s), 7.54 (1H, s), 8.27 (1H, s), 8.45 (1H, s), 8.68 (1H, s) | 1.24 |
| 400 | 403.00 | (d6-DMSO, 400 MHz) 3.90-3.95 (2H, m), 4.12 (2H, d), 7.97 (1H, t), 8.15 (1H, s), 8.24 (1H, d), 8.27 (1H, d), 8.63 (1H, d), 8.75 (1H, t), 12.34 (1H, brs) | 2.93 |
| 401 | 350.00 | NMR (DMSO) 1.3 (3H, d, CH3), 2.6-2.8 (2H, m, CH2), 4.65 (H, m, alpha), 7.15 (H, m, ar), 8.15 (H, m, ar), 8.25 (2H, s, ar), 8.7 (H, s, NH), 12.1-12.5 (2H, NH and COOH, brs × 2) | 2.59 |
| 402 | 363.00 | NMR (DMSO) 1.25 (3H, d, CH3), 1.75 (3H, m, CH3), 3.0 (2H, CH2, m), 4.65 (H, m, alpha), 7.5 (H, d, ar), 8.0 (H, m, NH), 8.1 (H, d, ar), 8.15 (H, s, ar), 8.25 (H, s, ar), 8.7 (H, s, NH) and 12.45 (H, s, NH). | 2.90 |
| 403 | 379.38 | 1H NMR (DMSO-d6): 1.73 (2H, m), 1.99 (2H, m), 2.84 (2H, m), 4.55 (1H, m), 7.74 (2H, br s), 7.95 (1H, d), 8.19 (1H, s), 8.28 (2H, m), 8.73 (1H, s), 12.38 (1H, s), 12.99 (1H, br s) | 2.21 |
| 404 | 418.49 | 1H NMR (DMSO-d6): 1.74 (3H, m), 5.82 (1H, m), 7.20 (2H, m), 7.61 (2H, m), 7.70 (1H, s), 7.84 (1H, s), 7.99 (1H, s), 8.39 (1H, s), 8.54 (1H, s), 8.66 (1H, s), 8.79 (1H, br s), 9.82 (1H, br s), 13.08 (1H, br s) | 3.85 |
| 405 | 344.00 | 2.82-2.88 (4H, m), 3.47-3.52 (4H, m), 4.50 (2H, s), 5.31 (1H, br s), 6.61 (1H, s), 7.15 (1H, s), 8.20 (1H, s), 8.25 (1H, s), 8.70 (1H, s), 12.25 (1H, br s) | 2.34 |
| 406 | 417.00 | 1H NMR (CD3OD): 1.1-1.4 (6H, m), 1.6-2.0 (7H, m), 3.0-3.15 (1H, m), 3.65-3.80 (1H, m), 5.6-5.7 (1H, m), 8.15 (1H, m), 8.20-8.25 (2H, m), 8.80 (1H, s) | 3.37 |
| 407 | 429.00 | 1H NMR (DMSO-d6): 1.45-1.50 (3H, d), 3.80-4.00 (5H, m), 4.60-4.65 (1H, m), 6.80-6.85 (1H, m), 7.95 (1H, s), 8.10 (1H, s), 8.25 (1H, s), 8.70 (2H, m), 12.2 (1H, s) | 3.13 |
| 408 | 443.00 | 1H NMR (DMSO-d6): 1.37-1.47 (6H, m), 3.85-4.05 (2H, m), 4.10-4.20 (2H, qd), 4.60-4.65 (1H, m), 6.65-6.70 (1H, d), 7.95 (1H, s), 8.10 (1H, s), 8.25 (1H, s), 8.70-8.80 (2H, m), 12.2 (1H, s) | 3.33 |
| 409 | 342.80 | DMSO D6 3.22-3.30 (4H, m), 3.86-3.91 (4H, m), 7.22 (1H, m), 7.69 (1H, s), 8.33 (1H, s), 8.46 (1H, s), 8.68 (1H, s), 10.07 (1H, s), 12.48 (1H, s) | 2.80 |
| 410 | 457.00 | 1H NMR (DMSO-d6): 1.35-1.40 (6H, m), 1.45-1.50 (3H, d), 3.80-4.10 (2H, m), 4.60-4.65 (2H, m), 6.50-6.60 (1H, m), 7.95 (1H, s), 8.10 (1H, s), 8.25 (1H, s), 8.70-8.80 (2H, m), 12.5 (1H, s) | 3.46 |
| 411 | 423.00 | 1H NMR (DMSO-d6): 1.45-1.50 (3H, d), 3.80-4.00 (2H, m), 4.50-4.60 (1H, m), 4.75 (1H, s), 8.05 (1H, m), 8.30-8.40 (2H, m), 8.50-8.60 (1H, m), 8.95-9.000 (1H, m), 9.20 (1H, m), 12.5 (1H, s) | 3.22 |

TABLE 4-continued

| Cmpd No. | LC_MASS_PLUS M + 1 (obs) | NMR_RESULT (1H NMR) | RT (mins) |
|---|---|---|---|
| 412 | 338.70 | DMSO D6 2.80-2.90 (4H, m), 3.48-3.61 (4H, m), 4.43 (1H, s), 6.66 (1H, s), 7.25 (1H, s), 8.27 (1H, s), 8.35 (1H, s), 8.66 (1H, s), 12.28 (1H, br s). | 3.16 |
| 413 | 399.00 | 1H NMR (CD3OD): 1.5-1.6 (3H, d), 3.85-4.10 (2H, m), 4.60-4.75 (1H, m), 6.40-6.50 (1H, s), 8.15 (1H, d), 8.20-8.25 (2H, m), 8.90 (1H, s) | 2.93 |
| 414 | 497.00 | 1H NMR (CD3OD): 1.5-1.6 (3H, d), 3.00-3.10 (3H, s), 3.30-3.60 (6H, brm), 3.90-4.05 (2H, m), 4.45-4.55 (1H, m), 6.50-6.60 (1H, s), 8.20 (1H, s), 8.30 (1H, s), 8.50 (1H, s), 8.70-8.80 (1H, m) | 3.08 |
| 415 | 583.00 | 1H NMR (DMSO-d6): 1.30-1.35 (3H, d), 1.40 (9H, s), 3.35-3.40 (4H, m), 3.65-3.72 (4H, m), 3.9-4.0 (2H, m), 4.40-4.50 (1H, m), 6.35-6.40 (1H, s), 7.10-7.20 (1H, m), 8.15 (1H, s), 8.25 (1H, s), 8.50 (1H, s), 8.60-8.70 (1H, m), 12.5 (1H, s) | 3.69 |
| 416 | 483.00 | 1H NMR (CD3OD): 1.50-1.60 (3H, d), 3.40-3.45 (4H, m), 3.95-4.05 (2H, m), 4.10-4.20 (2H, m), 4.6-4.7 (1H, m), 6.55 (1H, s), 8.35 (1H, s), 8.40 (2H, m), 8.90 (1H, s) | 2.73 |
| 417 | 458.00 | 1H NMR (CD3OD): 1.40-1.50 (3H, d), 3.50-3.55 (2H, m), 3.75-3.85 (2H, m), 3.95-4.05 (2H, m), 4.10-4.20 (2H, m), 4.45-4.55 (1H, m), 6.30-6.35 (1H, s), 8.00-8.05 (1H, s), 8.25 (2H, m), 8.75 (1H, s) | 2.88 |
| 418 | 467.74 | 1H NMR (DMSO-d6): 1.43 (3H, d), 3.93 (2H, m), 4.56 (1H, m), 8.04 (1H, s), 8.35 (1H, d), 8.39 (1H, d), 8.57 (1H, m), 8.66 (1H, m), 8.99 (1H, s), 12.67 (1H, s) | 3.35 |
| 419 | 485.00 | 1H NMR (CDCl3): 1.50-1.55 (3H, d), 2.25-2.30 (6H, s), 2.5-2.7 (2H, m), 3.50-3.60 (2H, m), 3.80-4.10 (2H, m), 4.50-4.60 (1H, m), 5.55-5.60 (1H, m), 5.90 (1H, s), 7.60-7.90 (2H, m), 8.20 (1H, s), 8.45-8.55 (1H, brs), 10.5-10.8 (1H, brs) | 2.82 |
| 420 | 424.80 | 1H NMR (DMSO): 1.44 (3H, d), 3.91 (2H, m), 4.58 (1H, m), 8.38 (1H, m), 8.66-8.72 (3H, m), 9.20 (1H, d) | 3.12 |
| 421 | 453.77 | 1H NMR (DMSO-d6): 3.92 (2H, m), 4.06 (2H, s), 8.06 (1H, s), 8.33 (1H, d), 8.44 (1H, s), 8.59 (2H, m), 8.95 (1H, s), 12.76 (1H, s) | 3.22 |
| 422 | 413.02 | 1H NMR (DMSO): 1.68 (3H, d), 5.67 (1H, m), 7.19 (2H, m), 7.61 (2H, m), 8.32 (1H, s), 8.47 (2H, m), 8.85 (1H, m), 9.18 (1H, s), 12.83 (1H, br s) | 3.90 |
| 423 | 383.76 | 1H NMR (DMSO): 1.65 (2H, m), 5.56 (1H, m), 5.75 (1H, br s), 7.22 (2H, m), 7.50 (2H, m), 7.56 (1H, s), 8.35 (2H, s), 8.39 (1H, m), 12.75 (1H, br s), 13.5 (1H, s) | 3.45 |
| 424 | 481.00 | 1H NMR (DMSO-d6): 1.45-1.50 (3H, d), 3.05-3.20 (3H, m), 3.80-4.00 (2H, m), 5.30-5.50 (1H, m), 8.00-8.10 (1H, m), 8.30-8.40 (1H, m), 8.50-8.80 (2H, m), 12.5 (1H, s) | 3.67 |
| 425 | 439.81 | 1H NMR (DMSO): 1.52 (3H, d), 2.99 (6H, s), 5.36 (1H, m), 6.43 (1H, br s), 7.16 (2H, m), 7.49 (2H, m), 8.11 (1H, m), 8.22 (2H, m), 8.51 (1H, br s), 12.36 (1H, s) | 3.56 |
| 426 | 478.00 | 1H NMR (DMSO-d6): 1.28 (9H, s), 1.40-1.50 (3H, d), 2.90-3.15 (4H, m), 4.50-4.60 (1H, m), 6.70-6.80 (1H, m), 7.60-7.65 (1H, d), 8.08-8.13 (1H, m), 8.15-8.20 (2H, m), 8.25 (1H, s), 8.70 (1H, s), 12 (1H, s) | 3.23 |
| 427 | 435.82 | 1H NMR (DMSO-d6): 3.92 (2H, m), 4.24 (2H, s), 7.43 (1H, m), 7.59 (1H, m), 7.77 (2H, m), 8.22 (2H, s), 8.78 (1H, m), 8.81 (1H, m), 8.92 (1H, s), 12.35 (1H, s) | 3.28 |
| 428 | 293.63 | 1H NMR (DMSO-d6): 1.25 (3H, t), 2.93 (2H, q), 8.34 (1H, s), 8.37 (1H, s), 8.57 (1H, s), 8.07 (1H, s), 12.84 (1H, br s) | 3.28 |
| 429 | 441.00 | 1H NMR (CD3OD): 1.30-1.50 (6H, dd), 1.60-1.70 (3H, d), 3.05-3.15 (1H, m), 3.85-4.05 (2H, m), 4.80-4.90 (1H, m), 8.10 (1H, s), 8.20-8.25 (2H, m), 8.80 (1H, s) | 3.45 |
| 430 | 359.00 | 1H NMR (CD3OD): 1.30-1.40 (6H, d), 2.88 (3H, s), 2.95-3.05 (1H, m), 4.20-4.25 (2H, m), 8.05 (1H, s), 8.20-8.25 (2H, m), 8.80 (1H, s) | 3.00 |
| 431 | 378.73 | 1H NMR (CD3OD): 1.70-1.75 (3H, d), 2.90-3.15 (2H, m), 3.5-3.6 (2H, m); 3.80-3.85 (1H, m), 8.35-8.45 (3H, m), 8.60-8.70 (1H, m) | 2.54 |
| 432 | 470.19 | 1H NMR (CD3OD): 1.30-1.40 (6H, d), 1.60 (3H, d), 2.95 (3H, s), 3.85-4.20 (2H, m), 4.80-4.90 (1H, qd), 7.60 (1H, s), 8.05 (1H, s), 8.20 (1H, s) | 3.43 |
| 433 | 439.00 | 1H NMR (CD3OD): 1.45-1.55 (3H, d), 1.80-1.90 (2H, m), 2.65-2.80 (2H, m); 4.50-4.60 (1H, m), 7.00-7.10 (5H, m), 8.10-8.20 (3H, m), 8.80 (1H, s) | 3.33 |
| 434 | 443.00 | 1H NMR (CD3OD): 1.65-1.75 (3H, d), 2.90-2.95 (2H, m), 3.50-3.60 (2H, m); 3.70-3.80 (3H, m), 4.90-5.00 (1H, m), 7.30 (1H, s), 8.40-8.45 (2H, m), 8.50 (1H, s), 8.60 (1H, s), 8.80 (1H, s) | 2.77 |
| 435 | 448.00 | 1H NMR (CD3OD): 1.75-1.85 (3H, d), 3.05-3.15 (2H, m), 3.25-3.30 (2H, m); 3.45-3.55 (2H, m), 3.60-3.80 (4H, m), | 2.81 |

TABLE 4-continued

| Cmpd No. | LC_MASS_PLUS M + 1 (obs) | NMR_RESULT (1H NMR) | RT (mins) |
|---|---|---|---|
| | | 3.90-4.00 (2H, m), 4.95-5.00 (1H, m), 8.40-8.45 (2H, m), 8.50 (1H, s), 8.60 (1H, s) | |
| 436 | 432.00 | 1H NMR (CD3OD): 1.75-1.85 (3H, d), 2.90-2.10 (4H, m), 3.00-3.10 (2H, m); 3.20-3.30 (2H, m), 3.55-3.75 (4H, m), 4.95-5.00 (1H, m), 8.40-8.45 (2H, m), 8.50 (1H, s), 8.60 (2H, s) | 2.64 |
| 437 | 478.19 | 1H NMR (CD3OD): 1.65-1.70 (3H, d), 2.90-3.00 (2H, m), 3.50-3.70 (2H, m), 4.80-4.90 (1H, m), 6.80-6.90 (1H, t), 6.95-7.05 (3H, m), 7.20-7.25 (1H, d), 7.35-7.40 (1H, d), 8.35-8.40 (3H, m), 8.50 (1H, m) | 3.18 |
| 438 | 440.00 | 1H NMR (CD3OD): 1.65-1.70 (3H, d), 3.70-3.90 (4H, m), 4.80-4.90 (1H, m), 7.80-7.85 (1H, t), 7.90-7.95 (1H, t), 8.35-8.45 (3H, m), 8.50 (2H, s), 8.60 (1H, m) | 2.93 |
| 439 | 446.00 | 1H NMR (CD3OD): 1.75-1.85 (3H, d), 1.90-2.10 (6H, m), 2.80-2.90 (2H, m); 3.00-3.10 (2H, m), 3.40-3.75 (4H, m), 4.95-5.00 (1H, m), 8.40-8.45 (2H, m), 8.50 (1H, s), 8.60 (2H, s) | 2.59 |
| 440 | 435.14 | 1H NMR (CD3OD): 1.00-1.05 (6H, d), 1.75-1.85 (3H, d), 3.20-3.40 (5H, m), 4.60-4.70 (1H, m), 8.10-8.30 (3H, m), 8.80 (1H, s) | 3.15 |
| 441 | 447.00 | 1H NMR (CD3OD): 1.75-1.85 (3H, d), 3.10-3.80 (8H, m), 4.95-5.00 (1H, m), 8.40-8.45 (2H, m), 8.50 (1H, s), 8.60 (1H, s) | 2.66 |
| 442 | 443.00 | 1H NMR (CD3OD): 1.75-1.85 (3H, d), 2.05-2.15 (2H, m), 3.55-3.60 (1H, m); 3.75-3.80 (1H, m), 4.10-4.20 (2H, m), 4.95-5.00 (1H, m), 7.50 (2H, s), 8.35 (1H, s), 8.40-8.60 (3H, m), 8.63 (1H, s), 8.87 (1H, s) | 2.75 |
| 443 | 428.00 | 1H NMR (CD3OD): 1.60-1.70 (3H, d), 3.40-3.50 (1H, m), 3.70-3.80 (1H, m); 4.00-4.05 (2H, m), 4.80-4.90 (1H, m), 5.90 (1H, s), 6.60 (1H, s), 8.35-8.55 (7H, m), 8.6 (2H, s) | 3.16 |
| 444 | 420.09 | 1H NMR (DMSO-d6): 1.26 (3H, d), 1.68 (3H, s), 3.05 (4H, m), 4.54 (1H, m), 7.78 (2H, m), 8.13 (1H, s), 8.27 (3H, s), 8.66 (1H, s), 12.40 (1H, s) | 2.68 |
| 445 | 470.12 | 1H NMR (CDCl3 + CD3OD drops): 1.19 (5H, m), 1.66 (3H, d), 2.76 (2H, m), 3.06 (2H, m), 4.69 (1H, m), 8.10 (1H, s), 8.18 (1H, s), 8.30 (1H, s), 8.64 (1H, s) | 2.88 |
| 446 | 518.19 | 1H NMR (CDCl3 + CD3OD drops): 2.83 (2H, t), 3.33 (1H, s), 3.40 (1H, m), 3.58 (1H, m), 4.05 (2H, m), 4.59 (1H, m), 6.94 (1H, br s), 7.06 (2H, d), 7.56 (2H, d), 7.92 (1H, s), 8.03 (1H, s), 8.12 (1H, s), 8.12 (1H, s), 8.71 (1H, s) | 2.88 |
| 447 | 423.00 | 1H NMR (CD3OD): 1.05-1.10 (3H, t), 1.60-1.70 (3H, d), 2.35-2.40 (2H, m), 2.45-2.55 (2H, m); 3.40-3.50 (2H, m), 4.55-4.60 (1H, m), 8.10 (1H, s), 8.15 (1H, s), 8.20 (1H, s), 8.80 (1H, s) | 3.23 |
| 448 | 446.00 | 1H NMR (CD3OD): 1.60-1.70 (4H, m), 1.90-2.05 (2H, m), 2.10-2.20 (1H, m), 2.25-2.40 (1H, m); 2.70-2.80 (3H, m), 2.90-3.00 (1H, m), 3.05-3.10 (1H, m), 3.35-3.45 (2H, m), 3.50-3.60 (2H, m), 3.65-3.75 (2H, m), 4.90-5.00 (1H, m), 8.35-8.40 (2H, m), 8.50 (1H, s), 8.60-8.65 (1H, s) | 2.62 |
| 449 | 440.00 | 1H NMR (CD3OD): 1.65-1.70 (3H, d), 3.70-3.90 (4H, m), 4.80-4.90 (1H, m), 7.80-7.85 (1H, t), 8.35-8.45 (3H, m), 8.45-8.55 (2H, s), 8.60 (1H, s), 8.75 (1H, s) | 2.90 |
| 450 | 452.00 | (d6-DMSO, 400 MHz) 1.36 (3H, d), 2.28 (3H, s), 2.78 (3H, s), 2.79-2.99 (2H, m), 3.15-3.25 (2H, m), 4.50 (1H, brs), 6.22 (1H, brs), 7.05 (1H, brs), 7.38 (1H, d), 8.13 (1H, brs), 8.22 (1H, s), 8.26 (1H, d), 8.77 (1H, brs), 12.30 (1H, s) | 2.76 |
| 451 | 492.00 | 1H NMR (CD3OD): 1.40-1.45 (9H, s), 1.65-1.70 (3H, d), 2.80-2.85 (3H, m), 2.95-3.00 (1H, m), 3.05-3.10 (1H, m), 3.40-3.50 (2H, m), 4.60-4.70 (1H, m), 8.15 (1H, s), 8.25 (1H, s), 8.30 (1H, s), 8.80 (1H, s) | 3.42 |
| 452 | 392.00 | 1H NMR (CD3OD): 1.65-1.70 (3H, d), 3.20-3.40 (2H, m), 3.70 (3H, s), 3.75-3.80 (2H, m), 4.50-4.60 (1H, m), 6.25-6.30 (1H, d), 6.35-6.40 (1H, t), 6.55-6.65 (2H, m), 7.90 (1H, s), 8.05 (1H, s), 8.15 (1H, s), 8.55 (1H, s) | 2.59 |
| 453 | 485.00 | 1H NMR (CD3OD): 1.65-1.70 (3H, d), 3.20-3.40 (2H, m), 3.70 (3H, s), 3.75-3.80 (2H, m), 4.50-4.60 (1H, m), 6.25-6.30 (1H, d), 6.35-6.40 (1H, t), 6.55-6.65 (2H, m), 7.90 (1H, s), 8.05 (1H, s), 8.15 (1H, s), 8.55 (1H, s) | 3.13 |
| 454 | 484.00 | 1H NMR (CD3OD): 1.08-1.13 (6H, m), 1.55-1.60 (3H, d), 2.85-3.05 (2H, m), 3.10-3.25 (2H, m), 3.35-3.40 (1H, m), 4.60-4.70 (1H, m), 8.10 (1H, s), 8.15 (1H, s), 8.20 (1H, s), 8.80 (1H, s) | 2.94 |
| 455 | 468.00 | (d6-DMSO, 400 MHz) 1.39 (3H, brs), 2.70-2.96 (5H, m), 3.16-3.26 (2H, m), 3.84 (3H, s), 4.31-4.36 (1H, m), 6.60 (1H, s), 7.03 (1.4H, brs), 7.43 (0.6H, brs), 8.01 (1H, t), 8.26 (1H, s), 8.41 (1H, s), 8.70 (0.4H, brs), 9.09 (0.6H, brs), 12.39 (1H, s) | 2.96 |

TABLE 4-continued

| Cmpd No. | LC_MASS_PLUS M + 1 (obs) | NMR_RESULT (1H NMR) | RT (mins) |
|---|---|---|---|
| 456 | 420.00 | (d6-DMSO, 400 MHz) 1.81-1.88 (1H, m), 1.94-1.98 (1H, m), 2.15 (6H, s), 2.24-2.28 (1H, m), 2.38-2.44 (1H, m), 2.86 (3H, s), 3.23 (3H, s), 5.38-5.40 (1H, m), 7.83 (1H, d), 8.15 (1H, s), 8.20 (1H, d), 8.28 (1H, d), 8.72 (1H, d), 12.35 (1H, s) | 2.90 |
| 457 | 455.13 | 1H NMR (DMSO): 1.47 (3H, d), 3.36 (1H, m), 3.51 (1H, m), 3.80 (2H, m), 6.64 (2H, d), 6.82 (1H, t), 7.09 (2H, t), 8.07 (1H, br s), 8.28 (4H, m), 8.66 (1H, s), 12.50 (1H, s) | 3.29 |
| 458 | 512.22 | 1H NMR (DMSO): 1.45 (3H, d), 3.07 (4H, m), 4.55 (1H, m), 4.93 (2H, m), 7.21 (1H, m), 7.29 (5H, m), 8.01 (1H, br s), 8.17 (1H, m), 8.28 (3H, m), 8.65 (1H, s), 12.44 (1H, s) | 3.34 |
| 459 | 479.16 | 1H NMR (DMSO + CD3OD drops): 1.41 (3H, d), 3.27 (2H, m), 3.58 (1H, m), 3.60 (1H, m), 4.53 (1H, m), 7.42 (2H, m), 7.60 (2H, m), 8.13 (1H, s), 8.24 (2H, m), 8.43 (1H, s), 8.51 (1H, s) | 3.09 |
| 460 | 460.17 | 1H NMR (DMSO): 1.48 (5H, m), 1.75 (2H, m), 2.10 (2H, t), 2.92 (2H, m), 3.05 (4H, m), 4.53 (1H, m), 7.90 (1H, br s), 8.04 (1H, m), 8.28 (3H, m), 8.66 (1H, s), 12.41 (1H, s) | 2.86 |
| 461 | 388.04 | 1H NMR (DMSO): 1.46 (3H, d), 2.59 (2H, m), 3.35 (1H, m), 4.57 (1H, m), 7.95 (1H, br s), 8.23 (1H, s), 8.28 (2H, s), 8.47 (1H, t), 8.65 (1H, s) | 2.84 |
| 462 | 555.18 | 1H NMR (DMSO): 1.45 (3H, d), 2.60 (2H, m), 3.26 (2H, m), 3.85 (2H, d), 4.56 (1H, m), 7.22 (1H, t), 7.37 (2H, d), 7.69 (1H, d), 8.21 (4H, m), 8.66 (1H, s), 12.31 (1H, s) | 3.59 |
| 463 | 419.00 | 1H NMR (CD3OD): 0.70-0.75 (3H, t), 1.05-1.15 (7H, m), 1.35-1.45 (2H, m), 1.55-1.60 (3H, d), 3.90-4.00 (1H, m), 4.60-4.65 (1H, m), 8.10 (1H, s), 8.15 (1H, s), 8.20 (1H, s), 8.80 (1H, s) | 3.50 |
| 464 | 405.00 | 1H NMR (CD3OD): 0.70-0.75 (6H, t), 1.30-1.40 (2H, m), 1.40-1.50 (1H, m), 1.55-1.60 (3H, d), 2.90-3.00 (1H, m), 3.15-3.20 (1H, m), 4.70-4.75 (1H, m), 8.10 (1H, s), 8.15 (1H, s), 8.20 (1H, s), 8.80 (1H, s) | 3.40 |
| 465 | 391.00 | 1H NMR (CD3OD): 0.70-0.75 (3H, t), 1.05-1.10 (3H, d), 1.35-1.45 (2H, m), 1.55-1.60 (3H, d), 3.80-3.90 (1H, m), 4.70-4.75 (1H, m), 8.10 (1H, s), 8.15 (1H, s), 8.20 (1H, s), 8.80 (1H, s) | 3.30 |
| 466 | 407.00 | 1H NMR (CD3OD): 1.55-1.60 (3H, d), 2.40-2.50 (2H, m), 3.35-3.55 (2H. m), 4.65-4.70 (1H, m), 8.25 (1H, s), 8.30-8.40 (2H, m), 8.70 (1H, s) | 2.50 |
| 467 | 420.00 | 1H NMR (CD3OD): 1.55-1.60 (3H, d), 2.30-2.40 (2H, m), 3.35-3.60 (5H, m), 4.60-4.70 (1H, m), 8.15 (1H, s), 8.20 (1H, s), 8.25 (1H, s), 8.80 (1H, s) | 2.80 |
| 468 | 448.00 | 1H NMR (CD3OD): 1.00-1.10 (6H, m), 1.55-1.60 (3H, d), 2.30-2.40 (2H, m), 3.35-3.50 (3H, m), 3.80-3.90 (2H, m), 4.60-4.70 (1H, m), 8.15 (1H, s), 8.20 (1H, s), 8.25 (1H, s), 8.80 (1H, s) | 3.00 |
| 469 | 484.00 | 1H NMR (CD3OD): 0.90-1.00 (6H, m), 1.55-1.60 (3H, d), 2.95-3.05 (1H, m), 3.10-3.25 (2H. m). 3.50-3.60 (1H. m), 3.70-3.80 (1H, m), 4.65-4.70 (1H, m), 8.10 (1H, s), 8.30-8.40 (2H, m), 8.70 (1H, s) | 3.00 |

B) Biological Data:

Example 1

JAK3 Inhibition Assay

Compounds were screened for their ability to inhibit JAK3 using a standard radioactive enzyme assay. 1.5 μL/well of a DMSO stock containing serial dilutions of a compound of the present invention (concentrations ranging from 667 μM to 46 nM) was placed in a 96 well polycarbonate plate. 50 μL per well of kinase buffer (100 mM HEPES (pH 7.4), 10 mM $MgCl_2$, 25 mM NaCl, 1 mM DTT, and 0.01% bovine serum albumin (BSA)) containing 2 μM poly(Glu)$_4$Tyr and 10 μM ATP was also added to the plate. To initiate the reaction, 50 μL kinase buffer containing 2 nM JAK3 enzyme was added. Final ATP concentration was 5 μM [γ-$^{33}$P] ATP (200 μCi $^{33}$P ATP/μmol ATP (Perkin Elmer, Cambridge, Mass.). After 20 minutes at room temperature (25° C.), the reaction was stopped by adding 50 μL 20% trichloroacetic acid (TCA)/0.4 mM ATP to each well. The entire content of each well was then transferred to a 96 well glass fiber filter plate using a TomTek Cell Harvester. After washing, 60 μL scintillation fluid was added and $^{33}$P incorporation detected using a Perkin Elmer TopCount. After removing mean background values for all of the data points the data was fit using Prism software to obtain a $K_i$(app). Inhibition of JAK2 was measured as above except that final poly(Glu)$_4$Tyr concentration was 15 μM and final ATP concentration was 12 μM.

Example 2

ROCK Inhibition Assays

Compounds were screened for their ability to inhibit ROCK I (AA 6-553) activity using a standard coupled enzyme system (Fox et al. (1998) *Protein Sci*. 7, 2249). Reactions were carried out in a solution containing 100 mM HEPES (pH 7.5), 10 mM $MgCl_2$, 25 mM NaCl, 2 mM DTT and 1.5% DMSO. Final substrate concentrations in the assay were 45 µM ATP (Sigma Chemicals, St Louis, Mo.) and 200 µM peptide (American Peptide, Sunnyvale, Calif.). Reactions were carried out at 30° C. and 45 nM ROCK I. Final concentrations of the components of the coupled enzyme system were 2.5 mM phosphoenolpyruvate, 350 µM NADH, 30 µg/ml pyruvate kinase and 10 µg/ml lactate dehydrogenase.

Some compounds were screened for their ability to inhibit ROCK using a standard radioactive enzyme assay. Assays were carried out in a solution containing 100 mM HEPES (pH 7.5), 10 mM MgCl$_2$, 25 mM NaCl, 2 mM DTT, and 1.5% DMSO. Final substrate concentrations in the assay were 13 µM [γ-$^{33}$P] ATP (25mCi $^{33}$P ATP/mmol ATP, Perkin Elmer, Cambridge, Mass./Sigma Chemicals, St Louis, Mo.) and 27 µM Myelin Basic Protein (MBP). Final enzyme concentration in the assay was 5 nM ROCK. Assays were carried out at room temperature. 1.5 µl of DMSO stock containing serial dilutions of the compound of the present invention (concentrations ranging from 10 µM to 2.6 nM) was placed in a 96 well plate. 50 µl of Solution 1 (100 mM HEPES (pH 7.5), 10 mM MgCl$_2$, 26 mM [γ-$^{33}$P] ATP) was added to the plate. The reaction was initiated by addition of 50 µl of Solution 2 (100 mM HEPES (pH 7.5), 10 mM MgCl$_2$, 4 mM DTT, 54 mM MBP and 10 nM ROCK). After 2 hours the reaction was quenched with 50 µL of 30% trichloroacetic acid (TCA, Fisher) containing 9 mM ATP. Transfer of 140 µL of the quenched reaction to a glass fiber filter plate (Corning, Cat. No. 3511) was followed by washing 3 times with 5% TCA. 50 µL of Optima Gold scintillation fluid (Perkin Elmer) was added and the plates were counted on a Top Count (Perkin Elmer). After removing mean background values for all of the data points the data was fit using Prism software to obtain a K$_i$(app).

Example 3

Aurora Inhibition Assay

Compounds were screened for their ability to inhibit full length Aurora-A (AA 1-403) activity using a standard coupled enzyme system (Fox et al., Protein Sci. 7, pp. 2249 (1998)). Reactions were carried out in a solution containing 100 mM HEPES (pH 7.5), 10 mM MgCl$_2$, 25 mM NaCl, 300 µM NADH, 1 mM DTT and 3% DMSO. Final substrate concentrations in the assay were 200 µM ATP (Sigma Chemicals, St Louis, Mo.) and 800 µM peptide (LRRASLG, American Peptide, Sunnyvale, Calif.). Reactions were carried out at 30° C. and 35 nM Aurora-A. Final concentrations of the components of the coupled enzyme system were 2.5 mM phosphoenolpyruvate, 200 µM NADH, 60 µg/ml pyruvate kinase and 20 µg/ml lactate dehydrogenase.

An assay stock buffer solution was prepared containing all of the reagents listed above with the exception of ATP and the test compound of interest. The assay stock buffer solution (60 µl) was incubated in a 96 well plate with 2 µl of the test compound of interest at final concentrations spanning 0.002 µM to 30 µM at 30° C. for 10 min. Typically, a 12 point titration was conducted by preparing serial dilutions (from 1 mM compound stocks) with DMSO of the test compounds in daughter plates. The reaction was initiated by the addition of 5 µl of ATP (final concentration 200 µM). Rates of reaction were obtained using a Molecular Devices Spectramax plate reader (Sunnyvale, Calif.) over 10 min at 30° C. The K$_i$ values were determined from the rate data as a function of inhibitor concentration using computerized nonlinear regression (Prism 3.0, Graphpad Software, San Diego, Calif.). Aurora-C activity was screened in a similar manner using Aurora-C protein. Aurora-B activity was screened using a radioactive assay, such as described in Examples 1 and 2, but using Aurora-B protein.

Table 5 below depicts enzyme inhibition data (K$_i$) for certain exemplary compounds. Compound numbers correspond to those compounds depicted in Table Table 6 below depicts enzyme inhibition data (K$_i$) for certain exemplary compounds. Compound numbers correspond to those compounds depicted in Table 2.

In Tables 5 and 6, "A" represents a K$_i$ of less than 0.5 µM, "B" represents a K$_i$ of between 0.5 and 5.0 µM, and "C" represents a K$_i$ greater than 5.0 µM for the indicated enzyme. If more than one value of K$_i$ has been determined, the average K$_i$ is indicated. If no value is indicated, then the K$_i$ was not determined. For ROCK, the term "Enzyme" indicates that an enzyme-linked assay was used; the term "$^{33}$P" indicates that a radioactive assay was used.

TABLE 5

Enzyme Inhibition Data for Compounds of Table 1

| Compound Number | Aurora A | JAK2 | JAK3 | ROCK Enzyme | $^{33}$P |
|---|---|---|---|---|---|
| 1 | | | | A | A |
| 2 | B | | | | A |
| 3 | A | A | A | | B |
| 4 | | B | A | | A |
| 5 | | B | C | | A |
| 6 | | B | B | | A |
| 7 | B | A | A | | A |
| 8 | B | A | A | | A |
| 9 | B | B | B | | B |
| 10 | | A | A | | A |
| 11 | | A | A | | A |
| 12 | | A | B | | B |
| 13 | | B | B | | A |
| 14 | | A | A | | A |
| 15 | | | | | A |
| 16 | A | A | A | | A |
| 17 | B | A | B | | B |
| 18 | B | A | A | | A |
| 19 | | A | A | | A |
| 20 | | A | A | | A |
| 21 | A | | | | A |
| 22 | | | | | A |
| 23 | | | | | A |
| 24 | | | | | A |
| 25 | B | | | | A |
| 26 | | B | B | | B |
| 27 | | | | | A |
| 28 | | | | | A |
| 29 | | | | | A |
| 30 | A | | | | A |
| 31 | A | | | | A |
| 32 | | B | A | | A |
| 33 | B | A | A | | A |
| 34 | | A | A | | A |
| 35 | | B | C | | B |
| 36 | | B | B | | B |
| 37 | | A | A | | A |
| 38 | B | A | A | | A |
| 39 | | C | C | | B |
| 40 | | A | A | | A |
| 41 | | A | A | | B |
| 42 | | A | A | | B |
| 43 | B | A | A | | A |
| 44 | B | B | B | | A |
| 45 | | B | B | | B |
| 46 | | B | A | | A |
| 47 | | B | B | | B |
| 48 | | B | B | | B |
| 49 | | B | A | | B |
| 50 | | B | B | | B |
| 51 | B | B | A | | A |

TABLE 5-continued

Enzyme Inhibition Data for Compounds of Table 1

| Compound Number | Aurora A | JAK2 | JAK3 | ROCK Enzyme | $^{33}$P |
|---|---|---|---|---|---|
| 52 | | C | C | | B |
| 53 | | C | B | | B |
| 54 | | C | C | | B |
| 55 | | B | B | | A |

TABLE 6

Enzyme Inhibition Data for Compounds of Table 2

| Compound No. | Aurora A | Aurora B | Aurora C | JAK2 | JAK3 | ROCK Enzyme | $^{33}$P |
|---|---|---|---|---|---|---|---|
| 1 | | | | A | A | | B |
| 2 | | | | A | A | | B |
| 3 | | | | A | A | | A |
| 4 | A | | | A | A | | A |
| 5 | | | | A | A | | B |
| 6 | | | | A | A | | A |
| 7 | | | | B | B | | B |
| 8 | A | | | A | A | | A |
| 9 | | | | A | A | | B |
| 10 | A | | | A | A | | A |
| 11 | | | | A | A | | B |
| 12 | | | | A | A | | A |
| 13 | | | | A | A | | B |
| 14 | B | | | A | A | | A |
| 15 | | | | B | B | | B |
| 16 | | | | A | A | | A |
| 17 | | | | B | B | | A |
| 18 | B | | | A | A | B | B |
| 19 | A | | | A | A | A | A |
| 20 | A | | | A | A | | B |
| 21 | | | | A | A | | A |
| 22 | | | | A | A | | A |
| 23 | | | | B | B | | A |
| 24 | B | | | A | A | | A |
| 25 | A | | | A | A | | A |
| 26 | | | | A | A | | A |
| 27 | | | | A | A | | A |
| 28 | | | | A | A | | A |
| 29 | | | | A | A | | A |
| 30 | A | | | A | A | | A |
| 31 | | | | A | A | | A |
| 32 | A | | | A | A | | B |
| 33 | A | | | A | A | A | A |
| 34 | | | | A | A | A | B |
| 35 | A | | | A | A | A | A |
| 36 | A | | | A | A | B | B |
| 37 | | | | A | A | B | A |
| 38 | B | | | A | A | B | B |
| 39 | A | | | A | A | | B |
| 40 | | | | A | A | | B |
| 41 | A | | | A | A | | B |
| 42 | A | | | A | A | | B |
| 43 | A | | | B | B | | B |
| 44 | A | | | B | B | | B |
| 45 | A | | | A | A | | B |
| 46 | A | | | A | A | | B |
| 47 | B | | | A | A | | B |
| 48 | A | | | A | A | | B |
| 49 | B | | | A | A | | B |
| 50 | B | | | A | A | | A |
| 51 | | | | B | B | | B |
| 52 | B | | | C | C | | B |
| 53 | A | | | A | A | | A |
| 54 | A | | | B | B | | B |
| 55 | | | | B | B | | |
| 56 | B | | | C | B | | |
| 57 | B | | | C | B | | B |
| 58 | B | | | A | A | | B |

TABLE 6-continued

Enzyme Inhibition Data for Compounds of Table 2

| Compound No. | Aurora A | Aurora B | Aurora C | JAK2 | JAK3 | ROCK Enzyme | $^{33}$P |
|---|---|---|---|---|---|---|---|
| 59 | B | | | A | A | | B |
| 60 | B | | | B | B | | B |
| 61 | | | | A | A | | B |
| 62 | | | | A | A | | A |
| 63 | | | | A | A | | A |
| 64 | | | | A | A | | B |
| 65 | | | | A | A | | B |
| 66 | B | | | A | A | | B |
| 67 | A | | | A | A | | B |
| 68 | A | | | A | A | | B |
| 69 | B | | | A | A | | B |
| 70 | B | | | A | A | | B |
| 71 | | | | A | A | | B |
| 72 | A | | | B | A | | B |
| 73 | | | | A | A | | A |
| 74 | | | | A | A | | A |
| 75 | A | | | A | A | | A |
| 76 | A | | | A | A | | B |
| 77 | | | | A | A | | B |
| 78 | A | | | A | A | | B |
| 79 | A | | | A | A | | B |
| 80 | A | | | A | A | | B |
| 81 | A | | | B | B | | B |
| 82 | | | | A | A | | A |
| 83 | | | | A | A | | B |
| 84 | | | | A | A | | B |
| 85 | | | | A | A | | B |
| 86 | | | | A | A | | B |
| 87 | | | | A | A | | B |
| 88 | | | | A | A | | B |
| 89 | | | | A | A | | B |
| 90 | | | | A | A | | B |
| 91 | | | | B | B | | B |
| 92 | A | | | A | A | | A |
| 93 | A | | | A | A | | B |
| 94 | | | | B | B | | B |
| 95 | B | | | B | B | | B |
| 96 | B | | | A | A | | B |
| 97 | A | | | A | A | | B |
| 98 | A | | | A | A | | B |
| 99 | A | | | A | A | | A |
| 100 | A | | | A | A | | B |
| 101 | A | | | A | A | | B |
| 102 | B | | | A | A | | B |
| 103 | B | | | A | A | | B |
| 104 | | | | A | A | | B |
| 105 | | | | A | A | | B |
| 106 | | | | A | A | | B |
| 107 | | | | A | A | | B |
| 108 | | | | A | A | | B |
| 109 | | | | A | A | | B |
| 110 | B | | | B | B | | B |
| 111 | | | | A | A | | B |
| 112 | | | | A | A | | B |
| 113 | B | | | A | A | | B |
| 114 | B | | | A | A | | B |
| 115 | | | | A | A | | B |
| 116 | | | | A | A | | B |
| 117 | B | | | A | A | | B |
| 118 | B | | | A | A | | B |
| 119 | B | | | A | A | | B |
| 120 | A | | | A | A | | B |
| 121 | B | | | A | A | | B |
| 122 | B | | | A | A | | B |
| 123 | B | | | A | A | | B |
| 124 | B | | | A | A | | B |
| 125 | B | | | A | A | | B |
| 126 | | | | C | B | | B |
| 127 | | | | A | A | | B |
| 128 | B | | | A | A | | B |
| 129 | | | | B | A | | B |
| 130 | A | | | A | A | | B |
| 131 | A | | | A | A | | B |
| 132 | A | | | A | A | | B |

TABLE 6-continued

Enzyme Inhibition Data for Compounds of Table 2

| Compound No. | Aurora A | Aurora B | Aurora C | JAK2 | JAK3 | ROCK Enzyme | $^{33}$P |
|---|---|---|---|---|---|---|---|
| 133 | | | | A | A | B | |
| 134 | | | | A | A | B | |
| 135 | | | | A | A | A | |
| 136 | | | | A | A | A | |
| 137 | | | | A | A | B | |
| 138 | | | | A | A | B | |
| 139 | | | | A | A | B | |
| 140 | | | | A | A | B | |
| 141 | | | | A | A | B | |
| 142 | | | | B | A | B | |
| 143 | | | | B | A | B | |
| 144 | | | | A | A | B | |
| 145 | | | | A | A | B | |
| 146 | | | | A | A | B | |
| 147 | | | | A | A | B | |
| 148 | | | | B | A | A | |
| 149 | | | | A | A | B | |
| 150 | B | | | A | A | B | |
| 151 | A | | | A | A | A | |
| 152 | B | | | A | A | B | |
| 153 | B | | | A | A | B | |
| 154 | B | | | A | A | B | |
| 155 | B | | | A | A | B | |
| 156 | B | | | A | A | A | |
| 157 | B | | | A | A | B | |
| 158 | B | | | A | A | B | |
| 159 | B | | | A | A | B | |
| 160 | | | | A | A | B | |
| 161 | B | | | A | A | B | |
| 162 | B | | | A | A | B | |
| 163 | B | | | A | A | B | |
| 164 | B | | | A | A | B | |
| 165 | B | | | A | A | B | |
| 166 | B | | | A | A | B | |
| 167 | B | | | A | A | B | |
| 168 | B | | | A | A | B | |
| 169 | B | | | A | A | B | |
| 170 | B | | | A | A | B | |
| 171 | | | | A | A | B | |
| 172 | B | | | A | A | A | |
| 173 | | | | A | A | A | |
| 174 | | | | A | A | | |
| 175 | | | | A | A | | |
| 176 | | | | A | A | | |
| 177 | A | | | A | A | B | |
| 178 | | | | B | B | B | |
| 179 | B | | | A | A | B | |
| 180 | | | | A | A | B | |
| 181 | B | | | A | A | B | |
| 182 | B | | | A | A | B | |
| 183 | | | | A | A | B | |
| 184 | | | | B | A | B | |
| 185 | | | | B | A | | |
| 186 | A | | | A | A | | |
| 187 | | | | B | A | | |
| 188 | | | | C | B | | |
| 189 | | | | A | A | B | |
| 190 | B | | | A | A | B | |
| 191 | B | | | A | A | A | |
| 192 | B | | | A | A | A | |
| 193 | | | | A | A | A | |
| 194 | | | | A | A | B | |
| 195 | | | | B | A | B | |
| 196 | | | | C | B | B | |
| 197 | | | | B | B | B | |
| 198 | | | | C | B | B | |
| 199 | | | | B | A | B | |
| 200 | | | | B | A | B | |
| 201 | | | | A | A | B | |
| 202 | | | | B | B | B | |
| 203 | | | | A | A | B | |
| 204 | | | | | A | B | |
| 205 | | | | | A | B | |
| 206 | | | | | A | B | |
| 207 | | | | | A | B | |
| 208 | | | | | A | B | |
| 209 | | | | | A | B | |
| 210 | B | | | | | | |
| 211 | A | | | | | | B |
| 212 | A | B | | | | | B |
| 213 | A | | | | | | B |
| 214 | B | | | | | | B |
| 215 | B | | | | | | B |
| 216 | A | | | | | | B |
| 217 | A | | | | | B | B |
| 218 | A | | | | | A | A |
| 219 | A | | | | | B | B |
| 220 | B | | | | | B | |
| 221 | A | | | | | A | |
| 222 | A | | | | | A | |
| 223 | B | | | | | B | |
| 224 | A | | | | | A | |
| 225 | B | | | | | B | |
| 226 | B | | | | | | |
| 227 | A | | | | | A | |
| 228 | A | | | | | A | |
| 229 | A | | | | | B | |
| 230 | B | | | | | B | |
| 231 | A | | | | | A | |
| 232 | A | | | | | B | |
| 233 | | | | | | B | |
| 234 | A | | | | | | |
| 235 | A | | | | | A | |
| 236 | A | | | | | | |
| 237 | A | A | A | | | B | |
| 238 | A | A | A | | | B | |
| 239 | A | | | | | A | |
| 240 | A | | | | | B | |
| 241 | B | | | | | | |
| 242 | A | B | A | | | B | |
| 243 | A | | | | | B | |
| 244 | B | | | | | B | |
| 245 | A | | | | | | |
| 246 | B | | | | | B | |
| 247 | A | | | | | B | |
| 248 | A | | | | | B | |
| 249 | A | | | | | B | |
| 250 | A | | | | | B | |
| 251 | A | | | | | B | |
| 252 | A | | A | | | B | |
| 253 | A | | | | | A | |
| 254 | A | | | | | B | |
| 255 | A | | | | | A | |
| 256 | A | | | | | A | |
| 257 | B | | | | | B | |
| 258 | A | | | | | B | |
| 259 | A | | | | | A | |
| 260 | A | | A | | | B | |
| 261 | B | | | | | B | |
| 262 | B | | | | | B | |
| 263 | A | | | | | B | |
| 264 | A | | | | | B | |
| 265 | A | | | | | B | |
| 266 | A | | | | | B | |
| 267 | A | | | | | A | |
| 268 | B | | | | | | |
| 269 | A | | | | | | |
| 270 | B | | | | | B | |
| 271 | A | | | | | B | |
| 272 | B | | | | | | |
| 273 | A | | | | | B | |
| 274 | A | | | | | B | |
| 275 | B | | | | | B | |
| 276 | A | | | | | B | |
| 277 | A | | | | | A | |
| 278 | A | | | | | A | |
| 279 | B | | | | | | |
| 280 | A | | | | | | |

TABLE 6-continued

Enzyme Inhibition Data for Compounds of Table 2

| Compound No. | Aurora A | Aurora B | Aurora C | JAK2 | JAK3 | ROCK Enzyme | 33P |
|---|---|---|---|---|---|---|---|
| 281 | A | | | | | | |
| 282 | A | | | | | | |
| 283 | B | | | | | | |
| 284 | B | | | | | | B |
| 285 | A | A | A | | | | B |
| 286 | A | | | | | | B |
| 287 | A | | | | | | |
| 288 | A | | | | | | |
| 289 | A | | | | | | B |
| 290 | A | B | B | | | | B |
| 291 | A | B | | | | | B |
| 292 | C | | | | | | B |
| 293 | B | | | | | | B |
| 294 | A | | | | | | B |
| 295 | A | | | | | | B |
| 296 | A | | | | | | B |
| 297 | A | | | | | | B |
| 298 | B | | | | | | B |
| 299 | A | A | | | | | A |
| 300 | A | A | | | | | A |
| 301 | B | | | | | | B |
| 302 | A | A | | | | | B |
| 303 | | | | | | | A |
| 304 | | | | | | | B |
| 305 | A | A | | | | | B |
| 306 | A | A | A | | | | B |
| 307 | A | | | | | | A |
| 308 | B | | | | | | B |
| 309 | B | | | | | | B |
| 310 | A | A | | | | | B |
| 311 | A | | | | | | B |
| 312 | A | A | A | | | | B |
| 313 | A | | | | | | B |
| 314 | B | | | | | | |
| 315 | A | B | | | | | B |
| 316 | A | A | A | | | | B |
| 317 | A | A | A | | | | B |
| 318 | A | | | | | | B |
| 319 | B | | | | | | |
| 320 | A | | | | | | |
| 321 | A | B | A | | | | B |
| 322 | A | A | | | | | B |
| 323 | A | A | A | | | | B |
| 324 | A | A | A | | | | B |
| 325 | A | A | A | | | | B |
| 326 | A | A | A | | | | A |
| 327 | A | A | A | | | | A |
| 328 | A | A | A | | | | B |
| 329 | A | A | A | | | | A |
| 330 | A | A | | | | | B |
| 331 | A | | A | | | | B |
| 332 | A | | | | | | |
| 333 | A | A | A | | | | B |
| 334 | A | | | | | | |
| 335 | A | A | | | | | |
| 336 | A | | | | | | B |
| 337 | A | | | | | | B |
| 338 | A | | | | | | B |
| 339 | A | A | A | | | | B |
| 340 | A | A | A | | | | B |
| 341 | A | A | | | | | B |
| 342 | A | | | | | | B |
| 343 | B | | | | | | |
| 344 | A | | | | | | A |
| 345 | A | B | B | | | | A |
| 346 | B | | | | | | |
| 347 | A | B | B | | | | A |
| 348 | A | A | A | | | | B |
| 349 | A | A | A | | | | B |
| 350 | B | | | | | | |
| 351 | A | | | | | | B |
| 352 | A | | | | | | |
| 353 | | | | | | | B |
| 354 | A | A | | | | | B |
| 355 | A | A | A | | | | B |
| 356 | A | A | A | | | | B |
| 357 | A | | | | | | B |
| 358 | B | | | | | | |
| 359 | A | A | A | | | | B |
| 360 | B | | | | | | B |
| 361 | A | A | A | | | | B |
| 362 | A | A | A | | | | B |
| 363 | A | | | | | | B |
| 364 | A | | | | | | B |
| 365 | A | | | | | | B |
| 366 | A | | | | | | B |
| 367 | A | | | | | | B |
| 368 | A | A | A | | | | B |
| 369 | A | A | A | | A | | B |
| 370 | A | A | A | | | | B |
| 371 | A | A | A | A | | | B |
| 372 | A | | | | | | B |
| 373 | A | | | | | | B |
| 374 | A | A | A | | | | B |
| 375 | A | A | | | | | B |
| 376 | A | | | | | | B |
| 377 | A | | | | | | B |
| 378 | A | | | | | | B |
| 379 | A | | | | | | A |
| 380 | A | A | | | | | B |
| 381 | A | | | | | | A |
| 382 | A | B | | | | | |
| 383 | A | | | | | | B |
| 384 | A | | | | | | B |
| 385 | A | A | | | | | B |
| 386 | A | A | A | A | | | B |
| 387 | A | A | A | | | | B |
| 388 | A | A | | | | | |
| 389 | A | | | | | | B |
| 390 | B | | | | | | B |
| 391 | A | | A | | A | | B |
| 392 | A | | | | | | B |
| 393 | A | | | | | | B |
| 394 | A | | | | | | B |
| 395 | A | A | | A | A | | B |
| 396 | A | | | | | | B |
| 397 | A | A | | | | | B |
| 398 | A | | | | | | B |
| 399 | A | | | | | | A |
| 400 | A | | A | | | | B |
| 401 | A | | | | | | B |
| 402 | B | | | | | | B |
| 403 | B | | | | | | |
| 404 | A | B | | | | | B |
| 405 | A | | | | | | |
| 406 | A | B | | | | | B |
| 407 | A | | A | | | | B |
| 408 | A | | | | | | B |
| 409 | A | | | | | | A |
| 410 | A | | | | | | B |
| 411 | A | | A | | | | B |
| 412 | A | | | | | | |
| 413 | A | A | | | | | B |
| 414 | B | B | | | | | B |
| 415 | A | A | | | | | B |
| 416 | A | B | | | | | B |
| 417 | A | A | | | | | B |
| 418 | A | A | | | | | B |
| 419 | B | B | | | | | B |
| 420 | A | A | A | | | | B |
| 421 | A | B | | | | | B |
| 422 | A | A | | | | | B |
| 423 | A | A | | | | | B |
| 424 | A | A | | | | | B |
| 425 | A | A | | | | | B |
| 426 | A | A | | | | | B |
| 427 | A | B | B | | | | B |
| 428 | A | B | | | | | B |

TABLE 6-continued

Enzyme Inhibition Data for Compounds of Table 2

| Compound No. | Aurora A | Aurora B | Aurora C | JAK2 | JAK3 | ROCK Enzyme $^{33}$P |
|---|---|---|---|---|---|---|
| 429 | A | B | B | | | B |
| 430 | A | B | B | | | B |
| 431 | A | A | A | | | B |
| 432 | B | B | | | | B |
| 433 | B | B | | | | B |
| 434 | B | B | | | | B |
| 435 | B | B | | | | B |
| 436 | B | A | | | | B |
| 437 | A | B | | | | B |
| 438 | B | B | | | | B |
| 439 | A | A | | | | B |
| 440 | B | B | | | | B |
| 441 | B | B | B | | | B |
| 442 | A | B | B | | | B |
| 443 | A | A | A | A | | B |
| 444 | A | A | A | B | | B |
| 445 | A | B | A | | | B |
| 446 | A | A | A | B | | B |
| 447 | A | B | B | | | B |
| 448 | B | B | | | | B |
| 449 | A | B | | | | B |
| 450 | A | A | A | B | | B |
| 451 | B | B | | | | B |
| 452 | A | A | A | | | B |
| 453 | B | B | | | | B |
| 454 | A | B | B | | | B |
| 455 | A | B | B | | | B |
| 456 | A | B | | | | B |
| 457 | B | B | | | | B |
| 458 | A | A | A | | | |
| 459 | B | B | | | | |
| 460 | B | B | | | | |
| 461 | A | A | A | | | |
| 462 | B | B | | | | |
| 463 | A | B | | | | |
| 464 | B | | | | | |
| 465 | A | | | | | |
| 466 | B | | | | | |
| 467 | A | | | | | |
| 468 | A | | | | | |
| 469 | A | | | | | |

The invention claimed is:

1. A compound of Formula (I-B)

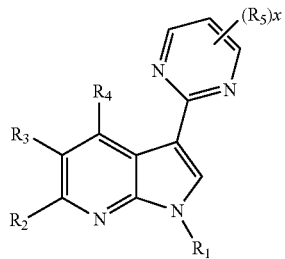

I-B or pharmaceutically acceptable salts thereof, wherein:
$R^1$ is T-R' or —Si(R')$_3$;
$R^2$, $R^3$, and $R^4$ are each independently halogen, —CN, —NO$_2$, or V—R';
x is 1, 2 or 3; and
T and V are each independently a bond or an optionally substituted C$_1$-C$_6$ alkylidene chain, wherein up to two methylene units of the chain are optionally and independently replaced by —NR'—, —S—, —O—, —CS—, —CO$_2$—, —OCO—, —CO—, —COCO—, —CONR'—, —NR'CO—, —NR'CO$_2$—, —SO$_2$NR'—, —NR'SO$_2$—, —CONR'NR'—, —NR'CONR'—, —OCONR'—, —NR'NR'—, —NR'SO$_2$NR'—, —SO—, —SO$_2$—, —PO—, —PO$_2$—, or —POR'—;

each occurrence of $R^5$ is independently halogen or —N(R')$_2$ wherein one R' in $R^5$ is hydrogen and the second R' in $R^5$ is a ring selected from

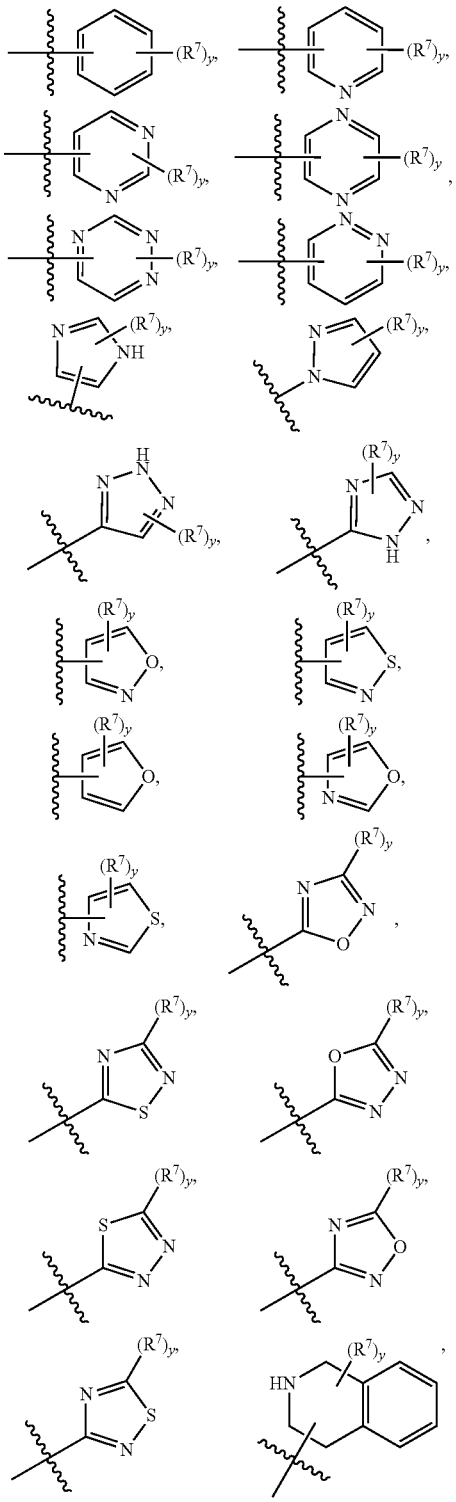

-continued

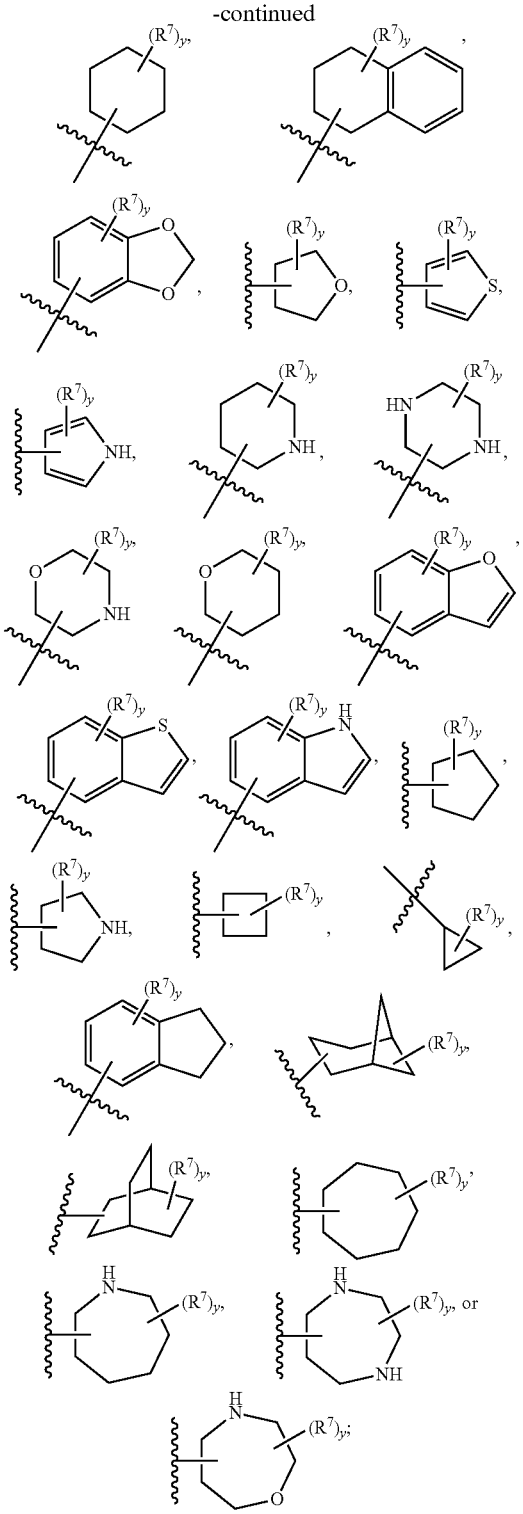

y is 0-5, each occurrence of $R^7$ is independently =O, =NR', =S, halogen, —CN, —$NO_2$, or W—R" wherein:

each W is independently a bond or an optionally substituted $C_1$-$C_6$ alkylidine chain, wherein up to two methylene units of the chain are optionally and independently replaced by —NR"—, —S—, —O—, —CS—, —$CO_2$—, —OCO—, —CO—, —COCO—, —CONR"—, —NR"CO—, —NR"$CO_2$—, —$SO_2$NR"—, —NR"$SO_2$—, —CONR"NR"—, —NR"CONR"—, —OCONR"—, —NR"NR"—, —NR"$SO_2$NR"—, —SO—, —$SO_2$—, —PO—, —$PO_2$— or —POR", and each occurrence of R" is independently hydrogen or an optionally substituted $C_1$-$C_6$ aliphatic group, a 3-8 membered saturated, partially unsaturated, or fully unsaturated monocyclic ring having 0-3 heteroatoms independently selected from nitrogen, oxygen, or sulfur, or an 8-12 membered saturated, partially saturated, or fully unsaturated bicyclic ring system having 0-5 heteroatoms independently selected from nitrogen, oxygen, or sulfur;

each occurrence of R' in T, V, $R^1$, $R^2$, $R^3$, $R^4$, and $R^7$ is independently hydrogen or an optionally substituted group selected from a $C_1$-$C_6$ aliphatic group, a 3-8 membered saturated or partially unsaturated monocyclic ring having 0-3 heteroatoms independently selected from nitrogen, oxygen, or sulfur, an 8-12 membered saturated, partially unsaturated, or fully unsaturated bicyclic ring system having 0-5 heteroatoms independently selected from nitrogen, oxygen, or sulfur, or two occurrences of R' are taken together with the atom(s) to which they are bound to form an optionally substituted 3-12 membered saturated or partially unsaturated monocyclic or bicyclic ring having 0-4 heteroatoms independently selected from nitrogen, oxygen, or sulfur, wherein an optional substituent on an unsaturated carbon atom on an aryl or heteroaryl group is selected from halogen; —R°; —OR°; —SR°; phenyl (Ph) optionally substituted with R°; —O(Ph) optionally substituted with R°; —$(CH_2)_{1-2}$(Ph), optionally substituted with R°; —CH=CH(Ph), optionally substituted with R°; a 5-6 membered heteroaryl or heterocyclic ring optionally substituted with R°; —$NO_2$; —CN; —N(R°)$_2$; —NR°C(O)R°; —NR°C(S)R°; —NR°C(O)N(R°)$_2$; —NR°C(S)N(R°)$_2$; —NR°$CO_2$R°; —NR°NR°C(O)R°; —NR°NR°C(O)N(R°)$_2$; —NR°NR°$CO_2$R°; —C(O)C(O)R°; —C(O)$CH_2$C(O)R°; —$CO_2$R°; —C(O)R°; —C(S)R°; —C(O)N(R°)$_2$; —C(S)N(R°$_2$; —OC(O)N(R°)$_2$; —OC(O)R°; —C(O)N(OR°)R°; —C(NOR°)R°; —S(O)$_2$R°; —S(O)$_3$R°; —$SO_2$N(R°)$_2$; —S(O)R°; —NR°$SO_2$N(R°)$_2$; —NR°$SO_2$R°; —N(OR°)R°; —C(=NH)—N(R°)$_2$; —P(O)$_2$R°; —PO(R°)$_2$; —OPO(R°)$_2$; or —$(CH_2)_{0-2}$NHC(O)R°; wherein each independent occurrence of R° is selected from hydrogen, optionally substituted $C_1$-$C_6$ aliphatic, an unsubstituted 5-6 membered heteroaryl or heterocyclic ring, phenyl, —O(Ph), or —$CH_2$(Ph), or two independent occurrences of R° on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur;

wherein an optional substituent on a saturated carbon on an aliphatic or heteroaliphatic group, or on a non-aromatic heterocyclic ring are selected from halogen; —R°; —OR°; —SR°; phenyl (Ph) optionally substituted with R°; —O(Ph) optionally substituted with R°; —$(CH_2)_{1-2}$(Ph), optionally substituted with R°; —CH=CH(Ph), optionally substituted with R°; a 5-6 membered heteroaryl or heterocyclic ring optionally substituted with R°; —$NO_2$; —CN; —N($R^1$)$_2$; —NR°C(O)R°; —NR°C(S)R°; —NR°C(O)N(R°)$_2$; —NR°C(S)N(R°)$_2$; —NR°$CO_2$R°; —NR°NR°C(O)R°; —NR°NR°C(O)N (R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₃ R°; —SO₂N(R°)₂; —S(O)R°; —NR°SO₂N(R°)₂; —NR°SO₂R°; —N(OR°)R°; —C(=NH)—N(R°)₂; —P(O)₂R°; —PO(R°)₂; —OPO(R°)₂; —(CH₂)₀₋₂ NHC(O)R°; =O; =S; =NNHR*; =NN(R*)₂; =NNHC(O)R*; =NNHCO₂(alkyl); =NNHSO₂(alkyl); or =NR*, where each R* is independently selected from hydrogen or an optionally substituted C₁₋₆ aliphatic group;

wherein an optional substituent on a nitrogen of a non-aromatic heterocyclic ring is independently selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺₂, —C(=S)N(R⁺¹)₂, —C(=NH)—N(R⁺)₂, or —NR⁺SO₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or two independent occurrences of R⁺, on the same substituent or different substituents, taken together with the atom(s) to which each R⁺ group is bound, form an optionally substituted 3-12 membered saturated, partially unsaturated, or fully unsaturated monocyclic or bicyclic ring having 0-4 heteroatoms independently selected from nitrogen, oxygen, or sulfur, provided that A) if R², R³, and R⁴ are simultaneously H, then R¹ is not —Si(R')₃; and
B) if R¹, R² and R⁴ are simultaneously H, then R³ is not phenyl or phenyl substituted with O-phenyl or —N(Me)₂.

2. The compound according to claim 1, wherein y is 1, 2, or 3 and each occurrence of R⁷ is independently —F, —Cl, —Br, —CN, —OH, —NH₂, —CH₂OH, C₁-C₆ alkyl, —O(C₁-C₆ alkyl), —CH₂O(C₁-C₆ alkyl), —CO(C₁-C₆ alkyl), —COO(C₁-C₆ alkyl), —NHSO₂(C₁-C₆ alkyl), —SO₂NH₂, —CONH₂, —CONH(C₁-C₆ alkyl), —SO₂(C₁-C₆ alkyl), —SO₂-phenyl, phenyl, benzyl, —N(C₁-C₆ alkyl)₂, or —S(C₁-C₆ alkyl), wherein each of the foregoing phenyl, benzyl, and C₁-C₆ alkyl groups is independently and optionally substituted, and wherein each of the foregoing C₁-C₆ alkyl groups is linear, branched, or cyclic.

3. The compound according to claim 1, wherein R², R³, and R⁴ are each independently selected from hydrogen, R', halogen, —CN, —NO₂, —N(R')₂, —CH₂N(R')₂, —CH₂OR', —SR', —CH₂SR', —COOR', —NR'COR', —CON(R')₂, —SO₂N(R')₂, —CONR'(CH₂)₂N(R')₂, —CONR'(CH₂)₃N(R')₂, —CONR(CH₂)₄N(R')₂, —O(CH₂)₂OR', —O(CH₂)₃OR', —O(CH₂)₄OR', —O(CH₂)₂N(R')₂, —O(CH₂)₃N(R')₂, or —O(CH₂)₄N(R')₂, wherein each occurrence of R' in R², R³, and R⁴ is independently hydrogen or an optionally substituted group selected from a C₁-C₆ aliphatic group, a 3-8 membered saturated or partially unsaturated monocyclic ring having 0-3 heteroatoms independently selected from nitrogen, oxygen, or sulfur, an 8-12 membered saturated, partially unsaturated, or fully unsaturated bicyclic ring system having 0-5 heteroatoms independently selected from nitrogen, oxygen, or sulfur, or two occurrences of R' are taken together with the atom(s) to which they are bound to form an optionally substituted 3-12 membered saturated or partially unsaturated monocyclic or bicyclic ring having 0-4 heteroatoms independently selected from nitrogen, oxygen, or sulfur.

4. The compound according to claim 1 wherein R² and R⁴ are both hydrogen.

5. The compound according to claim 1, wherein R' is selected from hydrogen, C₁-C₄ alkyl, —COR', —SO₂R', or —Si(R')₃, wherein each occurrence of R' in R¹ is independently hydrogen or an optionally substituted group selected from a C₁-C₆ aliphatic group, a 3-8 membered saturated or partially unsaturated monocyclic ring having 0-3 heteroatoms independently selected from nitrogen, oxygen, or sulfur, an 8-12 membered saturated, partially unsaturated, or fully unsaturated bicyclic ring system having 0-5 heteroatoms independently selected from nitrogen, oxygen, or sulfur, or two occurrences of R' are taken together with the atom(s) to which they are bound to form an optionally substituted 3-12 membered saturated or partially unsaturated monocyclic or bicyclic ring having 0-4 heteroatoms independently selected from nitrogen, oxygen, or sulfur.

6. The compound according to claim 5, wherein R¹ is hydrogen.

7. The compound according to claim 3, wherein R², R³, and R⁴ are each independently selected from hydrogen, —Cl, —Br, —F, —CN, —COOH, —COOMe, —NH₂, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, —SO₂N(Me)₂, or an optionally substituted group selected from C₁-C₄ alkyl, C₁-C₄ alkyloxy, a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur.

8. The compound according to claim 1, wherein R³ is selected from —H, —Cl, —F, —Br, —CN, —COOH, —COOMe, —NH₂, —N(R')₂, —NO₂, —OR', —CON(R')₂, —COOR', —OH, —SR', —C(R')₂OR', —N(R')COR', —N(R')C(O)OR', —SO₂NH₂, —SO₂N(R')₂, or an optionally substituted group selected from C₁-C₄ aliphatic, C₁-C₄ alkyloxy, or —C≡C—C₁-C₄ aliphatic.

9. The compound according to claim 8, wherein R² and R⁴ are both hydrogen.

10. The compound according to claim 9, wherein x is 2 or 3, and at least one occurrence of R⁵ is halogen.

11. The compound according to claim 1, wherein at least one occurrence of R⁵ is —N(R')₂, wherein one R' in R⁵ is hydrogen and the second R' in R⁵ is a ring selected from

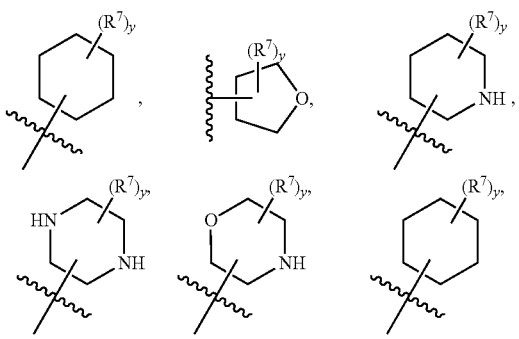

-continued

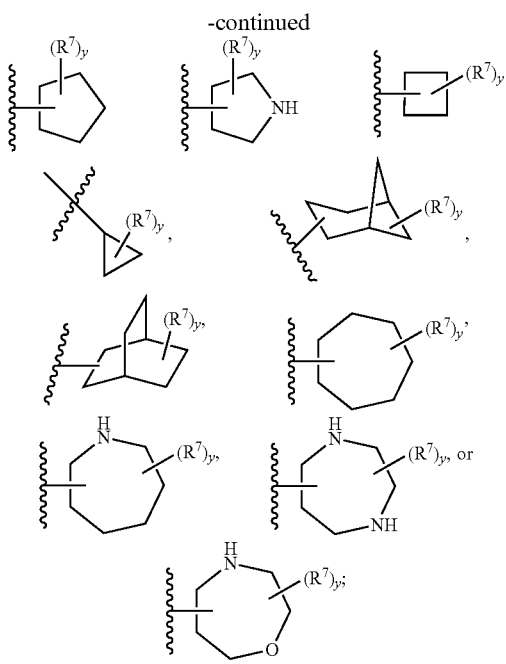

wherein y is 1, 2, or 3, and $R^7$ is =O, =S, halogen, —NO$_2$, or W—R", wherein each W is independently a bond or an optionally substituted C$_1$-C$_6$ alkylidine chain, wherein up to two methylene units of the chain are optionally and independently replaced by —NR"—, —S—, —O—, —CS—, —CO$_2$—, —OCO—, —CO—, —COCO—, —CONR"—, —NR"CO—, —NR"CO$_2$—, —SO$_2$NR"—, —NR"SO$_2$—, —CONR"NR"—, —NR"CONR"—, —OCONR"—, —NR"NR"—, —NR"SO$_2$NR"—, —SO—, —SO$_2$—, —PO—, —PO$_2$— or POR", and each occurrence of R" is independently hydrogen or an optionally substituted C$_1$-C$_6$ aliphatic group, a 3-8 membered saturated, partially unsaturated, or fully unsaturated monocyclic ring having 0-3 heteroatoms independently selected from nitrogen, oxygen, or sulfur, or an 8-12 membered saturated, partially saturated, or fully unsaturated bicyclic ring system having 0-5 heteroatoms independently selected from nitrogen, oxygen, or sulfur.

12. The compound according to claim 11, wherein y is 1, 2, or 3 and each occurrence of $R^7$ is independently —F, —Cl, —Br, —OH, —NH$_2$, —CH$_2$OH, C$_1$-C$_6$ alkyl, —O(C$_1$-C$_6$ alkyl), —CH$_2$O(C$_1$-C$_6$ alkyl), —CO(C$_1$-C$_6$ alkyl), —COO(C$_1$-C$_6$ alkyl), —NHSO$_2$(C$_1$-C$_6$ alkyl), —SO$_2$NH$_2$, —CONH$_2$, —CONH(C$_1$-C$_6$ alkyl), —SO$_2$(C$_1$-C$_6$ alkyl), —SO$_2$-phenyl, phenyl, benzyl, —N(C$_1$-C$_6$ alkyl)$_2$, or —S(C$_1$-C$_6$ alkyl), wherein each of the foregoing phenyl, benzyl, and C$_1$-C$_6$ alkyl groups is independently and optionally substituted, and wherein each of the foregoing C$_1$-C$_6$ alkyl groups is linear, branched, or cyclic.

13. The compound according to claim 12, wherein x is 2 or 3, and at least one occurrence of $R^5$ is halogen.

14. A pharmaceutical composition comprising a compound according to any one of claim 1 or 11 and a pharmaceutically acceptable carrier, adjuvant, or vehicle.

15. The composition of claim 14, further comprising an additional therapeutic agent selected from a chemotherapeutic or anti-proliferative agent, a treatment for Alzheimer's Disease, a treatment for Parkinson's Disease, an agent for treating Multiple Sclerosis (MS), a treatment for asthma, an agent for treating schizophrenia, an anti-inflammatory agent, an immunomodulatory or immunosuppressive agent, a neurotrophic factor, an agent for treating cardiovascular disease, an agent for treating destructive bone disorders, an agent for treating liver disease, an agent for treating a blood disorder, or an agent for treating an immunodeficiency disorder.

* * * * *